(12) United States Patent
Bozikis et al.

(10) Patent No.: US 11,492,346 B2
(45) Date of Patent: Nov. 8, 2022

(54) BENZISOXAZOLE SULFONAMIDE DERIVATIVES

(71) Applicants: Pfizer Inc., New York, NY (US); CTXT PTY LTD, Melbourne (AU)

(72) Inventors: Ylva Elisabet Bergman Bozikis, Parkville (AU); Michelle Ang Camerino, Parkville (AU); Pei-Pei Kung, San Diego, CA (US); Paul Anthony Stupple, Melbourne (AU); Scott Channing Sutton, San Diego, CA (US)

(73) Assignees: Pfizer Inc., New York, NY (US); CTXT PTY LTD, Melbourne (AU)

( * ) Notice: Subject to any disclaimer, the term of this patent is extended or adjusted under 35 U.S.C. 154(b) by 0 days.

(21) Appl. No.: 16/902,515

(22) Filed: Jun. 16, 2020

(65) Prior Publication Data
US 2020/0399258 A1     Dec. 24, 2020

Related U.S. Application Data

(60) Provisional application No. 63/025,278, filed on May 15, 2020, provisional application No. 62/953,223, filed on Dec. 24, 2019, provisional application No. 62/863,199, filed on Jun. 18, 2019.

(51) Int. Cl.
| | | |
|---|---|---|
| *C07D 413/06* | (2006.01) | |
| *A61P 35/04* | (2006.01) | |
| *A61K 45/06* | (2006.01) | |

(52) U.S. Cl.
CPC ............ *C07D 413/06* (2013.01); *A61P 35/04* (2018.01); *A61K 45/06* (2013.01); *C07B 2200/13* (2013.01)

(58) Field of Classification Search
None
See application file for complete search history.

(56) References Cited

U.S. PATENT DOCUMENTS

| | | |
|---|---|---|
| 2,358,031 A | 9/1944 | Roblin et al. |
| 2,525,321 A | 10/1950 | Hultquist et al. |
| 3,064,003 A | 11/1962 | Satzinger et al. |
| 3,332,942 A | 7/1967 | Breivogel et al. |
| 3,951,967 A | 4/1976 | Novello |
| 3,960,854 A | 6/1976 | Novello |
| 4,172,896 A | 10/1979 | Uno et al. |
| 4,251,664 A | 2/1981 | Spitzner |
| 6,248,767 B1 | 6/2001 | Blok et al. |
| 9,493,429 B2 | 11/2016 | Chen et al. |
| 2006/0025415 A1 | 2/2006 | Gonzalez et al. |
| 2006/0128706 A1 | 6/2006 | Bruncko et al. |
| 2006/0258657 A1 | 11/2006 | Bruncko et al. |
| 2007/0015787 A1 | 1/2007 | Bruncko et al. |
| 2007/0072860 A1 | 3/2007 | Bruncko et al. |
| 2009/0042945 A1 | 2/2009 | Frank et al. |
| 2009/0163545 A1 | 6/2009 | Goldfarb |
| 2013/0022629 A1 | 1/2013 | Sharpe et al. |
| 2015/0183802 A1 | 7/2015 | Chen et al. |
| 2016/0009667 A1 | 1/2016 | Chen et al. |
| 2020/0039945 A1 | 2/2020 | Lagiakos et al. |
| 2020/0399258 A1 | 12/2020 | Bozikis et al. |

FOREIGN PATENT DOCUMENTS

| | | |
|---|---|---|
| BE | 617370 A | 11/1962 |
| CA | 2121724 A1 | 10/1994 |
| CN | 101747325 A | 6/2010 |
| CN | 101845043 A | 9/2010 |
| DE | 1102745 B | 3/1961 |
| EP | 181018 A2 | 5/1986 |
| EP | 371438 A2 | 6/1990 |
| EP | 0558258 A1 | 9/1993 |
| EP | 0569193 A1 | 11/1993 |

(Continued)

OTHER PUBLICATIONS

Bruncko et al., database CAPLUS Acc. No. 2007:359148, CAS SciFinder abstract of US 2007/0072860 A1 (Mar. 29, 2007).*
Melero et al. Nature Reviews Cancer, 2015, 15, 457-472 doi:10.1038/nrc3973.
Meng et al., Zhongguo Yaowu Huaxue Zazhi, 1996, 6(4), 257-261.
Merson et al., J. Neurosci., 2006, 26, 11359-11370 doi :10.1523/JNEUROSCI.2247-6.2006.
Miller, A.M. et al. J. Immunol., 2006, 177, 7398-7405 doi:10.4049/jimmunol.177.10.7398.
Mochona et al, Bioorg. & Med. Chem. Lett., 2016, 26(12), 2847-2851.

(Continued)

*Primary Examiner* — Brian J Davis
(74) *Attorney, Agent, or Firm* — Banner & Witcoff, Ltd.

(57) ABSTRACT

The present invention relates to compounds of formula (I)

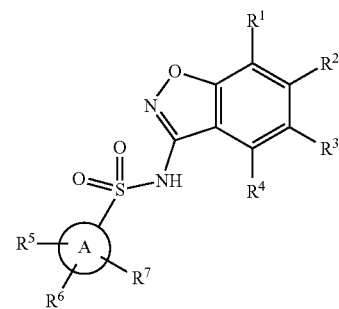

or pharmaceutically acceptable salts thereof, wherein Ring A, $R^1$-$R^8$, and n are defined herein. The novel benzisoxazole sulfonamide derivatives are useful in the treatment of abnormal cell growth, such as cancer, in patients. Additional embodiments relate to pharmaceutical compositions containing the compounds and to methods of using the compounds and compositions in the treatment of abnormal cell growth in patients.

6 Claims, 1 Drawing Sheet
Specification includes a Sequence Listing.

(56) References Cited

FOREIGN PATENT DOCUMENTS

| | | |
|---|---|---|
| EP | 1963295 A1 | 9/2008 |
| FR | 2690160 A1 | 10/1993 |
| GB | 689281 A | 3/1953 |
| JP | 29002834 B | 5/1927 |
| JP | 36003685 B | 4/1936 |
| JP | 36019566 B | 10/1936 |
| JP | 3901229 B | 2/1939 |
| JP | 49008255 B | 2/1974 |
| JP | 5452075 A | 4/1979 |
| JP | 03-258771 A | 11/1991 |
| JP | 63238006 A | 10/1998 |
| JP | 2003292485 A | 10/2003 |
| PL | 220630 B1 | 11/2015 |
| WO | 199321171 A1 | 10/1993 |
| WO | 199427979 A1 | 12/1994 |
| WO | 199631492 A1 | 10/1996 |
| WO | 199739000 A1 | 10/1997 |
| WO | 199813366 A1 | 4/1998 |
| WO | 199821186 A1 | 5/1998 |
| WO | 199849162 A1 | 11/1998 |
| WO | 2001019798 A2 | 3/2001 |
| WO | 200149289 A1 | 7/2001 |
| WO | 200164642 A2 | 9/2001 |
| WO | 200164643 A2 | 9/2001 |
| WO | 2003042700 A2 | 5/2003 |
| WO | 2003044000 A1 | 5/2003 |
| WO | 2004085385 A2 | 10/2004 |
| WO | 2004103980 A1 | 12/2004 |
| WO | 2004113310 A1 | 12/2004 |
| WO | 2005009967 A2 | 2/2005 |
| WO | 2005013914 A2 | 2/2005 |
| WO | 2006044405 A1 | 4/2006 |
| WO | 2006122799 A1 | 11/2006 |
| WO | 2006124744 A1 | 11/2006 |
| WO | 2007039174 A2 | 4/2007 |
| WO | 2007039175 A1 | 4/2007 |
| WO | 2007057093 A1 | 5/2007 |
| WO | 2007075895 A2 | 7/2007 |
| WO | 2008022286 A2 | 2/2008 |
| WO | 2008063668 A1 | 5/2008 |
| WO | 2008064116 A2 | 5/2008 |
| WO | 2008089307 A2 | 7/2008 |
| WO | 2009012242 A1 | 1/2009 |
| WO | 2009058348 A1 | 5/2009 |
| WO | 2009080223 A1 | 7/2009 |
| WO | 201019788 A1 | 2/2010 |
| WO | 2010046780 A2 | 4/2010 |
| WO | 2010121963 A1 | 10/2010 |
| WO | 2011017561 A1 | 2/2011 |
| WO | 2011082400 A2 | 7/2011 |
| WO | 2011085575 A1 | 7/2011 |
| WO | 2011137089 A1 | 11/2011 |
| WO | 2011156610 A2 | 12/2011 |
| WO | 20120007868 A2 | 1/2012 |
| WO | 2012080729 A2 | 6/2012 |
| WO | 2012088438 A1 | 6/2012 |
| WO | 2012129562 A2 | 9/2012 |
| WO | 2014144545 A2 | 9/2014 |
| WO | 2015112465 A1 | 7/2015 |
| WO | 2016198507 A1 | 12/2016 |
| WO | 2017002120 A1 | 1/2017 |
| WO | 2017098421 A1 | 6/2017 |
| WO | 2018081167 A1 | 5/2018 |
| WO | 2018102419 A1 | 6/2018 |
| WO | 2018226976 A1 | 12/2018 |
| WO | 2019243491 A1 | 12/2019 |

OTHER PUBLICATIONS

Morrow et al., PCT/EP2018/073431 International Search Report and Written Opinion dated Dec. 3, 2018.
Morrow et al., U.S. Appl. No. 16/642,290 Application filed Feb. 26, 2020.
Morrow et al., U.S. Appl. No. 16/642,290 Preliminary Amendment filed Feb. 26, 2020.
Neidlein & Hausmann, Zeitschrift fur Naturforschung, Teil B. Chemie, Biochemie, Biophysik, Biologie und wervandte Gebeite, 1966, 21(9), 898.
Neidlein & J. Tauber, Pharmazeutische Zentralhalle, 1968, 107(6), 430-432.
Pachhamia J. Indian Chem. Soc., 1988, 65(5), 357-361.
Pattan et al., Asian Journal of Research in Chemistry, 2009, 2(2), 123-126.
Pattan et al., Iranian Journal of Pharmaceutical Sciences, 2009, 5(4), 225-230.
Persa et al., Cancer Letters, 2015 368(2), 252-261 doi:10.1016/j.canlet.2015.03.003.
Polozov et al., Tetrahedron Letters, 2010, 51(4), 575-578.
Potkin et al., Russian Journal of Organic Chemistry, 2009, 45(6), 879-883.
Rosenthal et al., Bioorganic & Medicinal Chemistry Letters, 2013, 23(20), 5660-5666.
Savastre et al., Bulletin of University of Agricultural Sciences and Veterinary Medicine Cluj-Napoca, Veterinary Medicine, 2013, 70(1), 134-139.
U.S. Appl. No. 16/446,868 amendment filed Jan. 5, 2021.
Sheikh et al., Blood, 2015, 125(12), 1910-21 doi:10.1182/blood-2014-08-594655.
Shi et al., Nature Biotech, 2015, 33, 661-667 doi:10.1038/nbt.3235.
Singh et al., International Journal of Chemical Sciences, 2012, 10(3), 1487-1492.
Smaine et al., Bioorganic & Medicinal Chemistry Letters, 2008, 18(24), 6332-6335.
Spillane et al., Journal of Agricultural and Food Chemistry (2009), 57(12), 5486-5493.
Stachel, Chemische Berichte, 1963, 96, 1088-97.
Stein et al., Journal of Medicinal Chemistry, 1995, 38, 1344-1354.
Stern et al., Crit. Rev. Oncol. Hematol., 2005, 54, 11-29 doi:10.1016/j.critrevonc.2004.10.011.
Su et al., Int. J. Mol. Sci., 2016, 17, 1-18 doi:10.3390/ijms17101594.
Sugai et al., Chemical & Pharmaceutical Bulletin, 1984, 32(2), 530-7.
Suyama et al., Heterocycles, 2003, 60(1), 121-129.
Tait et al., Bollettino chimico Farmaceutico, 1990, 129(9), 273-275.
Tan et al., Yingyong Huaxue, 2016, 33(9), 1067-1072.
Tao, H. et al., Lung Cancer, 2012, 75, 95-101 doi:10.1016/j.lungcan.2011.06.002.
Thomas et al., Development, 2000, 127, 2537-2548 PMID:10821753.
Thomas et al., Genes Dev, 2006, 20(9), 1175.
Turner-Ivey et al., Neoplasia, 2014, 16(8): 644-655 doi:10.1016/j.neo.2014.07.007.
Valerio et al., Cancer Research, 2017, 77(7), 1753-62 doi:10.1158/0008-5472.CAN-16-2374.
Vikani et al., Journal of the Indian Chemical Society, 1990, 67(10), 859-61.
Vizmanos et al., Genes Chromosomes Cancer, 2003, 36(4), 402-405 doi:10.1002/gcc.10174.
Voss et al., BioEssays, 2009, 31(10), 1050-1061 doi:10.1002/bies.200900051.
Wang et al. EBioMedicine, 2016, 13, 99-112 doi:10.1016/j.ebiom.2016.10.018.
Wang et al., Gaodeng Xuexiao Huaxue Xuebao, 1987, 8(2), 133-6.
Wang et al., Oncogene, 2017, 36, 3048-3058 doi:10.1038/onc.2016.458.
Wells et al., Journal of Medicinal Chemistry, 2001, 44(21), 3488-3503.
Xiao et al., Cell reports, 2014, 7, 1471-1480 doi :10.1016/j.celrep.2014.04.021.
Xiao-Jian et al., Frontiers in Oncology, 2015, 5, 108.
Yan et al., Breast Cancer Research, 2011, 13, R47 doi:10.1186/bcr2869.
Yoshida et al., Yakugaku Zasshi 1954, 74, 948-50.
Young et al., Blood Res 2016 51(3), 152-154 doi:10.5045/br.2016.51.3.152.

(56) References Cited

OTHER PUBLICATIONS

Dhuban et al., Sci. Immunol., 2017, 2, 9297 doi:10.1126/sciimmunol.aai9297.
Doyon et al., Mol. Cell., 2006, 21, 51-64 doi:10.1016/j.molcel.2005.12.007.
Duong et al., Cancer Res., 2013, 73, 5556-5568 doi:10.1158/0008-5472.CAN-13-0013.
Dzhemukhadze et al., Fenol'nye Soedineniya i Ikh Biologicheskie Funktsii, Materialy Vsesoyuznogo Simpoziuma po Fenol'nym Soedineniyam 1968, 196-202.
Fairley et al., Synlett, 2013, 24(5), 570-574.
Falk et al., J. Biomalecular Screening 16(10): 2011 DOI:10.1177/1087057111421631.
Fan et al., Oncogene, 2015, 1-12.
Fernandes et al., Journal of the Institution of Chemists (India), 1991, 63(3), 83-4.
Fujita et al., Yakugaku Zasshi, 1964, 84(11), 1061-7.
Seng et al., Nature Immunology, 2017, (online) doi:10.1038/ni.3748.
Ghizzoni et al., Eur. J. Med. Chem., 2012, 47, 337-344 doi:10.1016/j.ejmech.2011.11.001.
Gil et al., J. Proteomics, 2017, 150, 297-309 doi:10.1016/j.jprot.2016.10.003.
Giri et al., Journal of the Indian Chemical Society, 1964, 41(4), 295-8.
Gobert et al., Cancer Research, 2009, 69, 2000-2009 doi:10.1158/0008-5472.CAN-08-2360.
Grashey et al., Chemiker-Zeitung 1976, 100(11), 497-8.
Grashey et al., Chemiker-Zeitung, 1973, 97(11), 623.
Grashey et al., Tetrahedron Letters, 1972, (29), 2943-6.
Gregory J. Wells et al, "1, 2-Benzothiazine 1, 1-Dioxide P2-P3 Peptide Mimetic Aldehyde Calpain I Inhibitors", Journal of Medicinal Chemistry, vol. 44, No. 21, Oct. 1, 2001, pp. 3488-3503.
Hangan et al., Farmacia, 2012, 60(6), 932-938.
Hangan et al., Journal of Chemical Sciences (Bedin, Germany), 2016, 128(5), 815-824.
Hangan et al., Russian Journal of Coordination Chemistry, 2015, 41(6), 395-404.
Hassan et al., Journal of Chemical Technology and Biotechnology, 1982, 32(2), 416-20.
Hategan et al., Bioorganic & Medicinal Chemistry Letters, 2009, 19(23), 6797-6800.
Hirsch et al., J. Mol. Biol., 2017, 429(13), 1958-1977.
Hitchin et al., Med. Chem. Common., 2013, 4, 1513-1522.
Holbert et al., J. Biol. Chem., 2007, 282, 36603-36613 doi:10.1074/jbc.M705812200.
Hultquist et al., Journal of the American Chemical Society, 1951, 73, 2558-66.
Iizuka et al., Cancer Sci., 2013, 104, 1647-1655 doi:10.1111/cas.12303.
Iizuka et al., Mol. Cell. Biol., 2006, 26, 1098-1108 doi:10.1128/MCB.26.3.1098-1108.2006.
International Preliminary Report on Patentability for PCT/EP2019/066337, dated Dec. 22, 2020.
International Search Report and Written Opinion for PCT/EP2018/073431 dated Dec. 3, 2018, 9 pages.
International Search Report and Written Opinion for PCT/IB2020/055589, dated Jul. 9, 2020.
International Search Report for PCT/EP2019/067309 dated Nov. 21, 2019, 17 pages.
J. A. L. Brown et al: "Targeting cancer using KAT inhibitors to mimic lethal knockouts", Biochemical Society Transactions, vol. 44, No. 4, Aug. 15, 2016, pp. 979-986.
Joshi et al., Immunity 2015, 43, 579-590 doi:10.1016/j.immuni.2015.08.006.
Judes et al., Epigenomics, 2015, 7(8), 1351-1363.
Keil et al., ChemMedChem, 2011, 6(4), 633-653.
King et al., Journal of Biological Chemistry, 2009, 284(14), 9059-9065.
Klosa, Archiv der Pharmazie und Berichte der Deutschen Pharmazeutischen Gesellschaft, 1954, 287, 12-14.
Kurihara et al., Yakugaku Zasshi, 1965, 85(10), 920-5.
Kuznetsov et al., Izvestiya Akademii Nauk SSSR, Seriya Khimicheskaya 1976, (2), 319-22.
Lagiakos et al., U.S. Appl. No. 16/445,868 Application filed Jun. 20, 2019.
Lagiakos et al., U.S. Appl. No. 16/445,868 Notice of Allowance dated Oct. 5, 2020.
Lagiakos et al., U.S. Appl. No. 16/445,868 Response to Non-Final Office Action filed Aug. 19, 2020.
Lalezari et al., Journal of Heterocyclic Chemistry, 1966, 3(3), 336-7.
Lazaris et al., Khimiya Geterotsiklicheskikh Soedinenii, 1973, (10), 1345-50.
Lee, Archives of Pharmacal Research, 2004, 27(3), 305-313.
Li et al., PNAS, 2007, 104, 4571-4576 doi:10.1073/pnas.0700298104.
Liu, Workman and Vignali, The FEBS journal, 2016, 283, 2731-2748.
Malev, Metody Polucheniya Khimicheskikh Reaktivov i Preparatov 1964, No. 8, 44-8.
Zack et al., Nature Genetics 2013 45, 1134-1140 doi:10.1038/ng.2760.
Zhang et al., Mini. Rev. Med. Chem., 2017, 17, 1-8 doi:10.2174/1389557516666160923125031.
Aggarwal and Calvi, Nature, 2004, 430, 372-376 doi:10.1038/nature02694.
Aiello et al., Ricerca Scientifica, Parte 2: Rendiconti, Sezione B: Biologica, 1964, 4(4), 575-80.
Avvakumov et al., Oncogene, 2007, 26, 5395-5407 doi:10.1038/sj.onc.1210608.
Baell et al., Nature, doi:/10.1038/s41586-018-0387-5, 2018.
Berge et al., J. Pharm. Sci., 1977, 66, 1-19 doi:10.1002/jps.2600660104.
Borrow et al., Nat. Genet., 1996, 14, 33-41 doi:10.1038/ng0996-33.
Brown et al., Biocehmical Society Transactions, 2016, 44(4), 979-986.
Chavan et al., Indian Journal of Heterocyclic Chemistry, 2007, 17(1), 45-48.
Czudor et al., Bioorganic & Med. Chem. Let., 2018, vol. 28, p. 769-773.
Dekker et al., Drug, Discov. Today, 2014, 19, 654-660 doi:10.1016/j.drudis.2013.11.012.
Lagiakos et al., U.S. Appl. No. 17/392,356, claims filed Aug. 3, 2021, 5 pages.
Database CA [Online] Chemical Abstracts Service, Columbus, Ohio, US, compound with RN 1032507-60-0, retrieved from STN, entered Jul. 3, 2008.
Database CA [Online] Chemical Abstracts Service, Columbus, Ohio, US, compound with RN 1207646-75-0, retrieved from STN, entered Mar. 2, 2010.
Database CA [Online] Chemical Abstracts Service, Columbus, Ohio, US, compound with RN 1207661-17-3, retrieved from STN, entered Mar. 2, 2010.
Database CA [Online] Chemical Abstracts Service, Columbus, Ohio, US, compound with RN 1808493-75-5, retrieved from STN, entered Sep. 29, 2015.
Database CA [Online] Chemical Abstracts Service, Columbus, Ohio, US, compound with RN 1808522-80-6, retrieved from STN, entered Sep. 29, 2015.
Database CA [Online] Chemical Abstracts Service, Columbus, Ohio, US, compound with RN 1808570-72-0, retrieved from STN, entered Sep. 29, 2015.
Database CA [Online] Chemical Abstracts Service, Columbus, Ohio, US, compound with RN 1808779-04-5, retrieved from STN, entered Sep. 29, 2015.
Database CA [Online] Chemical Abstracts Service, Columbus, Ohio, US, compound with RN 1808779-26-1, retrieved from STN, entered Sep. 29, 2015.
Database CA [Online] Chemical Abstracts Service, Columbus, Ohio, US, compound with RN 2094188-03-9, retrieved from STN, entered May 2, 2017.

(56) References Cited

OTHER PUBLICATIONS

Database CA [Online] Chemical Abstracts Service, Columbus, Ohio, US, compound with RN 2094235-06-8, retrieved from STN, entered May 2, 2017.
Database CA [Online] Chemical Abstracts Service, Columbus, Ohio, US, compound with RN 2094317-93-6, retrieved from STN, entered May 2, 2017.
Database CA [Online] Chemical Abstracts Service, Columbus, Ohio, US, compound with RN 2094373-00-7, retrieved from STN, entered May 2, 2017.
Database CA [Online] Chemical Abstracts Service, Columbus, Ohio, US, compound with RN 2094434-40-7, retrieved from STN, entered May 2, 2017.
Database CA [Online] Chemical Abstracts Service, Columbus, Ohio, US, compound with RN 2094666-45-0, retrieved from STN, entered May 2, 2017.
Database CA [Online] Chemical Abstracts Service, Columbus, Ohio, US, compound with RN 2094857-16-4, retrieved from STN, entered May 3, 2017.
Database CA [Online] Chemical Abstracts Service, Columbus, Ohio, US, compound with RN 2094888-54-5, retrieved from STN, entered May 3, 2017.
Database CA [Online] Chemical Abstracts Service, Columbus, Ohio, US, compound with RN 2138109-21-2, retrieved from STN, entered Nov. 2, 2017.
Database CA [Online] Chemical Abstracts Service, Columbus, Ohio, US, compound with RN 2138573-90-5, retrieved from STN, entered Nov. 6, 2017.
Database CA [Online] Chemical Abstracts Service, Columbus, Ohio, US, compound with RN 2178688-56-5, retrieved from STN, entered Feb. 22, 2018.
Database CA [Online] Chemical Abstracts Service, Columbus, Ohio, US, compound with RN 2189108-08-3, retrieved from STN, entered Mar. 12, 2018.
Database CA [Online] Chemical Abstracts Service, Columbus, Ohio, US, compound with RN 2224022-18-6, retrieved from STN, entered May 20, 2018.
Database CA [Online] Chemical Abstracts Service, Columbus, Ohio, US, compound with RN 2224161-46-8, retrieved from STN, entered May 20, 2018.
Database CA [Online] Chemical Abstracts Service, Columbus, Ohio, US, compound with RN 891026-69-0, retrieved from STN, entered Jul. 9, 2006.
Database CA [Online] Chemical Abstracts Service, Columbus, Ohio, US, compound with RN 891026-77-0, retrieved from STN, entered Jul. 9, 2006.
Database CA [Online] Chemical Abstracts Service, Columbus, Ohio, US, compound with RN 891027-33-1, retrieved from STN, entered Jul. 9, 2006.
Database CA [Online] Chemical Abstracts Service, Columbus, Ohio, US, compound with RN 891027-41-1, retrieved from STN, entered Jul. 9, 2006.
Database CA [Online] Chemical Abstracts Service, Columbus, Ohio, US, compound with RN 891027-49-9, retrieved from STN, entered Jul. 9, 2006.
Database CA [Online] Chemical Abstracts Service, Columbus, Ohio, US, compound with RN 891027-57-9, retrieved from STN, entered Jul. 9, 2006.
Database CA [Online] Chemical Abstracts Service, Columbus, Ohio, US, compound with RN 891027-65-9, retrieved from STN, entered Jul. 9, 2006.
Database CA [Online] Chemical Abstracts Service, Columbus, Ohio, US, compound with RN 891027-73-9, retrieved from STN, entered Jul. 9, 2006.
Database CA [Online] Chemical Abstracts Service, Columbus, Ohio, US, compound with RN 891027-89-7, retrieved from STN, entered Jul. 9, 2006.
Database CA [Online] Chemical Abstracts Service, Columbus, Ohio, US, compound with RN 891027-97-7, retrieved from STN, entered Jul. 9, 2006.
Database CA [Online] Chemical Abstracts Service, Columbus, Ohio, US, compound with RN 891028-05-0, retrieved from STN, entered Jul. 9, 2006.
Database CA [Online] Chemical Abstracts Service, Columbus, Ohio, US, compound with RN 891028-12-9, retrieved from STN, entered Jul. 9, 2006.
Database CA [Online] Chemical Abstracts Service, Columbus, Ohio, US, compound with RN 891028-89-0, retrieved from STN, entered Jul. 9, 2006.
Database CA [Online] Chemical Abstracts Service, Columbus, Ohio, US, compound with RN 892699-07-9, retrieved from STN, entered Jul. 14, 2006.
Database CA [Online] Chemical Abstracts Service, Columbus, Ohio, US, compound with RN 892699-21-7, retrieved from STN, entered Jul. 14, 2006.
Database CA [Online] Chemical Abstracts Service, Columbus, Ohio, US, compound with RN 892699-30-8, retrieved from STN, entered Jul. 14, 2006.
Database CA [Online] Chemical Abstracts Service, Columbus, Ohio, US, compound with RN 892699-39-7, retrieved from STN, entered Jul. 14, 2006.
Database CA [Online] Chemical Abstracts Service, Columbus, Ohio, US, compound with RN 892699-67-1, retrieved from STN, entered Jul. 14, 2006.

* cited by examiner

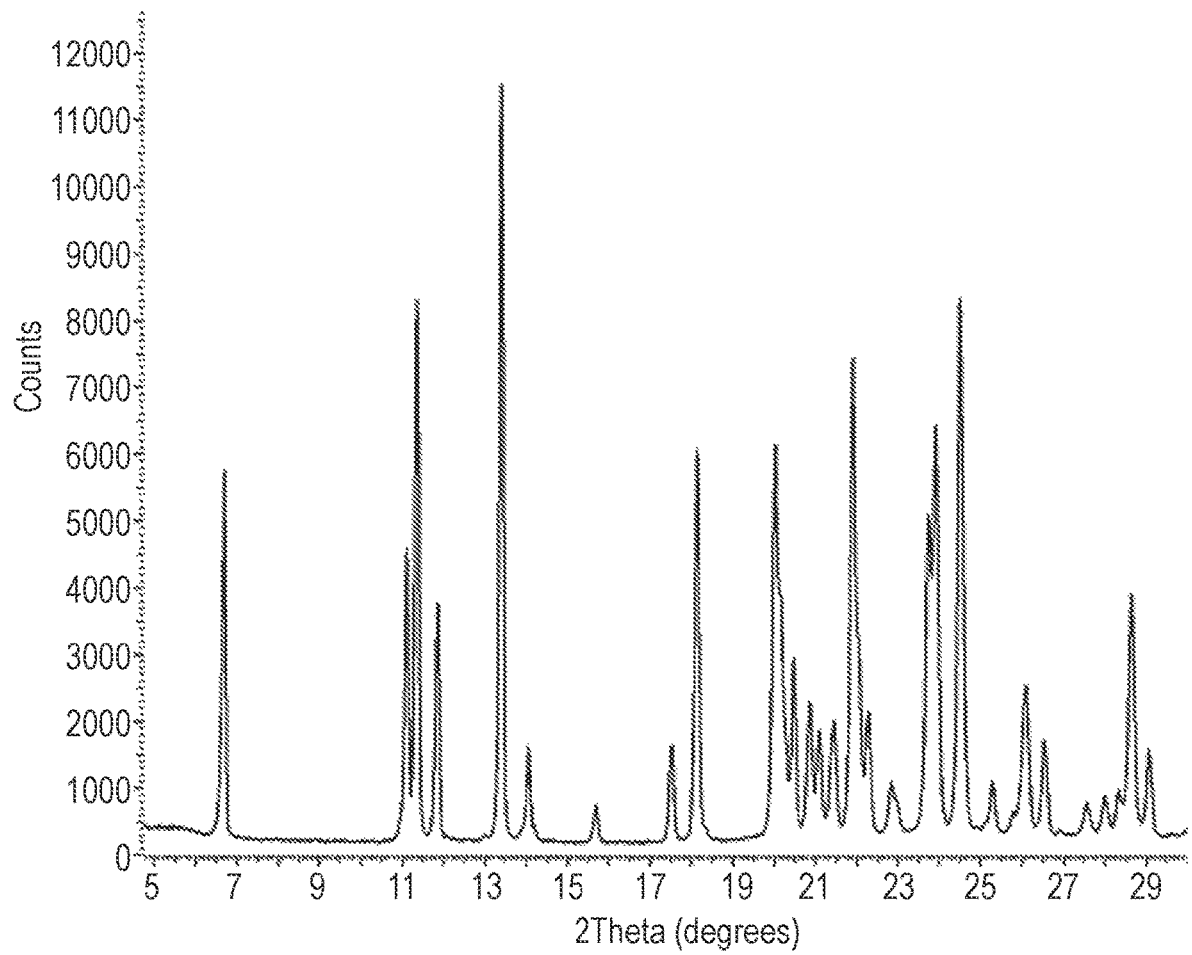

BENZISOXAZOLE SULFONAMIDE DERIVATIVES

CROSS-REFERENCE TO RELATED APPLICATIONS

This application claims the benefit of priority to U.S. provisional patent application Ser. No. 62/863,199, filed Jun. 18, 2019; U.S. provisional patent application Ser. No. 62/953,223, filed Dec. 24, 2020; and U.S. provisional patent application Ser. No. 63/025,278, filed May 15, 2020; the entire contents of which are incorporated herein by reference.

SEQUENCE LISTING

This application incorporates by reference the contents of a 13.2 kb file created on Jun. 15, 2020 and named "PC072525Asequencelisting.txt," which is the sequence listing for this application.

FIELD OF THE INVENTION

The present invention relates to novel benzisoxazole sulfonamide derivatives, which act as Lysine Acetyl Transferase (KAT) inhibitors of the MYST family and are useful in the treatment of abnormal cell growth, such as cancer, in patients. The present invention also relates to pharmaceutical compositions containing the compounds and to methods of using the compounds and compositions in the treatment of abnormal cell growth in patients.

BACKGROUND OF THE INVENTION

The MYST family is the largest family of KATs and is named after the founding members in yeast and mammals: MOZ, Ybf2/Sas3, Sas2 and TIP60 (Dekker 2014). MYST proteins mediate many biological functions including gene regulation, DNA repair, cell-cycle regulation and development (Avvakumov 2007; Voss 2009). The KAT proteins of the MYST family play key roles in post-translational modification of histones and thus have a profound effect on chromatin structure in the eukaryotic nucleus (Avvakumov 2007). The family currently comprises five mammalian KATs: TIP60 (KAT5; HTATIP; MIM 601409), MOZ (KAT6A; MIM 601408; MYST3), MORF (KAT6b; QKF; MYST4), HBO (KAT7; HBO1; MYST2) and MOF (KAT8; MYST1) (Voss 2009). These five members of the MYST family are present in humans and malfunction of MYST proteins is known to be associated with cancer (Avvakumov 2007). The most frequently used names for members of the MYST family are:

| Common name | MYST name | Systematic name |
|---|---|---|
| MOF | MYST1 | KAT8 |
| HBO | MYST2 | KAT7 |
| MOZ | MYST3 | KAT6A |
| MORF | MYST4 | KAT6B |
| TIP60 | | KAT5 |

MYST Functional Domains

MYST proteins function in multisubunit protein complexes including adaptors such as ING proteins that mediate DNA binding (Avvakumov 2007). For instance, TIP60 is affiliated to the NuA4 multiprotein complex (which embraces more than 16 members) (Zhang 2017). However, there have also been some reports of a helix-turn-helix DNA-binding motif within the structure of the MOZ protein itself (Holbert 2007), which suggests the capacity to bind directly to DNA.

The acetyltransferase activity of MYST proteins is effected by the MYST domain (the catalytic domain). The MYST domain contains an acetyl-coenzyme A binding motif, which is structurally conserved with other HATs, and an unusual $C_2HC$-type zinc finger (Voss 2009). The highly conserved MYST domain, including the acetyl-CoA binding motif and zinc finger, is considered to be the defining feature of this family of enzymes (Avvakumov 2007).

Role of MYST Proteins

Acetylation of histone residues is generally associated with transcriptional activation. However, in some instances, transcriptional repression has also been attributed to MYST proteins (Voss 2009). The individual members of the MYST family are known to participate in a broad range of important biochemical interactions:

HBO1 positively regulates initiation of DNA replication (Avvakumov 2007; Aggarwal 2004; Doyon 2006; Iizuka 2006) via acetylation of histone substrates, which presumably leads to a more accessible chromatin conformation (Avvakumov 2007, Iizuka 2006). HBO1 is also known to play a role in the pathogenesis of breast cancer by promoting an enrichment of cancer stem-like cells (Duong 2013) and by destabilising the estrogen receptor α (ERα) through ubiquinitiation, which proceeds via the histone-acetylating activity of HBO1 (Iizuka 2013). HBO1 has also been implicated in Acute myeloid leukemia (AML) (Shi 2015).

TIP60 (KAT5) is the most studied member of the MYST family. TIP60 plays an important role not only in the regulation of transcription but also in the process of DNA damage repair, particularly in DNA double-strand breaks (DSB) (Gil 2017). TIP60 can acetylate p53, ATM and c-Myc. TIP60 and MOF specifically acetylate lysine 120 (K120) of p53 upon DNA damage (Avvakumov 2007). TIP60 has also been implicated in being important for regulatory T-cell (Treg) biology. FOXP3 is the master regulator in the development and function of Tregs and it has been shown that acetylation of FOXP3 by TIP60 is essential for FOXP3 activity (Li 2007, Xiao 2014). Underscoring this, conditional TIP60 deletion in mice leads to a scurfy-like fatal autoimmune disease, mimicking a phenotype seen in FOXP3 knock out mice (Xiao 2014). In cancer, Treg cells can facilitate tumor progression by suppressing adaptive immunity against the tumor.

MOF ("males absent on the first") was originally identified as one of the components of the dosage compensation in Drosophila, and was classified as a member of the MYST family based on functional studies and sequence analysis (Su 2016). The human ortholog exhibits significant similarity to drosophila MOF; containing an acetyl-CoA-binding site, a chromodomain (which binds histones) and a $C_2HC$-type zinc finger (Su 2016). MOF is a key enzyme for acetylating histone H4K16, and MOF-containing complexes are implicated in various essential cell functions with links to cancer (Su 2016). Besides the global reduction of histone acetylation, depletion of MOF in mammalian cells can result in abnormal gene transcription, particularly causing abnormal expression of certain tumor suppressor genes or oncogenes, suggesting a critical role of MOF in tumorigenesis (Su 2016). For example, KAT activity of MOF has been shown to be required to sustain MLL-AF9 leukemia and may be important for multiple AML subtypes (Valerio 2017).

KAT6B (Querkopf) was first identified in a mutation screen for genes regulating the balance between proliferation and differentiation during embryonic development (Thomas 2000). Mice homozygous for the KAT6B mutant allele have severe defects in cerebral cortex development resulting from a severe reduction in both proliferation and differentiation of specifically the cortical progenitor population during embryonic development. KAT6B is required for the maintenance of the adult neural stem cell population and is part of a system regulating differentiation of stem cells into neurons (Merson 2006). KAT6B is also mutated in rare forms of leukemia (Vizmanos 2003).

The MOZ locus ranks as the 12th most commonly amplified region across all cancer types (Zack 2013). MOZ is within the 8p11-p12 amplicon, which is seen at frequencies around 10-15% in various cancers, especially breast and ovarian (Turner-Ivey 2014). MOZ was first identified as a fusion partner of the CREB-binding protein (CBP) during examination of a specific chromosomal translocation in acute myeloid leukemia (AML) (Avvakumov 2007; Borrow 1996). MOZ KAT activity is necessary for promoting the expression of MEIS1 and HOXa9, proteins that are typically seen overexpressed in some lymphomas and leukemias. Increased survival of $MOZ^{+/-}$-heterozygote mice in the Ep-Myc transgenic model of B-cell lymphoma is seen, where loss of a single MOZ allele leads to a biologically relevant reduction in Meis1 and Hoxa9 levels in pre-B-cells (Sheikh 2015).

Inhibitors of some MYSTs are known. For example, the following Anacardic acid derivative is reported (Ghizzoni 2012) as inhibiting TIP60 ($IC_{50}$=74 μM) and MOF ($IC_{50}$=47 μM):

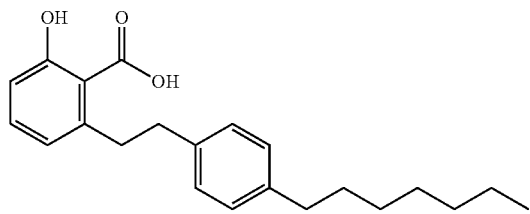 [SMILES: CCCCCCCc1ccc(CCc2cccc(O)c2C(=O)O)cc1]

Other known inhibitors include (Zhana 2017):

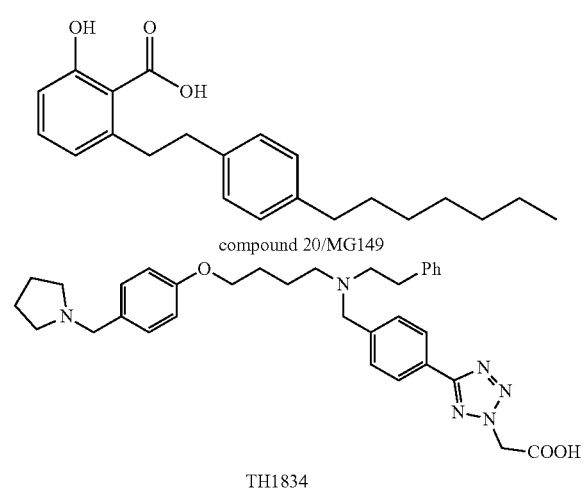

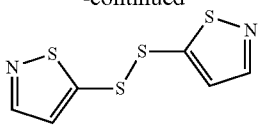

NU9056

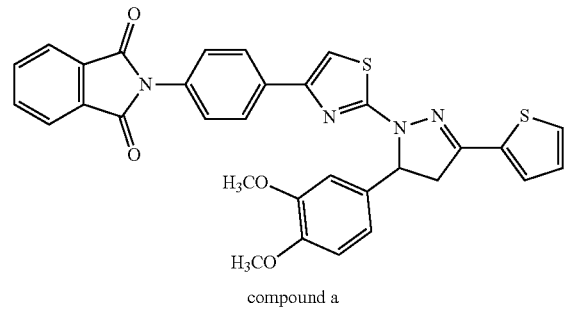

compound a

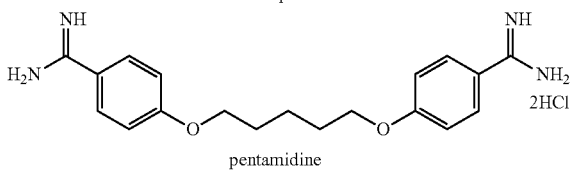

pentamidine

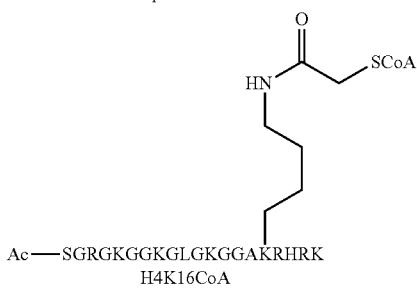

Ac—SGRGKGGKGLGKGGAKRHRK
H4K16CoA
SGRGKGGKGLGKGGAKRHRK, SEQ ID NO: 1

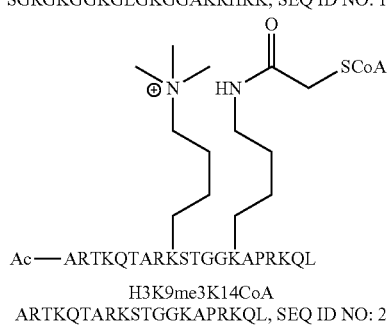

Ac—ARTKQTARKSTGGKAPRKQL
H3K9me3K14CoA
ARTKQTARKSTGGKAPRKQL, SEQ ID NO: 2

In light of the established role of KATs in general, and MYSTs in particular, in diseases such as cancer, a need exists for new inhibitors of these proteins.

SUMMARY OF THE INVENTION

Each of the embodiments of the present invention described below may be combined with one or more other embodiments of the present invention described herein which is not inconsistent with the embodiment(s) with which it is combined. In addition, each of the embodiments below describing the invention envisions within its scope the pharmaceutically acceptable salts of the compounds of the invention.

Accordingly, the phrase "or a pharmaceutically acceptable salt thereof" is implicit in the description of all compounds described herein.

This invention relates to a compound of formula (I)

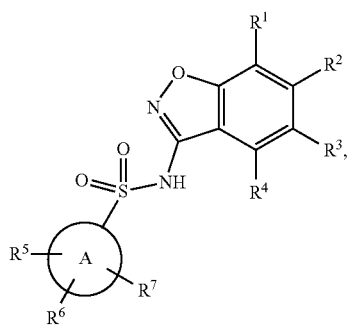

or a pharmaceutically acceptable salt thereof,
wherein
$R^1$ is hydrogen or 5-6 membered heteroaryl optionally substituted by methyl;
$R^2$ is hydrogen or —$(CHR_8)_n$-(5-9 membered heteroaryl) optionally substituted by halogen, $C_1$-$C_3$ alkyl, —$CH_2OH$, or —OH, provided that one of $R^1$ and $R^2$ is hydrogen, further provided that $R^1$ and $R^2$ are not both hydrogen;
$R^3$ is hydrogen, halogen, $C_1$-$C_3$ alkyl, cyclopropyl, —$CHF_2$, —$CF_3$, $C_1$-$C_4$ alkoxy, —$OCHF_2$, or —$OCF_3$;
$R^4$ is hydrogen, halogen, $C_1$-$C_3$ alkyl, cyclopropyl, $C_1$-$C_4$ alkoxy, or —O-cyclopropyl,
Ring A is $C_6$-$C_{10}$ aryl or 9-10 membered heteroaryl;
$R^5$ is hydrogen, fluoro, cyano, $C_1$-$C_3$ alkyl, —$CHF_2$, —$CF_3$, cyclopropyl, $C_1$-$C_3$ alkoxy, —$OCHF_2$, —$OCF_3$, —O-cyclopropyl, —$CH_2$—O—$CH_3$, —$C(O)OCH_3$, or —$C(O)N(H)CH_3$;
$R^6$ is hydrogen, fluoro, methyl, —OH, or methoxy;
$R^7$ is hydrogen, bromo, chloro, fluoro, or methoxy;
$R^8$ is hydrogen or —OH; and
n is 0 or 1.

One embodiment of the present invention relates to a compound of formula (I), or a pharmaceutically acceptable salt thereof, wherein $R^1$ is 5-6 membered heteroaryl and $R^2$ is hydrogen; $R^1$ is 5 membered heteroaryl and $R^2$ is hydrogen; or $R^1$ is pyrazolyl and $R^2$ is hydrogen.

One embodiment of the present invention relates to a compound of formula (I), or a pharmaceutically acceptable salt thereof, wherein $R^1$ is hydrogen and $R^2$ is 5-6 membered heteroaryl; $R^1$ is hydrogen and $R^2$ is 5 membered heteroaryl; $R^1$ is hydrogen and $R^2$ is pyrazolyl; $R^1$ is hydrogen, $R^2$ is —$(CHR_8)$-(5-6 membered heteroaryl) optionally substituted by halogen, $C_1$-$C_3$ alkyl, —$CH_2OH$, or —OH, and $R^8$ is —OH; $R^1$ is hydrogen and $R^2$ is —$(CH_2)$-(5-6 membered heteroaryl) optionally substituted by halogen, $C_1$-$C_3$ alkyl, —$CH_2OH$, or —OH; $R^1$ is hydrogen, $R^2$ is —$(CHR_8)$-(5-6 membered heteroaryl), and $R^8$ is —OH; $R^1$ is hydrogen and $R^2$ is —$(CH_2)$-(5-6 membered heteroaryl); $R^1$ is hydrogen, $R^2$ is —$(CHR_8)$-(5 membered heteroaryl) optionally substituted by halogen, $C_1$-$C_3$ alkyl, —$CH_2OH$, or —OH, and $R^8$ is —OH; $R^1$ is hydrogen and $R^2$ is —$(CH_2)$-(5 membered heteroaryl) optionally substituted by halogen, $C_1$-$C_3$ alkyl, —$CH_2OH$, or —OH; $R^1$ is hydrogen, $R^2$ is —$(CHR_8)$-(5 membered heteroaryl), and $R^8$ is —OH; $R^1$ is hydrogen and $R^2$ is —$(CH_2)$-(5 membered heteroaryl); $R^1$ is hydrogen and $R^2$ is —$(CH_2)$-triazolyl; $R^1$ is hydrogen and $R^2$ is —$(CH_2)$-pyrazolyl optionally substituted by halogen or $C_1$-$C_3$ alkyl; $R^1$ is hydrogen and $R^2$ is —$(CH_2)$-pyrazolyl optionally substituted by halogen; $R^1$ is hydrogen and $R^2$ is —$(CH_2)$-pyrazolyl optionally substituted by $C_1$-$C_3$ alkyl; $R^1$ is hydrogen and $R^2$ is —$(CH_2)$-pyrazolyl substituted by methyl; $R^1$ is hydrogen and $R^2$ is —$(CH_2)$-pyrazolyl; $R^1$ is hydrogen and $R^2$ is —$(CH_2)$-(6 membered heteroaryl); $R^1$ is hydrogen and $R^2$ is —$(CHR_8)$-(6 membered heteroaryl), and $R^8$ is —OH; $R^1$ is hydrogen and $R^2$ is —$(CH_2)$-pyridine, —$(CH_2)$-pyrazine, or —$(CH_2)$-pyrimidine; $R^1$ is hydrogen and $R^2$ is —$(CH_2)$-(5-9 membered heteroaryl); or $R^1$ is hydrogen and $R^2$ is —$(CH_2)$-indazolyl.

One embodiment of the present invention relates to a compound of formula (I), or a pharmaceutically acceptable salt thereof, wherein $R^3$ is halogen, $C_1$-$C_3$ alkyl, cyclopropyl, —$CHF_2$, —$CF_3$, $C_1$-$C_4$ alkoxy, —$OCHF_2$, or —$OCF_3$; and $R^4$ is hydrogen.

One embodiment of the present invention relates to a compound of formula (I), or a pharmaceutically acceptable salt thereof, wherein $R^3$ is hydrogen and $R^4$ is halogen, $C_1$-$C_3$ alkyl, cyclopropyl, $C_1$-$C_4$ alkoxy, or —O-cyclopropyl.

One embodiment of the present invention relates to a compound of formula (I), or a pharmaceutically acceptable salt thereof, wherein $R^3$ is hydrogen, halogen, or $C_1$-$C_3$ alkyl; $R^3$ is hydrogen, fluoro, bromo, or methyl; $R^3$ is fluoro: $R^3$ is methyl; $R^3$ is hydrogen; $R^4$ is hydrogen, fluoro, methyl, ethyl, cyclopropyl, —O-cyclopropyl, or $C_1$-$C_4$ alkoxy; $R^4$ is hydrogen; $R^4$ is $C_1$-$C_3$ alkoxy; or $R^4$ is methoxy, and any combination of $R^3$ and $R^4$ thereof.

One embodiment of the present invention relates to a compound of formula (I), or a pharmaceutically acceptable salt thereof, wherein at least one of $R^3$ and $R^4$ is hydrogen.

One embodiment of the present invention relates to a compound of formula (I), or a pharmaceutically acceptable salt thereof, wherein $R^3$ is hydrogen, halogen, or $C_1$-$C_3$ alkyl and $R^4$ is hydrogen; $R^3$ is hydrogen, fluoro, bromo, or methyl and $R^4$ is hydrogen; $R^3$ is methyl and $R^4$ is hydrogen; $R^3$ is hydrogen and $R^4$ is hydrogen, fluoro, methyl, ethyl, cyclopropyl, —O-cyclopropyl, or $C_1$-$C_4$ alkoxy; $R^3$ is hydrogen and $R^4$ is hydrogen; $R^3$ is hydrogen and $R^4$ is $C_1$-$C_3$ alkoxy; $R^3$ is hydrogen and $R^4$ is methoxy; or $R^3$ is fluoro and $R^4$ is methoxy.

One embodiment of the present invention relates to a compound of formula (I), or a pharmaceutically acceptable salt thereof, wherein Ring A is phenyl, quinolinyl, benzoxazolyl, indanyl, or tetrahydronaphthyl.

One embodiment of the present invention relates to a compound of formula (I), or a pharmaceutically acceptable salt thereof, wherein Ring A is phenyl.

One embodiment of the present invention relates to a compound of formula (I), or a pharmaceutically acceptable salt thereof, wherein Ring A is phenyl and $R^5$ is methoxy.

One embodiment of the present invention relates to a compound of formula (I), or a pharmaceutically acceptable salt thereof, wherein Ring A is phenyl and $R^6$ is methoxy.

One embodiment of the present invention relates to a compound of formula (I), or a pharmaceutically acceptable salt thereof, wherein Ring A is phenyl and $R^6$ is hydrogen.

One embodiment of the present invention relates to a compound of formula (I), or a pharmaceutically acceptable salt thereof, wherein Ring A is phenyl and $R^7$ is hydrogen.

One embodiment of the present invention relates to a compound of formula (I), or a pharmaceutically acceptable salt thereof, wherein Ring A is phenyl, $R^5$ is methoxy, and $R^6$ is methoxy.

One embodiment of the present invention relates to a compound of formula (I), or a pharmaceutically acceptable salt thereof, wherein Ring A is phenyl, $R^5$ is methoxy, $R^6$ is methoxy, and $R^7$ is hydrogen.

One embodiment of the present invention relates to a compound of formula (I), or a pharmaceutically acceptable salt thereof, wherein Ring A is phenyl, $R^5$ is methoxy, $R^6$ is hydrogen, and $R^7$ is hydrogen.

One embodiment of the present invention relates to a compound of formula (I), or a pharmaceutically acceptable salt thereof wherein Ring A is indanyl.

One embodiment of the present invention relates to a compound of formula (I), or a pharmaceutically acceptable salt thereof, wherein Ring A is tetrahydronaphthyl.

One embodiment of the present invention relates to a compound of formula (I), or a pharmaceutically acceptable salt thereof, wherein Ring A is indanyl or tetrahydronaphthyl, $R^5$ is methoxy, $R^6$ is hydrogen, and $R^7$ is hydrogen.

One embodiment of the present invention relates to a compound of formula (I), or a pharmaceutically acceptable salt thereof, wherein Ring A is quinolinyl.

One embodiment of the present invention relates to a compound of formula (I), or a pharmaceutically acceptable salt thereof, wherein Ring A is benzoxazolyl.

One embodiment of the present invention relates to a compound of formula (I), or a pharmaceutically acceptable salt thereof, wherein Ring A is quinolinyl or benzoxazolyl, $R^5$ is methyl or ethyl, $R^6$ is hydrogen, and $R^7$ is hydrogen.

It is to be understood that any of the above-mentioned embodiment(s) for formula (I) can be combined with any other embodiment(s) above to the extent they are not incompatible.

This invention relates to a compound of formula (Ia)

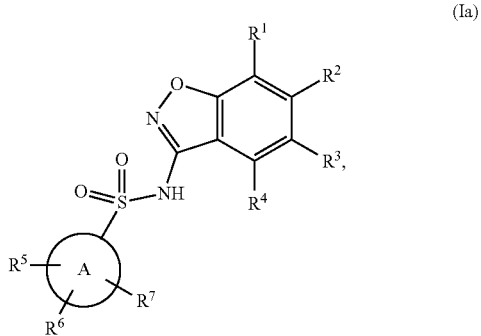

(Ia)

or a pharmaceutically acceptable salt thereof,
wherein
$R^1$ is hydrogen or 5-6 membered heteroaryl optionally substituted by methyl;
$R^2$ is hydrogen or —$(CH_2)_n$-(5-6 membered heteroaryl) optionally substituted by halogen, $C_1$-$C_3$ alkyl, —$CH_2OH$, or —OH,
provided that one of $R^1$ and $R^2$ is hydrogen,
further provided that $R^1$ and $R^2$ are not both hydrogen;
$R^3$ is hydrogen, halogen, $C_1$-$C_3$ alkyl, —$CF_2H$, —$CF_3$, $C_1$-$C_4$ alkoxy, —$OCHF_2$, or —$OCF_3$;
$R^4$ is hydrogen, halogen, $C_1$-$C_3$ alkyl, cyclopropyl, $C_1$-$C_4$ alkoxy, or —O— cyclopropyl,
provided that at least one of $R^3$ and $R^4$ is hydrogen;
Ring A is $C_6$-$C_{10}$ aryl or 9-10 membered heteroaryl;
$R^5$ is hydrogen, fluoro, cyano, $C_1$-$C_3$ alkyl, —$CHF_2$, —$CF_3$, cyclopropyl, $C_1$-$C_3$ alkoxy, —$OCHF_2$, —$OCF_3$, —O-cyclopropyl, —$CH_2$—O—$CH_3$, —C(O)$OCH_3$, or —C(O)N(H)$CH_3$;

$R^6$ is hydrogen, fluoro, methyl, —OH, or methoxy;
$R^7$ is hydrogen, bromo, chloro, fluoro, or methoxy; and
n is 0 or 1.

One embodiment of the present invention relates to a compound of formula (Ia), or a pharmaceutically acceptable salt thereof, wherein $R^1$ is 5-6 membered heteroaryl and $R^2$ is hydrogen.

One embodiment of the present invention relates to a compound of formula (Ia), or a pharmaceutically acceptable salt thereof, wherein $R^1$ is 5 membered heteroaryl and $R^2$ is hydrogen.

One embodiment of the present invention relates to a compound of formula (Ia), or a pharmaceutically acceptable salt thereof, wherein $R^1$ is pyrazolyl and $R^2$ is hydrogen; $R^1$ is hydrogen and $R^2$ is 5-6 membered heteroaryl; $R^1$ is hydrogen and $R^2$ is membered heteroaryl; $R^1$ is hydrogen and $R^2$ is pyrazolyl; $R^1$ is hydrogen and $R^2$ is —$(CH_2)$-(5-6 membered heteroaryl) optionally substituted by halogen, $C_1$-$C_3$ alkyl, —$CH_2OH$, or —OH; $R^1$ is hydrogen and $R^2$ is —$(CH_2)$-(5-6 membered heteroaryl); $R^1$ is hydrogen and $R^2$ is —$(CH_2)$-(5 membered heteroaryl) optionally substituted by halogen, $C_1$-$C_3$ alkyl, —$CH_2OH$, or —OH; $R^1$ is hydrogen and $R^2$ is —$(CH_2)$-(5 membered heteroaryl); $R^1$ is hydrogen and $R^2$ is —$(CH_2)$-triazolyl; $R^1$ is hydrogen and $R^2$ is —$(CH_2)$-pyrazolyl optionally substituted by halogen or $C_1$-$C_3$ alkyl; $R^1$ is hydrogen and $R^2$ is —$(CH_2)$-pyrazolyl optionally substituted by halogen; $R^1$ is hydrogen and $R^2$ is —$(CH_2)$-pyrazolyl optionally substituted by $C_1$-$C_3$ alkyl; $R^1$ is hydrogen and $R^2$ is —$(CH_2)$-pyrazolyl substituted by methyl; or $R^1$ is hydrogen and $R^2$ is —$(CH_2)$-pyrazolyl.

One embodiment of the present invention relates to a compound of formula (I), or a pharmaceutically acceptable salt thereof, wherein $R^3$ is halogen, $C_1$-$C_3$ alkyl, —$CF_2H$, —$CF_3$, $C_1$-$C_4$ alkoxy, —$OCHF_2$, or —$OCF_3$; and $R^4$ is hydrogen.

One embodiment of the present invention relates to a compound of formula (I), or a pharmaceutically acceptable salt thereof, wherein $R^3$ is hydrogen and $R^4$ is halogen, $C_1$-$C_3$ alkyl, cyclopropyl, $C_1$-$C_4$ alkoxy, or —O-cyclopropyl.

One embodiment of the present invention relates to a compound of formula (I), or a pharmaceutically acceptable salt thereof, wherein at least one of $R^3$ and $R^4$ is hydrogen.

One embodiment of the present invention relates to a compound of formula (Ia), or a pharmaceutically acceptable salt thereof, wherein $R^3$ is hydrogen, halogen, or $C_1$-$C_3$ alkyl and $R^4$ is hydrogen; $R^3$ is hydrogen, fluoro, bromo, or methyl and $R^4$ is hydrogen; $R^3$ is methyl and $R^4$ is hydrogen; $R^3$ is hydrogen and $R^4$ is hydrogen, fluoro, methyl, ethyl, cyclopropyl, —O-cyclopropyl, or $C_1$-$C_4$ alkoxy; $R^3$ is hydrogen and $R^4$ is hydrogen; $R^3$ is hydrogen and $R^4$ is $C_1$-$C_3$ alkoxy; or $R^3$ is hydrogen and $R^4$ is methoxy.

One embodiment of the present invention relates to a compound of formula (Ia), or a pharmaceutically acceptable salt thereof, wherein Ring A is phenyl, quinolinyl, benzoxazolyl, indanyl, or tetrahydronaphthyl.

One embodiment of the present invention relates to a compound of formula (Ia), or a pharmaceutically acceptable salt thereof, wherein Ring A is phenyl.

One embodiment of the present invention relates to a compound of formula (Ia), or a pharmaceutically acceptable salt thereof, wherein Ring A is phenyl and $R^5$ is methoxy.

One embodiment of the present invention relates to a compound of formula (Ia), or a pharmaceutically acceptable salt thereof, wherein Ring A is phenyl and $R^6$ is methoxy.

One embodiment of the present invention relates to a compound of formula (Ia), or a pharmaceutically acceptable salt thereof, wherein Ring A is phenyl and $R^6$ is hydrogen.

One embodiment of the present invention relates to a compound of formula (Ia), or a pharmaceutically acceptable salt thereof, wherein Ring A is phenyl and $R^7$ is hydrogen.

One embodiment of the present invention relates to a compound of formula (Ia), or a pharmaceutically acceptable salt thereof, wherein Ring A is phenyl, $R^5$ is methoxy, and $R^6$ is methoxy.

One embodiment of the present invention relates to a compound of formula (Ia), or a pharmaceutically acceptable salt thereof, wherein Ring A is phenyl, $R^5$ is methoxy, and $R^6$ is hydrogen.

One embodiment of the present invention relates to a compound of formula (Ia), or a pharmaceutically acceptable salt thereof, wherein Ring A is phenyl, $R^5$ is methoxy, $R^6$ is methoxy, and $R^7$ is hydrogen.

One embodiment of the present invention relates to a compound of formula (Ia), or a pharmaceutically acceptable salt thereof, wherein Ring A is phenyl, $R^5$ is methoxy, $R^6$ is hydrogen, and $R^7$ is hydrogen.

One embodiment of the present invention relates to a compound of formula (Ia), or a pharmaceutically acceptable salt thereof, wherein Ring A is indanyl.

One embodiment of the present invention relates to a compound of formula (Ia), or a pharmaceutically acceptable salt thereof, wherein Ring A is tetrahydronaphthyl.

One embodiment of the present invention relates to a compound of formula (Ia), or a pharmaceutically acceptable salt thereof, wherein Ring A is indanyl or tetrahydronaphthyl, $R^5$ is methoxy, $R^6$ is hydrogen, and $R^7$ is hydrogen.

One embodiment of the present invention relates to a compound of formula (Ia), or a pharmaceutically acceptable salt thereof, wherein Ring A is quinolinyl.

One embodiment of the present invention relates to a compound of formula (Ia), or a pharmaceutically acceptable salt thereof, wherein Ring A is benzoxazolyl.

One embodiment of the present invention relates to a compound of formula (Ia), or a pharmaceutically acceptable salt thereof, wherein Ring A is quinolinyl or benzoxazolyl, $R^5$ is methyl or ethyl, $R^6$ is hydrogen, and $R^7$ is hydrogen.

It is to be understood that any of the above-mentioned embodiment(s) for Formula (Ia) can be combined with any other embodiment(s) above to the extent they are not incompatible.

This invention relates to a compound of formula (II)

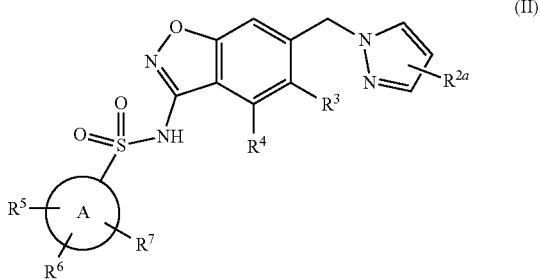

(II)

or a pharmaceutically acceptable salt thereof, wherein
$R^{2a}$ is absent, halogen, $C_1$-$C_3$ alkyl, —$CH_2OH$, or —OH;
$R^3$ is hydrogen, halogen, $C_1$-$C_3$ alkyl, cyclopropyl, —$CHF_2$, —$CF_3$, $C_1$-$C_4$ alkoxy, —$OCHF_2$, or —$OCF_3$;
$R^4$ is hydrogen, halogen, $C_1$-$C_3$ alkyl, cyclopropyl, $C_1$-$C_4$ alkoxy, or —O— cyclopropyl;
Ring A is $C_6$-$C_1$ aryl or 9-10 membered heteroaryl;
$R^5$ is hydrogen, fluoro, cyano, $C_1$-$C_3$ alkyl, —$CHF_2$, —$CF_3$, cyclopropyl, $C_1$-$C_3$ alkoxy, —$OCHF_2$, —$OCF_3$, —O-cyclopropyl, —$CH_2$—O—$CH_3$, —$C(O)OCH_3$, or —$C(O)N(H)CH_3$;
$R^6$ is hydrogen, fluoro, methyl, —OH, or methoxy; and
$R^7$ is hydrogen, bromo, chloro, fluoro, or methoxy.

One embodiment of the present invention relates to a compound of formula (II), or a pharmaceutically acceptable salt thereof, wherein $R^{2a}$ is absent, fluoro, methyl, —$CH_2OH$ or —OH; $R^{2a}$ is absent, fluoro, or methyl; $R^{2a}$ is absent; $R^{2a}$ is fluoro; or $R^{2a}$ is methyl.

One embodiment of the present invention relates to a compound of formula (II), or a pharmaceutically acceptable salt thereof, wherein $R^3$ is hydrogen, halogen, $C_1$-$C_3$ alkyl, —$CHF_2$, —$CF_3$, $C_1$-$C_4$ alkoxy, —$OCHF_2$, or —$OCF_3$.

One embodiment of the present invention relates to a compound of formula (II), or a pharmaceutically acceptable salt thereof, wherein $R^3$ is hydrogen, halogen, or $C_1$-$C_3$ alkyl; $R^3$ is hydrogen, fluoro, bromo, or methyl; $R^3$ is fluoro; $R^3$ is methyl; $R^4$ is hydrogen, fluoro, methyl, ethyl, cyclopropyl, —O-cyclopropyl, or $C_1$-$C_4$ alkoxy; $R^4$ is hydrogen: $R^4$ is $C_1$-$C_3$ alkoxy; or $R^4$ is methoxy, and any combination of $R^3$ and $R^4$ thereof.

One embodiment of the present invention relates to a compound of formula (II), or a pharmaceutically acceptable salt thereof, wherein $R^3$ is fluoro and $R^4$ is methoxy.

One embodiment of the present invention relates to a compound of formula (II), or a pharmaceutically acceptable salt thereof, wherein at least one of $R^3$ and $R^4$ is hydrogen.

One embodiment of the present invention relates to a compound of formula (II), or a pharmaceutically acceptable salt thereof, wherein $R^3$ is hydrogen, halogen, or $C_1$-$C_3$ alkyl and $R^4$ is hydrogen; $R^3$ is hydrogen, fluoro, bromo, or methyl and $R^4$ is hydrogen; $R^3$ is methyl and $R^4$ is hydrogen; $R^3$ is hydrogen and $R^4$ is hydrogen, fluoro, methyl, ethyl, cyclopropyl, —O-cyclopropyl, or $C_1$-$C_4$ alkoxy; $R^3$ is hydrogen and $R^4$ is hydrogen; $R^3$ is hydrogen and $R^4$ is $C_1$-$C_3$ alkoxy; $R^3$ is hydrogen and $R^4$ is methoxy.

One embodiment of the present invention relates to a compound of formula (II), or a pharmaceutically acceptable salt thereof, wherein Ring A is phenyl, quinolinyl, benzoxazolyl, indanyl, or tetrahydronaphthyl.

One embodiment of the present invention relates to a compound of formula (II), or a pharmaceutically acceptable salt thereof, wherein Ring A is phenyl.

One embodiment of the present invention relates to a compound of formula (II), or a pharmaceutically acceptable salt thereof, wherein Ring A is phenyl and $R^5$ is methoxy.

One embodiment of the present invention relates to a compound of formula (II), or a pharmaceutically acceptable salt thereof, wherein Ring A is phenyl and $R^6$ is methoxy.

One embodiment of the present invention relates to a compound of formula (II), or a pharmaceutically acceptable salt thereof, wherein Ring A is phenyl and $R^6$ is hydrogen.

One embodiment of the present invention relates to a compound of formula (II), or a pharmaceutically acceptable salt thereof, wherein Ring A is phenyl and $R^7$ is hydrogen.

One embodiment of the present invention relates to a compound of formula (II), or a pharmaceutically acceptable salt thereof, wherein Ring A is phenyl, $R^5$ is methoxy, and $R^6$ is methoxy.

One embodiment of the present invention relates to a compound of formula (II), or a pharmaceutically acceptable salt thereof, wherein Ring A is phenyl $R^5$ is methoxy, $R^6$ is methoxy, and $R^7$ is hydrogen.

One embodiment of the present invention relates to a compound of formula (II), or a pharmaceutically acceptable salt thereof, wherein Ring A is phenyl $R^5$ is methoxy, $R^6$ is hydrogen, and $R^7$ is hydrogen.

One embodiment of the present invention relates to a compound of formula (II), or a pharmaceutically acceptable salt thereof, wherein Ring A is indanyl.

One embodiment of the present invention relates to a compound of formula (II), or a pharmaceutically acceptable salt thereof, wherein Ring A is tetrahydronaphthyl.

One embodiment of the present invention relates to a compound of formula (II), or a pharmaceutically acceptable salt thereof, wherein Ring A is indanyl or tetrahydronaphthyl, $R^5$ is methoxy, $R^6$ is hydrogen, and $R^7$ is hydrogen.

One embodiment of the present invention relates to a compound of formula (II), or a pharmaceutically acceptable salt thereof, wherein Ring A is quinolinyl.

One embodiment of the present invention relates to a compound of formula (II), or a pharmaceutically acceptable salt thereof, wherein Ring A is benzoxazolyl.

One embodiment of the present invention relates to a compound of formula (II), or a pharmaceutically acceptable salt thereof, wherein Ring A is quinolinyl, $R^5$ is methyl or ethyl, $R^6$ is hydrogen, and $R^7$ is hydrogen.

It is to be understood that any of the above-mentioned embodiment(s) for formula (II) can be combined with any other embodiment(s) above to the extent they are not incompatible.

This invention relates to a compound of formula (III)

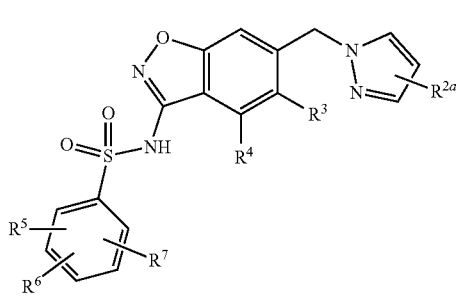

(III)

or a pharmaceutically acceptable salt thereof,
wherein
$R^{2a}$ is absent, halogen, $C_1$-$C_3$ alkyl, —$CH_2OH$, or —OH;
$R^3$ is hydrogen, halogen, $C_1$-$C_3$ alkyl, cyclopropyl, —$CHF_2$, —$CF_3$, $C_1$-$C_4$ alkoxy, —$OCHF_2$, or —$OCF_3$;
$R^4$ is hydrogen, halogen, $C_1$-$C_3$ alkyl, cyclopropyl, $C_1$-$C_4$ alkoxy, or —O— cyclopropyl;
$R^5$ is hydrogen, fluoro, cyano, $C_1$-$C_3$ alkyl, —$CHF_2$, —$CF_3$, cyclopropyl, $C_1$-$C_3$ alkoxy, —$OCHF_2$, —$OCF_3$, —O-cyclopropyl, —$CH_2$—O—$CH_3$, —$C(O)OCH_3$, or —$C(O)N(H)CH_3$;
$R^6$ is hydrogen, fluoro, methyl, —OH, or methoxy; and
$R^7$ is hydrogen, bromo, chloro, fluoro, or methoxy.

One embodiment of the present invention relates to a compound of formula (III), or a pharmaceutically acceptable salt thereof, wherein $R^{2a}$ is absent, fluoro, methyl, —$CH_2OH$ or —OH; $R^{2a}$ is absent, fluoro, or methyl; $R^{2a}$ is absent; $R^{2a}$ is fluoro; or $R^{2a}$ is methyl.

One embodiment of the present invention relates to a compound of formula (III), or a pharmaceutically acceptable salt thereof, wherein $R^3$ is hydrogen, halogen, or $C_1$-$C_3$ alkyl; $R^3$ is hydrogen, fluoro, bromo, or methyl; $R^3$ is fluoro; $R^3$ is methyl; $R^4$ is hydrogen, fluoro, methyl, ethyl, cyclopropyl, —O-cyclopropyl, or $C_1$-$C_4$ alkoxy; $R^4$ is hydrogen; $R^4$ is $C_1$-$C_3$ alkoxy; $R^4$ is methoxy; or $R^3$ is fluoro and $R^4$ is methoxy.

One embodiment of the present invention relates to a compound of formula (III), or a pharmaceutically acceptable salt thereof, wherein at least one of $R^3$ and $R^4$ is hydrogen.

One embodiment of the present invention relates to a compound of formula (III), or a pharmaceutically acceptable salt thereof, wherein $R^3$ is hydrogen, halogen, or $C_1$-$C_3$ alkyl and $R^4$ is hydrogen; $R^3$ is hydrogen, fluoro, bromo, or methyl and $R^4$ is hydrogen; $R^3$ is methyl and $R^4$ is hydrogen; $R^3$ is hydrogen and $R^4$ is hydrogen, fluoro, methyl, ethyl, cyclopropyl, —O-cyclopropyl, or $C_1$-$C_4$ alkoxy; $R^3$ is hydrogen and $R^4$ is hydrogen; $R^3$ is hydrogen and $R^4$ is $C_1$-$C_3$ alkoxy; or $R^3$ is hydrogen and $R^4$ is methoxy.

One embodiment of the present invention relates to a compound of formula (III), or a pharmaceutically acceptable salt thereof, wherein $R^5$ is methoxy, $R^6$ is methoxy, and $R^7$ is hydrogen.

One embodiment of the present invention relates to a compound of formula (III), or a pharmaceutically acceptable salt thereof, wherein $R^5$ is methoxy, $R^6$ is hydrogen, and $R^7$ is hydrogen.

It is to be understood that any of the above-mentioned embodiment(s) for formula (III) can be combined with any other embodiment(s) above to the extent they are not incompatible.

This invention relates to a compound of formula (IV)

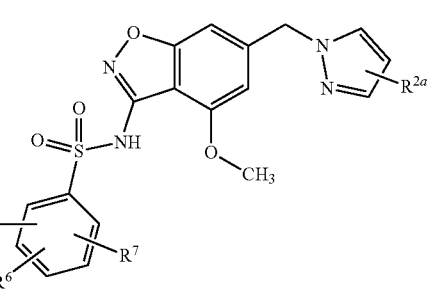

(IV)

or a pharmaceutically acceptable salt thereof,
wherein
$R^{2a}$ is absent, halogen, $C_1$-$C_3$ alkyl, —$CH_2OH$, or —OH;
$R^5$ is hydrogen, fluoro, cyano, $C_1$-$C_3$ alkyl, —$CHF_2$, —$CF_3$, cyclopropyl, $C_1$-$C_3$ alkoxy, —$OCHF_2$, —$OCF_3$, —O-cyclopropyl, —$CH_2$—O—$CH_3$, —$C(O)OCH_3$, or —$C(O)N(H)CH_3$;
$R^6$ is hydrogen, fluoro, methyl, —OH, or methoxy; and
$R^7$ is hydrogen, bromo, chloro, fluoro, or methoxy.

One embodiment of the present invention relates to a compound of formula (IV), or a pharmaceutically acceptable salt thereof, wherein $R^{2a}$ is absent, fluoro, methyl, —$CH_2OH$ or —OH; $R^{2a}$ is absent, fluoro, or methyl; $R^{2a}$ is absent; $R^{2a}$ is fluoro; or $R^{2a}$ is methyl.

One embodiment of the present invention relates to a compound of formula (IV), or a pharmaceutically acceptable salt thereof, wherein $R^5$ is methoxy, $R^6$ is methoxy, and $R^7$ is hydrogen.

One embodiment of the present invention relates to a compound of formula (IV), or a pharmaceutically acceptable salt thereof, wherein $R^5$ is methoxy, $R^6$ is hydrogen, and $R^7$ are hydrogen.

It is to be understood that any of the above-mentioned embodiment(s) for formula (IV) can be combined with any other embodiment(s) above to the extent they are not incompatible.

This invention relates to a compound of formula (V)

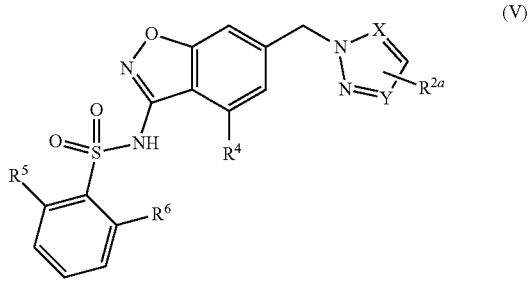

or a pharmaceutically acceptable salt thereof,
wherein
X is N or —C(H)—;
Y is N or —C(H)—,
provided that at least one of X and Y is —C(H)—;
$R^{2a}$ is absent, halogen, $C_1$-$C_3$ alkyl, —$CH_2OH$, or —OH;
$R^4$ is hydrogen, halogen, $C_1$-$C_3$ alkyl, cyclopropyl, $C_1$-$C_4$ alkoxy, or —O-cyclopropyl;
$R^5$ is hydrogen, methyl, —$CF_3$, $C_1$-$C_3$ alkoxy, —$CH_2$—$OCH_3$, or —$C(O)OCH_3$; and
$R^6$ is hydrogen, fluoro, methyl, —OH, or methoxy.

One embodiment of the present invention relates to a compound of formula (V), or a pharmaceutically acceptable salt thereof, wherein X is N and Y is —C(H)—.

One embodiment of the present invention relates to a compound of formula (V), or a pharmaceutically acceptable salt thereof, wherein X is —C(H)— and Y is N.

One embodiment of the present invention relates to a compound of formula (V), or a pharmaceutically acceptable salt thereof, wherein X is —C(H)— and Y is —C(H)—.

One embodiment of the present invention relates to a compound of formula (V), or a pharmaceutically acceptable salt thereof, wherein $R^{2a}$ is absent, fluoro, methyl, —$CH_2OH$ or —OH; $R^{2a}$ is absent, fluoro, or methyl; $R^{2a}$ is absent; $R^{2a}$ is fluoro; or $R^{2a}$ is methyl.

One embodiment of the present invention relates to a compound of formula (V), or a pharmaceutically acceptable salt thereof, wherein $R^4$ is hydrogen, fluoro, ethyl, cyclopropyl, $C_1$-$C_4$ alkoxy, or —O-cyclopropyl; $R^4$ is $C_1$-$C_4$ alkoxy; $R^4$ is methoxy; or $R^4$ is hydrogen.

One embodiment of the present invention relates to a compound of formula (V), or a pharmaceutically acceptable salt thereof, wherein $R^5$ is methoxy.

One embodiment of the present invention relates to a compound of formula (V), or a pharmaceutically acceptable salt thereof, wherein $R^6$ is methoxy.

One embodiment of the present invention relates to a compound of formula (V), or a pharmaceutically acceptable salt thereof, wherein $R^6$ is hydrogen.

One embodiment of the present invention relates to a compound of formula (V), or a pharmaceutically acceptable salt thereof, wherein $R^5$ is methoxy and $R^6$ is methoxy.

One embodiment of the present invention relates to a compound of formula (V), or a pharmaceutically acceptable salt thereof, wherein $R^5$ is methoxy and $R^6$ is hydrogen.

It is to be understood that any of the above-mentioned embodiment(s) for formula (V) can be combined with any other embodiment(s) above to the extent they are not incompatible.

This invention relates to a compound of formula (VI)

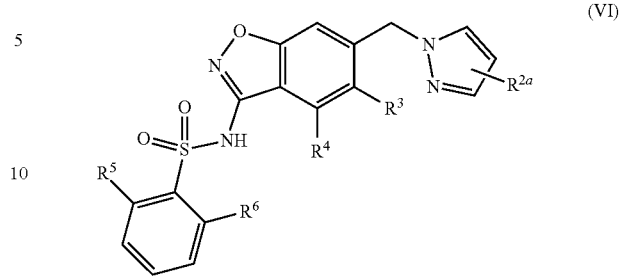

or a pharmaceutically acceptable salt thereof,
wherein
$R^{2a}$ is absent, halogen, $C_1$-$C_3$ alkyl, —$CH_2OH$, or —OH;
$R^3$ is hydrogen, halogen, or $C_1$-$C_3$ alkyl;
$R^4$ is hydrogen, halogen, $C_1$-$C_3$ alkyl, cyclopropyl, $C_1$-$C_4$ alkoxy, or —O-cyclopropyl, provided that at least one of $R^3$ and $R^4$ is hydrogen;
$R^5$ is hydrogen, methyl, —$CH_2$—$OCH_3$, —$CF_3$, $C_1$-$C_3$ alkoxy, or —$C(O)OCH_3$; and
$R^6$ is hydrogen, fluoro, methyl, —OH, or methoxy.

One embodiment of the present invention relates to a compound of formula (VI), or a pharmaceutically acceptable salt thereof, wherein $R^{2a}$ is absent, fluoro, methyl, —$CH_2OH$ or —OH; $R^{2a}$ is absent, fluoro, or methyl; $R^{2a}$ is absent; $R^{2a}$ is fluoro; or $R^{2a}$ is methyl.

One embodiment of the present invention relates to a compound of formula (VI), or a pharmaceutically acceptable salt thereof, wherein $R^3$ is hydrogen, fluoro, or methyl and $R^4$ is hydrogen; $R^3$ is hydrogen and $R^4$ is hydrogen; $R^3$ is methyl and $R^4$ is hydrogen; $R^3$ is hydrogen and $R^4$ is hydrogen, fluoro, ethyl, cyclopropyl, $C_1$-$C_4$ alkoxy, or —O-cyclopropyl; $R^3$ is hydrogen and $R^4$ is $C_1$-$C_4$ alkoxy; or $R^3$ is hydrogen and $R^4$ is methoxy.

One embodiment of the present invention relates to a compound of formula (VI), or a pharmaceutically acceptable salt thereof, wherein $R^5$ is methoxy.

One embodiment of the present invention relates to a compound of formula (VI), or a pharmaceutically acceptable salt thereof, wherein $R^6$ is methoxy.

One embodiment of the present invention relates to a compound of formula (VI), or a pharmaceutically acceptable salt thereof, wherein $R^6$ is hydrogen.

One embodiment of the present invention relates to a compound of formula (VI), or a pharmaceutically acceptable salt thereof, wherein $R^5$ is methoxy and $R^6$ is methoxy.

One embodiment of the present invention relates to a compound of formula (VI), or a pharmaceutically acceptable salt thereof, wherein $R^5$ is methoxy and $R^6$ is hydrogen.

It is to be understood that any of the above-mentioned embodiment(s) for formula (VI) can be combined with any other embodiment(s) above to the extent they are not incompatible.

One embodiment of the present invention provides a compound selected from the group consisting of the compounds exemplified in Examples 1 to 133, inclusive, or a pharmaceutically acceptable salt thereof.

This invention relates to a compound of any of the embodiments of the compounds of formula (I), formula (Ia), formula (II), formula (III), formula (IV), formula (V), or formula (VI), or a pharmaceutically acceptable salt thereof, which is deuterium-labeled.

This invention relates to a pharmaceutical composition comprising a compound of any of the embodiments of the compounds of formula (I), formula (Ia), formula (II), formula (III), formula (IV), formula (V), or formula (VI), or a pharmaceutically acceptable salt thereof, and a pharmaceutically acceptable carrier or diluent.

This invention relates to a pharmaceutical composition comprising a compound of any of the embodiments of the compounds of formula (I), formula (Ia), formula (II), formula (III), formula (IV), formula (V), or formula (VI), or a pharmaceutically acceptable salt thereof, and a pharmaceutically acceptable carrier or diluent, for treating cancer.

This invention relates to a method of treating cancer in a patient comprising administering to the patient an amount of a compound of any of the embodiments of the compounds of formula (I), formula (Ia), formula (II), formula (III), formula (IV), formula (V), or formula (VI), or formula (V), or a pharmaceutically acceptable salt thereof, that is effective in treating cancer.

This invention relates to a compound of any of the embodiments of the compounds of formula (I), formula (Ia), formula (II), formula (III), formula (IV), formula (V), or formula (VI), or a pharmaceutically acceptable salt thereof, for use in the treatment of cancer in a patient.

This invention relates to a use of a compound of any of the embodiments of the compounds of formula (I), formula (Ia), formula (II), formula (III), formula (IV), formula (V), or formula (VI), or a pharmaceutically acceptable salt thereof, in the manufacture of a medicament for the treatment of cancer.

This invention relates to a combination of a compound of any of the embodiments of the compounds of formula (I), formula (Ia), formula (II), formula (III), formula (IV), formula (V), or formula (VI), or a pharmaceutically acceptable salt thereof, with an anti-tumor agent or with radiation therapy, for the treatment of cancer.

This invention relates to a combination of a compound of any of the embodiments of the compounds formula (I), formula (Ia), formula (II), formula (III), formula (IV), formula (V), or formula (VI), or a pharmaceutically acceptable salt thereof, with an anti-tumor agent, for the treatment of cancer.

In one embodiment of the present invention the cancer is breast cancer.

In one embodiment of the present invention the cancer is breast cancer, which breast cancer is ER positive breast cancer.

BRIEF DESCRIPTION OF THE DRAWING

The FIGURE shows the PXRD spectrum of 2-methoxy-N-{4-methoxy-6-[(1H-pyrazol-1-yl)methyl]-1,2-benzoxazol-3-yl}benzene-1-sulfonamide anhydrous (Form 1).

DETAILED DESCRIPTION OF THE INVENTION

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

The invention described herein suitably may be practiced in the absence of any element(s) not specifically disclosed herein. Thus, for example, in each instance herein any of the terms "comprising", "consisting essentially of", and "consisting of" may be replaced with either of the other two terms.

For convenience, many chemical moieties and compounds are represented using well known abbreviations, including but not limited to, Ac (acetyl), AcOH (acetic acid), AIBN (azobisisobutyronitrile), n-BuLi (n-butyllithium), CN (cyano), CPME (cyclopentyl methyl ether), DCM (dichloromethane or methylene chloride), acetone-$d_6$ (deuterated acetone), $CDCl_3$ (deuterated chloroform), DMSO-$d_6$ (deuterated dimethylsulfoxide), methanol-$d_4$ (deuterated methanol), $D_2O$ (deuterated water), DIAD (diisopropyl azodicarboxylate), DMAP (N,N-dimethylpyridin-4-amine), DMF (N,N-dimethylformamide), DMSO (dimethylsulfoxide), dppf (1,1'-bis(diphenylphosphino)ferrocene), dppp (1,3-bis(diphenylphosphino)propane), Et (ethyl), ethyl acetate (EtOAc), EtOH (ethanol), LDA (lithium diisopropyl amide), Me (methyl), MeOH (methanol), MeCN (acetonitrile), MeOAc (methyl acetate), Ms (methanesulfonyl), MsCl (methanesulfonyl chloride), MTBE (methyl tert-butyl ether), NADPH (nicotinamide adenine dinucleotide phosphate), N/D (not determined); NaOMe (sodium methoxide), NaOtPn (sodium tert-pentoxide), $Pd(OAc)_2$ (palladium(II) acetate), $PdCl_2(dppf)$ or $Pd(dppf)Cl_2$ (1,1'-bis(diphenylphosphino)ferrocene dichloropalladium (II)), $Pd(PPh_3)_4$ (tetrakis(triphenylphosphine)palladium(0)), Pet. Ether (petroleum ether), Ph (phenyl), 2-PrOH (isopropanol, 2-propanyl), t-Bu (tert-butyl), TBAF (tetra-n-butylammonium fluoride), TBS (tert-butyldimethylsilyl), TMG (tetramethylguanidine), TBSCl (tert-butyldimethylsilyl chloride), TEA (triethylamine), TFA (trifluoroacetic acid), THF (tetrahydrofuran), TMEDA (tetramethylethylenediamine), and X-Phos (2-dicyclohexylphosphino-2',4',6'-triisopropylbiphenyl).

In addition, TLC refers to thin layer chromatography, HPLC refers to high-performance liquid chromatography, LCMS refers to liquid chromatography-mass spectrometry, and SFC (supercritical fluid chromatography).

Other abbreviations: rt or Rt (retention time), min (minute or minutes), h (hour or hours), RT (room temperature), aq. (aqueous), satd. (saturated), eq or eq. (equivalent(s)).

The term "halogen", as used herein, refers to a fluorine, chlorine, bromine, or iodine atom or fluoro (F), chloro (Cl), bromo (Br), or iodo (I).

The term "alkyl", as used herein, refers to saturated monovalent hydrocarbon radicals containing, in certain embodiments, from one to six, or from one to three carbon atoms, having straight or branched moieties. The term "$C_1$-$C_4$ alkyl" refers to an alkyl radical containing from one to four carbon atoms, having straight or branched moieties. The term "$C_1$-$C_4$ alkyl" includes within its definition the term "$C_1$-$C_3$ alkyl".

Examples of alkyl groups include, but are not limited to, methyl, ethyl, propyl, isopropyl, butyl, isobutyl, sec-butyl, and tert-butyl.

The term "alkoxy", as used herein, refers to an alkyl radical that is single bonded to an oxygen atom. The attachment point of an alkoxy radical to a molecule is through the oxygen atom. An alkoxy radical may be depicted as alkyl-O—. The terms "$C_1$-$C_4$ alkoxy" and "$C_1$-$C_3$ alkoxy", refer to an alkoxy radical containing from one to four carbon atoms and from one to three carbon atoms, respectively, having straight or branched moieties. Alkoxy groups, include, but are not limited to, methoxy, ethoxy, propoxy, isopropoxy, butoxy, and the like.

The term "aryl", as used herein, refers to a cyclic group derived from an aromatic hydrocarbon. The term "$C_6$-$C_{10}$ aryl" contains from six to ten carbon atoms. Examples of such groups include, but are not limited to, phenyl and naphthyl. The term "aryl" also includes fused polycyclic aromatic ring systems in which an aromatic ring is fused to one or more rings. Examples include, but are not limited to, 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl (2,3-dihydro-1H-indene) or tetrahydronaphthyl (also known as 1, 2, 3, 4-tetrahydronaphthyl), where the radical or point of attachment is on the aromatic ring.

The term "heterocycle" as used herein, refers to a group derived from an aryl group, in which at least one of the ring carbon atoms has been replaced with a heteroatom selected from oxygen, nitrogen and sulfur.

The term "heteroaryl", as used herein, refers to a group derived from an aromatic monocyclic or bicyclic heterocycle, and in particular with respect to the bicyclic heterocycle, to a benzo-fused heterocyclic group, in which an aromatic or non-aromatic heterocycle is fused to a phenyl group. As used herein, the term "5 membered heteroaryl" has a total of 5 atoms in its ring system, the term "5-6 membered heteroaryl", has a total of 5 or 6 atoms in its ring system, and the term "5-9 membered heteroaryl" has a total of 5, 6, 7, 8 or 9 atoms in its ring system. Additionally, each of the "5 membered heteroaryl", "5-6 membered heteroaryl" and "5-9 membered heteroaryl" groups have one, two or three heteroatoms independently selected from nitrogen and oxygen, with the proviso that the ring system does not contain two adjacent oxygen atoms. Examples include, but are not limited to, pyrazolyl and triazolyl. As used herein, the term "9-10 membered heteroaryl", has a total of 9 or 10 atoms in its ring system, and one or two heteroatoms each independently selected from nitrogen and oxygen, with the proviso that the ring system does not contain two adjacent oxygen atoms.

Examples of a "9-10 membered heteroaryl", according to the present invention, include, but are not limited to,

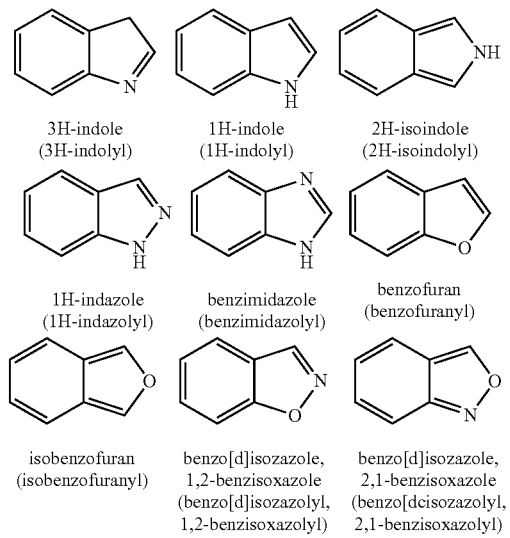

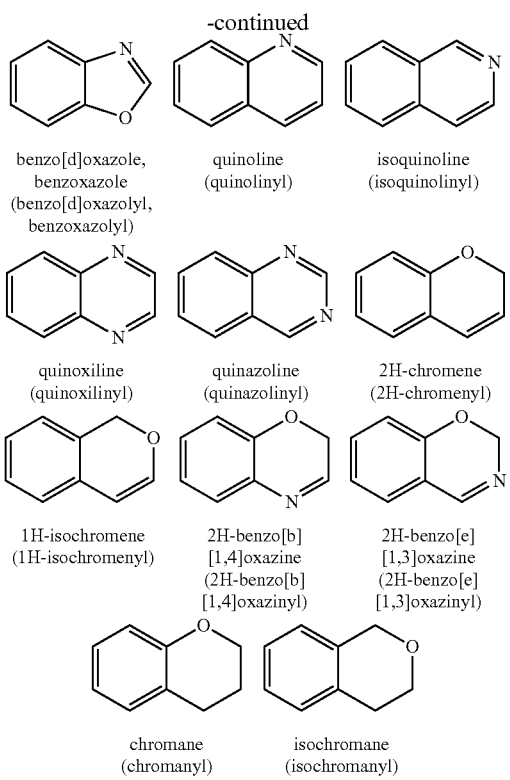

The term "treating", as used herein, unless otherwise indicated, means reversing, alleviating, inhibiting the progress of, or preventing the disease, disorder or condition to which such term applies, or one or more symptoms of such disease, disorder or condition. The term "treatment", as used herein, unless otherwise indicated, refers to the act of treating as "treating" is defined immediately above.

The term "combination", as used herein, unless otherwise indicated, means a fixed-dose combination or a combination of agents that is administered intermittently, concurrently or sequentially, according to the same or different route of administration.

As used herein, an "effective" amount refers to an amount of a substance, agent, compound, or composition that is of sufficient quantity to result in a decrease in severity of disease symptoms, an increase in frequency and duration of disease symptom-free periods, or a prevention of impairment or disability due to the disease affliction—either as a single dose or according to a multiple dose regimen, alone or in combination with other agents or substances. One of ordinary skill in the art would be able to determine such amounts based on such factors as the patient's size, the severity of the patient's symptoms, and the particular combination, composition or route of administration selected. The patient or subject may be a human or non-human mammal in need of treatment. In one embodiment, the patient is human.

Unless indicated otherwise, all references herein to the inventive compounds include references to salts, solvates, hydrates and complexes thereof, and to solvates, hydrates and complexes of salts thereof, including polymorphs, stereoisomers, and isotopically labelled versions thereof.

Embodiments disclosed herein include isotopically-labeled compounds, which are identical to those recited in formulas (I), (Ia) (II), (III), (IV), (V) or (VI) but for the fact that one or more atoms are replaced by an atom having an atomic mass or mass number different from the atomic mass or mass number usually found in nature. Examples of isotopes that can be incorporated into compounds of the embodiments disclosed herein include isotopes of hydrogen, carbon, nitrogen, oxygen, phosphorous, sulfur, fluorine and chlorine, such as, but not limited to, $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. In one embodiment, the isotope incorporated into compounds of formulas (I), (Ia) (II), (III), (IV), (V) or (VI) is $^2$H. Compounds described herein and pharmaceutically acceptable salts of said compounds which contain the aforementioned isotopes and/or other isotopes of other atoms are within the scope of the present embodiments. Certain isotopically-labeled compounds of the embodiments disclosed herein, for example, those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example, increased in vivo half-life or reduced dosage requirements and, hence, may be preferred in some circumstances. Isotopically-labeled compounds of embodiments disclosed herein can generally be prepared by carrying out the procedures disclosed in the Schemes and/or in the Examples below, by substituting a readily available isotopically-labeled reagent for a non-isotopically-labeled reagent. In one embodiment, the compounds of formulas (I), (Ia) (II), (III), (IV), (V) or (VI) are deuterium-labeled.

Some embodiments relate to the pharmaceutically acceptable salts of the compounds described herein. The compounds described herein that are basic in nature are capable of forming a wide variety of salts with various inorganic and organic acids. The acids that may be used to prepare pharmaceutically acceptable acid addition salts of such basic compounds described herein are those that form non-toxic acid addition salts, e.g., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, pamoate [i.e., 1,1'-methylene-bis-(2-hydroxy-3-naphthoate)] salts. The compounds described herein that include a basic moiety, such as an amino group, may form pharmaceutically acceptable salts with various amino acids, in addition to the acids mentioned above.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds described herein are known to one of skill in the art.

The term "solvate" is used herein to describe a molecular complex comprising a compound described herein and one or more pharmaceutically acceptable solvent molecules, for example, ethanol.

The compounds described herein may also exist in unsolvated and solvated forms. Accordingly, some embodiments relate to the hydrates and solvates of the compounds described herein. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of prodrugs in accordance with the invention include:

(i) where the compound contains a carboxylic acid functionality (—COOH), an ester thereof, for example, replacement of the hydrogen with $(C_1-C_8)$alkyl;

(ii) where the compound contains an alcohol functionality (—OH), an ether thereof, for example, replacement of the hydrogen with $(C_1-C_8)$alkanoyloxymethyl, or with a phosphate ether group; and (iii) where the compound contains a primary or secondary amino functionality (—NH$_2$ or —NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references. Finally, certain inventive compounds may themselves act as prodrugs of other of the inventive compounds.

Also included within the scope of the invention are metabolites of compounds of the formulae described herein, i.e., compounds formed in vivo upon administration of the drug.

Compounds described herein containing one or more asymmetric carbon atoms can exist as two or more stereoisomers. Where a compound described herein contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds described herein containing, for example, an imino, keto, or oxime group, or so-called valence tautomerism in compounds which contain an aromatic moiety. A single compound may exhibit more than one type of isomerism.

The compounds of the embodiments described herein include all stereoisomers (e.g., cis and trans isomers) and all optical isomers of compounds described herein (e.g., R and S enantiomers), as well as racemic, diastereomeric and other mixtures of such isomers. While all stereoisomers are encompassed within the scope of our claims, one skilled in the art will recognize that particular stereoisomers may be preferred.

In some embodiments, the compounds described herein can exist in several tautomeric forms, including the enol and imine form, and the keto and enamine form and geometric isomers and mixtures thereof. All such tautomeric forms are included within the scope of the present embodiments. Tautomers exist as mixtures of a tautomeric set in solution. In solid form, usually one tautomer predominates. Even though one tautomer may be described, the present embodiments include all tautomers of the present compounds.

The present embodiments also include atropisomers of the compounds described herein. Atropisomers refer to compounds that can be separated into rotationally restricted isomers.

Included within the scope of the present embodiments are all stereoisomers, geometric isomers and tautomeric forms of the compounds described herein, including compounds exhibiting more than one type of isomerism, and mixtures of one or more thereof.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC) or SFC.

Alternatively, the racemate (or a racemic precursor) may be reacted with a suitable optically active compound, for example, an alcohol, or, in the case where a compound described herein contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

"Abnormal cell growth" or "cancer" as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; (5) benign and malignant cells of other proliferative diseases in which aberrant serine/threonine kinase activation occurs; (6) any tumors that proliferate by aberrant signaling, metabolic, epigenetic and transcriptional mechanism; and (7) benign and malignant cells of other proliferative diseases in which aberrant signaling, metabolic, epigenetic and transcriptional mechanism.

For convenience, certain well-known abbreviations, may be used herein, including: estrogen receptor positive (ER+), human epidermal growth factor receptor 2 negative (HER2−), non-small cell lung cancer (NSCLC) and castration resistant prostate cancer (CRPC).

Further embodiments relate to methods of treating abnormal cell growth in a patient. Additional embodiments relate to a method of treating abnormal cell growth in a patient comprising administering to the patient an amount of a compound described herein that is effective in treating abnormal cell growth.

In other embodiments, the abnormal cell growth is cancer.

In some embodiments, the cancer is selected from the group consisting of lung cancer, mesothelioma, bone cancer, pancreatic cancer, skin cancer, cancer of the head or neck, cutaneous or intraocular melanoma, uterine cancer, ovarian cancer, rectal cancer, cancer of the anal region, stomach cancer, hepatic carcinoma, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, hematology malignancy, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, glioblastoma, brain stem glioma, pituitary adenoma, or a combination of two or more of the foregoing cancers.

Additional embodiments relate to methods of treating solid tumors in a patient. Some embodiments relate to the treatment of solid tumors in a patient comprising administering to the patient an amount of a compound described herein that is effective in treating the solid tumor.

In one embodiment, the solid tumor is breast, lung, colon, brain, prostate, stomach, pancreatic, ovarian, melanoma, endocrine, uterine, testicular, or bladder.

In one embodiment, the solid tumor is breast, lung, prostate, pancreatic, or ovarian.

In one embodiment, the cancer is breast cancer.

In one embodiment, the breast cancer is ER+ breast cancer.

In one embodiment, the breast cancer is ER+ HER2− breast cancer.

In one embodiment, the breast cancer is locally advanced or metastatic ER+ HER2− breast cancer.

In one embodiment, the lung cancer is non-small cell lung cancer.

In one embodiment, the lung cancer is locally advanced or metastatic non-small cell lung cancer.

In one embodiment, the prostate cancer is castration resistant prostate cancer.

In one embodiment, the prostate cancer is locally advanced or metastatic castration resistant prostate cancer.

Additional embodiments relate to methods of treating hematologic tumors in a patient. Some embodiments relate to the treatment of hematologic tumors in a patient comprising administering to the patient an amount of a compound described herein that is effective in treating the hematologic tumor.

In one embodiment, the hematologic tumor is leukemia, lymphoma or multiple myeloma.

In one embodiment, the hematologic tumor is leukemia or lymphoma.

Additional embodiments relate to methods of treating cancer in a patient comprising administering to the patient an amount of a compound described herein that is effective in treating cancer.

In one embodiment, the cancer is breast, lung, colon, brain, prostate, stomach, pancreatic, ovarian, melanoma, endocrine, uterine, testicular, bladder, or hematologic.

In one embodiment, the cancer is breast, lung, prostate, pancreatic, ovarian, or hematologic.

In one embodiment, the cancer is breast, lung, prostate, pancreatic, or ovarian.

In one embodiment, the cancer is breast cancer.

In one embodiment, the breast cancer is ER+ breast cancer.

In one embodiment, the breast cancer is ER+ HER2− breast cancer.

In one embodiment, the breast cancer is locally advanced or metastatic ER+ HER2− breast cancer.

In one embodiment, the lung cancer is non-small cell lung cancer.

In one embodiment, the lung cancer is locally advanced or metastatic non-small cell lung cancer.

In one embodiment, the prostate cancer is castration resistant prostate cancer.

In one embodiment, the prostate cancer is locally advanced or metastatic castration resistant prostate cancer.

In one embodiment, the cancer is hematologic.

In one embodiment, the hematologic tumor is leukemia or lymphoma.

Further embodiments relate to methods of treating cancer in a patient which comprises administering to the patient an amount of a compound described herein that is effective in treating cancer in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

More embodiments relate to pharmaceutical compositions for treating cancer in a patient comprising an amount of a compound described herein that is effective in treating cancer, and a pharmaceutically acceptable carrier.

Additional embodiments relate to a method of treating cancer in a patient, and in particular a human, comprising administering to the patient an amount of a compound described herein, or a pharmaceutically acceptable salt, solvate, hydrate or prodrug thereof, that is effective in treating cancer. In one embodiment of this method, the cancer, includes, but is not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises comprising administering to a patient an amount of a compound described herein that is effective in treating said cancer solid tumor. In one preferred embodiment the solid tumor is breast lung, colon, brain, prostate, stomach, pancreatic, ovarian, skin (melanoma), endocrine, uterine, testicular, and bladder cancer.

In another embodiment of said method, said cancer is a benign proliferative disease, including, but not limited to, psoriasis, benign prostatic hypertrophy or restenosis.

Some embodiments relate to a method of treating cancer in a patient which comprises administering to said patient an amount of a compound described herein, or a pharmaceutically acceptable salt, solvate, hydrate or prodrug thereof, that is effective in treating cancer in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Additional embodiments relate to a pharmaceutical composition for treating cancer in a patient, and in particular a human, comprising an amount of a compound described herein, or a pharmaceutically acceptable salt, solvate, hydrate or prodrug thereof, that is effective in treating cancer, and a pharmaceutically acceptable carrier. In one embodiment of said composition, the cancer, includes, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

Further embodiments relate to a method of treating cancer in a patient which comprises administering to said patient an amount of a compound described herein, or a pharmaceutically acceptable salt, solvate, or hydrate thereof, that is effective in treating cancer in combination with another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. Some embodiments contemplate a pharmaceutical composition for treating abnormal cell growth wherein the composition includes a compound described herein, or a pharmaceutically acceptable salt, solvate, or hydrate thereof, that is effective in treating abnormal cell growth, and another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Yet more embodiments relate to a method of treating a disorder associated with angiogenesis in a patient, including a human, comprising administering to said patient an amount of a compound described herein, as defined above, or a pharmaceutically acceptable salt, solvate, hydrate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

Some embodiments relate to a method of (and to a pharmaceutical composition for) treating cancer in a patient which comprise an amount of a compound described herein, or a pharmaceutically acceptable salt, solvate, or hydrate thereof, in combination with an amount of one or more substances selected from anti-angiogenesis agents, signal transduction inhibitors (e.g., inhibiting the means by which regulatory molecules that govern the fundamental processes of cell growth, differentiation, and survival communicated within the cell), and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound described herein in the methods and pharmaceutical compositions described herein.

Tyrosine kinase inhibitors can also be combined with a compound described herein.

VEGF inhibitors, for example, sutent and axitinib, can also be combined with a compound described herein.

ErbB2 receptor inhibitors may be administered in combination with a compound described herein. Various other compounds, such as styrene derivatives, have also been shown to possess tyrosine kinase inhibitory properties, and some of tyrosine kinase inhibitors have been identified as erbB2 receptor inhibitors.

Epidermal growth factor receptor (EGFR) inhibitors may be administered in combination with a compound of the present invention.

PI3K inhibitors, such as PI3K alpha or PI3K beta inhibitors, may be administered in combination with a compound of the present invention.

Mammalian target of rapamycin (mTOR) inhibitors may be administered in combination with a compound of the present invention. c-Met inhibitors may be administered in combination with a compound of the present invention.

CDK inhibitors may be administered in combination with a compound of the present invention.

MEK inhibitors may be administered in combination with a compound of the present invention.

PARP inhibitors may be administered in combination with a compound of the present invention.

JAK inhibitors may be administered in combination with a compound of the present invention.

An antagonist of a Programmed Death 1 protein (PD-1) may be administered in combination with a compound of the present invention.

An antagonist of Programmed Death-Ligand 1 (PD-L1) may be administered in combination with a compound of the present invention.

Other antiproliferative agents that may be used with the compounds described herein include inhibitors of the enzyme farnesyl protein transferase and inhibitors of the receptor tyrosine kinase PDGFr.

A compound described herein may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase.

A compound described herein may be applied as a sole therapy or may involve one or more other anti-tumor substances, for example those selected from, for example, mitotic inhibitors, alkylating agents, anti-metabolites, growth factor inhibitors, cell cycle inhibitors, intercalating antibiotics, enzymes, and anti-hormones.

The compounds described herein may be used alone or in combination with one or more of a variety of anti-cancer agents or supportive care agents. For example, the compounds described herein may be used with cytotoxic agents. Some embodiments also contemplate the use of the compounds described herein together with hormonal therapy. Further, some embodiments provide a compound described herein alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds described herein may be used with anti-tumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds described herein.

Some embodiments also relate to a pharmaceutical composition comprising a compound of formulas (I), (Ia) (II), (III), (IV), (V) or (VI), or a pharmaceutically acceptable salt or solvate thereof, as hereinbefore defined in association with a pharmaceutically acceptable adjuvant, diluent or carrier.

Further embodiments relate to a pharmaceutical composition which comprises mixing a compound of formulas (I), (Ia) (II), (III), (IV), (V) or (VI), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound formulas (I), (Ia) (II), (III), (IV), (V) or (VI), or pharmaceutically acceptable salt thereof, may be in the range from 1 mg to 1 gram; from 1 mg to 250 mg; from 1 mg to 100 mg; from 1 mg to 50 mg; from 1 mg to 25 mg; and from 1 mg to 10 mg.

The present embodiments also encompass sustained release compositions.

Administration of the compounds described herein (hereinafter the "active compound(s)") can be affected by any method that enables delivery of the compounds to the site of action. These methods include oral routes, intraduodenal routes, parenteral injection (including intravenous, subcutaneous, intramuscular, intravascular or infusion), topical, and rectal administration.

The active compound may be applied as a sole therapy or may involve one or more other anti-tumor substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound described herein as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The examples and preparations provided below further illustrate and exemplify the compounds described herein and methods of preparing such compounds. The scope of the embodiments described herein is not limited in any way by the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

In the examples shown, salt forms were occasionally isolated as a consequence of the mobile phase additives during HPLC based chromatographic purification. In these cases, salts such as formate, trifluoroacetate and acetate were isolated and tested without further processing. It will be recognized that one of ordinary skill in the art will be able to realize the free base form by standard methodology (such as using ion exchange columns, or performing simple basic extractions using a mild aqueous base).

In general, the compounds described herein may be prepared by processes known in the chemical arts, particularly in light of the description contained herein. Certain processes for the manufacture of the compounds described herein are provided as further features of the embodiments and are illustrated in the reaction schemes provided below and in the experimental section.

EXAMPLES

The following examples are provided solely to illustrate the present invention and are not intended to limit the scope of the invention, as described herein.

General Experimental Details

Unless otherwise stated the following generalizations apply. $^1$H NMR spectra were recorded on a Bruker Ultrashield Plus (400 MHz) or a Bruker AVANCE III (400 MHz). The multiplicity of a signal is designated by the following abbreviations: s, singlet; d, doublet; t, triplet; q, quartet; p, pentet; sept, septet; dd, doublet of doublets; dt, doublet of triplets; tt, triplet of triplets; br, broad; m, multiplet. All observed coupling constants, J, are reported in Hertz (Hz). Exchangeable protons are not always observed. LCMS data was generated using either an Agilent 6100 Series Single Quad, an Agilent 1260 Infinity Series UPLC/MS, an Agilent 1200 (LCMS-A), a Waters 2695 alliance, an Agilent 6120 Single Quad or mass-directed HPLC-MS. Chlorine isotopes are reported as $^3$Cl, Bromine isotopes are reported as either $^{79}$Br or 81Br or both $^{79}$Br/$^{81}$Br.

Representative LCMS Methodology is Provided Below:

Instrument: Agilent 6100 Series Single Quad LC/MS, Agilent 1200 Series HPLC, Pump: 1200 Series G1311A Quaternary pump, Autosampler: 1200 Series G1329A Thermostatted Autosampler, Detector: 1200 Series G1314B Variable Wavelength Detector LC conditions: Reverse Phase HPLC analysis, Column: Luna C8 (2) 5 µm 50×4.6 mm 100 Å, Column temperature: 30° C., Injection Volume: 5 µL, Solvent A: Water 0.1% Formic Acid, Solvent B: MeCN 0.1% Formic Acid, Gradient: 5-100% Solvent B over 10 min, Detection: 254 nm or 214 nm MS conditions: Ion Source: Quadrupole, Ion Mode: Multimode-ES, Drying gas temp: 300° C., Vaporizer temperature: 200° C., Capillary voltage (V): 2000 (positive), Capillary voltage (V): 4000 (negative), Scan Range: 100-1000, Step size: 0.1 sec, Acquisition time: 10 min LCMS method A (LCMS-A): LC model: Agilent 1200, Pump type: Binary Pump, Detector type: DAD, MS model: Agilent G6110A Quadrupole, LC conditions: Column: Xbridge-C18, 2.5 μm, 2.1×30 mm, Column temperature: 30° C., Acquisition of wavelength: 214 nm, 254 nm, Mobile phase: A: 0.07% HCOOH aqueous solution, B: MeOH; MS conditions: MS: Ion source: ES+ (or ES−) MS range: 50-900 m/z, Fragmentor: 60, Drying gas flow: 10 L/min, Nebulizer pressure: 35 psi Drying gas temperature: 350° C., Vcap: 3.5 kV

| Gradient Table : | | | |
|---|---|---|---|
| Flow (mL/min) | T (min) | A (%) | B (%) |
| 0.5 | 0.0 | 70 | 30 |
| 0.5 | 0.2 | 70 | 30 |
| 0.5 | 1.8 | 5 | 95 |
| 0.5 | 2.4 | 5 | 95 |
| 0.5 | 2.6 | 70 | 30 |
| 0.5 | 3.5 | 70 | 30 |

Sample Preparation:

The sample was dissolved in methanol, the concentration about 0.11-1 mg/mL, then filtered through syringe filter with 0.22 μm. (Injection volume: 1-10 μL)

General Methods:

Unless stated otherwise, the variables in Schemes I-VI have the same meanings as defined herein.

Scheme I

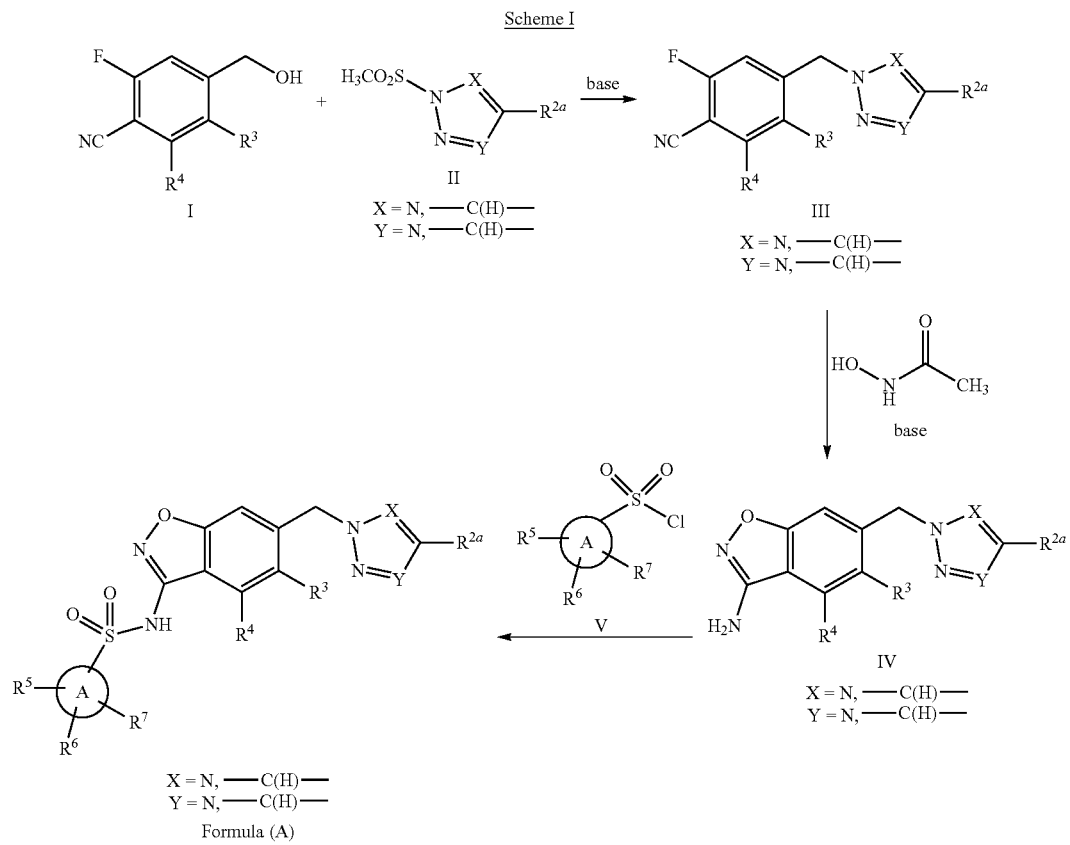

As exemplified in Scheme I, a compound of Type I can be treated with a compound of Type II in the presence of an effective base (such as $Cs_2CO_3$) in an appropriate solvent (such as MeCN) to provide a compound of Type III. A compound of Type III can be converted into a compound of Type IV by treatment with N-hydroxyacetamide in the presence of an effective base (such as $K_2CO_3$ or 1,1,3,3-tetramethylguanidine) in an appropriate solvent mixture (such as $DMF/H_2O$). A compound of Type IV can be treated with a compound of Type V in the presence of an effective base (such as pyridine, NaH, or NaOtPn), neat, or in an appropriate solvent (such as THF or DMF) to provide a compound of Formula (A). In some cases, compounds of Type II, III, and IV, or Formula (A) may contain protecting groups, which can be appended or removed by additional steps in the synthetic sequence using conditions known in the art (Protective Groups in Organic Synthesis, A. Wiley-Interscience Publication, 1981 or Protecting Groups, 10 Georg Thieme Verlag, 1994). Compounds at every step may be purified by standard techniques, such as column chromatography, crystallization, or reverse phase SFC or HPLC. Variables $R^{2a}$, $R^3$, $R^4$, $R^5$, $R^6$, $R^7$, and $R^8$ are as defined in the embodiments, schemes, examples, and claims herein.

Scheme II

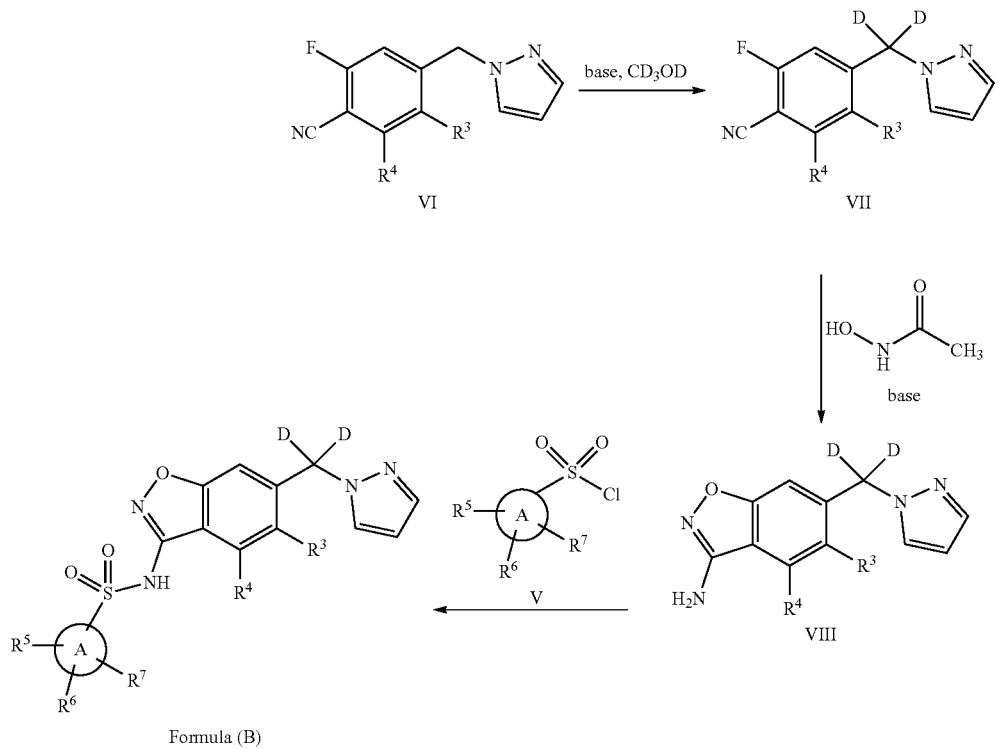

Formula (B)

As exemplified in Scheme II, a compound of Type VI can be deuterated by treatment with an effective base (such as $Cs_2CO_3$) in an appropriate solvent (such as $CD_3OD$) to provide a compound of Type VII. A compound of Type VII can be converted into a compound of Type VIII by treatment with N-hydroxyacetamide in the presence of an effective base (such as 1,1,3,3-tetramethylguanidine) in an appropriate solvent mixture (such as $MeCN/D_2O$). A compound of Type VIII can be treated with a compound of Type V in the presence of an effective base (such as pyridine), neat, to provide a compound of Formula (B). Compounds at every step may be purified by standard techniques, such as column chromatography, crystallization, or reverse phase SFC or HPLC. Variables $R^3$, $R^4$, $R^5$, $R^6$, and $R^7$ are as defined in the embodiments, schemes, examples, and claims herein.

Scheme III

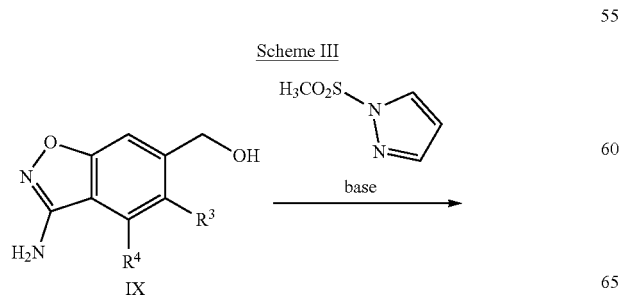

-continued

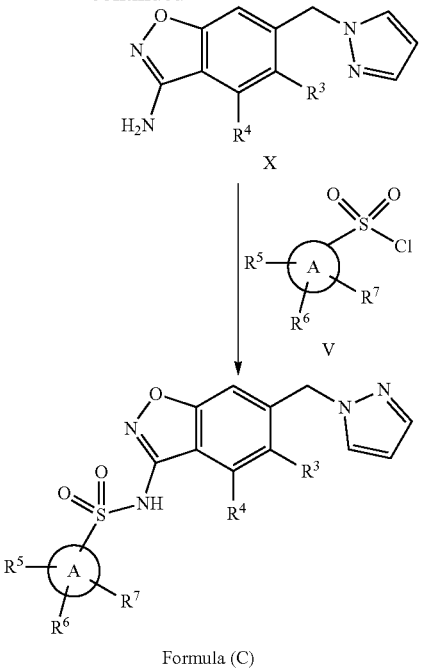

Formula (C)

As exemplified in Scheme III, a compound of Type IX can be converted to a compound of Type X by treatment with 1-(methanesulfonyl)-1H-pyrazole in the presence of an effective base (such as $Cs_2CO_3$) in an appropriate solvent (such as MeCN). A compound of Type X can be treated with a compound of Type V in the presence of an effective base (such as pyridine), neat, to provide a compound of Formula (C). Compounds at every step may be purified by standard techniques, such as column chromatography, crystallization, or reverse phase SFC or HPLC. Variables $R^3$, $R^4$, $R^5$, $R^6$, and $R^7$ are as defined in the embodiments, schemes, examples, and claims herein.

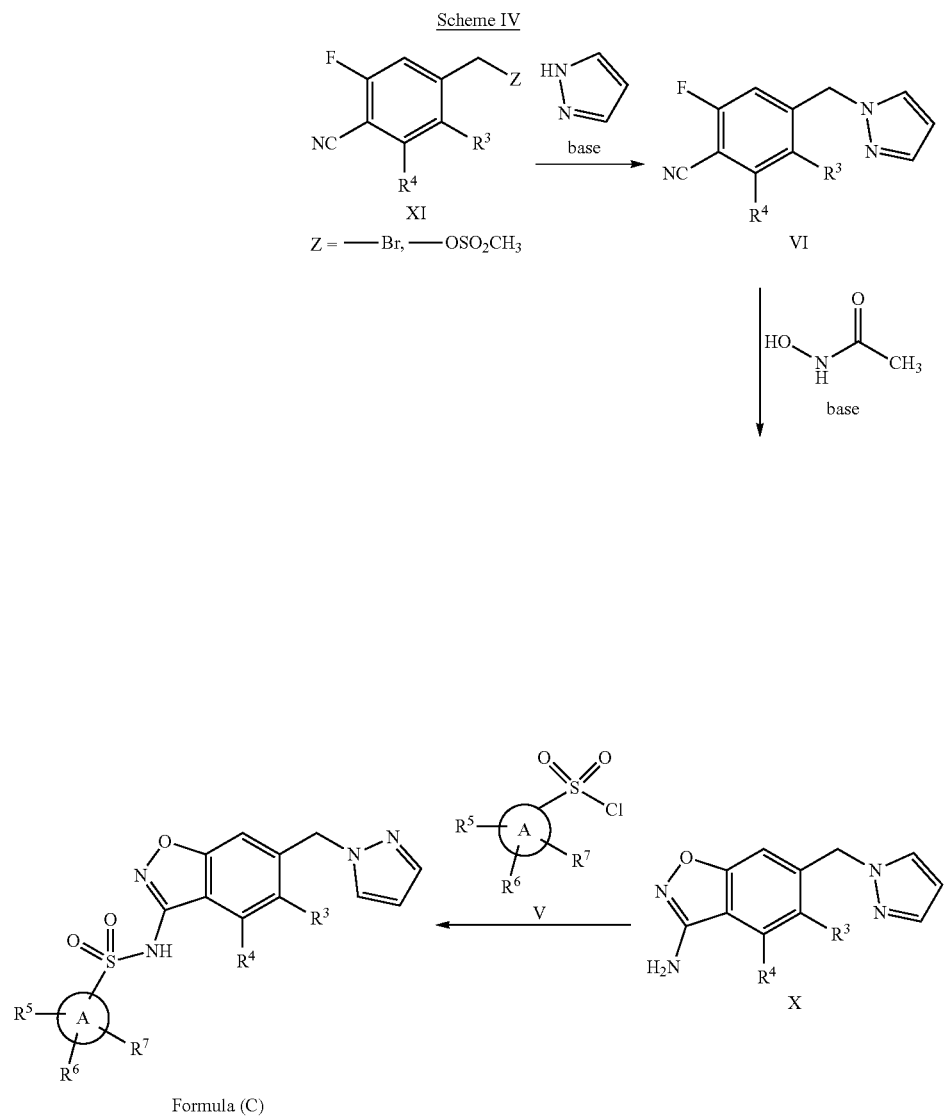

Scheme IV

As exemplified in Scheme IV, a compound of Type XI, with an appropriate leaving group (such as —Br or —SO$_2$CH$_3$) may be converted into a compound of Type VI by treatment with 1H-pyrazole in the presence of an effective base (such as Cs$_2$CO$_3$) in an appropriate solvent (such as MeCN). A compound of Type VI may be converted into a compound of Type X by treatment with N-hydroxyacetamide in the presence of an effective base (such 1,1,3,3-tetramethylguanidine) in an appropriate solvent mixture (such as DMF/H$_2$O). A compound of Type X can be treated with a compound of Type V in the presence of an appropriate base (such as pyridine), neat, to provide a compound of Formula (C). Compounds at every step may be purified by standard techniques, such as column chromatography, crystallization, or reverse phase SFC or HPLC. Variables $R^3$, $R^4$, $R^5$, $R^6$, and $R^7$ are as defined in the embodiments, schemes, examples, and claims herein.

Scheme V

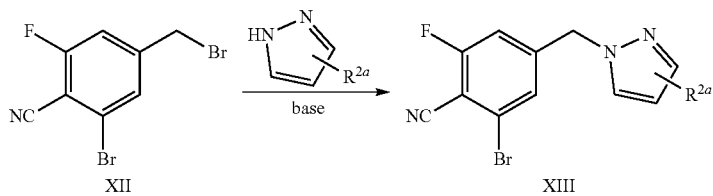

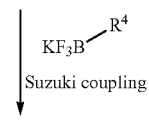

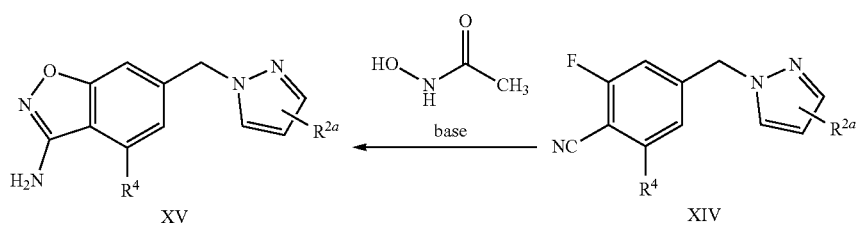

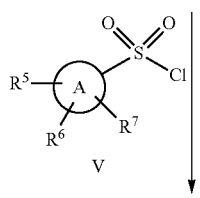

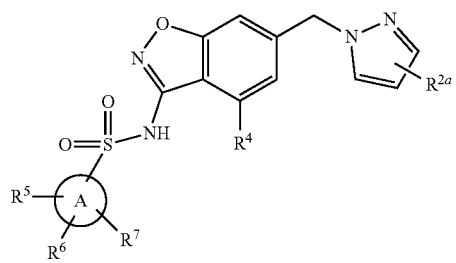

Formula (D)

As exemplified in Scheme V, a compound of Type XII may be converted into a compound of Type XIII by treatment with an appropriately optionally substituted 1H-pyrazole in the presence of an effective base (such as $Cs_2CO_3$) in an appropriate solvent (such as MeCN). A compound of Type XIII may be converted into a compound of Type XIV under Suzuki cross-coupling conditions in the presence of an effective catalyst (such as methanesulfonato(tri-t-butylphosphino)(2"amino-1,1-biphenyl-2-yl)palladium(II)) in an appropriate solvent mixture (such as $PhMe/H_2O$). A compound of Type XIV may be converted to a compound of Type XV by treatment with N-hydroxyacetamide in the presence of an effective base (such 1,1,3,3-tetramethylguanidine) in an appropriate solvent mixture (such as DMF/$H_2O$). A compound of Type XV can be treated with a compound of Type V in the presence of an appropriate base (such as pyridine), neat, to provide a compound of Formula (D). Compounds at every step may be purified by standard techniques, such as column chromatography, crystallization, or reverse phase SFC or HPLC. Variables $R^{2a}$, $R^4$, $R^5$, $R^6$, and $R^7$ are as defined in the embodiments, schemes, examples, and claims herein.

Scheme VI

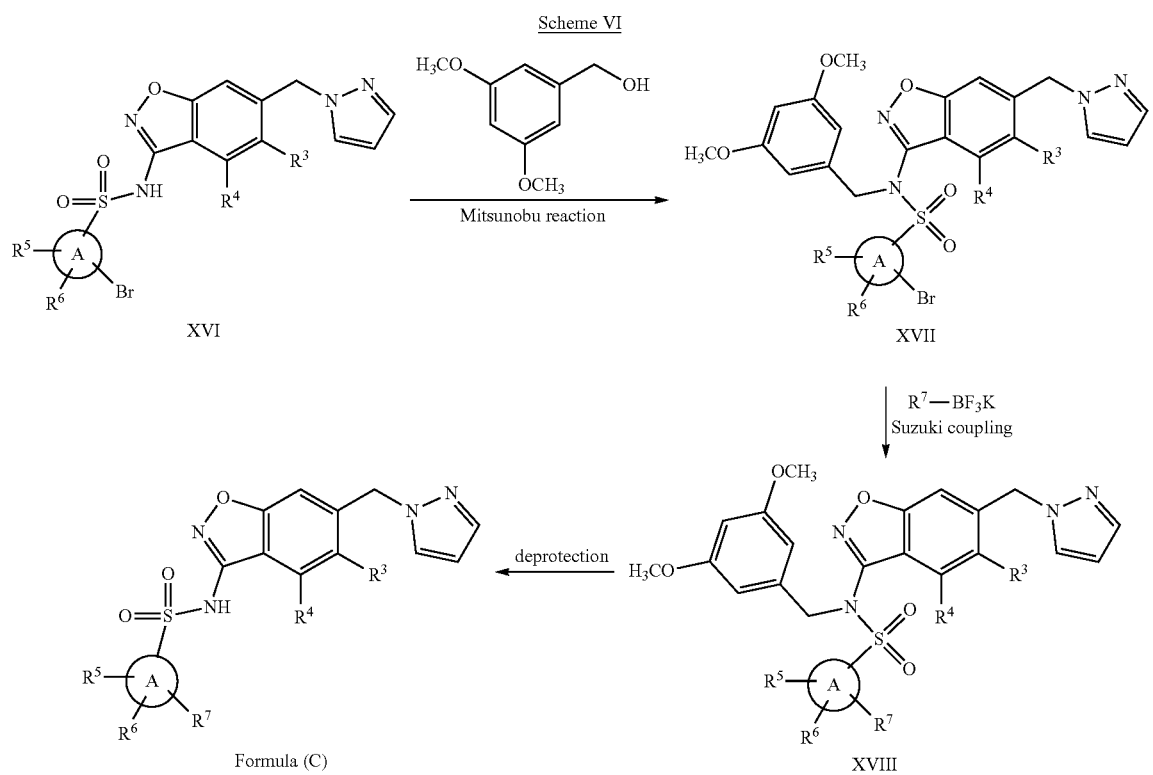

As exemplified in Scheme VI, a compound of Type XVI may be converted into a compound of Type XVII by treatment with (3,5-dimethoxyphenyl)methanol under Mitsunobu conditions (PPh$_3$, DIAD) in an appropriate solvent (such as 2-Me-THF). A compound of Type XVII may be converted into a compound of Type XVIII under Suzuki cross-coupling conditions in the presence of an effective catalyst/ligand combination (such as Pd(OAc)$_2$/X-Phos) in an appropriate solvent (such as CPME/H$_2$O). A compound of Type XVII may be converted to a compound of Formula (C) by treatment with an effective acid (such as TFA) in an appropriate solvent (such as DCM). Compounds at every step may be purified by standard techniques, such as column chromatography, crystallization, or reverse phase SFC or HPLC. Variables R$^3$, R$^4$, R$^5$, R$^6$, and R$^7$ are defined in the embodiments, schemes, examples, and claims herein.

Synthesis of Intermediates:

Preparation of
2-fluoro-4-(hydroxymethyl)-6-methoxybenzonitrile
(Int-01) According to Scheme 1

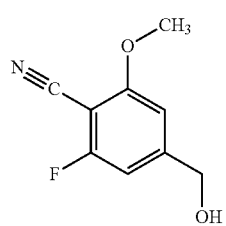

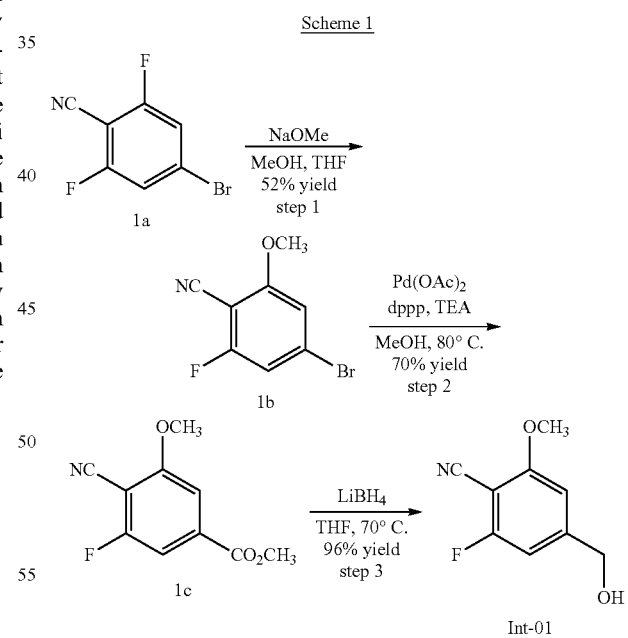

Step 1: Synthesis of
4-bromo-2-fluoro-6-methoxybenzonitrile (1 b)

To a solution of 4-bromo-2,6-difluorobenzonitrile (1a) (40.0 g, 183.5 mmol) in THF (210.0 mL) and MeOH (30.0 mL) was added NaOMe (11.9 g, 220 mmol) portion-wise at 0° C. The mixture was stirred at room temperature for 16 h.

TLC analysis (1:4 EtOAc/petroleum ether) showed consumption of the starting material. The mixture was transferred to a separatory funnel and washed with $H_2O$ (150 mL). The aqueous layer was extracted with EtOAc (300 mL). The combined organic layers were dried over $Na_2SO_4$, filtered, and concentrated. The crude product was purified by flash chromatography (330 g $SiO_2$, 10% EtOAc/petroleum ether) to provide 4-bromo-2-fluoro-6-methoxybenzonitrile (1b) (15.7 g, 52% yield) as a white solid. $^1$H NMR (400 MHz, DMSO-$d_6$) δ 7.49 (dd, J=1.5, 8.8 Hz, 1H), 7.41 (s, 1H), 3.98 (s, 3H).

Step 2: Synthesis of methyl 4-cyano-3-fluoro-5-methoxybenzoate (1c)

A solution of 4-bromo-2-fluoro-6-methoxybenzonitrile (1b) (15.7 g, 68.2 mmol), TEA (20.7 g, 205 mmol), dppp (2.8 g, 6.8 mmol), and Pd(OAc)$_2$ (766 mg, 3.4 mmol) in MeOH (150 mL) was stirred at 80° C. under an atmosphere of CO for 16 h. TLC analysis (1:4 EtOAc/petroleum ether) showed consumption of the starting material. The reaction was concentrated to dryness. The residue was purified by flash chromatography (120 g $SiO_2$, 1:4 EtOAc/petroleum ether) to provide methyl 4-cyano-3-fluoro-5-methoxybenzoate (1c) (10.0 g, 70% yield) as a yellow solid. $^1$H NMR (400 MHz, DMSO-$d_6$) δ 7.53-7.47 (m, 2H), 4.03 (s, 3H), 3.91 (s, 3H).

Step 3: Synthesis of 2-fluoro-4-(hydroxymethyl)-6-methoxybenzonitrile (Int-01)

To a solution of methyl 4-cyano-3-fluoro-5-methoxybenzoate (1c) (9.5 g, 45.4 mmol) in THF (50 mL) was added LiBH$_4$ (2.0 g, 90.8 mmol) portion-wise at 0° C. The mixture was stirred at 70° C. for 2 h. LCMS analysis showed consumption of the starting material with formation of the desired product mass. The reaction was quenched by slow addition of $H_2O$ (100 mL). The mixture was transferred to a separatory funnel and extracted with EtOAc (2×150 mL). The combined organic extracts were washed with brine and saturated aqueous NaHCO$_3$, dried over Na$_2$SO$_4$, filtered, and concentrated to provide 2-fluoro-4-(hydroxymethyl)-6-methoxybenzonitrile (Int-01) (7.9 g, 96% yield) as a brown oil. $^1$H NMR (400 MHz, DMSO-$d_6$) δ 7.05 (s, 1H), 6.98 (d, J=10.0 Hz, 1H), 4.58 (d, J=5.7 Hz, 2H), 3.95 (s, 3H).

The intermediates in the table below were prepared according to the methods used for the synthesis of 2-fluoro-4-(hydroxymethyl)-6-methoxybenzonitrile (Int-01). The following intermediates were synthesized with non-critical changes or substitutions to the exemplified procedures that one skilled in the art would be able to realize.

TABLE 1

| Compound Number | Structure/IUPAC Name | Analytical Data |
| --- | --- | --- |
| Int-02 | 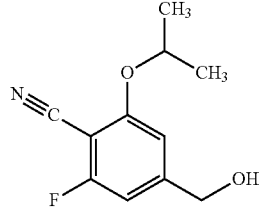<br>2-fluoro-4-(hydroxymethyl)-6-[(propan-2-yl)oxy]benzonitrile | $^1$H NMR (400 MHz, DMSO-$d_6$) δ 7.04 (s, 1H), 6.93 (d, J = 10.0 Hz, 1H), 5.58 (t, J = 5.8 Hz, 1H), 4.80 (sept, J = 6.1 Hz, 1H), 4.56 (d, J = 6.0 Hz, 2H), 1.32 (d, J = 6.0 Hz, 6H). |
| Int-03 | 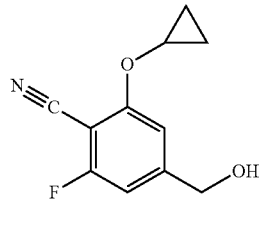 [SMILES: N#Cc1c(F)cc(CO)cc1OC1CC1]<br>2-(cyclopropyloxy)-6-fluoro-4-(hydroxymethyl)benzonitrile | $^1$H NMR (400 MHz, DMSO-$d_6$) δ 7.32 (s, 1H), 7.00 (d, J = 9.8 Hz, 1H), 5.64 (t, J = 5.8 Hz, 1H), 4.59 (d, J = 5.8 Hz, 2H), 4.13-4.01 (m, 1H), 0.91-0.73 (m, 4H). |
| Int-04 | 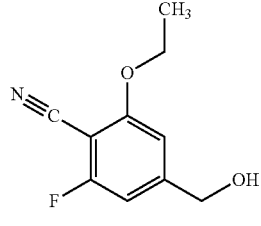<br>2-ethoxy-6-fluoro-4-(hydroxymethyl)benzonitrile | $^1$H NMR (400 MHz, DMSO-$d_6$) δ 7.02 (s, 1H), 6.95 (dd, J = 0.6, 10.0 Hz, 1H), 5.57 (t, J = 5.7 Hz, 1H), 4.56 (d, J = 5.9 Hz, 2H), 4.21 (q, J = 7.0 Hz, 2H), 1.42-1.34 (m, 3H). |

Alternative Preparation of
2-fluoro-4-(hydroxymethyl)-6-methoxybenzonitrile
(Int-01) According to Scheme 2

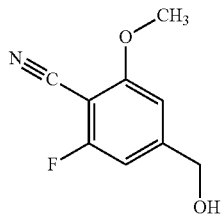

Scheme 2

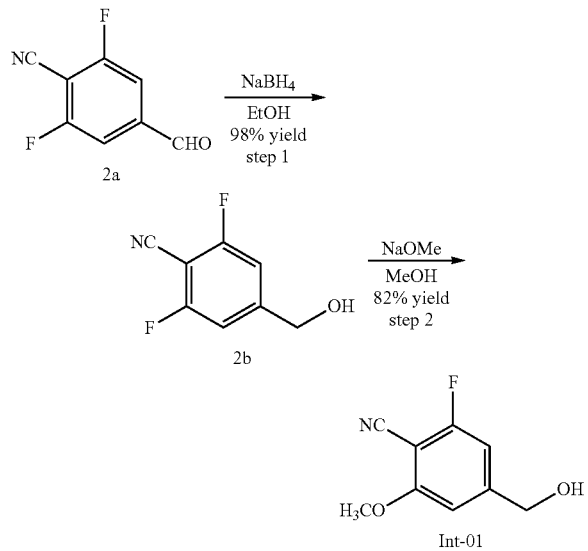

Step 1: Synthesis of
2,6-difluoro-4-(hydroxymethyl)benzonitrile (2b)

A solution of 2,6-difluoro-4-formylbenzonitrile (2a) (21.5 g, 129 mmol) in absolute EtOH (400 mL) was cooled in an ice-water bath to −3° C. (internal). Solid NaBH₄ (5×1 g pellets, 5.0 g, 130 mmol) was added, causing slight gas evolution. The mixture was stirred with ice-water bath cooling for 2 h and then quenched at the same temperature by drop-wise addition of deionized H₂O (100 mL over 5 min). Aqueous HCl (2.0 N, 50 mL over 30 min) was added slowly, maintaining the temperature <10° C. (internal). The solution was concentrated under vacuum to remove the EtOH. The aqueous residue was transferred to a separatory funnel, leaving behind a gummy white solid. The aqueous phase was extracted with EtOAc (2×). The combined organic extracts were washed with brine (2×), dried over MgSO₄, filtered, and concentrated. The crude material was triturated with heptane, filtered, and dried under vacuum to provide 2,6-difluoro-4-(hydroxymethyl)benzonitrile (2b) (21.3 g, 98%) as a free-flowing white solid. ¹H NMR (400 MHz, DMSO-d₆) δ 7.34 (d, J=9.3 Hz, 2H), 5.69 (br. s, 1H), 4.60 (br. s, 2H).

Step 2: Synthesis of
2-fluoro-4-(hydroxymethyl)-6-methoxybenzonitrile
(Int-01)

A solution of 2,6-difluoro-4-(hydroxymethyl)benzonitrile (2b) (21.3 g, 126 mmol) in anhydrous MeOH (400 mL) was cooled to −40° C. (internal) with a dry ice/acetonitrile bath. A solution of NaOMe (5.0 M in MeOH, 100 mL, 500 mmol) was added over a period of 10 min via dropping funnel addition. After the addition was complete the cooling bath was removed. The mixture was allowed to warm naturally to room temperature and stirred for a further 8 h. The reaction mixture was cooled to 0° C. (internal) and HCl (2.0 N, 200 mL) was added dropwise to provide a solution with pH ~5-6. The mixture was concentrated under vacuum to remove the MeOH. The aqueous solution was extracted with EtOAc (3×). The combined organic extracts were washed with brine (2×), dried over MgSO₄, and filtered. The mixture was concentrated to ~150 mL on the rotovap (bath temperature ~35° C.) and the resulting slurry was allowed to cool to room temperature. The solids were collected by filtration. The filter cake was washed with heptane (2×). The filtrate and heptane washes were further concentrated to afford a second crop of solids, which were collected by filtration. The combined solids were dried under vacuum to provide 2-fluoro-4-(hydroxymethyl)-6-methoxybenzonitrile (Int-01) (18.6 g, 82%) as a pale yellow solid. ¹H NMR (400 MHz, CDCl₃) δ 6.82 (s, 1H), 6.79 (d, J=9.2 Hz, 1H), 4.76 (s, 2H), 3.97 (s, 3H).

The intermediate in the table below was prepared according to the methods used for the synthesis of 2-fluoro-4-(hydroxymethyl)-6-methoxybenzonitrile (Int-01). The following intermediate was synthesized with non-critical changes or substitutions to the exemplified procedures that one skilled in the art would be able to realize.

TABLE 2

| Compound Number | Structure/IUPAC Name | Analytical Data |
| --- | --- | --- |
| Int-05 | (structure) | ¹H NMR (400 MHz, CDCl₃) δ 6.77-6.84 (m, 2H), 4.76 (d, J = 4.65 Hz, 2H), 1.89 (br. t, J = 5.69 Hz, 1H). |

TABLE 2-continued

| Compound Number | Structure/IUPAC Name | Analytical Data |
|---|---|---|
| | 2-fluoro-4-(hydroxymethyl)-6-[($^{2}H_{3}$)methyloxy]benzonitrile | |

Preparation of 2-fluoro-4-(hydroxymethyl)benzonitrile (Int-06) according to Scheme 3

Preparation of 5-bromo-4-(bromomethyl)-2-fluorobenzonitrile (Int-07) according to Scheme 4

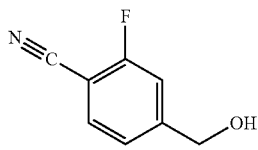 [SMILES: N#Cc1ccc(CO)cc1F]

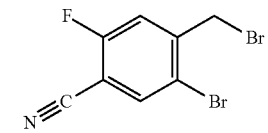

Scheme 3

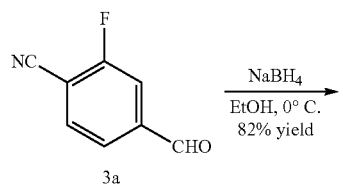

Scheme 4

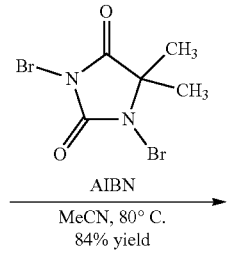

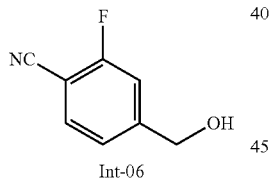

Int-06

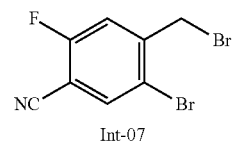

Int-07

A solution of (5.0 g, 33.5 mmol) 2-fluoro-4-formylbenzonitrile (3a) in EtOH (100 mL) was cooled to 0° C. NaBH$_4$ (1.3 g, 33 mmol) was added and the reaction was stirred at 0° C. for 2 h. The mixture was quenched by dropwise addition of H$_2$O (25 mL over 5 min). Dilute HCl (2 N, 13 mL) was added, maintaining the internal temperature <10° C. The solution was concentrated under vacuum to remove the EtOH. The aqueous mixture was extracted with EtOAc (2×). The combined organics were washed with brine, dried over Na$_2$SO$_4$, filtered, and concentrated. The residue was triturated with heptane and dried to provide 2-fluoro-4-(hydroxymethyl)benzonitrile (Int-06) (4.2 g, 82% yield) as a yellow solid. $^1$H NMR (400 MHz, DMSO-d$_6$) δ 7.87 (dd, J=7.9, 6.8 Hz, 1H), 7.42 (dd, J=10.6, 1.3 Hz, 1H), 7.35 (dd, J=8.0, 1.3 Hz, 1H), 5.55 (t, J=5.7 Hz, 1H), 4.60 (d, J=5.7 Hz, 2H).

To a solution of 5-bromo-2-fluoro-4-methylbenzonitrile (4a) (1.01 g, 4.72 mmol) in MeCN (10.0 mL) was added 1,3-dibromo-5,5-dimethylimidazolidine-2,4-dione (701 mg, 2.45 mmol) and AIBN (101 mg, 0.613 mmol). The mixture was stirred at 80° C. overnight and then concentrated to dryness. The residue was purified by flash chromatography (80 g SiO$_2$, 0-30% EtOAc/heptane) to provide (Int-07) (847 mg, 84% yield) as a white solid. $^1$H NMR (400 MHz, CDCl$_3$) δ 7.84 (d, J=6.0 Hz, 1H), 7.38 (d, J=8.9 Hz, 1H), 4.54 (s, 2H).

The intermediate in the table below was prepared according to the methods used for the synthesis of 5-bromo-4-(bromomethyl)-2-fluorobenzonitrile (Int-07). The following intermediate was synthesized with non-critical changes or substitutions to the exemplified procedures that one skilled in the art would be able to realize.

TABLE 3

| Compound number | Structure/IUPAC name | Analytical data |
|---|---|---|
| Int-08 | 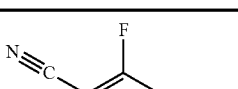<br>2-bromo-4-(bromomethyl)-6-fluorobenzonitrile | $^1$H NMR (400 MHz, CDCl$_3$) δ 7.53 (s, 1H), 7.18-7.22 (m, 1H), 4.40 (s, 2H). |

Preparation of (4-cyano-2,5-difluorophenyl)methyl methanesulfonate (Int-09) According to Scheme 5

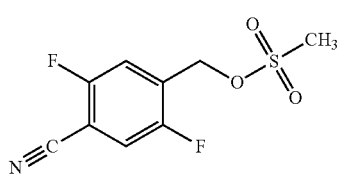 [SMILES: CS(=O)(=O)OCc1cc(F)c(C#N)cc1F]

Scheme 5

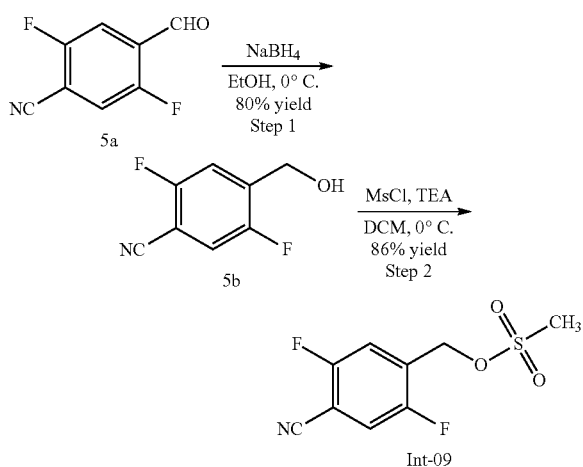

Step 1: Synthesis of 2,5-difluoro-4-(hydroxymethyl)benzonitrile (5b)

A solution of 2,5-difluoro-4-formylbenzonitrile (5a) (250 mg, 1.5 mmol) in EtOH (5.0 mL) was cooled to 0° C. with an ice bath and then NaBH$_4$ (60 mg, 1.6 mmol) was added. The mixture was stirred for 30 min at 0° C. The reaction was quenched at the same temperature by addition of H$_2$O (0.5 mL) and HCl (6.0 N, 0.32 mL). The mixture was extracted with EtOAc. The organic layer was washed with saturated aqueous NaHCO$_3$ and brine, dried over Na$_2$SO$_4$, filtered, and concentrated to provide 2,5-difluoro-4-(hydroxymethyl)benzonitrile (5b) (202 mg, 80% yield) as a white solid. $^1$H NMR (400 MHz, CDCl$_3$) δ 7.44 (dd, J=5.62, 8.80 Hz, 1H), 7.30 (dd, J=4.89, 8.56 Hz, 1H), 4.85 (s, 2H).

Step 2: Synthesis of (4-cyano-2,5-difluorophenyl)methyl methanesulfonate (Int-09)

A solution of 2,5-difluoro-4-(hydroxymethyl)benzonitrile (5b) (915 mg, 5.41 mmol) in DCM (25.0 mL) was cooled to 0° C. and then TEA (871 mg, 5.84 mmol) and MsCl (649 g, 5.66 mmol) were added. After 2 h, the reaction was loaded directly onto SiO$_2$ and purified by flash chromatography (40 g SiO$_2$, 0-75% EtOAc/heptane) to provide (4-cyano-2,5-difluorophenyl)methyl methanesulfonate (Int-09) (1.15 g, 86% yield) as a clear oil, which solidified upon standing. $^1$H NMR (400 MHz, CDCl$_3$) δ 7.44-7.39 (m, 2H), 5.34-5.32 (m, 2H), 3.14 (s, 3H).

The intermediate in the table below was prepared according to the methods used for the synthesis of (4-cyano-2,5-difluorophenyl)methyl methanesulfonate (Int-09). The following intermediate was synthesized with non-critical changes or substitutions to the exemplified procedures that someone who is skilled in the art would be able to realize.

TABLE 4

| Compound number | Structure/IUPAC name | Analytical data |
|---|---|---|
| Int-10 | 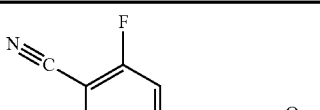<br>(4-cyano-3,5-difluorophenyl)methyl methanesulfonate | $^1$H NMR (400 MHz, CDCl$_3$) δ 7.12 (d, J = 7.5 Hz, 2H), 5.25 (s, 2H), 3.12 (s, 3H). |

Preparation of 2-fluoro-4-(hydroxymethyl)-5-methylbenzonitrile (Int-11) according to Scheme 6

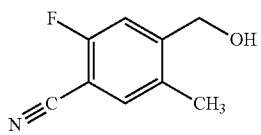

Scheme 6

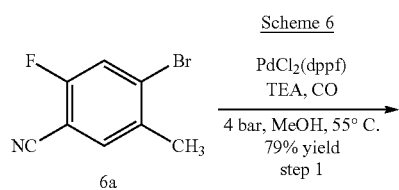

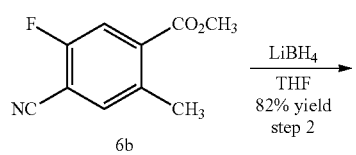

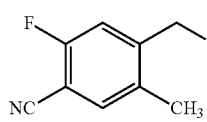

Int-11

Step 1: Synthesis of methyl 4-cyano-5-fluoro-2-methylbenzoate (6b)

To a solution of 4-bromo-2-fluoro-5-methylbenzonitrile (6a) (1.0 g, 4.67 mmol) and TEA (1.7 g, 17 mmol) in MeOH (30.0 mL) in a 100 mL stainless steel vessel was added PdCl$_2$(dppf) (247 mg, 0.327 mmol). The vessel was pressurized with CO to 4 bar and stirred at 55° C. for 20 h. The reaction was filtered and concentrated. The residue was purified by flash chromatography (40 g SiO$_2$, 0-55% EtOAc/heptane) to provide methyl 4-cyano-5-fluoro-2-methylbenzoate (6b) (716 mg, 79% yield) as a white solid. $^1$H NMR (400 MHz, CDCl$_3$) δ 7.74 (d, J=9.4 Hz, 1H), 7.52 (d, J=6.1 Hz, 1H), 3.95 (s, 3H), 2.59 (s, 3H).

Step 2: Synthesis of 2-fluoro-4-(hydroxymethyl)-5-methylbenzonitrile (Int-11)

To a solution of methyl 4-cyano-5-fluoro-2-methylbenzoate (6b) (710 mg, 3.68 mmol) in THF (18.4 mL) was added LiBH$_4$ (120 mg, 5.51 mmol) and the mixture was stirred at room temperature overnight. The reaction was quenched with H$_2$O (3 mL). The mixture was stirred for 30 min and then cooled with an ice bath. The mixture was carefully quenched with HCl (6.0 N, 0.60 mL). The THF was removed under vacuum and the residue was partitioned between EtOAc and 1:1 H$_2$O/saturated aqueous NaHCO$_3$. The organic layer was washed with brine, dried over Na$_2$SO$_4$, filtered, and concentrated.

The residue was purified by flash chromatography (24 g SiO$_2$, 0-80% EtOAc/heptane) to provide 2-fluoro-4-(hydroxymethyl)-5-methylbenzonitrile (Int-11) (495 mg, 82% yield) as a white solid. $^1$H NMR (400 MHz, CDCl$_3$) δ 7.44-7.35 (m, 2H), 4.74 (d, J=5.5 Hz, 2H), 2.26 (s, 3H), 1.84 (t, J=5.5 Hz, 1H); $^{19}$F NMR (376 MHz, CDCl$_3$) δ −110.29 (dd, J=5.7, 10.3 Hz).

Preparation of (3-amino-5-fluoro-4-methoxy-1,2-benzoxazol-6-yl)methanol (Int-12) According to Scheme 7

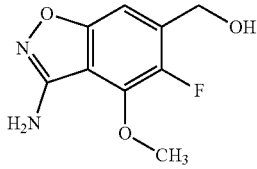

Scheme 7

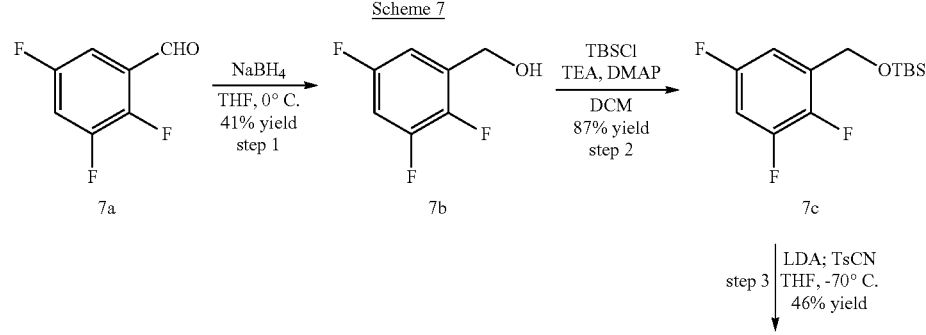

step 3 | LDA; TsCN
THF, -70° C.
46% yield

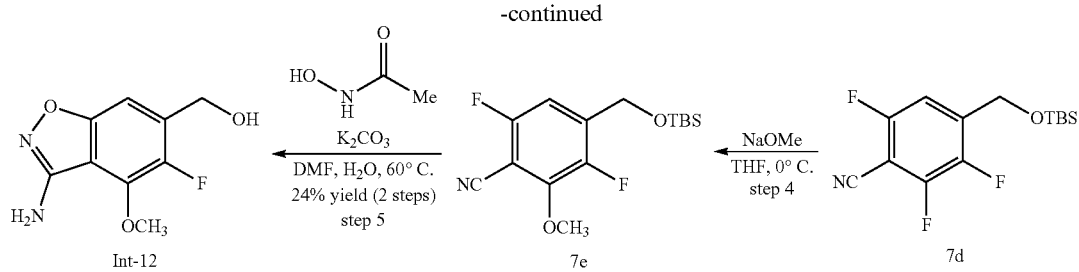

Step 1: Synthesis of (2,3,5-trifluorophenyl)methanol (7b)

To a solution of 2,3,5-trifluorobenzaldehyde (7a) (1.8 g, 11 mmol) in THF (30 mL) was added NaBH4 (468 mg, 12.4 mmol) portion-wise at 0° C. The mixture was stirred at 0° C. for 2 h. LCMS analysis showed consumption of the starting material. The reaction was quenched by slow addition of H$_2$O (10 mL) and concentrated to dryness. The residue was purified by flash chromatography (40 g SiO$_2$, 0-50% EtOAc/heptane) to provide (2,3,5-trifluorophenyl)methanol (7b) (740 mg, 41% yield) as a colorless oil. $^1$H NMR (400 MHz, CDCl$_3$) δ 7.10-6.96 (m, 1H), 6.94-6.78 (m, 1H), 4.81 (d, J=5.9 Hz, 2H), 1.91 (t, J=6.1 Hz, 1H).

Step 2: Synthesis of tert-butyl(dimethyl)[(2,3,5-trifluorophenyl)methoxy]silane (7c)

To a solution of (2,3,5-trifluorophenyl)methanol (7b) (740 mg, 4.56 mmol) in DCM (20 mL) was added DMAP (27.9 mg, 0.228 mmol), TEA (639 mg, 6.85 mmol), and a solution of TBSCl (894 mg, 5.93 mmol) in DCM (5 mL). The mixture was stirred at ambient temperature for 18 h. LCMS showed consumption of the starting material. The mixture was concentrated to dryness and the residue was purified by flash chromatography (40 g SiO$_2$, 0-10% EtOAc/petroleum ether) to provide tert-butyl(dimethyl)[(2,3,5-trifluorophenyl)methoxy]silane (7c) (1.1 g, 87% yield) as a colorless oil. $^1$H NMR (400 MHz, CDCl$_3$) δ 7.06-6.95 (m, 1H), 6.87-6.70 (m, 1H), 4.79 (s, 2H), 0.95 (s, 9H), 0.13 (s, 6H).

Step 3: Synthesis of 4-({[tert-butyl(dimethyl)silyl]oxy}methyl)-2,3,6-trifluorobenzonitrile (7d)

A solution of LDA (0.07 M in THF, 20.0 mL, 1.41 mmol) in THF (20 mL) at was cooled to −70° C. and then treated dropwise with a solution of tert-butyl(dimethyl)[(2,3,5-trifluorophenyl)methoxy]silane (7c) (300 mg, 1.09) in THF (5 mL) over 5 min. The mixture was stirred for 2 h at −70° C. and then treated dropwise with a solution of p-tolylsulfonyl cyanide (216 mg, 1.19 mmol) in THF (5 mL) over 10 min. The mixture was stirred at −70° C. for 1 h. The mixture was quenched by addition of saturated aqueous NH$_4$Cl and portioned between EtOAc (60 mL) and H$_2$O (60 mL). The organic layer was washed with brine, dried over Na$_2$SO$_4$, filtered, and concentrated. The residue was purified by flash chromatography (SiO$_2$, 3:1-10:1 EtOAc/petroleum ether). The combined product-containing fractions were repurified by preparative HPLC with an Agela DuraShell C18 column (150×25 mm, 5 m particle size), which was eluted with 70-100% MeCN/H$_2$O (+0.04% NH$_4$OH, +10 mM NH$_4$HCO$_3$) with a flow rate 25 mL/min to provide 4-({[tert-butyl(dimethyl)silyl]oxy}methyl)-2,3,6-trifluorobenzonitrile (7d) (150 mg, 46% yield) as a yellow oil. $^1$H NMR (400 MHz, CDCl$_3$) δ 7.10-7.02 (m, 1H), 4.69 (s, 2H), 0.81 (s, 9H), 0.00 (s, 6H).

Step 4: Synthesis of 4-({[tert-butyl(dimethyl)silyl]oxy}methyl)-3,6-difluoro-2-methoxybenzonitrile (7e)

To a solution of 4-({[tert-butyl(dimethyl)silyl]oxy}methyl)-2,3,6-trifluorobenzonitrile (7d) (150 mg, 0.498 mmol) in THF (20 mL) was added NaOMe (71.7 mg, 0.398 mmol) at 0° C. The mixture was stirred at 0° C. for 1 h. The mixture was quenched with H$_2$O and partitioned between EtOAc and H$_2$O. The organic layer was washed with brine, dried over Na$_2$SO$_4$, filtered, and concentrated to provide crude 4-({[tert-butyl(dimethyl)silyl]oxy}methyl)-3,6-difluoro-2-methoxybenzonitrile (7e) (150 mg, 96% yield) as a yellow oil, which was taken on without further purification.

Step 5: Synthesis of (3-amino-5-fluoro-4-methoxy-1,2-benzoxazol-6-yl)methanol (Int-12)

To a solution of crude 4-({[tert-butyl(dimethyl)silyl]oxy}methyl)-3,6-difluoro-2-methoxybenzonitrile (7e) (150 mg, 0.479 mmol) and N-hydroxyacetamide (108 mg, 1.33 mmol) in DMF (10 mL) and H$_2$O (2 mL) was added K$_2$CO$_3$ (397 mg, 2.87 mmol). The mixture was stirred at 60° C. for 16 h. The mixture was filtered and the filtrate was concentrated to dryness. The residue was purified by preparative HPLC with an Agela DuraShell C18 column (150×25 mm, 5 m particle size), which was eluted with 5-35% MeCN/H$_2$O H$_2$O (+0.04% NH$_4$OH, +10 mM NH$_4$HCO$_3$) with a flow rate 25 mL/min to provide (3-amino-5-fluoro-4-methoxy-1,2-benzoxazol-6-yl)methanol (Int-12) (25 mg, 24% yield over two steps) as a white solid. $^1$H NMR (400 MHz, DMSO-d$_6$) δ 7.12 (d, J=4.3 Hz, 1H), 6.03 (s, 2H), 5.47 (t, J=5.8 Hz, 1H), 4.62 (d, J=5.6 Hz, 2H), 4.05 (s, 3H); m/z (ESI+) 213.1 (M+H)$^+$.

Preparation of 1-(methanesulfonyl)-1H-pyrazole (Int-13) According to Scheme 8

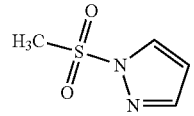

Scheme 8

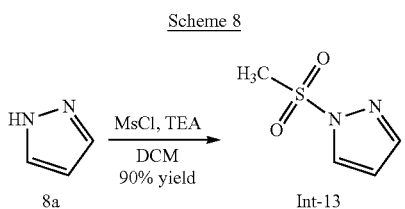

To a solution of 1H-pyrazole (8a) (33.0 g, 485 mmol) and TEA (73.6 mg, 727 mmol) in DCM was added MsCl (73.9 g, 645 mmol) slowly at 0° C. The mixture was stirred at 0° C. for 10 min and then room temperature for 1 h. TLC analysis (1:1 EtOAc/petroleum ether) showed consumption of the starting material. The reaction was diluted with saturated aqueous NH$_4$Cl (200 mL) and the mixture was separated. The aqueous layer was extracted with DCM (200 mL). The combined organic layers were washed with brine (300 mL) and saturated aqueous Na$_2$CO$_3$ (300 mL), dried over anhydrous Na$_2$SO$_4$, filtered, and concentrated to provide 1-(methanesulfonyl)-1H-pyrazole (Int-13) (64 g, 90% yield) as a pale-yellow oil. $^1$H NMR (400 MHz, CDCl$_3$) δ 8.04 (d, J=2.6 Hz, 1H), 7.86-7.79 (m, 1H), 6.46 (dd, J=1.6, 2.7 Hz, 1H), 3.33 (s, 3H). The intermediates in the table below were prepared according to the methods used for the synthesis of 1-(methanesulfonyl)-1H-pyrazole (Int-13). The following intermediates were synthesized with non-critical changes or substitutions to the exemplified procedures that one skilled in the art would be able to realize. If indicated, regioisomeric mixtures were isolated without further separation.

TABLE 5

| Compound Number | Structure/IUPAC Name | Analytical Data |
| --- | --- | --- |
| Int-14 | 4-fluoro-1-(methanesulfonyl)-1H-pyrazole | $^1$H NMR (400 MHz, CDCl$_3$) δ 7.91 (d, J = 5.0 Hz, 1H), 7.74 (d, J = 4.4 Hz, 1H), 3.32 (s, 3H) |
| Int-15 | 1-(methanesulfonyl)-5-methyl-1H-pyrazole and 1-(methanesulfonyl)-3-methyl-1H-pyrazole (~1:1 mixture) | $^1$H NMR (400 MHz, CDCl$_3$) δ 7.89 (d, J = 2.8 Hz, 1H), 7.61 (s, 1H), 6.23 (d, J = 2.8 Hz, 1H), 6.13 (s, 1H), 3.29 (s, 3H), 3.26 (s, 3H), 2.58-2.37 (m, 3H), 2.37-2.28 (m, 3H) |
| Int-16 | 1-(methanesulfonyl)-1H-1,2,3-triazole and 2-(methanesulfonyl)-2H-1,2,3-triazole (~5.5:1 mixture) | $^1$H NMR (400 MHz, CDCl$_3$) δ 8.18 (d, J = 1.3 Hz, 1H), 7.97 (s, 0.37H)*, 7.81 (d, J = 1.3 Hz, 1H), 3.56 (s, 3H), 3.44 (s, 0.6H)*; (*denotes peaks belonging only to minor regioisomer, multiple overlapping peaks). |

Preparation of 4-({[tert-butyl(dimethyl)silyl]oxy}methyl)-1-(methanesulfonyl)-1H-pyrazole (Int-17) According to Scheme 9

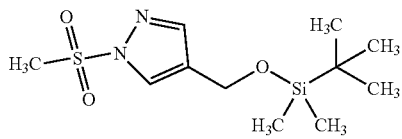 [SMILES: CC(C)(C)[Si](C)(C)OCc1cnn(S(C)(=O)=O)c1]

Scheme 9

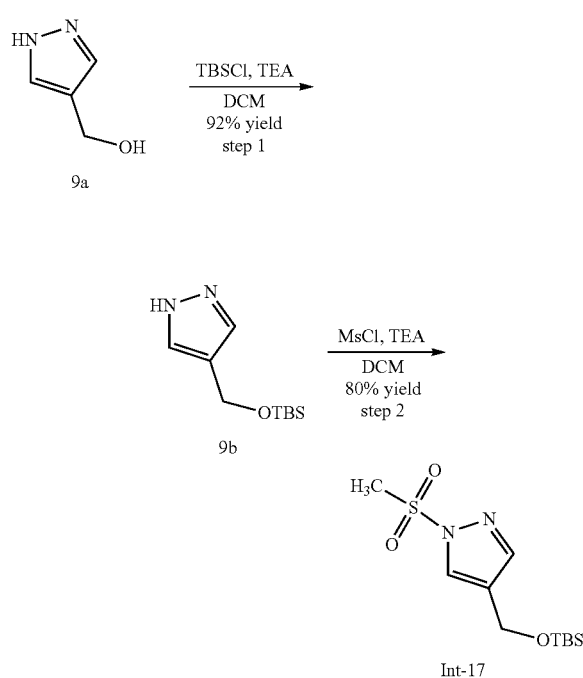

Step 1: Synthesis of 4-({[tert-butyl(dimethyl)silyl]oxy}methyl)-1H-pyrazole (9b)

To a solution of (1H-pyrazol-4-yl)methanol (9a) (500 mg, 5.1 mmol) in DCM (10.0 mL) was added TBSCl (845 mg, 5.6 mmol), TEA (774 mg, 7.7 mmol), and DMAP (31.1 mg, 0.26 mmol). The solution was stirred at room temperature for 16 h. LCMS analysis showed consumption of the starting material with formation of the desired product mass. The mixture was diluted with DCM (20 mL) and washed successively with $H_2O$ (20 mL), saturated aqueous $NaHCO_3$ (20 mL), and brine (20 mL). The organic phase was dried over $Na_2SO_4$, filtered, and concentrated to provide 4-({[tert-butyl(dimethyl)silyl]oxy}methyl)-1H-pyrazole (9b) (1.0 g, 92% yield), which was taken on without further purification. m/z (ESI+) 212.8 $(M+H)^+$.

Step 2: Synthesis of 4-({[tert-butyl(dimethyl)silyl]oxy}methyl)-1-(methanesulfonyl)-1H-pyrazole (Int-17)

To a solution of 4-({[tert-butyl(dimethyl)silyl]oxy}methyl)-1H-pyrazole (9b) (1.0 g, 4.7 mmol) in DCM (15.0 mL) was added TEA (619 mg, 6.1 mmol). The mixture was cooled to 0° C. with an ice-water bath. MsCl (3.8 g, 33.0 mmol) was added dropwise. The mixture was stirred for 2 h at 0° C. and room temperature for 16 h. LCMS analysis showed consumption of the starting material with formation of the desired product mass. The mixture was diluted with DCM (100 mL) and washed with successively with $H_2O$ (50 mL), saturated aqueous $NaHCO_3$ (50 mL), and brine (50 mL). The organic layer was dried over $Na_2SO_4$, filtered, and concentrated to provide 4-({[tert-butyl(dimethyl)silyl]oxy}methyl)-1-(methanesulfonyl)-1H-pyrazole (Int-17) (1.1 g, 80% yield), which was taken on without further purification. m/z (ESI+) 291.1 $(M+H)^+$. The intermediate in the table below was prepared according to the methods used for the synthesis of 4-({[tert-butyl(dimethyl)silyl]oxy}methyl)-1-(methanesulfonyl)-1H-pyrazole (Int-17). The following intermediate was synthesized with non-critical changes or substitutions to the exemplified procedures that one skilled in the art would be able to realize. If indicated, regioisomeric mixtures were isolated without further separation.

TABLE 6

| Compound Number | Structure/IUPAC Name | Analytical Data |
|---|---|---|
| Int-18 | (structure shown) + (structure shown) (unseparated mixture) 5-({[tert-butyl(dimethyl)silyl]oxy}methyl)-1-(methanesulfonyl)-1H-pyrazole and 3-({[tert-butyl(dimethyl)silyl]oxy}methyl)-1-(methanesulfonyl)-1H-pyrazole | m/z (ESI+) 291.1 $(M + H)^+$ |

Preparation of 2,4,6-trimethoxybenzene-1-sulfonyl chloride (Int-19) according to Scheme 10

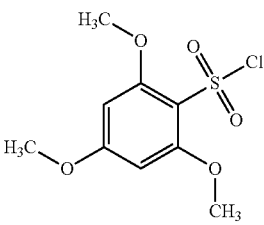 [SMILES: COc1cc(OC)c(S(=O)(=O)Cl)c(OC)c1]

Scheme 10

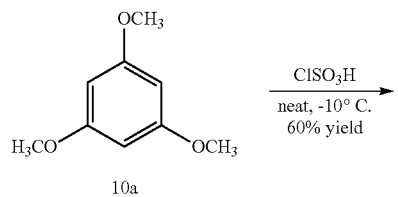

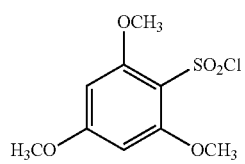

Int-19

Chlorosulfuric acid (15.0 mL) was cooled to −10° C. and 1,3,5-trimethoxybenzene (10a) (1.4 g, 8.4 mmol) was added in one portion. The mixture was stirred at −10° C. for 15 min. TLC analysis (1:1 EtOAc/petroleum ether) indicated consumption of the starting material. The reaction was quenched by carefully pouring over ice-water. The mixture was extracted with DCM (3×100 mL). The combined organic extracts were washed with saturated aqueous NaHCO$_3$ (50 mL), dried over Na$_2$SO$_4$, filtered, and concentrated. The residue was purified by flash chromatography (20 g SiO2, 0-50% EtOAc/petroleum ether) to provide 2,4,6-trimethoxybenzene-1-sulfonyl chloride (Int-19) (1.8 g, 60% yield) as a solid, which was taken on without further purification. $^1$H NMR (400 MHz, CDCl$_3$) b 6.12 (s, 2H), 3.96 (s, 6H), 3.89 (s, 3H).

The intermediate in the table below was prepared according to the methods used for the synthesis of 2,4,6-trimethoxybenzene-1-sulfonyl chloride (Int-19). The following intermediate was synthesized with non-critical changes or substitutions to the exemplified procedures that one skilled in the art would be able to realize.

TABLE 7

| Compound Number | Structure/IUPAC Name | Analytical Data |
|---|---|---|
| Int-20 | 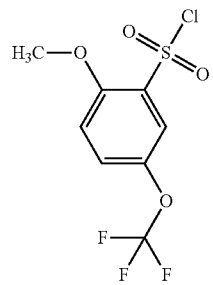 [SMILES: COc1ccc(OC(F)(F)F)cc1S(=O)(=O)Cl]<br>5-ethyl-2,4-dimethoxybenzene-1-sulfonyl chloride | $^1$H NMR (400 MHz, CDCl$_3$) δ 7.71 (s, 1H), 6.63-6.42 (m, 1H), 4.05 (s, 3H), 3.94 (s, 3H), 2.60 (q, J = 7.5 Hz, 2H), 1.20 (t, J = 7.5 Hz, 3H). |

Preparation of 2-methoxy-5-(trifluoromethoxy)benzene-1-sulfonyl chloride (Int-21) According to Scheme 11

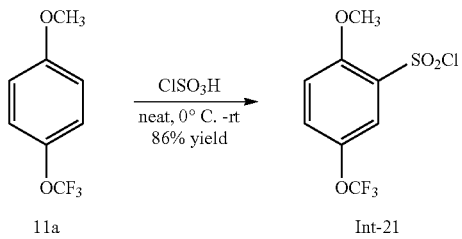

Scheme 11

Chlorosulfuric acid (26.0 mL) was cooled to 0° C. and 1-methoxy-4-(trifluoromethoxy)benzene (11a) (2.0 g, 10.4 mmol) was added in one portion. The mixture was stirred at room temperature for 18 h. The reaction was quenched by carefully pouring over ice-water. The mixture was extracted with EtOAc (2×60 mL). The combined organic extracts were washed with saturated aqueous Na$_2$CO$_3$ (50 mL), dried over Na$_2$SO$_4$, filtered, and concentrated to provide 2-methoxy-5-(trifluoromethoxy)benzene-1-sulfonyl chloride (Int-21) (2.6 g, 86% yield) as a yellow oil, which was taken on without further purification. $^1$H NMR (400 MHz, CDCl$_3$) δ 7.85 (d, J=2.8 Hz, 1H), 7.56 (dd, J=2.4, 9.1 Hz, 1H), 7.16 (d, J=9.2 Hz, 1H), 4.08 (s, 3H).

Preparation 2-methoxy-5,6,7,8-tetrahydronaphthalene-1-sulfonyl chloride and 3-methoxy-5,6,7,8-tetrahydronaphthalene-2-sulfonyl chloride (Int-22) according to Scheme 12

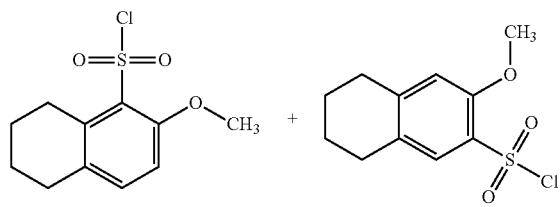 [SMILES: COc1ccc2c(c1S(=O)(=O)Cl)CCCC2 ; COc1cc2c(cc1S(=O)(=O)Cl)CCCC2]

Scheme 12

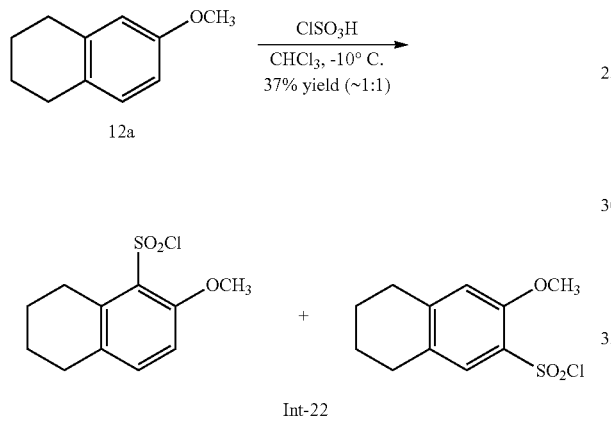

A mixture of CHCl$_3$ (10.0 mL) and chlorosulfuric acid (1.0 mL) was cooled to −10° C. and 6-methoxy-1,2,3,4-tetrahydronaphthalene (12a) (1.0 g, 6.1 mmol) was added. The mixture was stirred at −10° C. for 15 min. TLC analysis (1:1 EtOAc/petroleum ether) indicated consumption of the starting material. The reaction was quenched by carefully pouring over ice-water. The mixture was extracted with DCM (3×50 mL). The combined organic extracts were washed with saturated aqueous NaHCO$_3$ (50 mL), dried over Na$_2$SO$_4$, filtered, and concentrated. The residue was purified by flash chromatography (40 g SiO$_2$, 0-50% EtOAc/petroleum ether) to provide 2-methoxy-5,6,7,8-tetrahydronaphthalene-1-sulfonyl chloride and 3-methoxy-5,6,7,8-tetrahydronaphthalene-2-sulfonyl chloride (Int-22) (~1:1 mixture, 600 mg, 37% yield) as a pale yellow gum. $^1$H NMR (400 MHz, CDCl$_3$) δ 7.65 (s, 1H), 7.35 (d, J=8.5 Hz, 1H), 6.92 (d, J=8.5 Hz, 1H), 6.79 (s, 1H), 4.01 (s, 6H), 3.23 (t, J=6.0 Hz, 2H), 2.91-2.63 (m, 6H), 1.88-1.69 (m, 8H).

The intermediate in the table below was prepared according to the methods used for the synthesis of 2-methoxy-5,6,7,8-tetrahydronaphthalene-1-sulfonyl chloride and 3-methoxy-5,6,7,8-tetrahydronaphthalene-2-sulfonyl chloride (Int-22). The following intermediates were synthesized with non-critical changes or substitutions to the exemplified procedures that someone who is skilled in the art would be able to realize.

TABLE 8

| Compound Number | Structure/IUPAC name | Analytical Data |
|---|---|---|
| Int-23 | 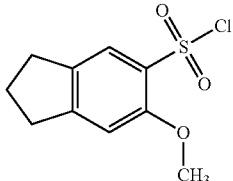<br>6-methoxy-2,3-dihydro-1H-indene-5-sulfonyl chloride | $^1$H NMR (400 MHz, CDCl$_3$) δ 7.77 (s, 1H), 6.99 (s, 1H), 4.03 (s, 3H), 3.00 (t, J = 7.5 Hz, 2H), 2.92 (t, J = 7.5 Hz, 2H), 2.16 (p, J = 7.5 Hz, 2H). |

Preparation of 4-cyclopropyl-2,6-dimethoxybenzene-1-sulfonyl chloride (Int-24) According to Scheme 13

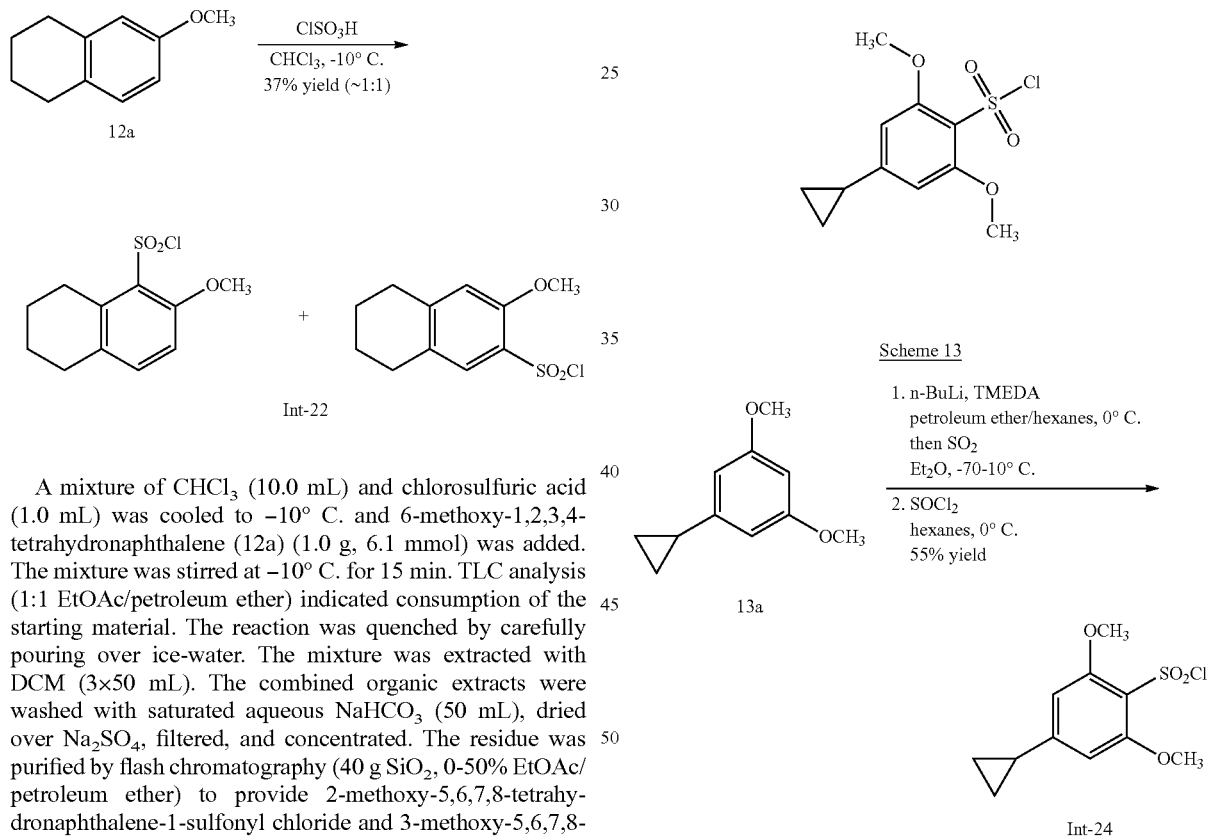

A solution of (13a) (1.0 g, 5.61 mmol) (J. Org. Chem. 2008, 7481-7485) and TMEDA (717 mg, 6.17 mmol) in petroleum ether (15.0 mL) was cooled in an ice-water bath and then treated dropwise with n-BuLi (2.5 M in hexanes, 2.5 mL, 6.17 mmol) via addition funnel, maintaining the temperature <5° C. (internal). The mixture was stirred at 0° C. for 20 min and then cooled to −70° C. with a dry-ice/acetone bath. A pre-cooled solution (−65° C.) of SO$_2$ (5.4 g, 84.2 mmol) in Et$_2$O (100 mL) was added slowly, maintaining the temperature <−60° C. (internal). The pale-yellow reaction mixture was slowly warmed to 10° C. The resultant solids were collected by filtration and washed with dry Et$_2$O.

The filter cake was suspended in hexane (30 mL) and the mixture was cooled to 0° C. To the cold suspension was added a solution of SOCl$_2$ (757 mg, 5.61 mmol) in hexane (20 mL) slowly, maintaining the temperature <3° C. (internal). The resulting mixture was stirred at 0° C. for 18 h. The solution was filtered and the filter cake was washed with cold hexane (20 mL). The solids were taken up in EtOAc (50 mL) and washed with H$_2$O (50 mL). The organic layer was dried over Na$_2$SO$_4$, filtered, and concentrated to provide 4-cyclopropyl-2,6-dimethoxybenzene-1-sulfonyl chloride (Int-24) (856 mg, 55% yield) as a white solid. $^1$H NMR (400 MHz, CDCl$_3$) δ 6.32 (s, 2H), 3.97 (s, 6H), 1.93 (tt, J=5.0, 8.3 Hz, 1H), 1.18-1.11 (m, 2H), 0.86-0.80 (m, 2H).

Preparation of 4-methoxy-6-((4-methyl-1H-pyrazol-1-yl)methyl)benzo[d]isoxazol-3-amine (Int-25) According to Scheme 14

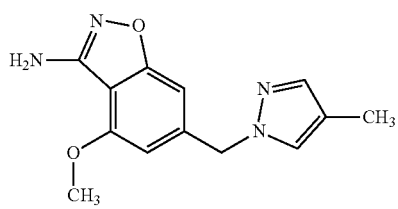 [SMILES: COc1cc(Cn2cc(C)cn2)cc2onc(N)c12]

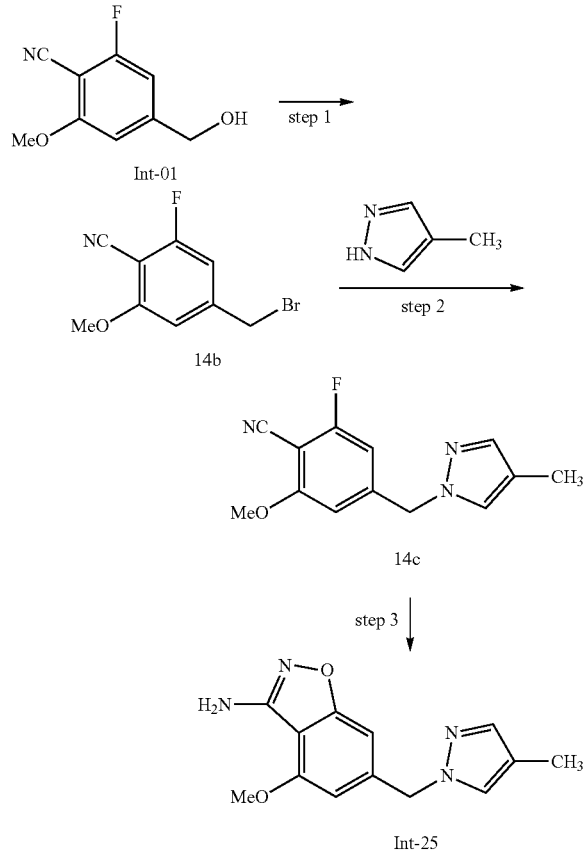

Step 1: Synthesis of 4-(bromomethyl)-2-fluoro-6-methoxybenzonitrile (14b)

To a solution of 2-fluoro-4-(hydroxymethyl)-6-methoxybenzonitrile (Int-01) (8.0 g, 44.2 mmol) and PPh$_3$ (18.7 g, 71.2 mmol) in acetonitrile (400 mL) was added Br$_2$ (11.8 g, 73.8 mmol) and the mixture was heated at 55° C. for 2 h. Water and excess Na$_2$SO$_3$ were added and the mixture was extracted with EtOAc. The combined organic layers were washed with brine, dried over anhydrous Na$_2$SO$_4$, filtered and concentrated under reduced pressure. The residue was purified by column chromatography (Pet. Ether/EtOAc=10/1) to give the title compound (9.7 g, 91%) as a white solid, which was used directly in the next step.

Step 2: Synthesis of 2-fluoro-6-methoxy-4-((4-methyl-1H-pyrazol-1-yl)methyl)benzonitrile (14c)

A mixture of 4-(bromomethyl)-2-fluoro-6-methoxybenzonitrile (14b) (100 mg, 0.41 mmol), 4-methyl-1H-pyrazole (40 mg, 0.49 mmol) and K$_2$CO$_3$ (113 mg, 0.82 mmol) in DMF (5 mL) was heated at 60° C. overnight. The mixture was diluted with water, extracted with EtOAc and the organic extract was washed with brine, dried over Na$_2$SO$_4$, filtered and concentrated under reduced pressure. The reaction was scaled up accordingly using 4-(bromomethyl)-2-fluoro-6-methoxybenzonitrile (14b) (500 mg, 2.05 mmol) and the two batches were combined and purified by column chromatography (DCM/MeOH=10/1) to give the title compound (380 mg, 63%) as a yellow solid. m/z 246.0 [M+H]$^+$.

Step 3: Synthesis of 4-methoxy-6-((4-methyl-1H-pyrazol-1-yl)methyl)benzo[d]isoxazol-3-amine (Int-25)

To a solution of N-hydroxyacetamide (238 mg, 3.18 mmol) in anhydrous DMF (13 mL) at 0° C. was added t-BuOK (357 mg, 3.18 mmol) and the mixture was stirred for 30 min. 2-Fluoro-6-methoxy-4-((4-methyl-1H-pyrazol-1-yl)methyl)benzonitrile (14c) (260 mg, 1.06 mmol) was then added and the mixture was allowed to warm to RT and stirred overnight. Water was added and the mixture was extracted with EtOAc. The combined organic layers were dried over Na$_2$SO$_4$, filtered and concentrated under reduced pressure. The residue was purified by column chromatography (DCM/MeOH=50/1) to give the title compound (150 mg, 55%) as a yellow solid. m/z 259.1 [M+H]$^+$. $^1$H NMR (400 MHz, CDCl$_3$) δ 7.37 (s, 1H), 7.20 (s, 1H), 6.76 (s, 1H), 6.43 (s, 1H), 5.31 (s, 2H), 3.90 (s, 3H), 2.07 (s, 3H).

Preparation of 2,6-dimethoxybenzenesulfonyl chloride (Int-26) according to Scheme 15

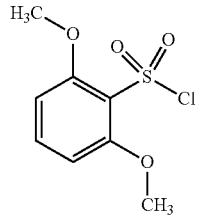

Scheme 15

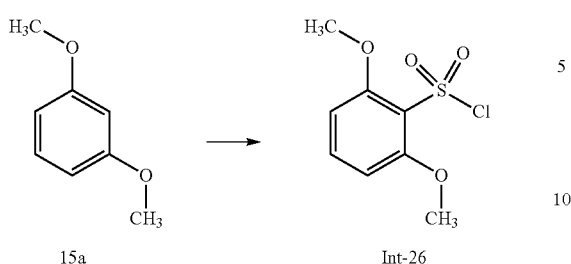

To a solution of 1,3-dimethoxybenzene (5.0 g, 36 mmol) and TMEDA (4.6 g, 39.8 mmol) in n-hexane (100 mL) at 0° C. under $N_2$ was added n-BuLi (2.5 M solution in hexanes, 16.0 mL, 39.8 mmol) dropwise while keeping the internal reaction temperature below 5° C. The mixture was stirred at 0° C. for 20 min then cooled to −78° C. and bubbled with $SO_2$ gas for 20 min. The mixture was then allowed to warm slowly to 10° C. and the resulting precipitate was collected by filtration and washed with dry diethyl ether. The solid was suspended in n-hexane (100 mL), cooled to 0° C. and a solution of $SO_2Cl_2$ (4.9 g, 36 mmol) in n-hexane (20 mL) was added dropwise while keeping the internal temperature below 3° C. The mixture was then stirred at 0° C. for 1 h and the solids were collected by filtration and washed with cold n-hexane. The solids were then partitioned between diethyl ether and water, the layers were separated and the aqueous layer was further extracted with diethyl ether. The combined organic extracts were dried over anhydrous $Na_2SO_4$, filtered and concentrated under reduced pressure to give the title compound (4.0 g, 47%) as a white solid. $^1$H NMR (400 MHz, $CDCl_3$) δ 7.54 (t, J=8.4 Hz, 1H), 6.66 (d, J=8.4 Hz, 2H), 3.97 (s, 6H).

Preparation of N-(6-bromo-4-methoxybenzo[d]isoxazol-3-yl)-2,6-dimethoxybenzenesulfonamide (Int-27) according to Method AA

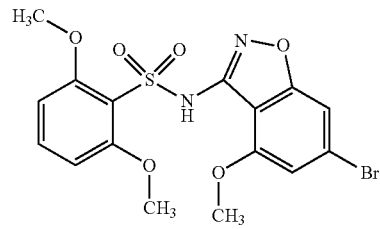 [SMILES: COc1cccc(OC)c1S(=O)(=O)Nc1noc2cc(Br)cc(OC)c12]

Method AA:

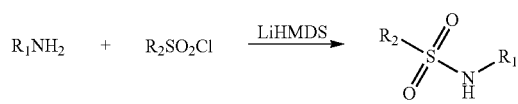

To a solution of the amine (0.5 mmol, 1.0 eq.) in anhydrous THF (10 mL) at −78° C. under $N_2$ was added LiHMDS (1 M solution in THF, 3 eq.) dropwise and the mixture was stirred at −78° C. for 30 min. A solution of the sulfonyl chloride (1.5 eq.) in anhydrous THF (2.0 mL) was then added dropwise and the mixture was allowed to warm to RT and stirred overnight. Water was added and the mixture was extracted with EtOAc. The combined organic extracts were washed with brine, dried over anhydrous $Na_2SO_4$, filtered and concentrated under reduced pressure. The residue was purified by column chromatography or prep. TLC to give the title compound. Variations to above conditions have been noted in the table immediately below.

TABLE 9

| Name and Structure | Analytical | Intermediates | Notes |
|---|---|---|---|
| N-(6-bromo-4-methoxybenzo[d]isoxazol-3-yl)-2,6-dimethoxybenzenesulfonamide, Int-27 | m/z 442.9 [M + H]$^+$; $^1$H NMR (400 MHz, DMSO-$d_6$) δ 9.80 (s, 1H), 7.54–7.48 (m, 2H), 7.05 (s, 1H), 6.78 (d, J = 8.4 Hz, 2H), 3.92 (s, 3H), 3.76 (s, 6H). | 2,6-dimethoxy benzenesulfonyl chloride (Int-26) 6-bromo-4-methoxybenzo[d]isoxazol-3-amine (14b) | 4 eq. LiHMDS used. Prep. TLC (DCM/MeOH = 100/1) |

Preparation of
7-bromo-5-methylbenzo[d]isoxazol-3-amine (Int-28)
according to Scheme 16

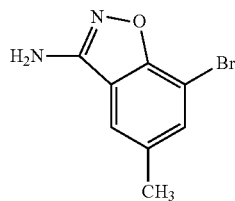

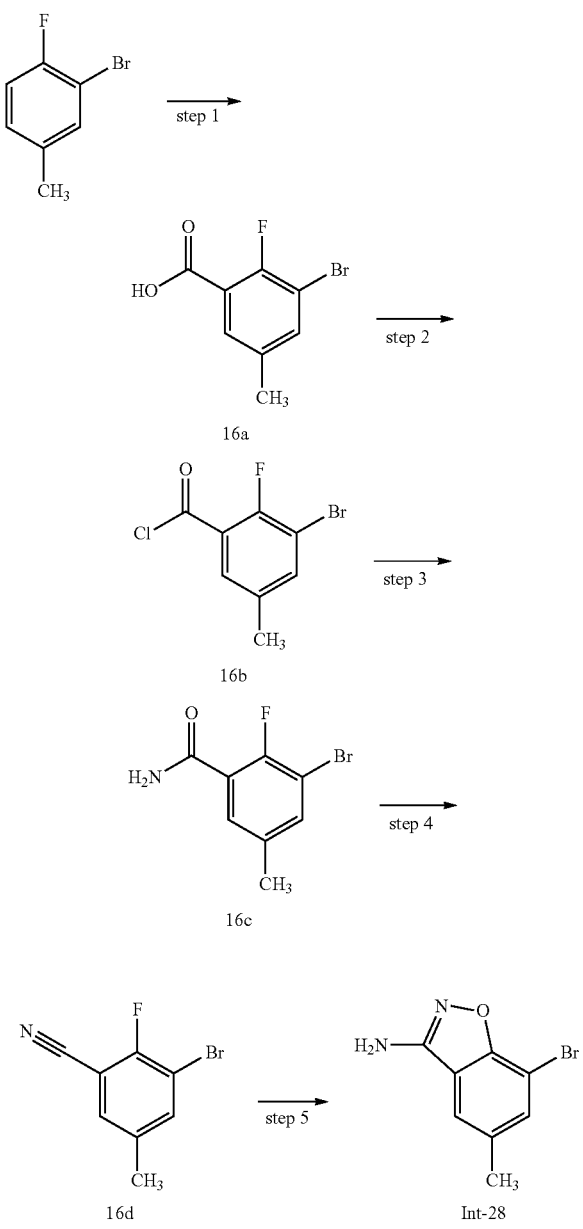

Scheme 16

Step 1: Synthesis of 3-bromo-2-fluoro-5-methylbenzoic acid (16a)

To a solution of 2-bromo-1-fluoro-4-methylbenzene (10.0 g, 53 mmol) and diisopropylamine (5.9 g, 58 mmol) in anhydrous THF (200 mL) at −78° C. under $N_2$ was added n-BuLi (2.5 M solution in hexanes, 25.6 mL, 64.0 mmol) dropwise and the mixture stirred at −78° C. for 1 h. Excess solid $CO_2$ (dry ice) was added and stirring was continued at −78° C. for 3 h. The mixture was diluted with water (500 mL) and extracted with EtOAc (500 mL). The organic layer was washed with brine, dried over $Na_2SO_4$, filtered and concentrated under reduced pressure to give the title compound (12.3 g, 100%) as a brown solid, which was used in the next step without further purification. m/z 232.8 $[M+H]^+$.

Step 2: Synthesis of 3-bromo-2-fluoro-5-methylbenzoyl chloride (16b)

To a solution of 3-bromo-2-fluoro-5-methylbenzoic acid (16a) (12.3 g, 53 mmol) and DMF (4 drops) in DCM (100 mL) at RT under $N_2$ was added oxalyl chloride (13.0 g, 106 mmol) dropwise and the mixture was stirred for 2 h. The mixture was concentrated under reduced pressure to give the title compound (14.0 g, 100%) as a brown solid, which was used in the next step without further purification.

Step 3: Synthesis of 3-bromo-2-fluoro-5-methylbenzamide (16c)

A solution of 3-bromo-2-fluoro-5-methylbenzoyl chloride (16b) (14.0 g, 53 mmol) in DCM (100 mL) was added dropwise to a 30% aqueous ammonium hydroxide solution (100 mL) and the mixture was stirred for 2 h. The mixture was diluted with EtOAc (200 mL), washed with water (200 mL×3), brine and the organic layer was dried over $Na_2SO_4$, filtered and concentrated under reduced pressure to give the title compound (12.0 g, 97%) as a brown solid, which was used in the next step without further purification. m/z 231.9 $[M+H]^+$.

Step 4: Synthesis of 3-bromo-2-fluoro-5-methylbenzonitrile (16d)

A solution of 3-bromo-2-fluoro-5-methylbenzamide (16c) (10.0 g, 43.0 mmol) and thionyl chloride (15.4 g, 129 mmol) in DMF (100 mL) was heated at 100° C. for 3 h. The mixture was diluted with EtOAc (200 mL) and washed with water (400 mL×5), brine and the organic layer was dried over $Na_2SO_4$, filtered and concentrated under reduced pressure to give the title compound (5.0 g, 54%) as a brown solid, which was used in the next step without further purification. m/z 213.9 $[M+H]^+$.

Step 5: Synthesis of 7-bromo-5-methylbenzo[d]isoxazol-3-amine (Int-28)

A suspension of N-hydroxyacetamide (5.27 g, 70.2 mmol) and t-BuOK (7.88 g, 70.2 mmol) in anhydrous DMF (200 mL) was stirred at 0° C. for 1 h. 3-Bromo-2-fluoro-5-methylbenzonitrile (16d) (5.0 g, 23.4 mmol) was then added and the mixture was allowed to warm to RT and stirred overnight. The mixture was diluted with EtOAc (300 mL), washed with water (600 mL×4), brine and the organic layer was dried over $Na_2SO_4$, filtered and concentrated under reduced pressure. The residue was purified by column chromatography (Pet. ether/EtOAc=10/1) to give the title compound (2.8 g, 52%) as a yellow solid. m/z 226.9 [M+H]⁺.

Preparation of N-(7-bromo-5-methylbenzo[d]isoxazol-3-yl)-2,6-dimethoxybenzenesulfonamide (Int-29) according to Method AB

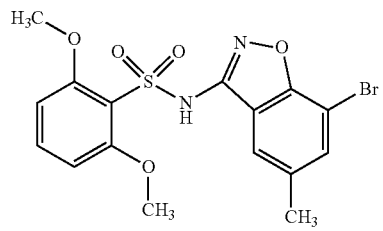 [SMILES: COc1cccc(OC)c1S(=O)(=O)Nc1noc2c(Br)cc(C)cc12]

Method AB:

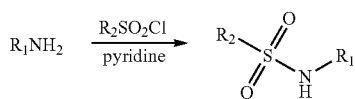

To a solution of the amine (0.2 mmol, 1.0 eq.) in pyridine (2 mL) was added the sulfonyl chloride (1.5 eq.) and the mixture was heated at 120° C. under microwave irradiation for 2 h. The mixture was partitioned between water and EtOAc, the layers were separated and the organic layer was washed with brine, dried over Na₂SO₄, filtered and concentrated under reduced pressure. The residue was purified by prep. TLC to give the title compound. Variations to above conditions have been noted in the table immediately below.

Sulfonamide Formation Methods:

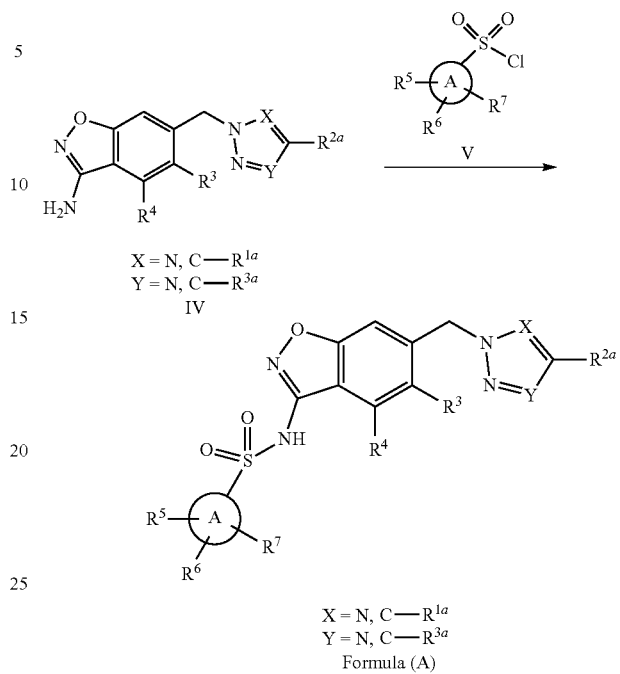

Method A:

To a solution of compound of Type IV (1.0 eq) in pyridine (c=0.1 M) was added compound of Type V (1.2 eq). The mixture was stirred at heated at a temperature between 80 and 120° C. for ~3-16 h. The reaction was cooled to room temperature, concentrated to dryness, and purified by standard methods known to those in the art to provide compound of Formula (A).

Method B:

To a suspension of NaH (60% dispersion in mineral oil, 3.0 eq) in THF (c=0.15 M) at 0° C. was added a solution of compound of Type IV (1.0 eq) in 1:1 THF/DMF (c=0.15 M) or THF (c=0.15 M) drop-wise. A solution of compound of Type V (1.3 eq) in 2:1 THF/DMF (c=0.15 M) or THF (c=0.15 M) was added at the same temperature. The reaction mixture was stirred at 60° C. for 16 h. The reaction was cooled to room temperature, concentrated to dryness, and

TABLE 10

| Name and structure | Analytical | Intermediates | Notes |
|---|---|---|---|
| ![structure] N-(7-bromo-5-methylbenzo[d]isoxazol-3-yl)-2,6-dimethoxybenzenesulfonamide, Int-29 | m/z 427.0, 429.0 [M + H]⁺; ¹H NMR (400 MHz, DMSO-d₆) δ 11.5 (s, 1H), 7.85 (s, 1H), 7.73 (s, 1H), 7.48 (t, J = 8.4 Hz, 1H), 6.75 (d, J = 8.4 Hz, 2H), 3.74 (s, 6H), 2.40 (s, 3H). | 2,6-dimethoxybenzenesulfonyl chloride (Int-26) 7-bromo-5-methylbenzo[d]isoxazol-3-amine (Int-28) | 0.2 eq. DMAP used. Organic layer washed with 0.1M aq. HCl in workup. Prep. TLC (DCM/MeOH, 20/1) | purified by standard methods known to those in the art to provide compound of Formula (A).

Method C:

To a solution of compound of Type IV (1.0 eq) in THF (c=0.3 M) was added NaOtPn (40% in PhMe, 1.0 eq) and a solution of compound of Type V (1.0 eq) in THF (c=0.3 M). The mixture was stirred at 60° C. for 16 h. The reaction was cooled to room temperature, concentrated to dryness, and purified by standard methods known to those in the art to provide compound of Formula (A).

Method D:

To a solution of compound of Type IV (1.0 eq) and compound of Type V (1.2 eq) in ACN (c=0.2 M) was added a 0.05 M solution of DMSO in ACN (1.0 mL/mmol compound of Type IV, 0.05 eq DMSO), followed by 3,5-lutidine (3.0 eq). The mixture was stirred at room temperature for 16 hours, concentrated to dryness, and purified by standard methods known to those in the art to provide compound of Formula (A).

PREPARATION OF EXAMPLES

Example 01: Preparation of 5-ethyl-2-methoxy-N-{4-methoxy-6-[(1H-pyrazol-1-yl)methyl]-1,2-benzoxazol-3-yl}benzene-1-sulfonamide According to Scheme A

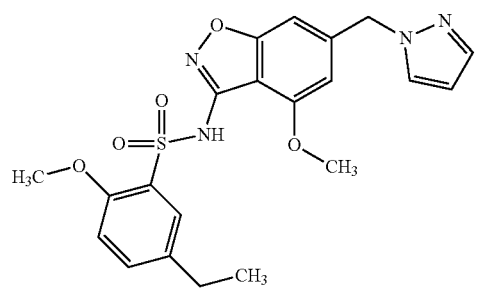 [SMILES: CCc1ccc(OC)c(S(=O)(=O)Nc2noc3cc(Cn4cccn4)cc(OC)c23)c1]

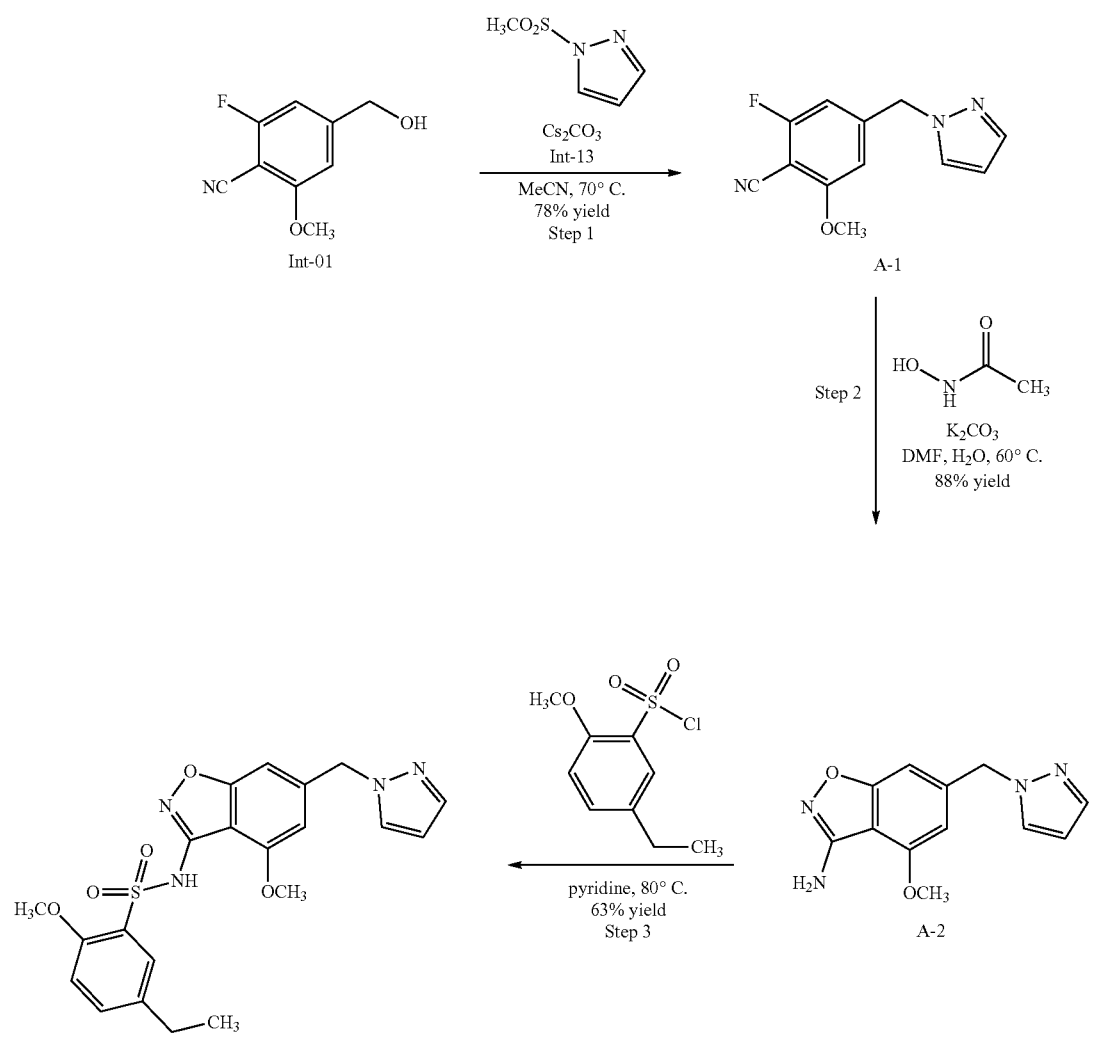

Scheme A

Example 01

Step 1: Synthesis of 2-fluoro-6-methoxy-4-[(1H-pyrazol-1-yl)methyl]benzonitrile (A-1)

To a solution of 2-fluoro-4-(hydroxymethyl)-6-methoxybenzonitrile (Int-01) (7.0 g, 38.6 mmol) and 1-(methanesulfonyl)-1H-pyrazole (Int-13) (6.2 g, 42.5 mmol) in MeCN (150 mL) was added $Cs_2CO_3$ (18.9 g, 58 mmol). The mixture was stirred at 70° C. for 2 h. LCMS analysis showed consumption of the starting material. The reaction was filtered and the filtrate was concentrated to dryness. The crude residue was purified by flash chromatography (40 g $SiO_2$, 1:1 EtOAc/petroleum ether) to provide 2-fluoro-6-methoxy-4-[(1H-pyrazol-1-yl)methyl]benzonitrile (A-1) (7.0 g, 78% yield) as a yellow solid. m/z (ESI+) 231.8 $(M+H)^+$.

Step 2: Synthesis of 4-methoxy-6-[(1H-pyrazol-1-yl)methyl]-1,2-benzoxazol-3-amine (A-2)

To a solution of 2-fluoro-6-methoxy-4-[(1H-pyrazol-1-yl)methyl]benzonitrile (A-1) (7.0 g, 30.3 mmol) and N-hydroxyacetamide (6.8 g, 90.8 mmol) in DMF (200 mL) and $H_2O$ (30 mL) was added $K_2CO_3$ (25.1 g, 182 mmol). The mixture was stirred at 60° C. for 16 h. TLC analysis (EtOAc) showed consumption of the starting material. The reaction mixture was concentrated to remove the majority of the DMF and then diluted with $H_2O$ (100 mL). The resultant precipitate was collected by filtration. The filter cake was washed with $H_2O$ (3×20 mL) and dried in vacuum to provide 4-methoxy-6-[(1H-pyrazol-1-yl)methyl]-1,2-benzoxazol-3-amine (A-2) (6.0 g). The above filtrate was extracted with EtOAc (2×30 mL). The combined organic layers were dried over $Na_2SO_4$, filtered, and concentrated. The residue was purified by flash chromatography ($SiO_2$, EtOAc) to provide an additional batch of 4-methoxy-6-[(1H-pyrazol-1-yl)methyl]-1,2-benzoxazol-3-amine (A-2) (0.5 g). The two batches of product were combined and dried under vacuum to provide 4-methoxy-6-[(1H-pyrazol-1-yl)methyl]-1,2-benzoxazol-3-amine (A-2) (6.5 g, 88% yield) as a yellow solid. $^1$H NMR (400 MHz, DMSO-$d_6$) δ 7.88 (d, J=2.0 Hz, 1H), 7.51 (d, J=1.3 Hz, 1H), 6.70 (s, 1H), 6.63 (s, 1H), 6.31 (t, J=2.0 Hz, 1H), 6.08-5.78 (m, 2H), 5.52-5.31 (m, 2H), 3.93-3.73 (m, 3H). m/z (ESI+) 244.8 $(M+H)^+$.

Step 3: Synthesis of 5-ethyl-2-methoxy-N-{4-methoxy-6-[(1H-pyrazol-1-yl)methyl]-1,2-benzoxazol-3-yl}benzene-1-sulfonamide (Example 01) according to Sulfonamide Formation Method A To a solution of 4-methoxy-6-[(1H-pyrazol-1-yl)methyl]-1,2-benzoxazol-3-amine (A-2) (1.23 g, 5.032 mmol) in pyridine (2.5 mL) was added 5-ethyl-2-methoxybenzene-1-sulfonyl chloride (1.54 g, 6.54 mmol). The reaction was stirred at 80° C. for 3.5 h. LCMS analysis showed consumption of the starting material with formation of the desired product mass. The reaction solidified upon cooling. The solid was dissolved in DCM and AcOH (1.4 mL) with a minimal amount of MeOH. The mixture was purified by flash chromatography (40 g $SiO_2$, 10-70% MeOAc/heptane). The pure fractions containing the title compound were collected. The impure fractions were repurified by flash chromatography (40 g $SiO_2$, 10-70% MeOAc/heptane). The pure fractions were combined with the previously isolated pure fractions and concentrated to provide a white solid. The solid was suspended in MeOAc, refluxed for 1 h, and allowed to cool to room temperature. The resultant solid was collected by filtration and dried under vacuum to provide 5-ethyl-2-methoxy-N-{4-methoxy-6-[(1H-pyrazol-1-yl)methyl]-1,2-benzoxazol-3-yl}benzene-1-sulfonamide (Example 01) (1.4 g, 63% yield) as a white solid. $^1$H NMR (400 MHz, DMSO-$d_6$) δ 9.98 (s, 1H), 7.87 (d, J=2.0 Hz, 1H), 7.62 (d, J=2.3 Hz, 1H), 7.49 (d, J=1.5 Hz, 1H), 7.46 (dd, J=2.0, 8.5 Hz, 1H), 7.10 (d, J=8.5 Hz, 1H), 6.83 (s, 1H), 6.74 (s, 1H), 6.30 (t, J=2.0 Hz, 1H), 5.43 (s, 2H), 3.81 (s, 3H), 3.74 (s, 3H), 2.59 (q, J=7.5 Hz, 2H), 1.13 (t, J=7.5 Hz, 3H); m/z (ESI+) 443.1 $(M+H)^+$.

Example 02: Preparation of 2,6-dimethoxy-N-{4-methoxy-6-[(3-methyl-1H-pyrazol-1-yl)methyl]-1,2-benzoxazol-3-yl}benzene-1-sulfonamide According to Scheme B

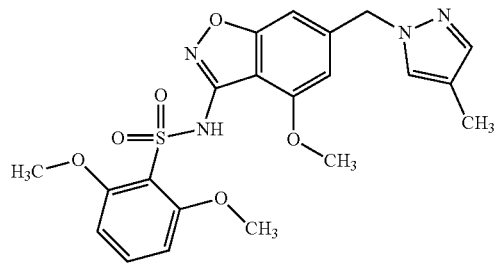 [SMILES: COc1cccc(OC)c1S(=O)(=O)Nc1noc2cc(Cn3cc(C)cn3)cc(OC)c12]

Example 03: Preparation of 2,6-dimethoxy-N-{4-methoxy-6-[(5-methyl-1H-pyrazol-1-yl)methyl]-1,2-benzoxazol-3-yl}benzene-1-sulfonamide According to Scheme B

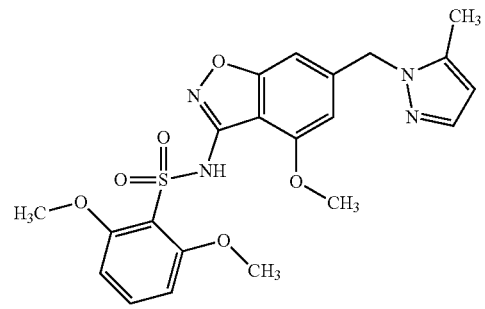 [SMILES: COc1cccc(OC)c1S(=O)(=O)Nc1noc2cc(Cn3nccc3C)cc(OC)c12]

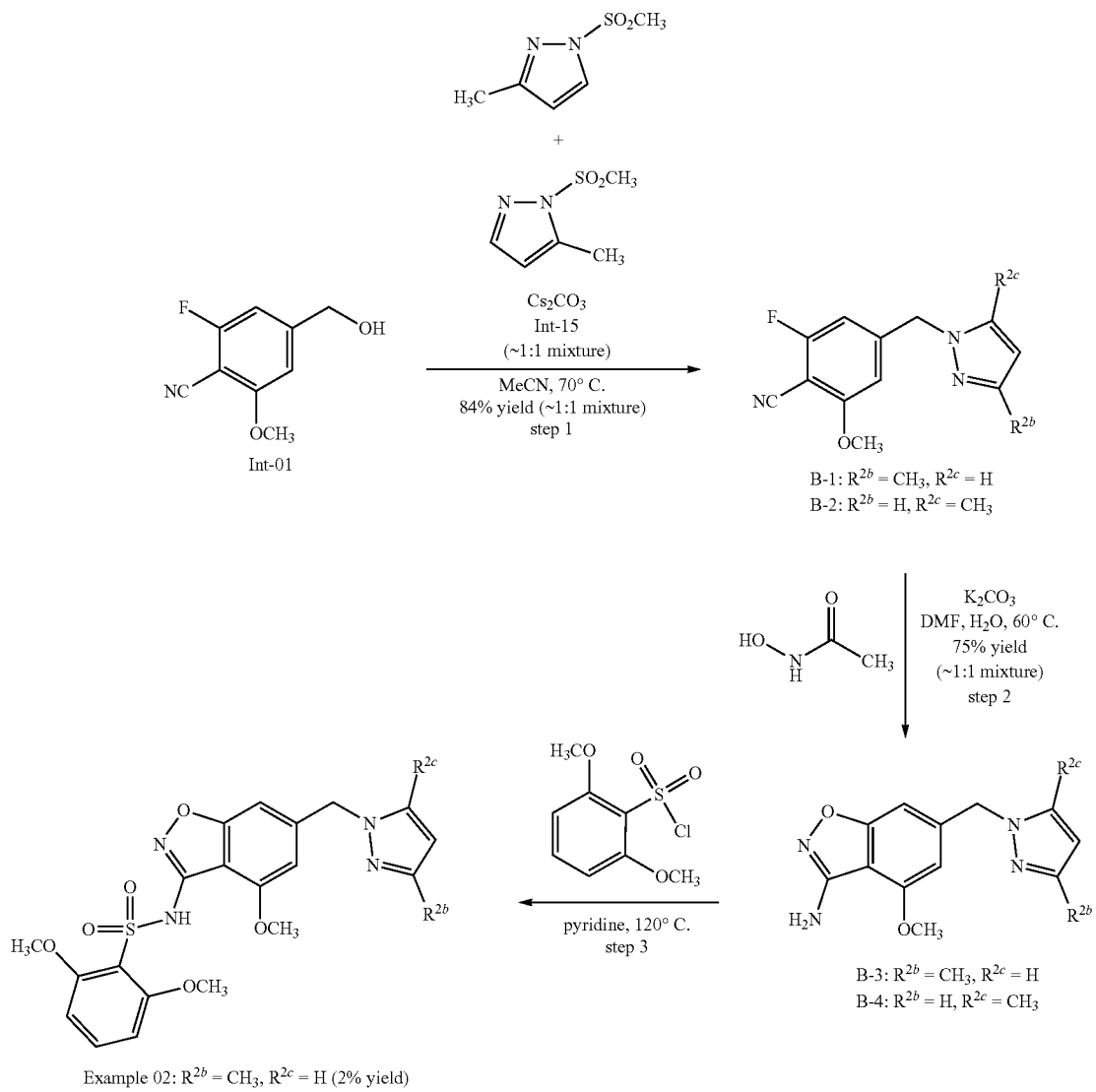

Example 02: R²ᵇ = CH₃, R²ᶜ = H (2% yield)
Example 03: R²ᵇ = H, R²ᶜ = CH₃ (4% yield)

Step 1: Synthesis of 2-fluoro-6-methoxy-4-[(3-methyl-1H-pyrazol-1-yl)methyl]benzonitrile (B-1) and 2-fluoro-6-methoxy-4-[(5-methyl-1H-pyrazol-1-yl)methyl]benzonitrile (B-2)

To a mixture (~1:1) of 1-(methanesulfonyl)-3-methyl-1H-pyrazole and 1-(methanesulfonyl)-5-methyl-1H-pyrazole (Int-15) in MeCN (25 mL) was added 2-fluoro-4-(hydroxymethyl)-6-methoxybenzonitrile (Int-01) (1.0 g, 5.5 mmol) and Cs₂CO₃ (2.3 g, 7.2 mmol). The mixture was stirred at 70° C. for 1 h. LCMS analysis showed consumption of the starting material with formation of the desired product mass. The reaction was cooled to room temperature and concentrated to dryness. The residue was purified by flash chromatography (20 g SiO₂, 100% EtOAc) to provide a mixture (~1:1) of 2-fluoro-6-methoxy-4-[(3-methyl-1H-pyrazol-1-yl)methyl]benzonitrile (B-1) and 2-fluoro-6-methoxy-4-[(5-methyl-1H-pyrazol-1-yl)methyl]benzonitrile (B-2) (1.13 g, 84% yield) as a yellow gum. m/z (ESI+) 245.8 (M+H)⁺.

Step 2: Synthesis of 4-methoxy-6-[(3-methyl-1H-pyrazol-1-yl)methyl]-1,2-benzoxazol-3-amine (B-3) and 4-methoxy-6-[(5-methyl-1H-pyrazol-1-yl)methyl]-1,2-benzoxazol-3-amine (B-4)

To a mixture (~1:1) of 2-fluoro-6-methoxy-4-[(3-methyl-1H-pyrazol-1-yl)methyl]benzonitrile (B-1) and 2-fluoro-6-methoxy-4-[(5-methyl-1H-pyrazol-1-yl)methyl]benzonitrile (B-2) (1.13 g, 4.73 mmol) in DMF (20 mL) and H₂O (3 mL) was added N-hydroxyacetamide (1.07 g, 14.2 mmol) and K₂CO₃ (3.9 g, 28.4 mmol). The mixture was stirred at 60° C. for 16 h. LCMS analysis showed consumption of the starting material with formation of the desired product mass. The mixture was concentrated to dryness. The residue was taken up in EtOAc (30 mL) and washed with H₂O (30 mL).

The organic layer was dried over Na$_2$SO$_4$, filtered, and concentrated. The residue was purified by flash chromatography (20 g SiO$_2$, 100% EtOAc) to provide a mixture (~1:1) of 4-methoxy-6-[(3-methyl-1H-pyrazol-1-yl)methyl]-1,2-benzoxazol-3-amine (B-3) and 4-methoxy-6-[(5-methyl-1H-pyrazol-1-yl)methyl]-1,2-benzoxazol-3-amine (B-4) (916 mg, 75% yield) as a solid. m/z (ESI+) 258.8 (M+H)$^+$.

Step 3: Synthesis of 2,6-dimethoxy-N-{4-methoxy-6-[(3-methyl-1H-pyrazol-1-yl)methyl]-1,2-benzoxazol-3-yl}benzene-1-sulfonamide (Example 02) and 2,6-dimethoxy-N-{4-methoxy-6-[(5-methyl-1H-pyrazol-1-yl)methyl]-1,2-benzoxazol-3-yl}benzene-1-sulfonamide (Example 03) according to Sulfonamide Formation Method A To a mixture (~1:1) of 4-methoxy-6-[(3-methyl-1H-pyrazol-1-yl)methyl]-1,2-benzoxazol-3-amine (B-3) and 4-methoxy-6-[(5-methyl-1H-pyrazol-1-yl)methyl]-1,2-benzoxazol-3-amine (B-4) (800 mg, 3.1 mmol) in pyridine (10.0 mL) was added 2,6-dimethoxybenzene-1-sulfonyl chloride (Int-26) (1.1 g, 4.65 mmol). The mixture was stirred at 120° C. for 2 h. The reaction was cooled to room temperature and concentrated to dryness. The residue was purified by flash chromatography (20 g SiO$_2$, 1:4 MeOH/EtOAc). The material was re-purified by preparative HPLC with a YMC Triart column (20×150 mm, 7 μm particle size), which was eluted with 23-63% MeCN/H$_2$O (+0.225% formic acid) with a flow rate of 25 mL/min. The material was re-purified by preparative SFC with a Diacel CHIRALCEL OD-H column (30× 250 mm, 5 μm particle size), which was eluted with 45% EtOH/CO$_2$ (+0.1% NH$_4$OH) with a flow rate of 60 mL/min to provide 2,6-dimethoxy-N-{4-methoxy-6-[(3-methyl-1H-pyrazol-1-yl)methyl]-1,2-benzoxazol-3-yl}benzene-1-sulfonamide (Example 02) (63 mg, 4% yield) as the first eluting peak as a white solid. $^1$H NMR (400 MHz, DMSO-d$_6$) δ 9.62 (br. s, 1H), 7.74 (d, J=2.1 Hz, 1H), 7.49 (t, J=8.4 Hz, 1H), 6.81 (s, 1H), 6.77 (d, J=8.3 Hz, 3H), 6.07 (d, J=2.1 Hz, 1H), 5.33 (s, 2H), 3.93-3.84 (m, 3H), 3.77 (s, 6H), 2.15 (s, 3H); m/z (ESI+) 458.8 (M+H)$^+$. 2,6-Dimethoxy-N-{4-methoxy-6-[(5-methyl-1H-pyrazol-1-yl)methyl]-1,2-benzoxazol-3-yl}benzene-1-sulfonamide (Example 03) (33 mg, 2% yield) was obtained as the second eluting peak as a white solid. $^1$H NMR (400 MHz, DMSO-d$_6$) δ 9.64 (br. s, 1H), 7.49 (t, J=8.6 Hz, 1H), 7.40 (d, J=1.7 Hz, 1H), 6.78 (s, 1H), 6.76 (s, 1H), 6.66 (s, 1H), 6.61 (s, 1H), 6.11 (dd, J=1.8, 0.9 Hz, 1H), 5.41 (s, 2H), 3.86 (s, 3H), 3.76 (s, 6H), 2.21 (s, 3H); m/z (ESI+) 458.8 (M+H)$^+$.

The examples in the table below were synthesized according to the methods used for the synthesis of 5-ethyl-2-methoxy-N-{4-methoxy-6-[(1H-pyrazol-1-yl)methyl]-1,2-benzoxazol-3-yl}benzene-1-sulfonamide (Example 01), 2,6-dimethoxy-N-{4-methoxy-6-[(3-methyl-1H-pyrazol-1-yl)methyl]-1,2-benzoxazol-3-yl}benzene-1-sulfonamide (Example 02), and 2,6-dimethoxy-N-{4-methoxy-6-[(5-methyl-1H-pyrazol-1-yl)methyl]-1,2-benzoxazol-3-yl}benzene-1-sulfonamide (Example 03) and the general sulfonamide formation methods A-D. The following examples were synthesized with non-critical changes or substitutions to the exemplified procedures that someone who is skilled in the art would be able to realize. If necessary, separation of regioisomeric mixtures was carried out under standard methods known in the art, such as SFC or HPLC, and was conducted at any suitable step in the synthetic sequence.

TABLE 11

| Example Number | Structure/IUPAC Name | Analytical Data | Sulfonamide Formation Method |
|---|---|---|---|
| 04 | 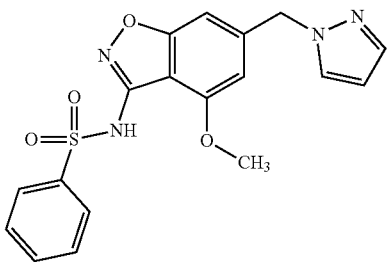<br>N-{4-methoxy-6-[(1H-pyrazol-1-yl)methyl]-1,2-benzoxazol-3-yl}benzenesulfonamide | $^1$H NMR (400 MHz, DMSO-d$_6$) δ 10.95 (br. s, 1H), 8.03-7.95 (m, 2H), 7.87 (d, J = 2.3 Hz, 1H), 7.71-7.65 (m, 1H), 7.64-7.58 (m, 2H), 7.49 (d, J = 1.8 Hz, 1H), 6.83 (s, 1H), 6.74 (s, 1H), 6.30 (t, J = 2.0 Hz, 1H), 5.44 (s, 2H), 3.85 (s, 3H); m/z (ESI+) 244.7 (M + H)$^+$. | A |

TABLE 11-continued

| Example Number | Structure/IUPAC Name | Analytical Data | Sulfonamide Formation Method |
|---|---|---|---|
| 05 | 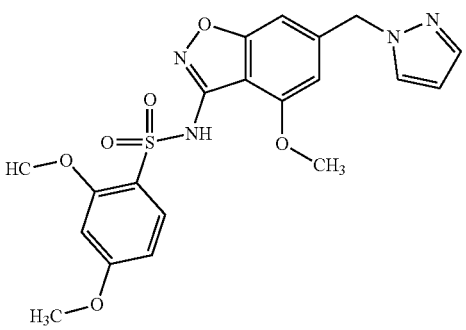<br>2,4-dimethoxy-N-{4-methoxy-6-[(1H-pyrazol-1-yl)methyl]-1,2-benzoxazol-3-yl}benzene-1-sulfonamide | $^1$H NMR (400 MHz, DMSO-$d_6$) δ 9.88 (br. s, 1H), 7.87 (d, J = 2.2 Hz, 1H), 7.72 (d, J = 8.5 Hz, 1H), 7.49 (d, J = 1.9 Hz, 1H), 6.81 (s, 1H), 6.74 (s, 1H), 6.69-6.57 (m, 2H), 6.30 (t, J = 2.1 Hz, 1H), 5.43 (s, 2H), 3.86 (s, 2H), 3.82 (s, 3H), 3.77 (s, 3H); m/z (ESI+) 445.0 (M + H)$^+$. | B |
| 06 | 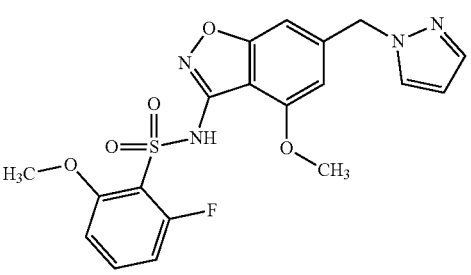<br>2-fluoro-6-methoxy-N-{4-methoxy-6-[(1H-pyrazol-1-yl)methyl]-1,2-benzoxazol-3-yl}benzene-1-sulfonamide | $^1$H NMR (400 MHz, DMSO-$d_6$) δ 10.67 (br. s, 1H), 7.89 (d, J = 2.3 Hz, 1H), 7.62 (td, J = 8.5, 6.0 Hz, 1H), 7.50 (d, J = 1.8 Hz, 1H), 7.03 (d, J = 8.5 Hz, 1H), 6.95 (dd, J = 10.9, 8.4 Hz, 1H), 6.85 (s, 1H), 6.76 (s, 1H), 6.31 (t, J = 2.1 Hz, 1H), 5.45 (s, 2H), 3.81 (s, 3H), 3.80 (s, 3H); m/z (ESI+) 432.9 (M + H)$^+$. | B |
| 07 | 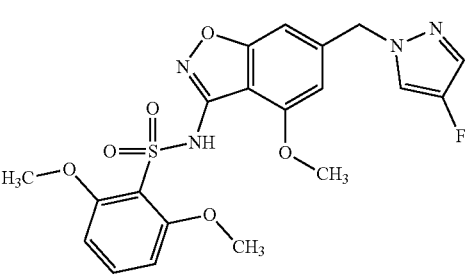<br>N-{6-[(4-fluoro-1H-pyrazol-1-yl)methyl]-4-methoxy-1,2-benzoxazol-3-yl}-2,6-dimethoxybenzene-1-sulfonamide | $^1$H NMR (400 MHz, DMSO-$d_6$) δ 8.85 (br. s, 1H), 8.02 (d, J = 4.6 Hz, 1H), 7.53 (d, J = 4.2 Hz, 1H), 7.46 (t, J = 8.5 Hz, 1H), 6.86 (s, 1H), 6.76-6.71 (m, 3H), 5.33 (s, 2H), 3.87 (s, 3H), 3.74 (s, 6H); m/z (ESI+) 463.0 (M + H)$^+$. | A |

TABLE 11-continued

| Example Number | Structure/IUPAC Name | Analytical Data | Sulfonamide Formation Method |
|---|---|---|---|
| 08 | 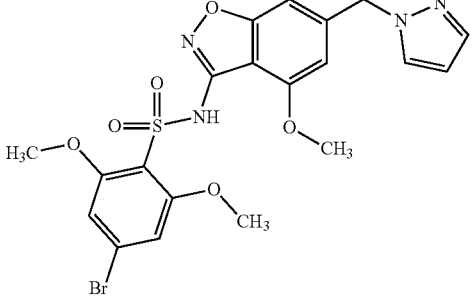<br>4-bromo-2,6-dimethoxy-N-{4-methoxy-6-[(1H-pyrazol-1-yl)methyl]-1,2-benzoxazol-3-yl}benzene-1-sulfonamide | $^1$H NMR (400 MHz, DMSO-$d_6$) δ 7.84 (d, J = 2.3 Hz, 1H), 7.48 (d, J = 1.9 Hz, 1H), 6.76 (s, 2H), 6.54 (s, 1H), 6.49 (s, 1H), 6.29 (t, J = 2.1 Hz, 1H), 5.37 (s, 2H), 4.09 (br. s, 1H), 3.83 (s, 3H), 3.59 (s, 6H); m/z (ESI+) 522.9, 524.9 (M + H)$^+$. | C |
| 09 | 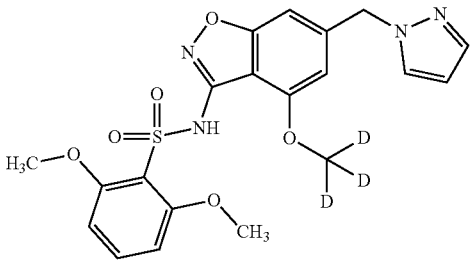<br>2,6-dimethoxy-N-{4-[($^2$H$_3$)methyloxy]-6-[(1H-pyrazol-1-yl)methyl]-1,2-benzoxazol-3-yl}benzene-1-sulfonamide | $^1$H NMR (400 MHz, DMSO-$d_6$) δ 9.56 (s, 1H), 7.87 (d, J = 1.96 Hz, 1H), 7.43-7.55 (m, 2H), 6.83 (s, 1H), 6.77 (d, J = 8.80 Hz, 3H), 6.30 (t, J = 2.08 Hz, 1H), 5.44 (s, 2H), 3.76 (s, 6H); m/z (ESI+) 448.1 (M + H)$^+$. | A |
| 10 | 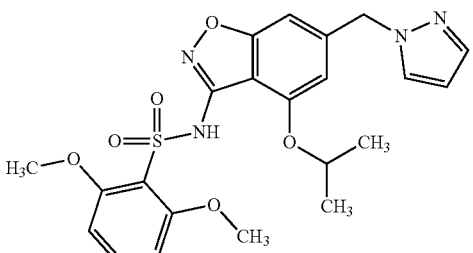<br>2,6-dimethoxy-N-{4-[(propan-2-yl)oxy]-6-[(1H-pyrazol-1-yl)methyl]-1,2-benzoxazol-3-yl}benzene-1-sulfonamide | $^1$H NMR (400 MHz, DMSO-$d_6$) δ 9.09 (s, 1H), 7.89 (d, J = 2.3 Hz, 1H), 7.60-7.34 (m, 2H), 6.81 (d, J = 13.0 Hz, 2H), 6.76 (d, J = 9.6 Hz, 2H), 6.31 (t, J = 2.1 Hz, 1H), 5.45 (s, 2H), 4.75 (sept, J = 6.1 Hz, 1H), 3.75 (s, 6H), 1.34 (d, J = 6.0 Hz, 6H); m/z (ESI+) 473.1 (M + H)$^+$. | A |
| 11 | 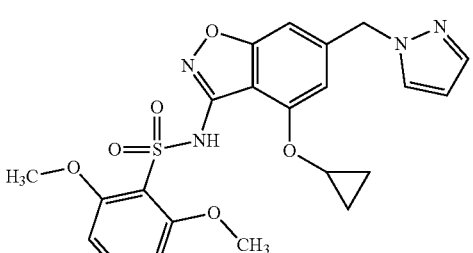<br>N-{4-(cyclopropyloxy)-6-[(1H-pyrazol-1-yl)methyl]-1,2-benzoxazol-3-yl}-2,6-dimethoxybenzene-1-sulfonamide | $^1$H NMR (400 MHz, DMSO-$d_6$) δ 9.56 (s, 1H), 7.89 (dd, J = 2.3, 0.7 Hz, 1H), 7.56-7.37 (m, 2H), 6.97 (s, 1H), 6.87 (s, 1H), 6.77 (s, 1H), 6.75 (s, 1H), 6.32 (t, J = 2.1 Hz, 1H), 5.48 (s, 2H), 3.99-3.88 (m, 1H), 3.73 (s, 6H), 0.87-0.77 (m, 2H), 0.75-0.68 (m, 2H); m/z (ESI+) 471.1 (M + H)$^+$. | B |

TABLE 11-continued

| Example Number | Structure/IUPAC Name | Analytical Data | Sulfonamide Formation Method |
|---|---|---|---|
| 12 | 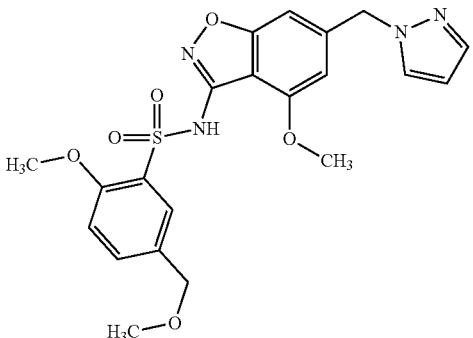<br>2-methoxy-5-(methoxymethyl)-N-{4-methoxy-6-[(1H-pyrazol-1-yl)methyl]-1,2-benzoxazol-3-yl}benzene-1-sulfonamide | $^1$H NMR (400 MHz, DMSO-$d_6$) δ 10.16 (br. s, 1H), 7.86 (d, J = 2.0 Hz, 1H), 7.75 (d, J = 1.6 Hz, 1H), 7.48 (s, 2H), 7.12 (br. d, J = 8.5 Hz, 1H), 6.77 (br. s, 1H), 6.68 (br. s, 1H), 6.29 (s, 1H), 5.42 (s, 2H), 4.37 (s, 2H), 3.81 (s, 3H), 3.75 (s, 3H), 3.25 (s, 3H); m/z (ESI+) 459.1 (M + H)$^+$. | B |
| 13 | 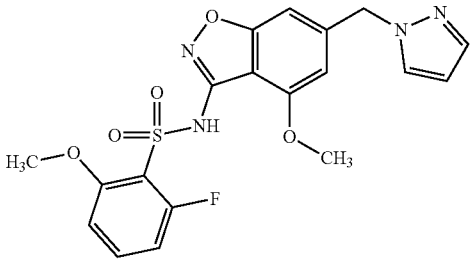<br>2-fluoro-N-{4-methoxy-6-[(1H-pyrazol-1-yl)methyl]-1,2-benzoxazol-3-yl}-6-methylbenzene-1-sulfonamide | $^1$H NMR (400 MHz, DMSO-$d_6$) δ 11.26 (br. s, 1H), 7.88 (d, J = 2.2 Hz, 1H), 7.62-7.43 (m, 1H), 7.27-7.15 (m, 2H), 6.82 (br. s, 1H), 6.72 (br. s, 1H), 6.31 (t, J = 2.1 Hz, 1H), 5.44 (s, 2H), 3.79 (s, 4H), 2.60 (s, 3H); m/z (ESI+) 417.0 (M + H)$^+$. | B |
| 14 | 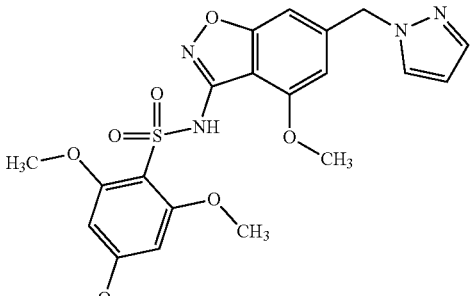<br>2,4,6-trimethoxy-N-{4-methoxy-6-[(1H-pyrazol-1-yl)methyl]-1,2-benzoxazol-3-yl}benzene-1-sulfonamide | $^1$H NMR (400 MHz, DMSO-$d_6$) δ 9.21 (br. s, 1H), 7.88 (d, J = 2.0 Hz, 1H), 7.49 (d, J = 1.3 Hz, 1H), 6.81 (s, 1H), 6.75 (s, 1H), 6.30 (t, J = 2.0 Hz, 1H), 6.26 (s, 2H), 5.44 (s, 2H), 3.91 (s, 3H), 3.80 (s, 3H), 3.75 (s, 6H); m/z (ESI+) 475.1 (M + H)$^+$. | A |

TABLE 11-continued

| Example Number | Structure/IUPAC Name | Analytical Data | Sulfonamide Formation Method |
|---|---|---|---|
| 15 | 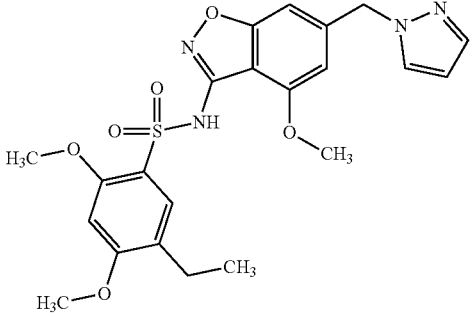<br>5-ethyl-2,4-dimethoxy-N-{4-methoxy-6-[(1H-pyrazol-1-yl)methyl]-1,2-benzoxazol-3-yl}benzene-1-sulfonamide | $^1$H NMR (400 MHz, CD$_3$OD) δ 7.78 (d, J = 2.4 Hz, 1H), 7.70 (s, 1H), 7.57 (d, J = 1.9 Hz, 1H), 6.79 (s, 1H), 6.68 (s, 1H), 6.61 (s, 1H), 6.38 (t, J = 2.2 Hz, 1H), 5.47 (s, 2H), 4.00 (s, 3H), 3.89 (s, 3H), 3.87 (s, 3H), 2.59 (q, J = 7.5 Hz, 2H), 1.17 (t, J = 7.5 Hz, 3H); m/z (ESI+) 473.1 (M + H)$^+$. | B |
| 16 | 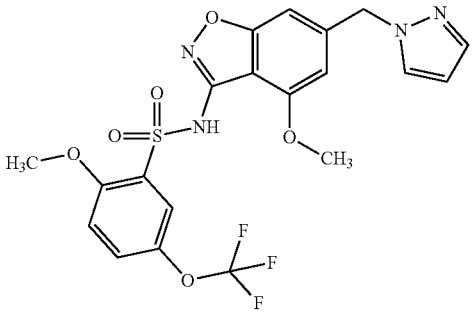<br>2-methoxy-N-{4-methoxy-6-[(1H-pyrazol-1-yl)methyl]-1,2-benzoxazol-3-yl}-5-(trifluoromethoxy)benzene-1-sulfonamide | $^1$H NMR (400 MHz, DMSO-d$_6$) δ 7.87 (d, J = 2.2 Hz, 1H), 7.72 (d, J = 3.0 Hz, 1H), 7.62-7.56 (m, 1H), 7.50 (d, J = 1.8 Hz, 1H), 7.29-7.21 (m, 1H), 7.14-6.97 (m, 1H), 6.80-6.75 (m, 1H), 6.72-6.64 (m, 1H), 6.30 (t, J = 2.1 Hz, 1H), 5.42 (s, 2H), 3.79 (s, 3H), 3.77 (s, 3H); m/z (ESI+) 499.0 (M + H)$^+$. | B |
| 17 | 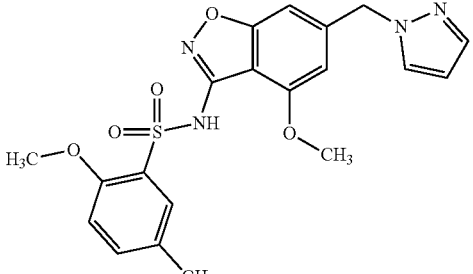<br>2-methoxy-N-{4-methoxy-6-[(1H-pyrazol-1-yl)methyl]-1,2-benzoxazol-3-yl}-5-methylbenzene-1-sulfonamide | $^1$H NMR (400 MHz, DMSO-d$_6$) δ 9.96 (s, 1H), 7.87 (d, J = 2.3 Hz, 1H), 7.61 (d, J = 2.3 Hz, 1H), 7.50 (d, J = 1.8 Hz, 1H), 7.36 (d, J = 5.1 Hz, 1H), 7.04 (d, J = 8.4 Hz, 1H), 6.78 (br. s, 1H), 6.70 (br. s, 1H), 6.30 (t, J = 2.2 Hz, 1H), 5.43 (s, 2H), 3.83 (s, 3H), 3.73 (s, 3H), 2.28 (s, 3H); m/z (ESI+) 429.0 (M + H)$^+$. | B |

TABLE 11-continued

| Example Number | Structure/IUPAC Name | Analytical Data | Sulfonamide Formation Method |
|---|---|---|---|
| 18 | 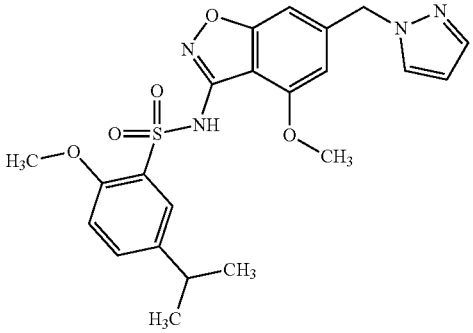

2-methoxy-N-{4-methoxy-6-[(1H-pyrazol-1-yl)methyl]-1,2-benzoxazol-3-yl}-5-(propan-2-yl)benzene-1-sulfonamide | $^1$H NMR (400 MHz, DMSO-d$_6$) δ 10.04 (s, 1H), 7.87 (d, J = 2.3 Hz, 1H), 7.65 (d, J = 2.3 Hz, 1H), 7.50 (s, 1H), 7.48-7.43 (m, 1H), 7.09 (d, J = 8.6 Hz, 1H), 6.81 (br. s, 1H), 6.71 (br. s, 1H), 6.30 (s, 1H), 5.43 (s, 2H), 3.81 (s, 3H), 3.73 (s, 3H), 2.90 (hept, J = 6.7 Hz, 1H), 1.17 (d, J = 6.9 Hz, 6H); m/z (ESI+) 457.2 (M + H)$^+$. | A |
| 19 | 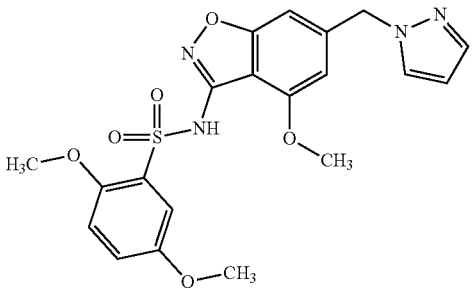

2,5-dimethoxy-N-{4-methoxy-6-[(1H-pyrazol-1-yl)methyl]-1,2-benzoxazol-3-yl}benzene-1-sulfonamide | $^1$H NMR (400 MHz, DMSO-d$_6$) δ 10.16 (s, 1H), 7.87 (d, J = 2.3 Hz, 1H), 7.50 (d, J = 1.8 Hz, 1H), 7.33 (d, J = 3.0 Hz, 1H), 7.18-7.00 (m, 2H), 6.78 (br. s, 1H), 6.69 (br. s, 1H), 6.30 (t, J = 2.1 Hz, 1H), 5.43 (s, 2H), 3.83 (s, 3H), 3.73 (s, 3H), 3.71 (s, 3H); m/z (ESI+) 445.0 (M + H)$^+$. | B |
| 20 | 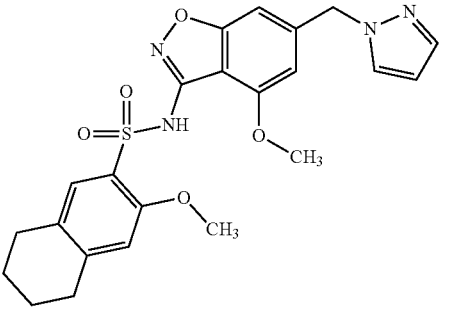

3-methoxy-N-{4-methoxy-6-[(1H-pyrazol-1-yl)methyl]-1,2-benzoxazol-3-yl}-5,6,7,8-tetrahydronaphthalene-2-sulfonamide | $^1$H NMR (400 MHz, DMSO-d$_6$) δ 9.84 (s, 1H), 7.88 (d, J = 2.3 Hz, 1H), 7.50 (d, J = 1.9 Hz, 1H), 7.49 (s, 1H), 6.86 (s, 1H), 6.84 (s, 1H), 6.75 (s, 1H), 6.31 (t, J = 2.1 Hz, 1H), 5.44 (s, 2H), 3.87 (s, 3H), 3.73 (s, 3H), 2.80-2.71 (m, 2H), 2.69-2.63 (m, 2H), 1.77-1.61 (m, 4H); (ESI+) 468.8 (M + H)$^+$. | A |

TABLE 11-continued

| Example Number | Structure/IUPAC Name | Analytical Data | Sulfonamide Formation Method |
|---|---|---|---|
| 21 | 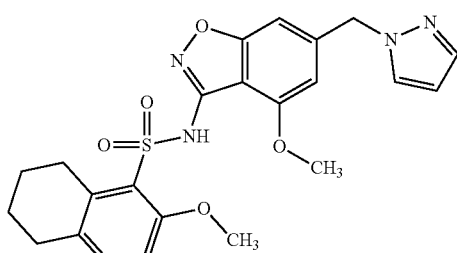/2-methoxy-N-{4-methoxy-6-[(1H-pyrazol-1-yl)methyl]-1,2-benzoxazol-3-yl}-5,6,7,8-tetrahydronaphthalene-1-sulfonamide | $^1$H NMR (400 MHz, DMSO-$d_6$) δ 9.56 (s, 1H), 7.88 (d, J = 2.0 Hz, 1H), 7.50 (d, J = 1.2 Hz, 1H), 7.29 (d, J = 8.6 Hz, 1H), 6.99 (d, J = 8.6 Hz, 1H), 6.83 (s, 1H), 6.76 (s, 1H), 6.30 (t, J = 2.1 Hz, 1H), 5.44 (s, 2H), 3.88 (s, 3H), 3.78 (s, 3H), 3.12 (t, J = 5.7 Hz, 2H), 2.72 (t, J = 6.0 Hz, 2H), 1.73-1.59 (m, 4H); m/z (ESI+) 468.8 (M + H)$^+$. | A |
| 22 | 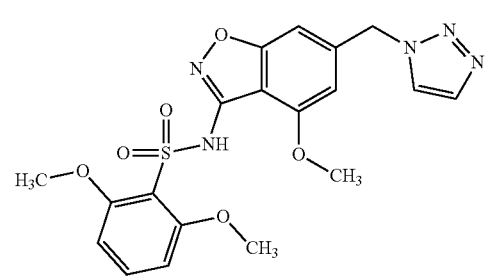/2,6-dimethoxy-N-{4-methoxy-6-[(1H-1,2,3-triazol-1-yl)methyl]-1,2-benzoxazol-3-yl}benzene-1-sulfonamide | $^1$H NMR (400 MHz, DMSO-$d_6$) δ 10.34 (br. s, 1H), 9.78 (br. s, 1H), 8.26 (s, 1H), 7.78 (s, 1H), 7.46 (t, J = 8.4 Hz, 1H), 6.98 (s, 1H), 6.82 (s, 1H), 6.76 (s, 1H), 6.74 (s, 1H), 5.72 (s, 2H), 3.89 (s, 3H), 3.74 (s, 6H); m/z (ESI+) 446.1 (M + H)$^+$. | A |
| 23 | 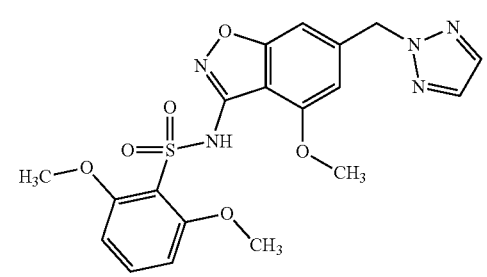/2,6-dimethoxy-N-{4-methoxy-6-[(2H-1,2,3-triazol-2-yl)methyl]-1,2-benzoxazol-3-yl}benzene-1-sulfonamide | $^1$H NMR (400 MHz, DMSO-$d_6$) δ 9.66 (br. s, 1H), 7.87 (s, 2H), 7.50 (t, J = 8.5 Hz, 1H), 6.92 (s, 1H), 6.79-6.77 (m, 2H), 6.76 (s, 1H), 5.79 (s, 2H), 3.88 (s, 3H), 3.77 (s, 6H); m/z (ESI+) 446.1 (M + H)$^+$. | A |

TABLE 11-continued

| Example Number | Structure/IUPAC Name | Analytical Data | Sulfonamide Formation Method |
|---|---|---|---|
| 24 | 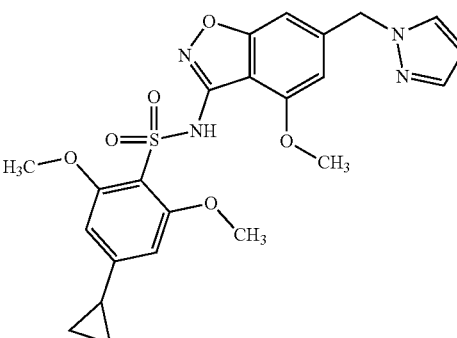<br>4-cyclopropyl-2,6-dimethoxy-N-{4-methoxy-6-[(1H-pyrazol-1-yl)methyl]-1,2-benzoxazol-3-yl}benzene-1-sulfonamide | $^1$H NMR (400 MHz, DMSO-$d_6$) δ 8.58 (br. s, 1H), 7.87 (d, J = 2.3 Hz, 1H), 7.50 (d, J = 1.9 Hz, 1H), 6.78 (s, 1H), 6.72 (s, 1H), 6.39 (s, 2H), 6.30 (t, J = 2.1 Hz, 1H), 5.43 (s, 2H), 3.89 (s, 3H), 3.72 (s, 6H), 2.00-1.83 (m, 1H), 1.03-0.90 (m, 2H), 0.87-0.68 (m, 2H); m/z (ESI+) 485.1 (M + H)$^+$. | A |
| 25 | 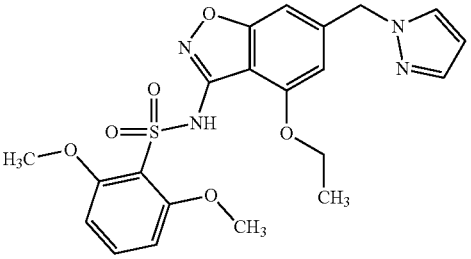<br>N-{4-ethoxy-6-[(1H-pyrazol-1-yl)methyl]-1,2-benzoxazol-3-yl}-2,6-dimethoxybenzene-1-sulfonamide | $^1$H NMR (400 MHz, DMSO-$d_6$) δ 9.34 (br. s, 1H), 7.89 (d, J = 2.0 Hz, 1H), 7.53-7.48 (m, 2H), 6.83 (s, 1H), 6.78 (d, J = 8.5 Hz, 2H), 6.75 (s, 1H), 6.31 (t, J = 2.1 Hz, 1H), 5.45 (s, 2H), 4.20 (q, J = 7.0 Hz, 2H), 3.75 (s, 6H), 1.38 (t, J = 7.0 Hz, 3H); m/z (ESI+) 459.1 (M + H)$^+$. | A |
| 26 | 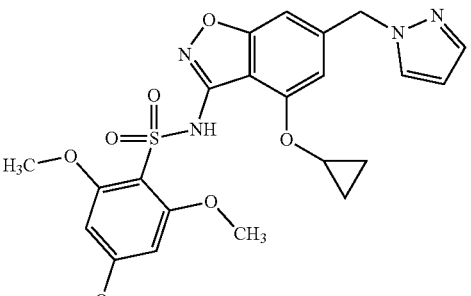<br>N-{4-(cyclopropyloxy)-6-[(1H-pyrazol-1-yl)methyl]-1,2-benzoxazol-3-yl}-2,4,6-trimethoxybenzene-1-sulfonamide | $^1$H NMR (400 MHz, CDCl$_3$) δ 7.99 (s, 1H), 7.59 (s, 1H), 7.48 (br. s, 1H), 6.77 (s, 2H), 6.34 (s, 1H), 6.08 (s, 2H), 5.42 (s, 2H), 3.90-3.83 (m, 7H), 3.81 (s, 3H), 0.92-0.86 (m, 4H); m/z (APCI+) 501.2 (M + H)$^+$. | A |

TABLE 11-continued

| Example Number | Structure/IUPAC Name | Analytical Data | Sulfonamide Formation Method |
|---|---|---|---|
| 27 | 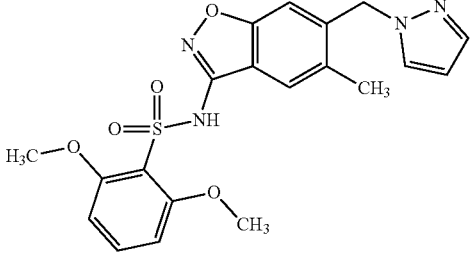<br>2,6-dimethoxy-N-{5-methyl-6-[(1H-pyrazol-1-yl)methyl]-1,2-benzoxazol-3-yl}benzene-1-sulfonamide | $^1$H NMR (400 MHz, DMSO-$d_6$) δ 11.30 (s, 1H), 7.83 (s, 1H), 7.79 (d, J = 2.2 Hz, 1H), 7.51 (d, J = 1.2 Hz, 1H), 7.46 (t, J = 8.5 Hz, 1H), 6.86 (s, 1H), 6.73 (d, J = 8.4 Hz, 2H), 6.32 (t, J = 2.0 Hz, 1H), 5.47 (s, 2H), 3.74 (s, 6H), 2.35 (s, 3H); m/z (ESI+) 429.1 (M + H)$^+$. | A |
| 28 | 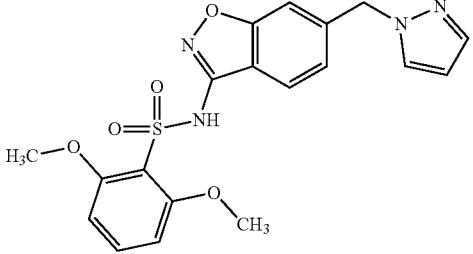<br>2,6-dimethoxy-N-{6-[(1H-pyrazol-1-yl)methyl]-1,2-benzoxazol-3-yl}benzene-1-sulfonamide | $^1$H NMR (400 MHz, DMSO-$d_6$) δ 11.41 (s, 1H), 8.01 (d, J = 8.3 Hz, 1H), 7.87 (d, J = 2.3 Hz, 1H), 7.49 (s, 1H), 7.46 (t, J = 8.5 Hz, 1H), 7.33 (s, 1H), 7.18 (d, J = 8.3 Hz, 1H), 6.72 (d, J = 8.5 Hz, 2H), 6.29 (t, J = 2.1 Hz, 1H), 5.49 (s, 2H), 3.72 (s, 6H); m/z (ESI+) 415.1 (M + H)$^+$. | A |
| 29 | 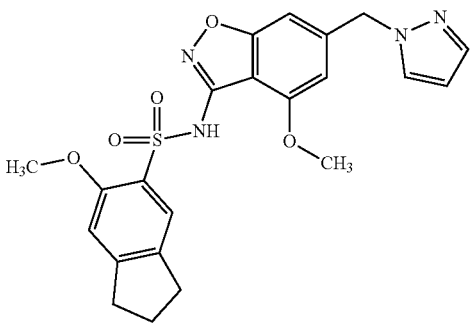<br>6-methoxy-N-{4-methoxy-6-[(1H-pyrazol-1-yl)methyl]-1,2-benzoxazol-3-yl}-2,3-dihydro-1H-indene-5-sulfonamide | $^1$H NMR (400 MHz, DMSO-$d_6$) δ 9.74 (s, 1H), 7.86 (d, J = 1.8 Hz, 1H), 7.63 (s, 1H), 7.49 (d, J = 1.3 Hz, 1H), 7.07 (s, 1H), 6.82 (s, 1H), 6.74 (s, 1H), 6.29 (t, J = 2.1 Hz, 1H), 5.43 (s, 2H), 3.86 (s, 3H), 3.76 (s, 3H), 2.89 (t, J = 7.5 Hz, 2H), 2.83 (t, J = 7.3 Hz, 2H), 2.07-1.96 (m, 2H); m/z (ESI+) 454.9 (M + H)$^+$. | A |
| 30 | 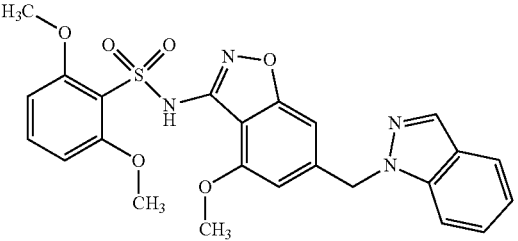<br>N-(6-((1H-indazol-1-yl)methyl)-4-methoxybenzo[d]isoxazol-3-yl)-2,6-dimethoxybenzenesulfonamide | $^1$H NMR (400 MHz, DMSO-d6) δ 9.60 (br s, 1H), 8.16 (s, 1H), 7.80 (d, J = 8.1 Hz, 1H), 7.72 (d, J = 8.4 Hz, 1H), 7.50-7.36 (m, 2H), 7.16 (t, J = 7.5 Hz, 1H), 6.81 (s, 2H), 6.75 (d, J = 8.4 Hz, 1H), 6.77-6.70 (m, 1H), 5.77 (s, 2H), 3.85 (s, 3H), 3.74 (s, 6H); m/z 495.0 (M + H)$^+$. | A |

TABLE 11-continued

| Example Number | Structure/IUPAC Name | Analytical Data | Sulfonamide Formation Method |
|---|---|---|---|
| 31 | 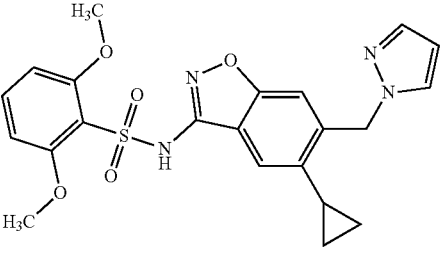<br>N-[5-cyclopropyl-6-(1H-pyrazol-1-ylmethyl)-1,2-benzoxazol-3-yl]-2,6-dimethoxybenzenesulfonamide | $^1$H NMR (400 MHz, DMSO-$d_6$) δ 11.29 (s, 1H), 7.84 (d, J = 2.1 Hz, 1H), 7.80 (s, 1H), 7.52 (d, J = 1.3 Hz, 1H), 7.46 (t, J = 8.5 Hz, 1H), 6.79 (s, 1H), 6.73 (d, J = 8.4 Hz, 2H), 6.33 (t, J = 2.1 Hz, 1H), 5.65 (s, 2H), 3.73 (s, 6H), 2.10-2.00 (m, 1H), 1.01-0.95 (m, 2H), 0.63-0.57 (m, 2H); m/z 455.2 (M + H)$^+$. | A |
| 32 | 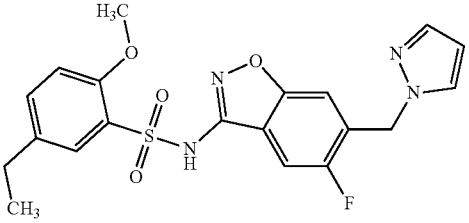<br>5-ethyl-N-[5-fluoro-6-(1H-pyrazol-1-ylmethyl)-1,2-benzoxazol-3-yl]-2-methoxybenzenesulfonamide | $^1$H NMR (400 MHz, DMSO-$d_6$) δ 11.68 (s, 1H), 7.84 (d, J = 2.2 Hz, 1H), 7.81 (d, J = 9.3 Hz, 1H), 7.69 (d, J = 2.2 Hz, 1H), 7.48 (d, J = 1.3 Hz, 1H), 7.45 (dd, J = 2.1, 8.6 Hz, 1H), 7.28 (d, J = 5.3 Hz, 1H), 7.08 (d, J = 8.4 Hz, 1H), 6.29 (t, J = 2.1 Hz, 1H), 5.50 (s, 2H), 3.70 (s, 3H), 2.60 (q, J = 7.5 Hz, 2H), 1.14 (t, J = 7.6 Hz, 3H); m/z 431.1 (M + H)$^+$. | A |
| 33 | 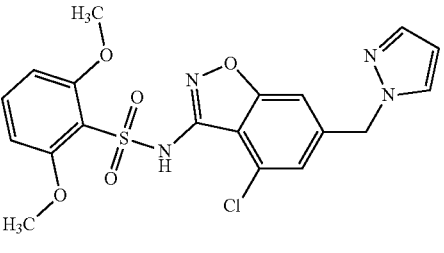<br>N-[4-chloro-6-(1H-pyrazol-1-ylmethyl)-1,2-benzoxazol-3-yl]-2,6-dimethoxybenzenesulfonamide | $^1$H NMR (400 MHz, DMSO-$d_6$) δ 10.20 (br. s, 1H), 7.92 (s, 1H), 7.57-7.50 (m, 2H), 7.47 (s, 1H), 7.27 (s, 1H), 6.79 (d, J = 8.4 Hz, 2H), 6.32 (s, 1H), 5.51 (s, 2H), 3.75 (s, 6H); m/z 449.0 (M + H)$^+$. | A |
| 34 | 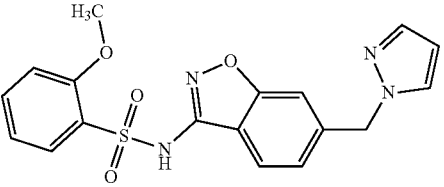<br>2-methoxy-N-[6-(1H-pyrazol-1-ylmethyl)-1,2-benzoxazol-3-yl]benzenesulfonamide | $^1$H NMR (400 MHz, DMSO-$d_6$) δ 11.69 (br. s, 1H), 7.88-7.80 (m, 3H), 7.51 (br. s, 1H), 7.47 (d, J = 1.3 Hz, 1H), 7.30-7.19 (m, 1H), 7.09 (br. t, J = 7.4 Hz, 2H), 7.05-6.96 (m, 1H), 6.28 (t, J = 2.0 Hz, 1H), 5.45 (s, 2H), 3.72 (s, 3H); m/z 385.1 (M + H)$^+$. | C |

TABLE 11-continued

| Example Number | Structure/IUPAC Name | Analytical Data | Sulfonamide Formation Method |
|---|---|---|---|
| 35 | 2,4-dimethoxy-N-[6-(1H-pyrazol-1-ylmethyl)-1,2-benzoxazol-3-yl]benzenesulfonamide | $^1$H NMR (400 MHz, DMSO-$d_6$) δ 7.82 (d, J = 2.2 Hz, 1H), 7.70 (d, J = 8.4 Hz, 1H), 7.56 (br. s, 1H), 7.46 (d, J = 1.7 Hz, 1H), 7.04 (br. s, 1H), 6.96 (br. s, 1H), 6.46 (br. s, 2H), 6.28-6.25 (m, 1H), 5.41 (s, 2H), 3.75 (s, 3H), 3.66 (s, 3H); m/z 415.1 (M + H)$^+$ | C |
| 36 | 5-chloro-2-methoxy-N-[6-(1H-pyrazol-1-ylmethyl)-1,2-benzoxazol-3-yl]benzenesulfonamide | $^1$H NMR (400 MHz, DMSO-$d_6$) δ 11.95 (br. s, 1H), 7.89-7.74 (m, 3H), 7.56 (br. d, J = 8.9 Hz, 1H), 7.49-7.45 (m, 1H), 7.32-7.19 (m, 1H), 7.12 (br. t, J = 7.3 Hz, 2H), 6.27 (t, J = 2.1 Hz, 1H), 5.45 (s, 2H), 3.72 (s, 3H); m/z 419.1 (M + H)$^+$. | C |
| 37 | 2-methoxy-5-(methoxymethyl)-N-[6-(1H-pyrazol-1-ylmethyl)-1,2-benzoxazol-3-yl]benzenesulfonamide | $^1$H NMR (400 MHz, DMSO-$d_6$) δ 11.70 (s, 1H), 7.91-8.05 (m, 1H), 7.85 (d, J = 2.0 Hz, 1H), 7.81 (d, J = 2.2 Hz, 1H), 7.49-7.56 (m, 1H), 7.48 (d, J = 1.7 Hz, 2H), 7.28-7.36 (m, 1H), 7.08-7.20 (m, 2H), 6.29 (t, J = 2.0 Hz, 1H), 5.47 (s, 2H), 4.38 (s, 2H), 3.74 (s, 3H), 3.25 (s, 3H); m/z 429.2 (M + H)$^+$. | C |
| 38 | 2-methoxy-4-methyl-N-[6-(1H-pyrazol-1-ylmethyl)-1,2-benzoxazol-3-yl]benzenesulfonamide | $^1$H NMR (400 MHz, DMSO-$d_6$) δ 7.81 (d, J = 1.7 Hz, 1H), 7.63 (d, J = 7.8 Hz, 1H), 7.56 (d, J = 7.9 Hz, 1H), 7.46 (d, J = 1.1 Hz, 1H), 7.03 (s, 1H), 6.95 (d, J = 8.1 Hz, 1H), 6.75 (s, 1H), 6.67 (d, J = 8.1 Hz, 1H), 6.26 (t, J = 2.0 Hz, 1H), 5.40 (s, 2H), 3.64 (s, 3H), 2.27 (s, 3H); m/z 399.2 (M + H)$^+$. | C |

TABLE 11-continued

| Example Number | Structure/IUPAC Name | Analytical Data | Sulfonamide Formation Method |
|---|---|---|---|
| 39 | 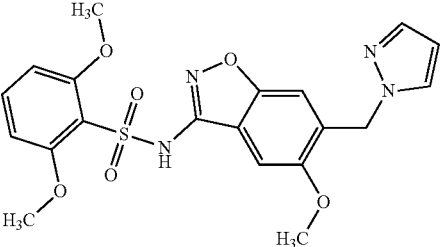<br>2,6-dimethoxy-N-[5-methoxy-6-(1H-pyrazol-1-ylmethyl)-1,2-benzoxazol-3-yl]benzenesulfonamide | $^1$H NMR (400 MHz, DMSO-d$_6$) δ 11.29 (br. s, 1H), 7.81 (d, J = 2.0 Hz, 1H), 7.62 (s, 1H), 7.52-7.41 (m, 2H), 6.79 (s, 1H), 6.73 (d, J = 8.6 Hz, 2H), 6.30 (t, J = 2.0 Hz, 1H), 5.39 (s, 2H), 3.85 (s, 3H), 3.73 (s, 6H); m/z 445.0 (M + H)$^+$. | A |
| 40 | 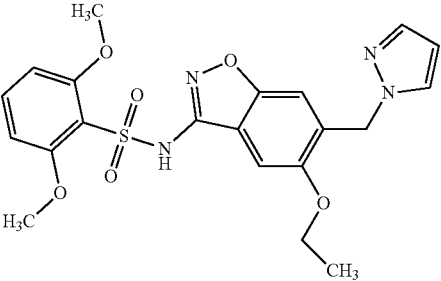<br>N-[5-ethoxy-6-(1H-pyrazol-1-ylmethyl)-1,2-benzoxazol-3-yl]-2,6-dimethoxybenzenesulfonamide | $^1$H NMR (400 MHz, CDCl$_3$) δ 8.12 (br. s, 1H), 7.49 (d, J = 1.4 Hz, 1H), 7.45 (s, 1H), 7.43 (d, J = 2.0 Hz, 1H), 7.32 (t, J = 8.5 Hz, 1H), 6.79 (s, 1H), 6.53 (d, J = 8.6 Hz, 2H), 6.23 (t, J = 1.9 Hz, 1H), 5.35 (s, 2H), 4.16-4.01 (m, 2H), 3.89-3.75 (m, 6H), 1.41 (t, J = 6.9 Hz, 3H); m/z 459.1 (M + H)$^+$. | A |
| 41 | 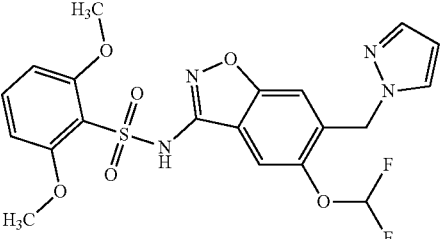<br>N-[5-(difluoromethoxy)-6-(1H-pyrazol-1-ylmethyl)-1,2-benzoxazol-3-yl]-2,6-dimethoxybenzenesulfonamide | $^1$H NMR (400 MHz, DMSO-d$_6$) δ 11.55 (s, 1H), 8.00 (s, 1H), 7.85 (d, J = 2.0 Hz, 1H), 7.51 (d, J = 1.3 Hz, 1H), 7.48 (t, J = 8.4 Hz, 1H), 7.38-6.94 (m, 2H), 6.74 (d, J = 8.5 Hz, 2H), 6.32 (t, J = 2.1 Hz, 1H), 5.48 (s, 2H), 3.73 (s, 6H); m/z 481.1 (M + H)$^+$. | B |
| 42 | 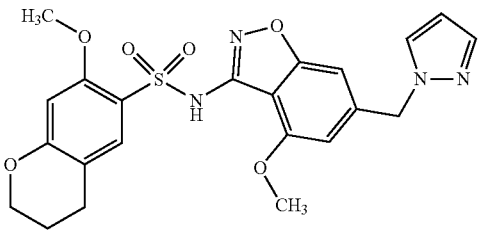<br>7-methoxy-N-[4-methoxy-6-(1H-pyrazol-1-ylmethyl)-1,2-benzoxazol-3-yl]-3,4-dihydro-2H-chromene-6-sulfonamide | $^1$H NMR (400 MHz, CDCl$_3$) δ 7.99 (br. s, 1H), 7.80 (s, 1H), 7.56 (s, 1H), 7.43 (d, J = 1.8 Hz, 1H), 6.77 (s, 1H), 6.43 (s, 1H), 6.31 (br. d, J = 7.5 Hz, 2H), 5.37 (s, 2H), 4.25-4.13 (m, 2H), 3.95 (s, 3H), 3.80 (s, 3H), 2.75 (br. t, J = 6.3 Hz, 2H), 2.02-1.92 (m, 2H); m/z 471.1 (M + H)$^+$. | B |

TABLE 11-continued

| Example Number | Structure/IUPAC Name | Analytical Data | Sulfonamide Formation Method |
|---|---|---|---|
| 43 | 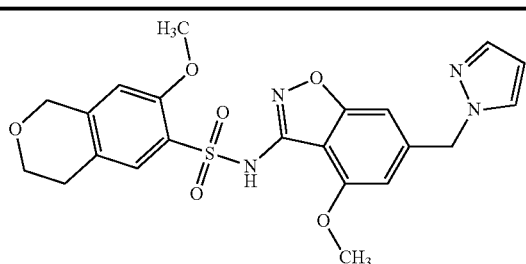<br>7-methoxy-N-[4-methoxy-6-(1H-pyrazol-1-ylmethyl)-1,2-benzoxazol-3-yl]-3,4-dihydro-1H-isochromene-6-sulfonamide | $^1$H NMR (400 MHz, DMSO-d$_6$) δ 10.02 (br. s, 1H), 7.88 (d, J = 2.0 Hz, 1H), 7.58 (s, 1H), 7.50 (d, J = 1.3 Hz, 1H), 7.23-7.08 (m, 1H), 6.94-6.63 (m, 2H), 6.30 (t, J = 2.0 Hz, 1H), 5.43 (s, 2H), 4.68 (s, 2H), 3.89-3.85 (m, 2H), 3.85 (s, 3H), 3.72 (s, 3H), 2.75 (br. s, 2H); m/z 471.1 (M + H)$^+$. | B |
| 44 | 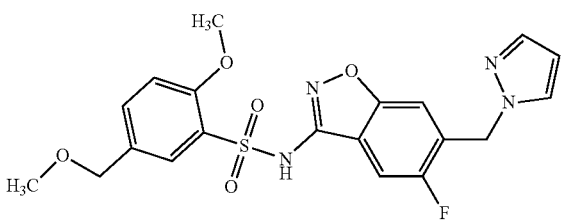<br>N-[5-fluoro-6-(1H-pyrazol-1-ylmethyl)-1,2-benzoxazol-3-yl]-2-methoxy-5-(methoxymethyl)benzenesulfonamide | $^1$H NMR (400 MHz, DMSO-d$_6$) δ 11.75 (s, 1H), 7.85-7.79 (m, 3H), 7.54 (dd, J = 1.5, 8.2 Hz, 1H), 7.48 (d, J = 1.2 Hz, 1H), 7.28 (br. d, J = 4.9 Hz, 1H), 7.15 (d, J = 8.6 Hz, 1H), 6.29 (t, J = 2.1 Hz, 1H), 5.50 (s, 2H), 4.39 (s, 2H), 3.74 (s, 3H), 3.25 (s, 3H); m/z 447.1 (M + H)$^+$. | A |

Example 45: Preparation of 2-methoxy-N-{4-methoxy-6-[(1H-pyrazol-1-yl)methyl]-1,2-benzoxazol-3-yl}benzene-1-sulfonamide According to Scheme C (Route A)

Scheme C

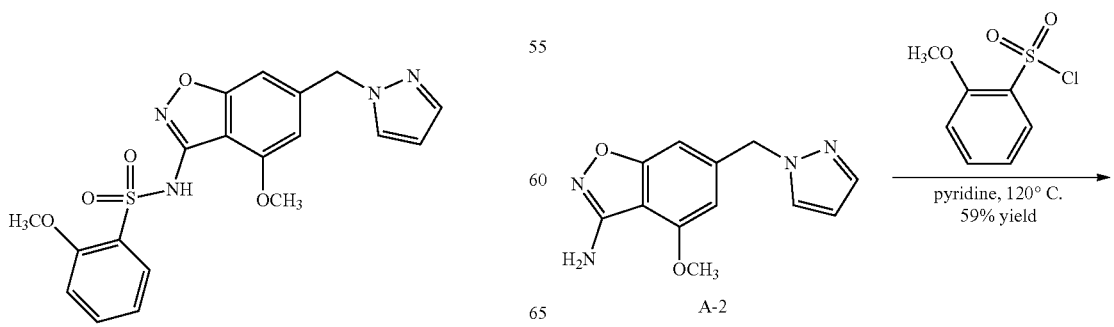

-continued

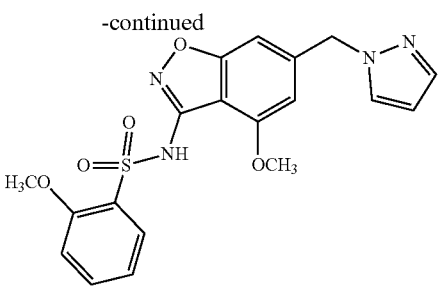

Example 45

-continued

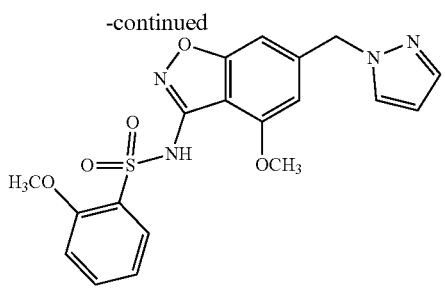

Example 45

To a suspension of 4-methoxy-6-[(1H-pyrazol-1-yl)methyl]-1,2-benzoxazol-3-amine (A-2) (2.5 g, 10 mmol) in pyridine (8.0 mL) was added 2-methoxybenzene-1-sulfonyl chloride (3.17 g, 15.4 mmol). The reaction was stirred at 120° C. for 1.5 h. The mixture was cooled to room temperature and diluted with MeOH. The resultant suspension was filtered. and the filter cake was washed with MeOH (30 mL). The solids were dissolved in DCM (50 mL) and MeOH (30 mL) was added. The DCM was removed under vacuum and the precipitate was collected by filtration. The filter cake was dried by lyophilization to provide 2-methoxy-N-{4-methoxy-6-[(1H-pyrazol-1-yl)methyl]-1,2-benzoxazol-3-yl}benzene-1-sulfonamide (Example 45) (2.5 g, 59% yield) as a white solid. $^1$H NMR (400 MHz, DMSO-$d_6$) δ 10.18 (s, 1H), 7.87 (d, J=2.0 Hz, 1H), 7.80 (dd, J=1.6, 7.9 Hz, 1H), 7.66-7.59 (m, 1H), 7.49 (d, J=1.5 Hz, 1H), 7.19 (d, J=8.3 Hz, 1H), 7.09 (t, J=7.7 Hz, 1H), 6.83 (s, 1H), 6.74 (s, 1H), 6.30 (t, J=2.0 Hz, 1H), 5.44 (s, 2H), 3.82 (s, 3H), 3.78 (s, 3H); m/z (ESI+) 415.0 (M+H)$^+$.

Example 45: Alternative preparation of 2-methoxy-N-{4-methoxy-6-[(1H-pyrazol-1-yl)methyl]-1,2-benzoxazol-3-yl}benzene-1-sulfonamide According to Scheme D

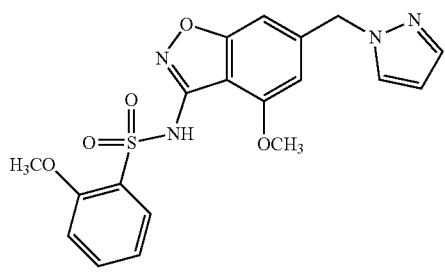 [SMILES: COc1ccccc1S(=O)(=O)Nc1noc2cc(Cn3cccn3)cc(OC)c12]

Scheme D

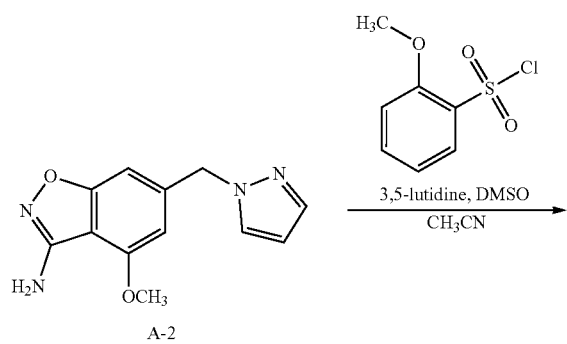

A 100 mL reactor equipped with an overhead stirrer was charged with 4-methoxy-6-(1H-pyrazol-1-ylmethyl)-1,2-benzoxazol-3-amine (A-2) (10.00 g, 40.94 mmol), 2-methoxybenzenesulfonyl chloride (10.15 g, 49.13 mmol), and acetonitrile (100 mL). The resulting suspension was stirred at 25° C. for 55 minutes. Via pipette, dimethylsulfoxide (0.36 mL, 4.09 mmol) was added in one portion. Via syringe, 3,5-lutidine (14.8 mL, 122.82 mmol) was added dropwise over 15 minutes. The resulting light-yellow suspension was stirred at 25° C. for 18 hours to reach >98% conversion as judged by LCMS. The reaction mixture was acidified with 1 M aq. HCl (100 mL), then concentrated to ~80 mL (rotary evaporator, 40° C., 85 mbar). The slurry was treated with additional 1 M aq. HCl (40 mL) to rinse down the walls of the vessel, then stirred at 20° C. for 2.5 hours. The resulting precipitate was collected by suction filtration. The filter cake was washed with water (2×50 mL), then dried under vacuum at 35° C. for 48 hours, affording crude 2-methoxy-N-{4-methoxy-6-[(1H-pyrazol-1-yl)methyl]-1,2-benzoxazol-3-yl}benzene-1-sulfonamide (Example 45) (15.2 g, 90% yield, 98% purity by LCMS) as a solid. m/z 415.1 (M+H)$^+$.

To purify the crude product, a suspension of crude 2-methoxy-N-{4-methoxy-6-[(1H-pyrazol-1-yl)methyl]-1,2-benzoxazol-3-yl}benzene-1-sulfonamide (Example 45) (14.00 g, 33.78 mmol) in dichloromethane (210 mL) was heated in a 40° C. bath until a clear solution was obtained (10 minutes). The mixture was filtered, and the filtrate returned to a clean reaction vessel, using additional dichloromethane (70 mL) to quantitate the transfer. Ethyl acetate (140 mL) was added to the solution over 2 minutes, then the mixture stirred for 2.5 hours. No crystallization was observed, so the solution was concentrated under reduced pressure (200 mbar) to remove dichloromethane (volume was reduced by about 70 mL). More ethyl acetate (140 mL) was added to the residue, and the mixture stirred at room temperature for 21 hours. The resulting suspension was concentrated under reduced pressure (40° C., 200 mbar) to about 280 mL, then stirred at room temperature for 3 hours. The solids were collected by filtration, with additional ethyl acetate (70 mL) used to rinse the reaction vessel and filter cake. The filter cake was dried in a vacuum oven at 35° C. for 23 hours, affording 2-methoxy-N-{4-methoxy-6-[(1H-pyrazol-1-yl)methyl]-1,2-benzoxazol-3-yl}benzene-1-sulfonamide (Example 45) (12.0 g, 85% yield, 97.9% purity by UPLC, no single impurity larger than 0.5%) as a solid. m/z 415.1 (M+H)$^+$.

To purify further, a suspension of 2-methoxy-N-{4-methoxy-6-[(1H-pyrazol-1-yl)methyl]-1,2-benzoxazol-3-yl}benzene-1-sulfonamide (Example 45) (2.0 g, 4.73 mmol) in acetone (80 mL) was heated to reflux (bath temperature 55° C.) with stirring for 2 hours. While the mixture was still heated, ethyl acetate (30 mL) was added slowly, so that the internal temperature remained above 45° C. The resulting slurry was concentrated to about 30 mL under mild vacuum (bath temp 65° C.), then cooled slowly at a rate of 1° C./min to 20° C. (~31 minutes). The resulting precipitate was collected by suction filtration. The filter cake dried under vacuum at 50° C. for 22 hours, yielding 2-methoxy-N-{4-methoxy-6-[(1H-pyrazol-1-yl)methyl]-1,2-benzoxazol-3-yl}benzene-1-sulfonamide (Example 45) (1.825 g, 93% yield, 99.5% purity by UPLC) as a crystalline solid. $^1$H NMR (400 MHz, CHLOROFORM-d) b 8.14 (dd, J=1.7, 7.8 Hz, 1H), 8.04 (s, 1H), 7.59-7.51 (m, 2H), 7.44 (d, J=2.2 Hz, 1H), 7.14-7.06 (m, 1H), 6.95 (d, J=8.3 Hz, 1H), 6.78 (d, J=0.6 Hz, 1H), 6.45 (s, 1H), 6.32 (t, J=2.1 Hz, 1H), 5.38 (s, 2H), 3.97 (s, 3H), 3.91 (s, 3H).

Example 45b: Preparation of 2-methoxy-N-{4-methoxy-6-[(1H-pyrazol-1-yl)methyl]-1,2-benzoxazol-3-yl}benzene-1-sulfonamide anhydrous free base (Form 1) According to Scheme C-1 (Route B)

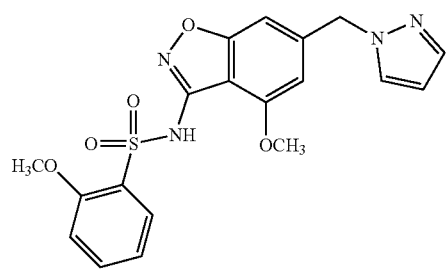 [SMILES: COc1ccccc1S(=O)(=O)Nc1noc2cc(Cn3cccn3)cc(OC)c12]

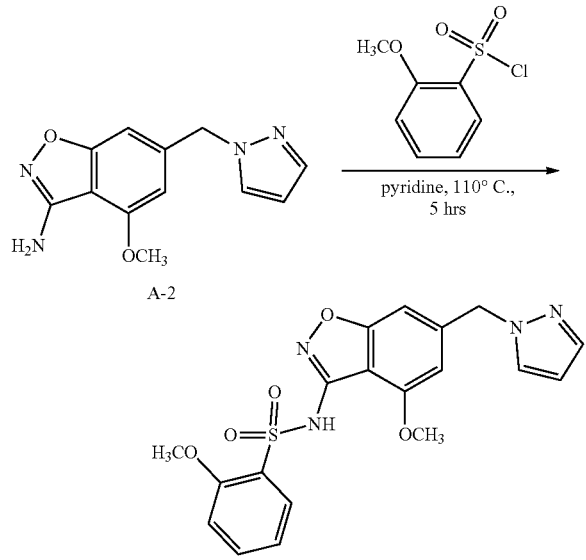

Scheme C-1

Example 45

2-methoxybenzene-1-sulfonyl chloride (7.6 g, 37 mmol) was placed in a 2-neck round bottom flask equipped with an internal thermometer. 4-methoxy-6-[(1H-pyrazol-1-yl)methyl]-1,2-benzoxazol-3-amine (A-2) (8.18 g, 33.5 mmol) was added and the contents dissolved in pyridine (55 mL, 0.6 M) with gentle heating. Heating was initiated with an oil bath temperature of 110° C. and internal temperature of 101° C. After 5 h of heating, the reaction was complete as determined by LCMS analysis. The reaction was cooled to room temperature and partitioned between DCM (200 mL), 6 N HCl (100 mL) and ice water (100 mL). The product was extracted into DCM (×3) and the combined DCM extract was washed with 1 N HCl (×3) to remove traces of pyridine. The DCM extract was dried over MgSO$_4$ and concentrated to a dark oil. The oil was purified via flash chromatography eluting with a gradient of 40-100% EtOAc in heptane to afford 4.6 g of the product, which was confirmed by NMR. The 4.6 g of the product was recrystallized by first dissolving in CH$_3$CN (60 mL) at reflux until most of the solids had dissolved. This hot solution was filtered using a pre-heated/hot glass funnel fitted with fluted filter paper. This step removes any inorganic or silica gel impurities. The filter paper was washed with small portions of CH$_3$CN adding up to a total wash volume of 10 mL. The filtrate was collected in a 250 mL beaker equipped with a stir bar. MTBE (45 mL) was added to the hot filtrate and stirring was initiated. After 30 seconds of stirring, a white precipitate began to form. Stirring was continued at 400 rpm while a gentle stream of N$_2$ gas was forced across the top of the solution to help speed up the evaporation process. The forced N$_2$ evaporation was continued for 3 h until the total volume was 50 mL. The white solid was filtered washing with MTBE (×2) and heptane (×2). The white powder was placed in a 3-inch diameter crystallizing dish, covered with piece of filter paper and heated in a 70° C. vacuum oven for 48 h using a slow flow of N$_2$ in and out of the drying oven to aid the drying process. After drying, 3.9 g of crystalline product was obtained, which was confirmed by NMR. Melting point=203-204° C. Anal. Calcd for C$_{19}$H$_{18}$N$_4$O$_5$S: C, 55.06; H, 4.38; N, 13.52. Found: C, 55.09; H, 4.41; N, 13.57.

The crystalline solid prepared above as anhydrous (Form 1) was further characterized by powder X-ray diffraction (PXRD). Powder X-ray diffraction analysis was conducted on a Bruker A25 D8 Advance Powder X-Ray diffractometer fitted with, a theta-2theta goniometer, and a Lynxeye detector with a PSD window size of 3.3°, primary soller slit set to 2.5° and divergence slits were set at 0.6 mm constant illumination. The X-ray tube voltage and amperage were set to 40 kV and 40 mA respectively. Data was collected at the Copper wavelength using a step size of 0.02 degrees, a step time of 0.3 s from 3.0 to 40.0° 2-theta. The sample was prepared by placing the powder in Si low background cavity holder. The sample powder was pressed using a spatula to ensure that a proper sample height was achieved. Data were collected using Bruker DIFFRAC software and analysis was performed by DIFFRAC EVA software. The PXRD patterns collected were imported into Bruker DIFFRAC EVA software. The peak selection carried out utilizing the software's "peak search function" and then was carefully checked and corrected to ensure that all peak positions had been accurately assigned. Peaks with a relative intensity 4.0% were chosen. A typical error of ±0.2° 2-theta in peak positions applies to this data. The minor error associated with this measurement can occur because of a variety of factors including: (a) sample preparation (e.g., sample height), (b) instrument, (c) calibration, (d) operator (including those errors present when determining the peak locations), and (e) the nature of the material (e.g. preferred orientation and transparency errors). Therefore, peaks are considered to have a typical associated error of ±0.2° 2-theta. When two peaks, in the list, are considered to overlap the less intense peak has been removed from the listing. Peaks existing as shoulders, on a higher intensity adjacent peak, have also been removed from the peak list. While the shoulders may be >0.2° 2-theta from the position of the adjacent peak, they are not considered as discernible from the adjacent peak.

To obtain the absolute peak positions, the powder pattern should be aligned against a reference. This could either be the simulated powder pattern from the crystal structure of the same form solved at room temperature, or an internal standard e.g. silica or corundum. Simulated powder pattern of 2-methoxy-N-{4-methoxy-6-[(1H-pyrazol-1-yl)methyl]-1,2-benzoxazol-3-yl}benzene-1-sulfonamide anhydrous (Form 1) was obtained from a single crystal structure. To prepare the single crystal 200 mg of the material of Example 45b was dissolved in $CH_3CN$ (3 mL) while heating to reflux. MTBE (2 mL) was added and the mixture was allowed to sit in a test tube open to the air for 48 h, resulting in slow evaporation of the solvents. Large crystals formed, which were filtered and rinsed with MTBE (×2) and heptane (×2) and dried under vacuum. 116 mg (58% recovery) of the material of Example 45b was obtained as a crystalline, white solid as confirmed by $^1H$ NMR. The crystals, visualized by polarized light microscopy, showed large particle size and were triclinic in shape. A simulated powder pattern from the single crystal structure was obtained via a calculation using Mercury 4.1.0 which is part of the CCDC Software Suite.

The PXRD pattern of 2-methoxy-N-{4-methoxy-6-[(1H-pyrazol-1-yl)methyl]-1,2-benzoxazol-3-yl}benzene-1-sulfonamide Form 1 anhydrous (Example 45a), is shown in The FIGURE. A PXRD peak list and relative intensity data for 2-methoxy-N-{4-methoxy-6-[(1H-pyrazol-1-yl)methyl]-1,2-benzoxazol-3-yl}benzene-1-sulfonamide anhydrous Form 1 (Example 45a) (2-Theta °) is provided in Table 12 below. Characteristic PXRD peak positions are indicated by an asterisk.

TABLE 12

PXRD peak list for Example 45 Form 1 Anhydrous Free Base.

| Angle °2-theta | % Relative Intensity |
|---|---|
| 6.7 | 47.7 |
| 11.1 | 38.5 |
| 11.4* | 70.9 |
| 11.9 | 31.3 |
| 13.4* | 100.0 |
| 14.1* | 12.3 |
| 15.7 | 4.9 |
| 17.5* | 12.6 |
| 18.1* | 51.5 |
| 20.0 | 51.5 |
| 20.5 | 23.1 |
| 20.9 | 17.3 |
| 21.1 | 13.6 |
| 21.4 | 14.9 |
| 21.9 | 62.6 |
| 22.3 | 15.7 |
| 22.8 | 6.3 |
| 23.7 | 41.4 |
| 23.9 | 53.3 |
| 24.5 | 69.9 |
| 25.3 | 6.5 |
| 26.1 | 19.2 |
| 26.5 | 12.0 |
| 27.6 | 4.2 |
| 28.0 | 5.2 |
| 28.3 | 5.9 |
| 28.6 | 31.9 |
| 29.1 | 11.4 |

One embodiment of the present invention relates to a crystalline form of 2-methoxy-N-{4-methoxy-6-[(1H-pyrazol-1-yl)methyl]-1,2-benzoxazol-3-yl}benzene-1-sulfonamide anhydrous free base, having a powder X-ray diffraction pattern comprising peaks at 2θ values of: 13.4 and 18.1 °2θ±0.2 °2θ, and further comprising at least one peak selected from the 2θ values of: 11.4, 14.1, and 17.5 °2θ±0.2 °2θ.

One embodiment of the present invention relates to a crystalline form of 2-methoxy-N-{4-methoxy-6-[(1H-pyrazol-1-yl)methyl]-1,2-benzoxazol-3-yl}benzene-1-sulfonamide anhydrous free base, having a powder X-ray diffraction pattern comprising peaks at 2θ values of: 13.4 and 18.1 °2θ±0.2 °2θ, and further comprising peaks at the values of: 11.4, 14.1, and 17.5 °2θ±0.2 °2θ.

One embodiment of the present invention relates to a crystalline form of 2-methoxy-N-{4-methoxy-6-[(1H-pyrazol-1-yl)methyl]-1,2-benzoxazol-3-yl}benzene-1-sulfonamide anhydrous free base, having a powder X-ray diffraction pattern comprising peaks at 2θ values of: 11.4, 13.4, 14.1, 17.5 and 18.1 °2θ±0.2 °2θ.

The examples in the table below were synthesized according to the methods used for the synthesis of 5-ethyl-2-methoxy-N-{4-methoxy-6-[(1H-pyrazol-1-yl)methyl]-1,2-benzoxazol-3-yl}benzene-1-sulfonamide (Example 01), 2,6-dimethoxy-N-{4-methoxy-6-[(3-methyl-1H-pyrazol-1-yl)methyl]-1,2-benzoxazol-3-yl}benzene-1-sulfonamide (Example 02), and 2,6-dimethoxy-N-{4-methoxy-6-[(5-methyl-1H-pyrazol-1-yl)methyl]-1,2-benzoxazol-3-yl}benzene-1-sulfonamide (Example 03) and the general sulfonamide formation method C in high-throughput library format. The following examples were synthesized with non-critical changes or substitutions to the exemplified procedures that one skilled in the art would be able to realize.

TABLE 13

| Example Number | Structure/IUPAC Name | Analytical data | Sulfonamide Formation Method |
|---|---|---|---|
| 46 | N-{4-methoxy-6-[(1H-pyrazol-1-yl)methyl]-1,2-benzoxazol-3-yl}-4-(trifluoromethyl)benzene-1-sulfonamide | m/z (ESI+) 453 (M + H)+. | C |
| 47 | 2-methoxy-N-{4-methoxy-6-[(1H-pyrazol-1-yl)methyl]-1,2-benzoxazol-3-yl}-4-methylbenzene-1-sulfonamide | m/z (ESI+) 429 (M + H)+. | C |
| 48 | N-{4-methoxy-6-[(1H-pyrazol-1-yl)methyl]-1,2-benzoxazol-3-yl}-3,5-dimethylbenzene-1-sulfonamide | m/z (ESI+) 413 (M + H)+. | C |

TABLE 13-continued

| Example Number | Structure/IUPAC Name | Analytical data | Sulfonamide Formation Method |
|---|---|---|---|
| 49 | 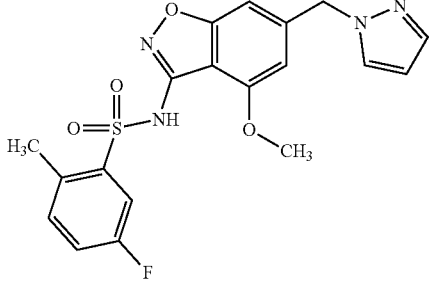<br>5-fluoro-N-{4-methoxy-6-[(1H-pyrazol-1-yl)methyl]-1,2-benzoxazol-3-yl}-2-methylbenzene-1-sulfonamide | m/z (ESI+) 417 (M + H)+. | C |
| 50 | 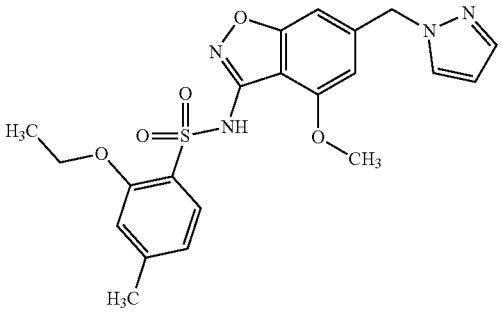<br>2-ethoxy-N-{4-methoxy-6-[(1H-pyrazol-1-yl)methyl]-1,2-benzoxazol-3-yl}-4-methylbenzene-1-sulfonamide | m/z (ESI+) 443 (M + H)+. | C |
| 51 | 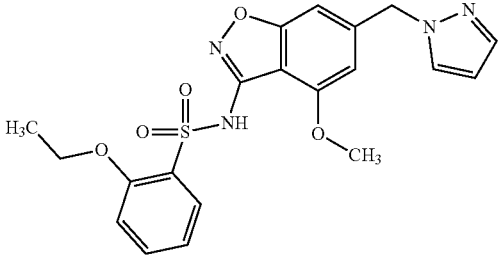<br>2-ethoxy-N-{4-methoxy-6-[(1H-pyrazol-1-yl)methyl]-1,2-benzoxazol-3-yl}benzene-1-sulfonamide | m/z (ESI+) 429 (M + H)+. | C |
| 52 | 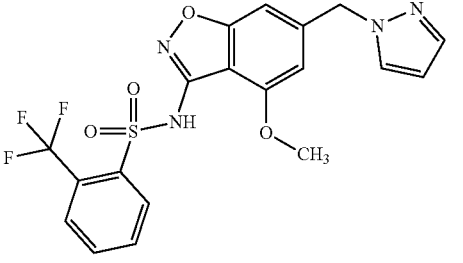<br>N-{4-methoxy-6-[(1H-pyrazol-1-yl)methyl]-1,2-benzoxazol-3-yl}-2-(trifluoromethyl)benzene-1-sulfonamide | m/z (ESI+) 453 (M + H)+. | C |

TABLE 13-continued

| Example Number | Structure/IUPAC Name | Analytical data | Sulfonamide Formation Method |
|---|---|---|---|
| 53 | 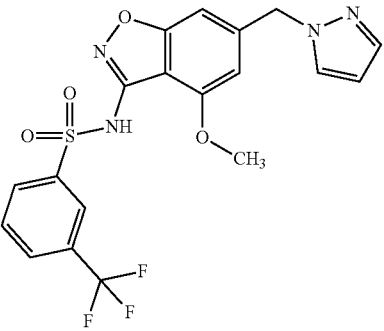<br>N-{4-methoxy-6-[(1H-pryazol-1-yl)methyl]-1,2-benzoxazol-3-yl}-3-(trifluoromethyl)benzene-1-sulfonamide | m/z (ESI+) 453 (M + H)+. | C |
| 54 | 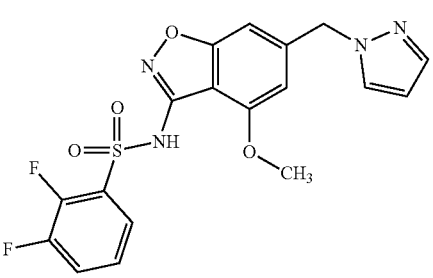<br>2,3-difluoro-N-{4-methoxy-6-[(1H-pyrazol-1-yl)methyl]-1,2-benzoxazol-3-yl}benzene-1-sulfonamide | m/z (ESI+) 421 (M + H)+. | C |
| 55 | 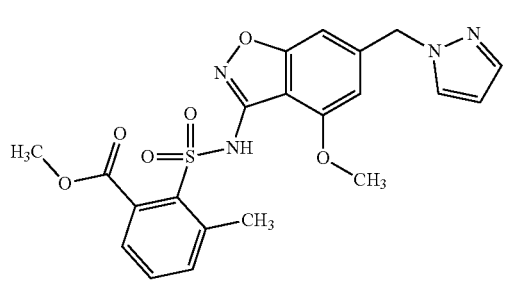<br>methyl 2-({4-methoxy-6-[(1H-pyrazol-1-yl)methyl]-1,2-benzoxazol-3-yl}sulfamoyl)-3-methylbenzoate | m/z (ESI+) 457 (M + H)+. | C |
| 56 | 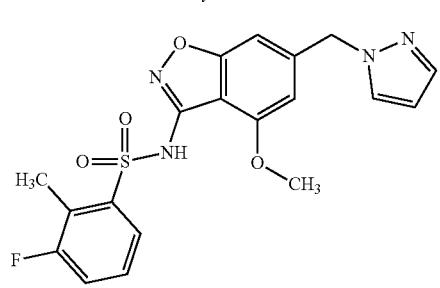<br>3-fluoro-N-{4-methoxy-6-[(1H-pyrazol-1-yl)methyl]-1,2-benzoxazol-3-yl}-2-methylbenzene-1-sulfonamide | m/z (ESI+) 417 (M + H)+. | C |

TABLE 13-continued

| Example Number | Structure/IUPAC Name | Analytical data | Sulfonamide Formation Method |
|---|---|---|---|
| 57 | 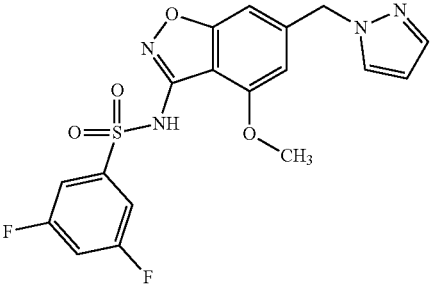<br>3,5-difluoro-N-{4-methoxy-6-[(1H-pyrazol-1-yl)methyl]-1,2-benzoxazol-3-yl}benzene-1-sulfonamide | m/z (ESI+) 421 (M + H)+. | C |
| 58 | 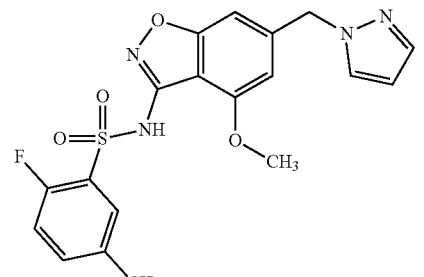<br>2-fluoro-N-{4-methoxy-6-[(1H-pyrazol-1-yl)methyl]-1,2-benzoxazol-3-yl}-5-methylbenzene-1-sulfonamide | m/z (ESI+) 417 (M + H)+. | C |
| 59 | 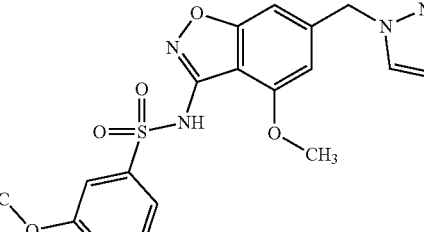<br>3-methoxy-N-{4-methoxy-6-[(1H-pyrazol-1-yl)methyl]-1,2-benzoxazol-3-yl}benzene-1-sulfonamide | m/z (ESI+) 415 (M + H)+. | C |

TABLE 13-continued

| Example Number | Structure/IUPAC Name | Analytical data | Sulfonamide Formation Method |
|---|---|---|---|
| 60 | 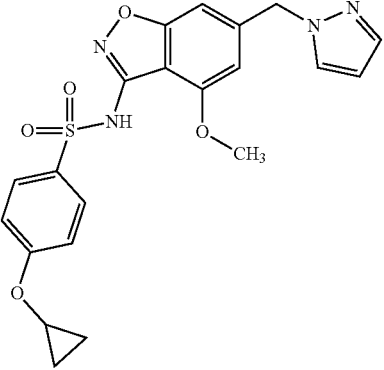　4-(cyclopropyloxy)-N-{4-methoxy-6-[(1H-pyrazol-1-yl)methyl]-1,2-benzoxazol-3-yl}benzene-1-sulfonamide | m/z (ESI+) 441 (M + H)+. | C |
| 61 | 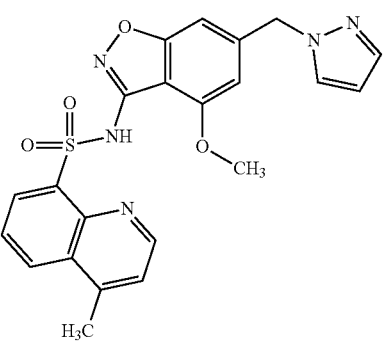　N-{4-methoxy-6-[(1H-pyrazol-1-yl)methyl]-1,2-benzoxazol-3-yl}-4-methylquinoline-8-sulfonamide | m/z (ESI+) 450 (M + H)+. | C |
| 62 | 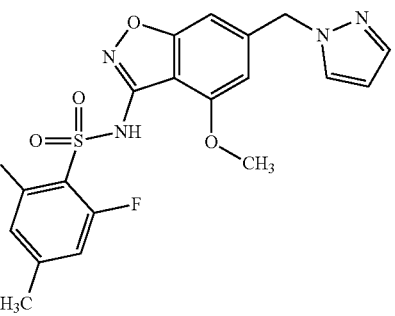　2,6-difluoro-N-{4-methoxy-6-[(1H-pyrazol-1-yl)methyl]-1,2-benzoxazol-3-yl}-4-methylbenzene-1-sulfonamide | m/z (ESI+) 435 (M + H)+. | C |

TABLE 13-continued

| Example Number | Structure/IUPAC Name | Analytical data | Sulfonamide Formation Method |
|---|---|---|---|
| 63 | 2-chloro-3-fluoro-N-{4-methoxy-6-[(1H-pyrazol-1-yl)methyl]-1,2-benzoxazol-3-yl}benzene-1-sulfonamide | m/z (ESI+) 437 (M + H)+. | C |
| 64 | 3,4,5-trifluoro-N-{4-methoxy-6-[(1H-pyrazol-1-yl)methyl]-1,2-benzoxazol-3-yl}benzene-1-sulfonamide | m/z (ESI+) 439 (M + H)+. | C |
| 65 | 2-fluoro-N-{4-methoxy-6-[(1H-pyrazol-1-yl)methyl]-1,2-benzoxazol-3-yl}-4-methylbenzene-1-sulfonamide | m/z (ESI+) 417 (M + H)+. | C |

TABLE 13-continued

| Example Number | Structure/IUPAC Name | Analytical data | Sulfonamide Formation Method |
|---|---|---|---|
| 66 | 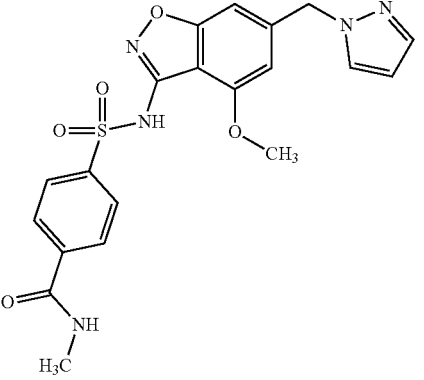<br>4-({4-methoxy-6-[(1H-pyrazol-1-yl)methyl]-1,2-benzoxazol-3-yl}sulfamoyl)-N-methylbenzamide | m/z (ESI+) 442 (M + H)+. | C |
| 67 | 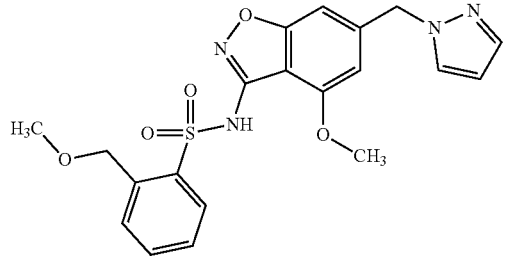<br>2-(methoxymethyl)-N-{4-methoxy-6-[(1H-pyrazol-1-yl)methyl]-1,2-benzoxazol-3-yl}benzene-1-sulfonamide | m/z (ESI+) 429 (M + H)+. | C |
| 68 | 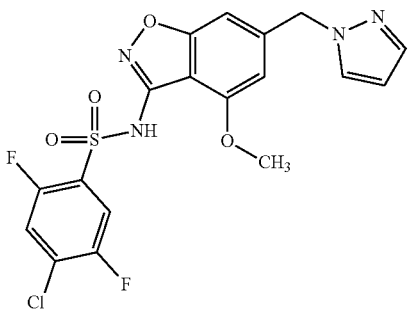<br>4-chloro-2,5-difluoro-N-{4-methoxy-6-[(1H-pyrazol-1-yl)methyl]-1,2-benzoxazol-3-yl}benzene-1-sulfonamide | m/z (ESI+) 455 (M + H)+. | C |

TABLE 13-continued

| Example Number | Structure/IUPAC Name | Analytical data | Sulfonamide Formation Method |
|---|---|---|---|
| 69 | 4-ethoxy-N-{4-methoxy-6-[(1H-pyrazol-1-yl)methyl]-1,2-benzoxazol-3-yl}benzene-1-sulfonamide | m/z (ESI+) 429 (M + H)+. | C |
| 70 | 2-fluoro-N-{4-methoxy-6-[(1H-pyrazol-1-yl)methyl]-1,2-benzoxazol-3-yl}-3-methylbenzene-1-sulfonamide | m/z (ESI+) 417 (M + H)+. | C |
| 71 | 4-chloro-2-methoxy-N-{4-methoxy-6-[(1H-pyrazol-1-yl)methyl]-1,2-benzoxazol-3-yl}benzene-1-sulfonamide | m/z (ESI+) 449 (M + H)+. | C |

TABLE 13-continued

| Example Number | Structure/IUPAC Name | Analytical data | Sulfonamide Formation Method |
|---|---|---|---|
| 72 | 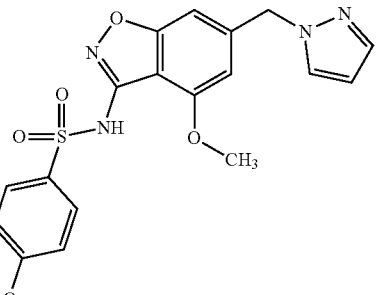<br>N-{4-methoxy-6-[(1H-pyrazol-1-yl)methyl]-1,2-benzoxazol-3-yl}-3,4-dimethylbenzene-1-sulfonamide | m/z (ESI+) 413 (M + H)+. | C |
| 73 | 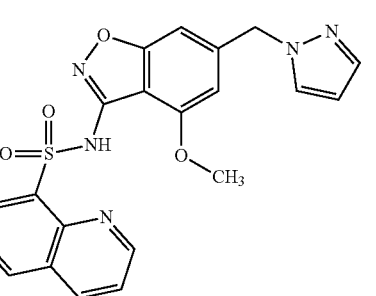<br>N-{4-methoxy-6-[(1H-pyrazol-1-yl)methyl]-1,2-benzoxazol-3-yl}-7-methylquinoline-8-sulfonamide | m/z (ESI+) 450 (M + H)+. | C |
| 74 | 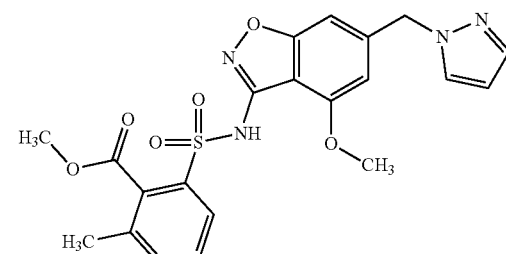<br>methyl 2-({4-methoxy-6-[(1H-pyrazol-1-yl)methyl]-1,2-benzoxazol-3-yl}sulfamoyl)-6-methylbenzoate | m/z (ESI+) 457 (M + H)+. | C |
| 75 | 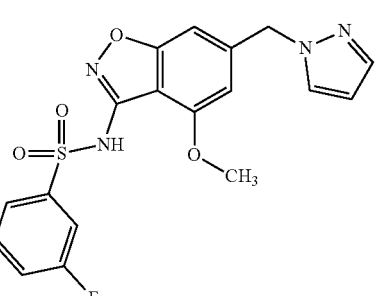<br>3-fluoro-N-{4-methoxy-6-[(1H-pyrazol-1-yl)methyl]-1,2-benzoxazol-3-yl}-5-methylbenzene-1-sulfonamide | m/z (ESI+) 417 (M + H)+. | C |

TABLE 13-continued

| Example Number | Structure/IUPAC Name | Analytical data | Sulfonamide Formation Method |
|---|---|---|---|
| 76 | 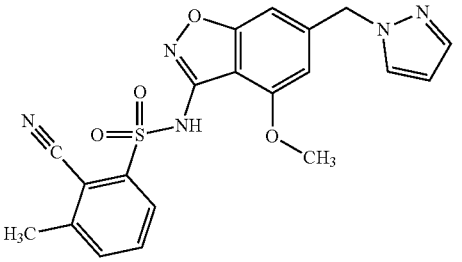

2-cyano-N-{4-methoxy-6-[(1H-pyrazol-1-yl)methyl]-1,2-benzoxazol-3-yl}-3-methylbenzene-1-sulfonamide | m/z (ESI+) 424 (M + H)+. | C |
| 77 | 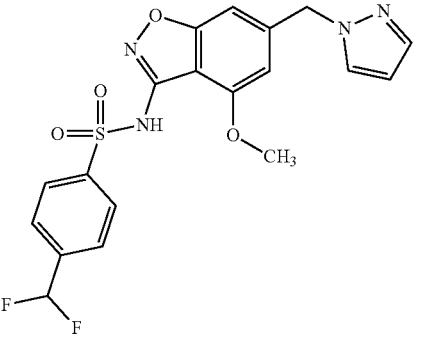

4-(difluoromethyl)-N-{4-methoxy-6-[(1H-pyrazol-1-yl)methyl]-1,2-benzoxazol-3-yl}benzene-1-sulfonamide | m/z (ESI+) 435 (M + H)+. | C |
| 78 | 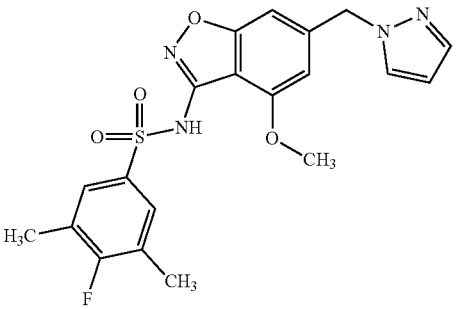

4-fluoro-N-{4-methoxy-6-[(1H-pyrazol-1-yl)methyl]-1,2-benzoxazol-3-yl}-3,5-dimethylbenzene-1-sulfonamide | m/z (ESI+) 431 (M + H)+. | C |

TABLE 13-continued

| Example Number | Structure/IUPAC Name | Analytical data | Sulfonamide Formation Method |
|---|---|---|---|
| 79 | 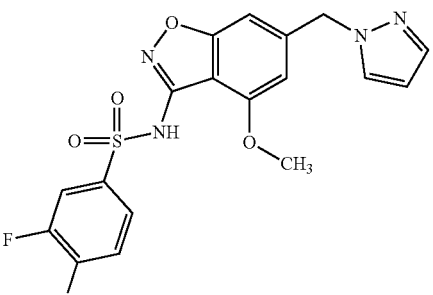<br>3-fluoro-N-{4-methoxy-6-[(1H-pyrazol-1-yl)methyl]-1,2-benzoxazol-3-yl}-4-methylbenzene-1-sulfonamide | m/z (ESI+) 417 (M + H)+. | C |
| 80 | 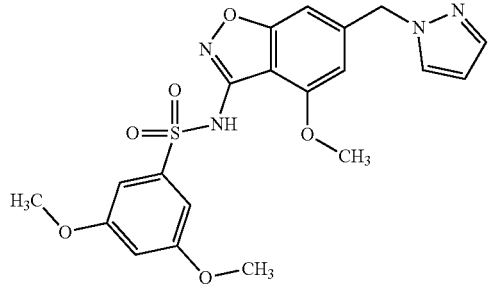<br>3,5-dimethoxy-N-{4-methoxy-6-[(1H-pyrazol-1-yl)methyl]-1,2-benzoxazol-3-yl}benzene-1-sulfonamide | m/z (ESI+) 445 (M + H)+. | C |
| 81 | 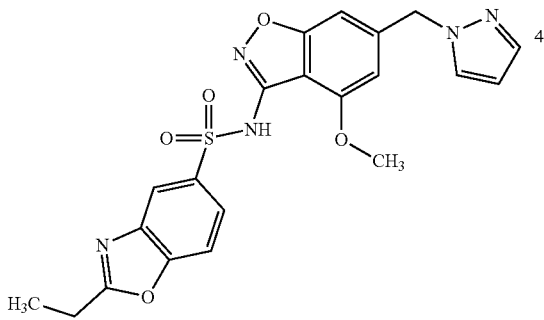<br>2-ethyl-N-{4-methoxy-6-[(1H-pyrazol-1-yl)methyl]-1,2-benzoxazol-3-yl}-1,3-benzoxazole-5-sulfonamide | m/z (ESI+) 454 (M + H)+. | C |

TABLE 13-continued

| Example Number | Structure/IUPAC Name | Analytical data | Sulfonamide Formation Method |
|---|---|---|---|
| 82 | 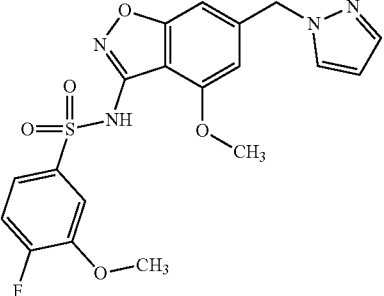<br>4-fluoro-3-methoxy-N-{4-methoxy-6-[(1H-pyrazol-1-yl)methyl]-1,2-benzoxazol-3-yl}benzene-1-sulfonamide | m/z (ESI+) 433 (M + H)+. | C |
| 83 | 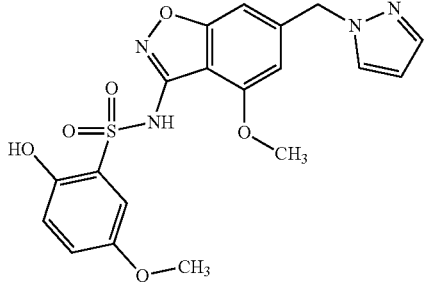<br>2-hydroxy-5-methoxy-N-{4-methoxy-6-[(1H-pyrazol-1-yl)methyl]-1,2-benzoxazol-3-yl}benzene-1-sulfonamide | m/z (ESI+) 431 (M + H)+. | C |
| 84 | 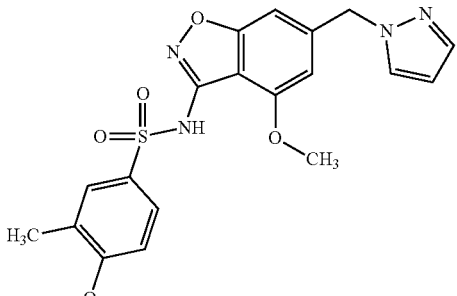<br>4-methoxy-N-{4-methoxy-6-[(1H-pyrazol-1-yl)methyl]-1,2-benzoxazol-3-yl}-3-methylbenzene-1-sulfonamide | m/z (ESI+) 429 (M + H)+. | C |

TABLE 13-continued

| Example Number | Structure/IUPAC Name | Analytical data | Sulfonamide Formation Method |
|---|---|---|---|
| 85 | 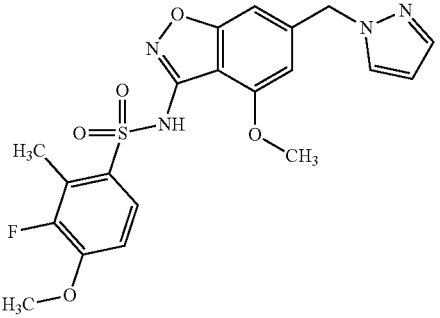<br>3-fluoro-4-methoxy-N-{4-methoxy-6-[(1H-pyrazol-1-yl)methyl]-1,2-benzoxazol-3-yl}-2-methylbenzene-1-sulfonamide | m/z (ESI+) 447 (M + H)+. | C |
| 86 | 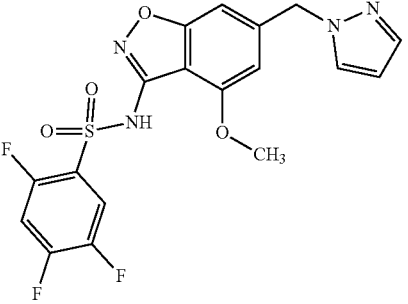<br>2,4,5-trifluoro-N-{4-methoxy-6-[(1H-pyrazol-1-yl)methyl]-1,2-benzoxazol-3-yl}benzene-1-sulfonamide | m/z (ESI+) 439 (M + H)+. | C |

Example 87: Preparation of N-(6-{[4-(hydroxymethyl)-1H-pyrazol-1-yl]methyl}-4-methoxy-1,2-benzoxazol-3-yl)-2,6-dimethoxybenzene-1-sulfonamide according to Scheme E

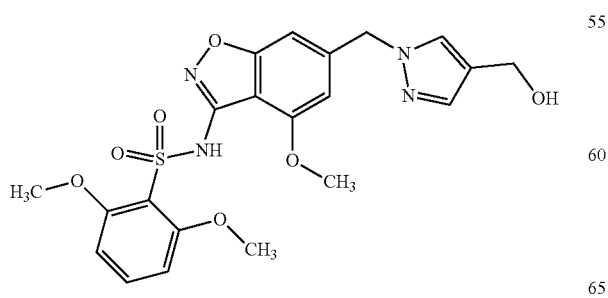

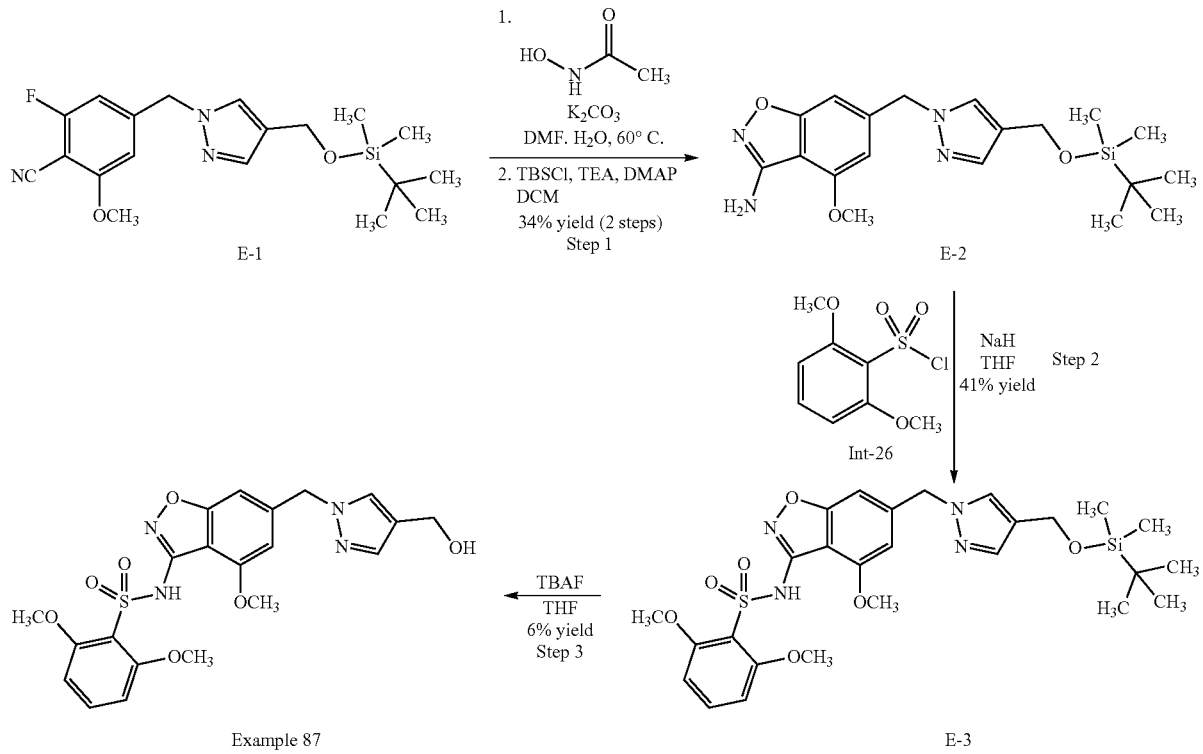

Scheme E

Example 87

Step 1: Synthesis of 6-{[4-({[tert-butyl(dimethyl)silyl]oxy}methyl)-1H-pyrazol-1-yl]methyl}-4-methoxy-1,2-benzoxazol-3-amine (E-2)

To a solution of 4-{[4-({[tert-butyl(dimethyl)silyl]oxy}methyl)-1H-pyrazol-1-yl]methyl}-2-fluoro-6-methoxybenzonitrile (E-1) (Prepared as in Example 01, 500 mg, 1.33 mmol) and N-hydroxyacetamide (300 mg, 3.99 mmol) in DMF (10.0 mL) and H₂O (2.0 mL) was added K₂CO₃ (1.1 g, 7.99 mmol). The mixture was stirred at 60° C. for 16 h. LCMS analysis showed consumption of the starting material. The reaction mixture was concentrated to remove the DMF and diluted with H₂O. The resultant precipitate was collected by filtration. The filter cake was dried under vacuum. LCMS analysis showed a mixture of the desired product and the des-TBS byproduct. The crude solids were combined with a parallel reaction run with 200 mg 4-{[4-({[tert-butyl(dimethyl)silyl]oxy}methyl)-1H-pyrazol-1-yl]methyl}-2-fluoro-6-methoxybenzonitrile. The combined solids were taken up in DCM (10.0 mL). TBSCl (178 mg, 1.18 mmol), TEA (149 mg, 1.48 mmol), and DMAP (6.0 mg, 0.49 mol) were added. The reaction was stirred at room temperature for 16 h. The mixture was diluted with DCM (100 mL) and washed successively with H₂O (50 mL), saturated NaHCO₃ (50 mL), and brine (50 mL). The organic phase was dried over Na₂SO₄, filtered, and concentrated. The residue was purified by flash chromatography (20 g SiO₂, 60-70% EtOAc/petroleum ether) to provide 6-{[4-({[tert-butyl(dimethyl)silyl]oxy}methyl)-1H-pyrazol-1-yl]methyl}-4-methoxy-1,2-benzoxazol-3-amine (E-2) (280 mg, 34% yield over 2 steps) as a white solid. m/z (ESI+) 388.9 (M+H)⁺.

Step 2: Synthesis of N-(6-{[4-({[tert-butyl(dimethyl)silyl]oxy}methyl)-1H-pyrazol-1-yl]methyl}-4-methoxy-1,2-benzoxazol-3-yl)-2,6-dimethoxybenzene-1-sulfonamide (E-3) according to sulfonamide formation Method B To a suspension of NaH (60% dispersion in mineral oil, 40.1 mg, 1.00 mmol) in THF (2.0 mL) was added a solution of 6-{[4-({[tert-butyl(dimethyl)silyl]oxy}methyl)-1H-pyrazol-1-yl]methyl}-4-methoxy-1,2-benzoxazol-3-amine (E-2) (130 mg, 0.335 mmol) in THF (2.0 mL). The reaction was stirred at room temperature for 15 min and then a solution of 2,6-dimethoxybenzene-1-sulfonyl chloride (Int-26) (95.0 mg, 0.402 mmol) in THF (2.0 mL) was added. The reaction mixture was stirred at room temperature for 17 h. The suspension was filtered and concentrated to dryness. The residue was purified by flash chromatography (12 g SiO₂, 1:1 EtOAc/petroleum ether) to provide N-(6-{[4-({[tert-butyl(dimethyl)silyl]oxy}methyl)-1H-pyrazol-1-yl]methyl}-4-methoxy-1,2-benzoxazol-3-yl)-2,6-dimethoxybenzene-1-sulfonamide (E3) (80 mg, 41% yield) as a pale-yellow gum. m/z (ESI+) 589.1 (M+H)⁺

Step 3: Synthesis of N-(6-{[4-(hydroxymethyl)-1H-pyrazol-1-yl]methyl}-4-methoxy-1,2-benzoxazol-3-yl)-2,6-dimethoxybenzene-1-sulfonamide (Example 87)

To a solution of N-(6-{[4-({[tert-butyl(dimethyl)silyl]oxy}methyl)-1H-pyrazol-1-yl]methyl}-4-methoxy-1,2-benzoxazol-3-yl)-2,6-dimethoxybenzene-1-sulfonamide (E-3) (80.0 mg, 0.16 mmol) in THF (2.0 mL) was added TBAF (76.3 mg, 0.32 mmol). The reaction solution was stirred for 1 h. LCMS analysis showed consumption of the starting material with formation of the desired product mass. The reaction was concentrated to dryness. The residue was taken up in EtOAc (15 mL) and washed with H$_2$O (10 mL). The organic layer was dried over Na$_2$SO$_4$, filtered, and concentrated to dryness. The residue was purified by preparative HPLC with a YMC-Actus Triart C-18 column (30×150 mm, 5 μm particle size), which was eluted with 5-25% MeCN/H$_2$O (0.05% NH$_4$OH) with a flow rate of 35 mL/min to provide N-(6-{[4-(hydroxymethyl)-1H-pyrazol-1-yl]methyl}-4-methoxy-1,2-benzoxazol-3-yl)-2,6-dimethoxybenzene-1-sulfonamide (Example 87) (4.5 mg, 6% yield) as a white solid. $^1$H NMR (400 MHz, DMSO-d$_6$) δ 7.73 (br. s, 1H), 7.40 (br. s, 2H), 6.74 (br. s, 4H), 5.35 (br. s, 2H), 4.81 (t, J=5.4 Hz, 1H), 4.34 (d, J=5.4 Hz, 2H), 3.97-3.59 (m, 9H); m/z (ESI+) 475.0 (M+H)$^+$.

The examples in the table below were synthesized according to the methods used for the synthesis of N-(6-{[4-(hydroxymethyl)-1H-pyrazol-1-yl]methyl}-4-methoxy-1,2-benzoxazol-3-yl)-2,6-dimethoxybenzene-1-sulfonamide (Example 87). The following examples were synthesized with non-critical changes or substitutions to the exemplified procedures that one skilled in the art would be able to realize. If necessary, separation of regioisomeric mixtures was carried out under standard methods known in the art, such as SFC or HPLC, and was conducted at any suitable step in the synthetic sequence.

TABLE 14

| Example Number | Structure/IUPAC Name | Analytical Data | Sulfonamide Formation Method |
|---|---|---|---|
| 88 | 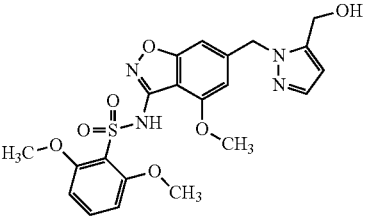<br>N-(6-{[5-(hydroxymethyl)-1H-pyrazol-1-yl]methyl}-4-methoxy-1,2-benzoxazol-3-yl)-2,6-dimethoxybenzene-1-sulfonamide | $^1$H NMR (400 MHz, DMSO-d$_6$) δ 9.60 (br. s, 1H), 7.79 (d, J = 2.2 Hz, 1H), 7.48 (br. t, J = 8.3 Hz, 1H), 6.84 (d, J = 0.9 Hz, 1H), 6.78 (s, 2H), 6.76 (s, 1H), 6.23 (d, J = 2.2 Hz, 1H), 5.37 (s, 2H), 4.97 (t, J = 5.7 Hz, 1H), 4.38 (d, J = 5.9 Hz, 2H), 3.88 (s, 3H), 3.76 (s, 6H); m/z (ESI+) 474.7 (M + H)$^+$ | B |
| 89 | 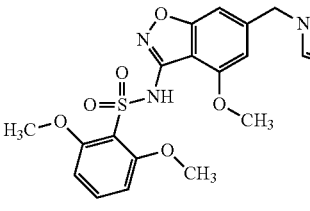<br>N-(6-{[3-(hydroxymethyl)-1H-pyrazol-1-yl]methyl}-4-methoxy-1,2-benzoxazol-3-yl)-2,6-dimethoxybenzene-1-sulfonamide | $^1$H NMR (400 MHz, CD$_3$OD) δ 7.52 (d, J = 1.5 Hz, 1H), 7.47 (t, J = 8.5 Hz, 1H), 6.74 (d, J = 8.5 Hz, 2H), 6.69 (s, 2H), 6.36 (s, 1H), 5.53 (s, 2H), 4.61 (s, 2H), 3.99 (s, 3H), 3.84 (s, 6H); m/z (ESI+) 474.7 (M + H)$^+$ | B |

Example 90: Preparation of 2,6-dimethoxy-N-{4-methoxy-6-[(1H-pyrazol-1-yl)($^2$H2)methyl]-1,2-benzoxazol-3-yl}benzene-1-sulfonamide According to Scheme F

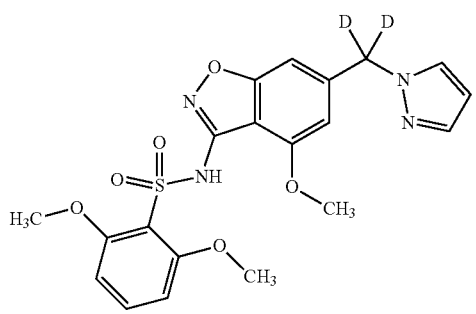 [SMILES: [2H]C([2H])(c1cc(OC)c2c(NS(=O)(=O)c3c(OC)cccc3OC)noc2c1)n1cccn1]

Step 1: Synthesis of 2-fluoro-6-methoxy-4-[(1H-pyrazol-1-yl)($^2$H$_2$)methyl]benzonitrile (F-1)

To a solution of 2-fluoro-6-methoxy-4-[(1H-pyrazol-1-yl)methyl]benzonitrile (164 mg, 0.703 mmol) (A-1) in CD$_3$OD (4.0 mL) was added Cs$_2$CO$_3$ (229 mg, 0.703 mmol). The mixture was stirred at 40° C. for 2 h. The reaction was cooled to room temperature and concentrated to dryness. The residue was purified by flash chromatography (24 g SiO$_2$, 0-40% EtOAc/DCM) to provide 2-fluoro-6-methoxy-4-[(1H-pyrazol-1-yl)($^2$H$_2$)methyl]benzonitrile (F-1) (81.0 mg, 49% yield) as a white solid. $^1$H NMR (400 MHz, CDCl$_3$) δ 7.61 (d, J=1.71 Hz, 1H), 7.47 (d, J=2.32 Hz, 1H), 6.52-6.57 (m, 2H), 6.37 (t, J=2.08 Hz, 1H), 3.88-3.91 (m, 3H); m/z (ESI+) 234.2 (M+H)$^+$.

Step 2: Synthesis of 4-methoxy-6-[(1H-pyrazol-1-yl)($^2$H2)methyl]-1,2-benzoxazol-3-amine (F-2)

To a suspension of 2-fluoro-6-methoxy-4-[(1H-pyrazol-1-yl)($^2$H$_2$)methyl]benzonitrile (F-1) (81.0 mg, 0.35 mmol)

Scheme F

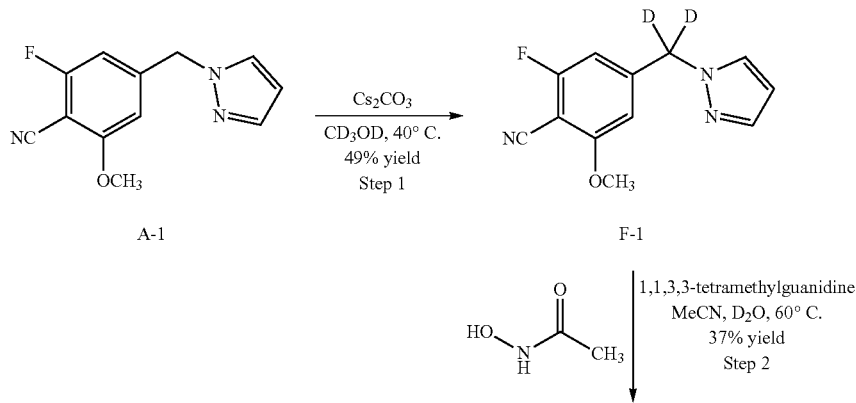

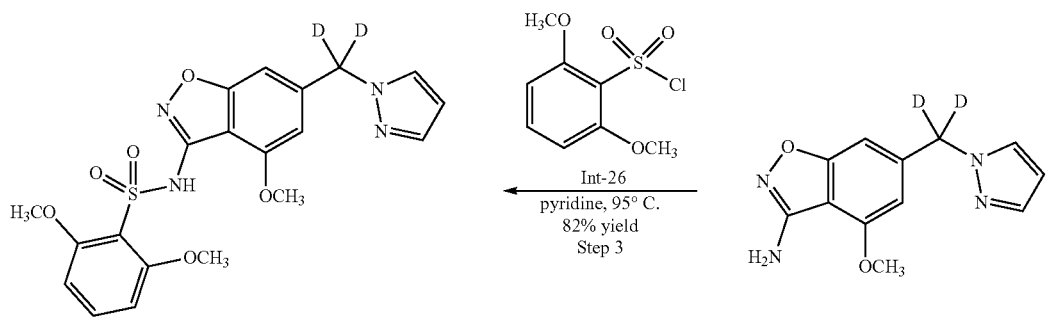

Example 90      F-2 and N-hydroxyacetamide (78.2 mg, 1.04 mmol) in MeCN (2.7 mL) and D$_2$O (0.3 mL) was added 1,1,3,3-tetramethylguanidine (240 mg, 2.08 mmol). The mixture was stirred at 60° C. for 7 h and 65° C. for an additional 2 h. The reaction was cooled to room temperature and concentrated to dryness. The residue was purified by flash chromatography (24 g SiO$_2$, 60-100% EtOAc/DCM) to provide 4-methoxy-6-[(1H-pyrazol-1-yl)($^2$H$_2$)methyl]-1,2-benzoxazol-3-amine (F-2) (32 mg, 37% yield) as a white solid. $^1$H NMR (400 MHz, DMSO-d$_6$) δ 7.85-7.89 (m, 1H), 7.49 (d, J=1.83 Hz, 1H), 6.70 (d, J=0.86 Hz, 1H), 6.63 (d, J=0.73 Hz, 1H), 6.30 (t, J=2.08 Hz, 1H), 5.93 (s, 2H), 3.83-3.87 (m, 3H); m/z (ESI+) 247.2 (M+H)$^+$.

Step 3: Synthesis of 2,6-dimethoxy-N-{4-methoxy-6-[(1H-pyrazol-1-yl)($^2$H$_2$)methyl]-1,2-benzoxazol-3-yl}benzene-1-sulfonamide (Example 90) According to Sulfonamide Formation Method A A mixture of 4-methoxy-6-[(1H-pyrazol-1-yl)($^2$H2)methyl]-1,2-benzoxazol-3-amine (F-2) (25.0 mg, 0.10 mmol) and 2,6-dimethoxybenzene-1-sulfonyl chloride (Int-26) (36.0 mg, 0.152 mmol) in pyridine was stirred at 95° C. for 2 h. The resulting gum was diluted with DCM and treated with AcOH (46 µL, 0.812 mmol). The mixture was purified directly by flash chromatography (24 g SiO$_2$, 70-100% EtOAc/heptane) to provide 2,6-dimethoxy-N-{4-methoxy-6-[(1H-pyrazol-1-yl)($^2$H2)methyl]-1,2-benzoxazol-3-yl}benzene-1-sulfonamide (Example 90) (37.0 mg, 82% yield) as a white solid. $^1$H NMR (400 MHz, DMSO-d$_6$) δ 9.60 (s, 1H), 7.88 (d, J=2.08 Hz, 1H), 7.43-7.54 (m, 2H), 6.84 (s, 1H), 6.73-6.80 (m, 3H), 6.30 (t, J=2.08 Hz, 1H), 3.87 (s, 3H), 3.76 (s, 6H); m/z (ESI+) 448.1 (M+H)$^+$.

The example in the table below was synthesized according to the methods used for the synthesis 2,6-dimethoxy-N-{4-methoxy-6-[(1H-pyrazol-1-yl)($^2$H2)methyl]-1,2-benzoxazol-3-yl}benzene-1-sulfonamide (Example 90). The following examples were synthesized with non-critical changes or substitutions to the exemplified procedures that someone who is skilled in the art would be able to realize.

TABLE 15

| Example Number | Structure/IUPAC Name | Analytical Data | Sulfonamide Formation Method |
|---|---|---|---|
| 91 | 2,6-dimethoxy-N-{4-[($^2$H$_3$)methoxy]-6-[(1H-pyrazol-1-yl)($^2$H$_2$)methyl]-1,2-benzoxazol-3-yl}benzene-1-sulfonamide | $^1$H NMR (400 MHz, DMSO-d$_6$) δ 9.59 (s, 1H), 7.87 (d, J = 1.83 Hz, 1H), 7.43-7.54 (m, 2H), 6.84 (s, 1H), 6.73-6.80 (m, 3H), 6.30 (t, J = 2.08 Hz, 1H), 3.76 (s, 6H), m/z (ESI+) 450.1 (M + H)$^+$. | A |

Example 92: Preparation of N-{5-bromo-6-[(1H-pyrazol-1-yl)methyl]-1,2-benzoxazol-3-yl}-2,6-dimethoxybenzene-1-sulfonamide According to Scheme G

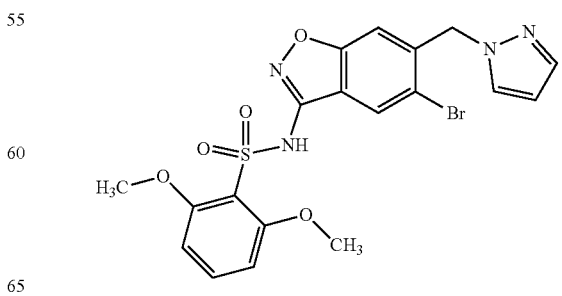

Scheme G

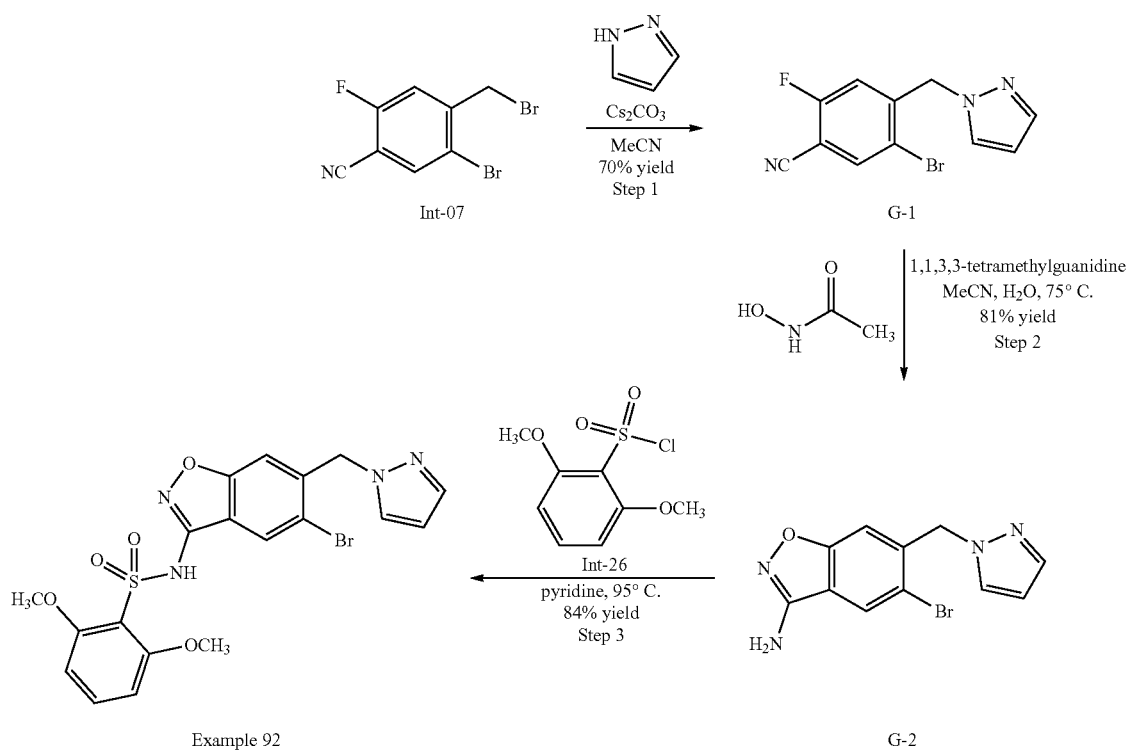

Example 92

Step 1: Synthesis of 5-bromo-2-fluoro-4-[(1H-pyrazol-1-yl)methyl]benzonitrile (G-1)

To a solution of 5-bromo-4-(bromomethyl)-2-fluorobenzonitrile (Int-07) (280 mg, 0.956 mmoL) in MeCN (6.4 mL) was added 1H-pyrazole (71.6 mg, 1.05 mmol) and $Cs_2CO_3$ (0.374 mg, 1.15 mmol). The mixture was stirred at room temperature for 6 h. The mixture was diluted with EtOAc and filtered. The filtrate was concentrated to dryness. The residue was purified by flash chromatography (40 g $SiO_2$, 10-100% EtOAc/heptane) to provide 5-bromo-2-fluoro-4-[(1H-pyrazol-1-yl)methyl]benzonitrile (G-1) (188 mg, 70% yield) as a clear oil, which solidified to a pale-yellow solid upon standing. $^1$H NMR (400 MHz, $CDCl_3$) δ 7.83 (d, J=5.7 Hz, 1H), 7.65 (d, J=1.7 Hz, 1H), 7.53 (d, J=2.2 Hz, 1H), 6.52 (d, J=9.3 Hz, 1H), 6.40 (t, J=2.1 Hz, 1H), 5.43 (s, 2H); m/z (ESI+) 280.0, 282.0 (M+H)$^+$.

Step 2: Synthesis of 5-bromo-6-[(1H-pyrazol-1-yl)methyl]-1,2-benzoxazol-3-amine (G-2)

To a solution of 5-bromo-2-fluoro-4-[(1H-pyrazol-1-yl)methyl]benzonitrile (G-1) (185 mg, 0.66 mmol) and N-hydroxyacetamide (149 mg, 1.98 mmol) in MeCN (3.5 mL) and $H_2O$ (0.35 mL) was added 1,1,3,3-tetramethylguanidine (45.9 mg, 0.399 mmol). The mixture was stirred at 75° C. for 4 h. The reaction was concentrated to dryness. The residue was purified by flash chromatography (40 g $SiO_2$, 30-90% EtOAc/heptane) to provide 5-bromo-6-[(1H-pyrazol-1-yl)methyl]-1,2-benzoxazol-3-amine (G-2) (157 mg, 81% yield) as a white solid. $^1$H NMR (400 MHz, DMSO-$d_6$) δ 8.18 (s, 1H), 7.87 (d, J=2.2 Hz, 1H), 7.55 (d, J=1.3 Hz, 1H), 6.80 (s, 1H), 6.50 (s, 2H), 6.34 (t, J=2.1 Hz, 1H), 5.51 (s, 2H); m/z (ESI+) 293.0, 295.0 (M+H)$^+$.

Step 3: Synthesis of N-{5-bromo-6-[(1H-pyrazol-1-yl)methyl]-1,2-benzoxazol-3-yl}-2,6-dimethoxybenzene-1-sulfonamide (Example 92)

A solution of 5-bromo-6-[(1H-pyrazol-1-yl)methyl]-1,2-benzoxazol-3-amine (G-2) (155 mg, 0.529 mmol) and 2,6-dimethoxybenzene-1-sulfonyl chloride (Int-26) (188 mg, 0.793 mmol)—in pyridine (0.31 mL) was heated to 95° C., at which point the reaction became homogeneous. The reaction was stirred at 95° C. for 2 h and then concentrated to dryness. The residue was taken up in a minimal amount of DCM and treated with AcOH (0.10 mL, 1.75 mmol). The mixture was loaded directly onto $SiO_2$ and purified by flash chromatography (40 g $SiO_2$, 35-100% MeOAc/heptane) to provide N-{5-bromo-6-[(1H-pyrazol-1-yl)methyl]-1,2-benzoxazol-3-yl}-2,6-dimethoxybenzene-1-sulfonamide (Example 92) (221 mg, 84% yield) as a white solid. $^1$H NMR (400 MHz, DMSO-$d_6$) b 11.55 (s, 1H), 8.39 (s, 1H), 7.87 (d, J=2.1 Hz, 1H), 7.54 (d, J=1.3 Hz, 1H), 7.47 (t, J=8.4 Hz, 1H), 6.88 (s, 1H), 6.74 (d, J=8.4 Hz, 2H), 6.34 (t, J=2.1 Hz, 1H), 5.52 (s, 2H), 3.75 (s, 6H); m/z (ESI+) 493.0, 495.0 (M+H)$^+$.

The examples in the table below were synthesized according to the methods used for the synthesis of N-{5-bromo-6-[(1H-pyrazol-1-yl)methyl]-1,2-benzoxazol-3-yl}-2,6-dimethoxybenzene-1-sulfonamide (Example 92). The following examples were synthesized with non-critical changes or substitutions to the exemplified procedures that one skilled in the art would be able to realize. If necessary, separation of regioisomeric mixtures was carried out under standard methods known in the art, such as SFC or HPLC, and was conducted at any suitable step in the synthetic sequence.

TABLE 16

| Example Number | Structure/IUPAC Name | Analytical Data | Sulfonamide formation method |
|---|---|---|---|
| 93 | N-{5-fluoro-6-[(1H-pyrazol-1-yl)methyl]-1,2-benzoxazol-3-yl}-2,6-dimethoxybenzene-1-sulfonamide | $^1$H NMR (400 MHz, DMSO-$d_6$) δ 11.50 (s, 1H), 7.83-7.90 (m, 2H), 7.43-7.52 (m, 2H), 7.25 (br. d, J = 4.52 Hz, 1H), 6.73 (d, J = 8.56 Hz, 2H), 6.30 (t, J = 2.08 Hz, 1H), 5.50 (s, 2H), 3.73 (s, 6H); m/z (ESI+) 433.1 (M + H)$^+$. | A |
| 94 | N-{4-fluoro-6-[(1H-pyrazol-1-yl)methyl]-1,2-benzoxazol-3-yl}-2,6-dimethoxybenzene-1-sulfonamide | $^1$H NMR (400 MHz, DMSO-$d_6$) δ 10.83 (s, 1H), 7.89 (d, J = 2.1 Hz, 1H), 7.55-7.46 (m, 2H), 7.27 (s, 1H), 6.98 (br. d, J = 10.1 Hz, 1H), 6.77 (d, J = 8.4 Hz, 2H), 6.31 (t, J = 2.0 Hz, 1H), 5.50 (s, 2H), 3.74 (s, 6H); m/z (ESI+) 433.1 (M + H)$^+$. | A |

Example 95: Preparation of N-{4-ethyl-6-[(1H-pyrazol-1-yl)methyl]-1,2-benzoxazol-3-yl}-2,6-dimethoxybenzene-1-sulfonamide According to Scheme H

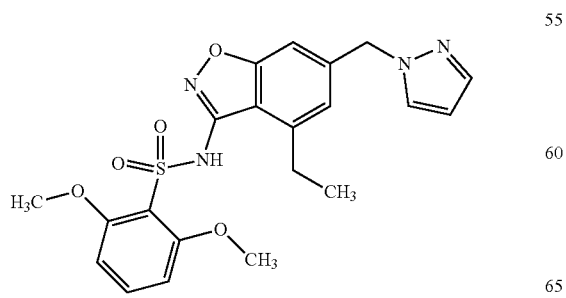

Scheme H

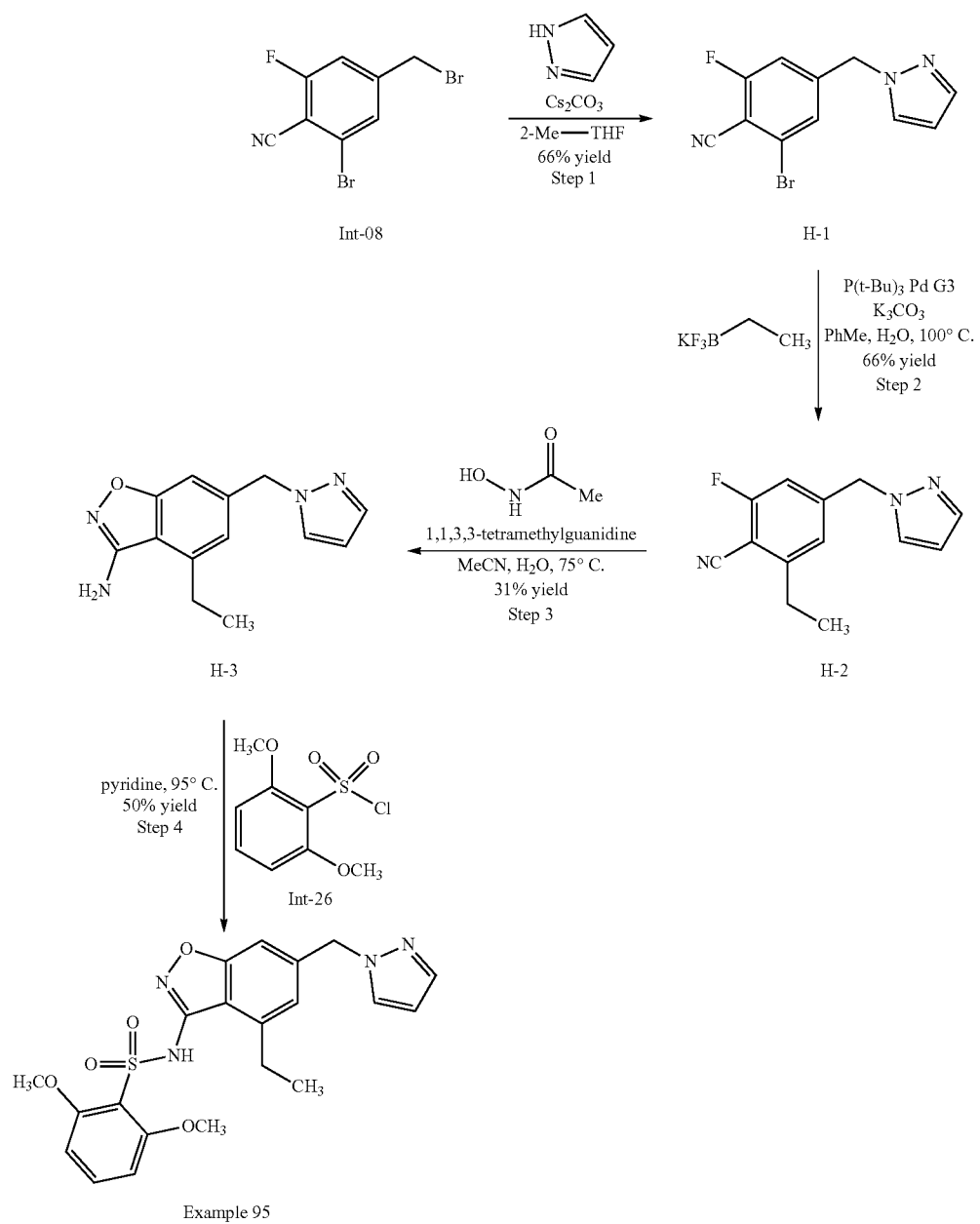

Example 95

Step 1: Synthesis of 2-bromo-6-fluoro-4-[(1H-pyrazol-1-yl)methyl]benzonitrile (H-1)

A suspension of 2-bromo-4-(bromomethyl)-6-fluorobenzonitrile (Int-08) (459 mg, 1.57 mmol), 1H-pyrazole (159 mg, 2.34 mmol), and Cs₂CO₃ (767 mg) in 2-Me-THF (3.1 mL) was stirred at room temperature for 5.5 h. LCMS analysis showed consumption of the starting material. The mixture was partitioned between H₂O (5 mL) and EtOAc (20 mL). The aqueous layer was extracted with EtOAc (20 mL). The combined organic layers were washed with brine (5 mL), dried over MgSO₄, filtered, and concentrated. The residue was purified by flash chromatography (40 g SiO₂, 0-100% EtOAc/heptane) to provide 2-bromo-6-fluoro-4-[(1H-pyrazol-1-yl)methyl]benzonitrile (H-1) (295 mg, 66% yield) as a yellow oil. $^1$H NMR (400 MHz, CDCl₃) δ 7.62 (d, J=1.7 Hz, 1H), 7.47 (d, J=2.3 Hz, 1H), 7.28 (s, 1H), 6.92 (d, J=8.9 Hz, 1H), 6.38 (t, J=2.1 Hz, 1H), 5.36 (s, 2H); m/z (ESI+) 280.0, 282.0 (M+H)⁺.

Step 2: Synthesis of 2-ethyl-6-fluoro-4-[(1H-pyrazol-1-yl)methyl]benzonitrile (H-2)

A microwave vial charged with 2-bromo-6-fluoro-4-[(1H-pyrazol-1-yl)methyl]benzonitrile (H-1) (79.3 mg, 0.283 mmol), potassium ethyltrifluoroborate (60.0 mg, 0.441 mmol), K₂CO₃ (108 mg, 0.778 mmol), and methanesulfonato(tri-t-butylphosphino)(2"amino-1,1-biphenyl-2-yl) palladium(II) (P(t-Bu)₃ Pd (7.9 mg, 0.014 mmol) was sealed, evacuated, and backfilled with N₂. PhMe (0.60 mL) and de-ionized H$_2$O (0.30 mL) were added and the mixture was stirred at 100° C. for 5 h. LCMS analysis showed formation of the desired product mass. The mixture was partitioned between saturated aqueous NH$_4$Cl (10 mL) and EtOAc (15 mL). The aqueous layer was extracted with EtOAc (15 mL). The combined organics were washed with brine, dried over MgSO$_4$, filtered, and concentrated. The residue was purified by flash chromatography (12 g SiO$_2$, 0-100% EtOAc/heptane) to provide 2-ethyl-6-fluoro-4-[(1H-pyrazol-1-yl)methyl]benzonitrile (H-2) (43.1 mg, 66% yield) as an off-white solid. $^1$H NMR (400 MHz, CDCl$_3$) δ 7.60 (d, J=1.6 Hz, 1H), 7.46 (d, J=2.2 Hz, 1H), 6.92 (s, 1H), 6.76 (d, J=9.2 Hz, 1H), 6.36 (t, J=2.1 Hz, 1H), 5.36 (s, 2H), 2.85 (q, J=7.6 Hz, 2H), 1.28 (t, J=7.6 Hz, 3H); m/z (APCI+) 230.1 (M+H)$^+$.

Step 3: Synthesis of 4-ethyl-6-[(1H-pyrazol-1-yl)methyl]-1,2-benzoxazol-3-amine (H-3)

To solution of 2-ethyl-6-fluoro-4-[(1H-pyrazol-1-yl)methyl]benzonitrile (H-2) (40.6 mg, 0.177 mmol) and N-hydroxyacetamide (43.9 mg, 0.585 mg) in MeCN (1.0 mL) and H$_2$O (0.1 mL) was added 1,1,3,3-tetramethylguanidine (120 mg, 1.0 mmol). The mixture was stirred at 75° C. for 24 h. The mixture was concentrated to dryness and purified by flash chromatography (12 g SiO$_2$, 0-100% EtOAc/heptane) to provide 4-ethyl-6-[(1H-pyrazol-1-yl)methyl]-1,2-benzoxazol-3-amine (H-3) (13.2 mg, 31% yield). $^1$H NMR (400 MHz, CDCl$_3$) δ 7.60 (d, J=1.6 Hz, 1H), 7.45 (d, J=2.0 Hz, 1H), 7.04 (s, 1H), 6.87 (s, 1H), 6.34 (t, J=2.0 Hz, 1H), 5.44 (s, 2H), 4.35 (br. s, 2H), 2.93 (q, J=7.6 Hz, 2H), 1.34 (t, J=7.6 Hz, 3H); m/z (APCI+) 243.1 (M+H)$^+$.

Step 4: Synthesis of N-{4-ethyl-6-[(1H-pyrazol-1-yl)methyl]-1,2-benzoxazol-3-yl}-2,6-dimethoxybenzene-1-sulfonamide (Example 95)

A suspension of 4-ethyl-6-[(1H-pyrazol-1-yl)methyl]-1,2-benzoxazol-3-amine (H-3) (13.2 mg, 0.055 mmol) and 2,6-dimethoxybenzene-1-sulfonyl chloride (Int-26) (21.3 mg, 0.090 mmol) in pyridine (0.15 mL) was stirred at 95° C. for 3 h. LCMS analysis showed consumption of the starting material. The reaction was concentrated to dryness and purified by flash chromatography (4 g SiO$_2$, 0-100% EtOAc/heptane) to provide N-{4-ethyl-6-[(1H-pyrazol-1-yl)methyl]-1,2-benzoxazol-3-yl}-2,6-dimethoxybenzene-1-sulfonamide (Example 95) (12.0 mg, 50% yield) as a white solid. $^1$H NMR (400 MHz, DMSO-d$_6$) δ10.14 (s, 1H), 7.87 (d, J=2.2 Hz, 1H), 7.57-7.50 (m, 1H), 7.49 (d, J=1.5 Hz, 1H), 7.20 (br. s, 1H), 7.06 (br. s, 1H), 6.79 (br. d, J=7.8 Hz, 2H), 6.29 (t, J=2.1 Hz, 1H), 5.46 (s, 2H), 3.77 (br. s, 6H), 3.07 (q, J=7.5 Hz, 2H), 1.21 (t, J=7.5 Hz, 3H); m/z (APCI+) 443.1 (M+H)$^+$.

The example in the table below was synthesized according to the methods used for the synthesis N-{4-ethyl-6-[(1H-pyrazol-1-yl)methyl]-1,2-benzoxazol-3-yl}-2,6-dimethoxybenzene-1-sulfonamide (Example 95). The following example was synthesized with non-critical changes or substitutions to the exemplified procedures that someone who is skilled in the art would be able to realize.

TABLE 17

| Example Number | Structure/IUPAC Name | Analytical Data | Sulfonamide formation method |
|---|---|---|---|
| 96 | 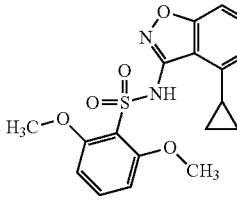<br>N-{4-cyclopropyl-6-[(1H-pyrazol-1-yl)methyl]-1,2-benzoxazol-3-yl}-2,6-dimethoxybenzene-1-sulfonamide | $^1$H NMR (400 MHz, DMSO-d$_6$) δ 10.15 (s, 1H), 7.85 (d, J = 2.1 Hz, 1H), 7.52 (br. t, J = 8.6 Hz, 1H), 7.48 (d, J = 1.5 Hz, 1H), 7.11 (s, 1H), 6.79 (d, J = 8.4 Hz, 2H), 6.73 (s, 1H), 6.29 (t, J = 2.0 Hz, 1H), 5.42 (s, 2H), 3.76 (s, 6H), 2.81-2.69 (m, 1H), 1.06-0.98 (m, 2H), 0.78-0.70 (m, 2H); m/z (APCI+) 455.1 (M + H)$^+$. | A |

Example 97: Preparation of 5-cyclopropyl-2-methoxy-N-{6-[(1H-pyrazol-1-yl)methyl]-1,2-benzoxazol-3-yl}benzene-1-sulfonamide According to Scheme J

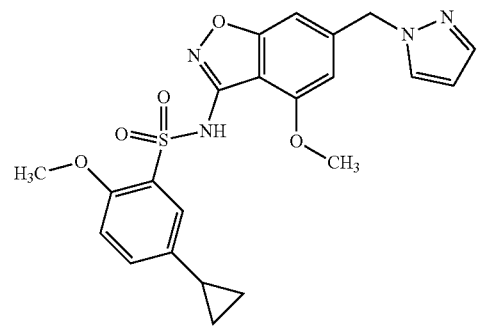 [SMILES: COc1ccc(C2CC2)cc1S(=O)(=O)Nc1noc2cc(Cn3cccn3)cc(OC)c12]

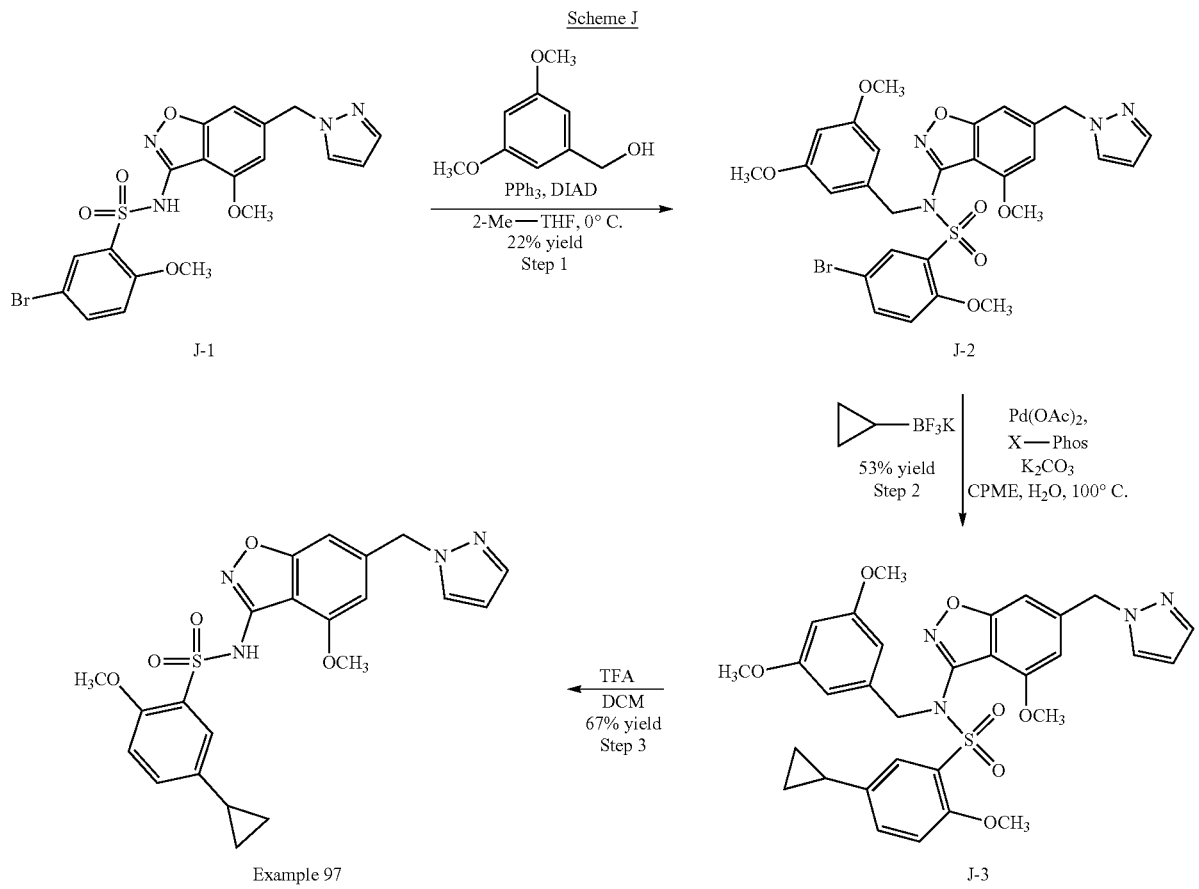

Scheme J

Example 97

Step 1: Synthesis of 5-bromo-N-[(3,5-dimethoxyphenyl)methyl]-2-methoxy-N-{4-methoxy-6-[(1H-pyrazol-1-yl)methyl]-1,2-benzoxazol-3-yl}benzene-1-sulfonamide (J-2)

To a solution of 5-bromo-2-methoxy-N-{4-methoxy-6-[(1H-pyrazol-1-yl)methyl]-1,2-benzoxazol-3-yl}benzene-1-sulfonamide (J-1) (Prepared as in Example 01, 700 mg, 1.42 mmol), PPh₃ (930 mg, 3.55 mmol), and (3,5-dimethoxyphenyl)methanol (358 mg, 2.13 mmol) in 2-Me-THF (30 mL) at 0° C. was added DIAD (574 mg, 2.84 mmol) dropwise. The solution was stirred for 16 h to provide a pale-yellow suspension. The suspension was filtered, and the filtrate was concentrated to dryness. The residue was purified by flash chromatography (40 g SiO₂, 1:2 petroleum ether/EtOAc) to provide 5-bromo-N-[(3,5-dimethoxyphenyl)methyl]-2-methoxy-N-{4-methoxy-6-[(1H-pyrazol-1-yl)methyl]-1,2-benzoxazol-3-yl}benzene-1-sulfonamide (J-2) (200 mg, 22% yield) as a white solid.

Step 2: Synthesis of 5-cyclopropyl-N-[(3,5-dimethoxyphenyl)methyl]-2-methoxy-N-{4-methoxy-6-[(1H-pyrazol-1-yl)methyl]-1,2-benzoxazol-3-yl}benzene-1-sulfonamide (J-3)

To a solution of 5-bromo-N-[(3,5-dimethoxyphenyl)methyl]-2-methoxy-N-{4-methoxy-6-[(1H-pyrazol-1-yl)methyl]-1,2-benzoxazol-3-yl}benzene-1-sulfonamide (J-2) (200 mg, 0.311 mmol) in CPME (10.0 mL) and H₂O (1.0 mL) was added potassium cyclopropyltrifluoroborate (138 mg, 0.932 mmol), Pd(OAc)₂ (14.0 mg, 0.062 mmol), K₂CO₃ (172 mg, 1.24 mmol), and X-Phos (44.4 mg, 0.093 mmol). The mixture was evacuated and back-filled with N₂ (3×) and then stirred at 100° C. under an atmosphere of N₂ for 16 h. The reaction was cooled to room temperature, diluted with EtOAc (20 mL), and filtered. The filtrate was concentrated to dryness. The residue was purified by flash chromatography (20 g SiO₂, EtOAc) to provide 5-cyclopropyl-N-[(3,5-dimethoxyphenyl)methyl]-2-methoxy-N-{4-methoxy-6-[(1H-pyrazol-1-yl)methyl]-1,2-benzoxazol-3-yl}benzene-1-sulfonamide (J-3) (100 mg, 53% yield) as a white solid. m/z (ESI+) 605.3 (M+H)⁺.

Step 3: Synthesis of 5-cyclopropyl-2-methoxy-N-{4-methoxy-6-[(1H-pyrazol-1-yl)methyl]-1,2-benzoxazol-3-yl}benzene-1-sulfonamide (Example 97)

To a solution of 5-cyclopropyl-N-[(3,5-dimethoxyphenyl)methyl]-2-methoxy-N-{4-methoxy-6-[(1H-pyrazol-1-yl)methyl]-1,2-benzoxazol-3-yl}benzene-1-sulfonamide (J-3) (100 mg, 0.165 mmol) in DCM (2.0 mL) was added TFA (2.0 mL). The mixture was stirred for 1 h and then concentrated to dryness. The residue was purified by flash chromatography (12 g SiO₂, 1:10 MeOH/EtOAc). The material was repurified by preparative HPLC with a Phenomenex Gemini-NX column (150×30 mm, 5 m particle size), which was eluted with 2-42% MeCN/H₂O (+0.05% NH₄OH) with a flow rate of 30 mL/min to provide 5-cyclopropyl-2-methoxy-N-{4-methoxy-6-[(1H-pyrazol-1-yl)methyl]-1,2-benzoxazol-3-yl}benzene-1-sulfonamide (Example 97) (50 mg, 67% yield) as a white solid. $^1$H NMR (400 MHz, DMSO-d$_6$) δ 10.10 (br s, 1H), 7.88 (d, J=1.9 Hz, 1H), 7.51 (dd, J=1.6, 11.0 Hz, 2H), 7.27 (br. d, J=6.8 Hz, 1H), 7.05 (br. d, J=8.9 Hz, 1H), 6.82 (br. s, 1H), 6.72 (br. s, 1H), 6.30 (t, J=1.9 Hz, 1H), 5.44 (s, 2H), 3.83 (s, 2H), 3.90 (br. d, J=8.3 Hz, 1H), 3.73 (s, 2H), 3.76-3.67 (m, 1H), 2.01-1.89 (m, 1H), 1.04-0.78 (m, 2H), 0.70-0.42 (m, 2H). m/z (ESI+) 454.8 (M+H)$^+$.

Example 98: Preparation of N-(6-((1H-pyrazol-1-yl)methyl)-4-methoxybenzo[d]isoxazol-3-yl)-2,6-dimethoxybenzenesulfonamide [or 2,6-dimethoxy-N-{4-methoxy-6-[(1H-pyrazol-1-yl)methyl]-1,2-benzoxazol-3-yl}benzene-1-sulfonamide] According to Scheme K

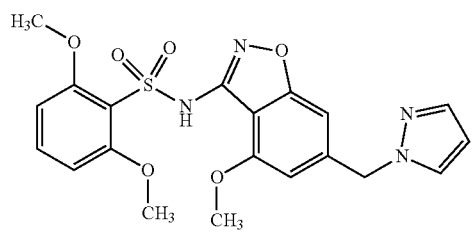 [SMILES: COc1cccc(OC)c1S(=O)(=O)Nc1noc2cc(Cn3cccn3)cc(OC)c12]

Scheme K

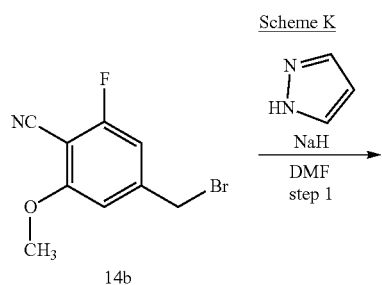

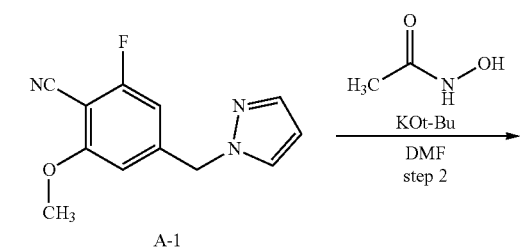

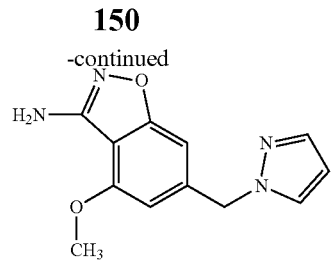

A-2

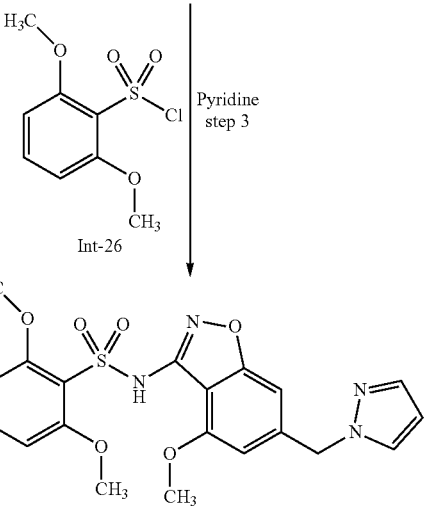

Example 98

Step 1: Alternate synthesis of 4-((1H-pyrazol-1-yl)methyl)-2-fluoro-6-methoxybenzonitrile (A-1) from 14b A solution of 1H-pyrazole (2.0 g, 29.6 mmol) and NaH (60% w/w dispersion in mineral oil, 1.5 g, 37.1 mmol) in DMF (520 mL) was stirred at 0° C. for 1 h. A solution of 4-(bromomethyl)-2-fluoro-6-methoxybenzonitrile (14b) (6.0 g, 24.7 mmol) in DMF (80 mL) was then added and the mixture was stirred at RT overnight. The reaction was quenched with water and the mixture was extracted with EtOAc. The combined organic layers were washed with brine, dried over anhydrous Na$_2$SO$_4$, filtered and concentrated under reduced pressure. The residue was purified by column chromatography (Pet. Ether/EtOAc=6/1) to give 4-((1H-pyrazol-1-yl)methyl)-2-fluoro-6-methoxybenzonitrile (A-1) (2.4 g, 42%) as a yellow solid. m/z 232.0 [M+H]$^+$.

Step 2: Alternate synthesis of 6-((1H-pyrazol-1-yl)methyl)-4-methoxybenzo[d]isoxazol-3-amine (A-2) using potassium tert-butoxide To a solution of acetohydroxamic acid (3.7 g, 49.5 mmol) in anhydrous DMF (150 mL) at RT was added potassium tert-butoxide (5.6 g, 49.5 mmol) and the mixture was stirred at RT for 1 h. 4-((1H-Pyrazol-1-yl)methyl)-2-fluoro-6-methoxybenzonitrile (A-1) (3.8 g, 16.5 mmol) was then added and stirring was continued at 60° C. for 4 h. Water was added and the mixture was extracted with EtOAc. The combined organic layers were dried over anhydrous Na$_2$SO$_4$, filtered and concentrated under reduced pressure. The residue was purified by column chromatography (Pet. Ether/EtOAc=5/1) to give 6-((1H-pyrazol-1-yl)methyl)-4- methoxybenzo[d]isoxazol-3-amine (A-2) (2.1 g, 53%) as a yellow solid. m/z 245.0 [M+H]+. 1H NMR (400 MHz, DMSO-d6) δ 7.87 (dd, J=1.6, 0.4 Hz, 1H), 7.50 (dd, J=1.6, 0.4 Hz, 1H), 6.69 (s, 1H), 6.62 (s, 1H), 6.30 (t, J=2.1 Hz, 1H), 5.93 (s, 2H), 5.41 (s, 2H), 3.86 (s, 3H).

Step 3: Synthesis of N-(6-((1H-pyrazol-1-yl)methyl)-4-methoxybenzo[d]isoxazol-3-yl)-2,6-dimethoxybenzenesulfonamide (Example 98)

A mixture of 6-((1H-pyrazol-1-yl)methyl)-4-methoxybenzo[d]isoxazol-3-amine (A-2) (50 mg, 0.205 mmol) and 2,6-dimethoxybenzenesulfonyl chloride (Int-26) (73 mg, 0.308 mmol) in pyridine (1 mL) was heated at 120° C. for 2 h under microwave irradiation (Batch 1).

A mixture of 6-((1H-pyrazol-1-yl)methyl)-4-methoxybenzo[d]isoxazol-3-amine (A-2)(500 mg, 2.1 mmol) and 2,6-dimethoxybenzenesulfonyl chloride (Int-26) (746 mg, 3.2 mmol) in pyridine (5 mL) was heated at 120° C. for 2 h under microwave irradiation (Batch 2). This reaction was repeated once again on exactly the same scale (Batch 3). A mixture of 6-((1H-pyrazol-1-yl)methyl)-4-methoxybenzo[d]isoxazol-3-amine (A-2)(350 mg, 1.4 mmol) and 2,6-dimethoxybenzenesulfonyl chloride (Int-26) (509 mg, 2.2 mmol) in pyridine (4 mL) was heated at 120° C. for 2 h under microwave irradiation (Batch 4). The four reaction mixtures were combined, diluted with water, adjusted to pH 5-6 with 2 M aqueous HCl and extracted with EtOAc (300 mL×3). The combined organic extracts were dried over anhydrous Na2SO4, filtered and concentrated under reduced pressure. The residue was purified by column chromatography (Pet. Ether/EtOAc=2/1) to give N-(6-((1H-pyrazol-1-yl)methyl)-4-methoxybenzo[d]isoxazol-3-yl)-2,6-dimethoxybenzenesulfonamide (Example 98) (1.07 g, 43%) as a white solid. m/z 445.0 [M+H]+. 1H NMR (400 MHz, DMSO-d6) δ 9.58 (s, 1H), 7.87 (d, J=2.0 Hz, 1H), 7.50-7.46 (m, 2H), 6.83 (s, 1H), 6.76 (m, 3H), 6.30 (s, 1H), 5.44 (s, 2H), 3.87 (s, 3H), 3.76 (s, 6H).

Example 98: Alternative preparation of 2,6-dimethoxy-N-{4-methoxy-6-[(1H-pyrazol-1-yl)methyl]-1,2-benzoxazol-3-yl}benzene-1-sulfonamide according to Scheme L

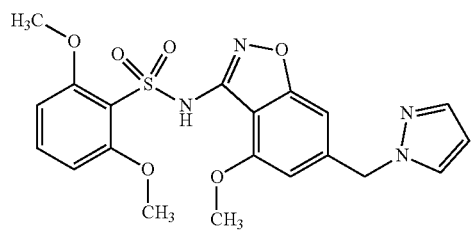 [SMILES: COc1cccc(OC)c1S(=O)(=O)Nc1noc2cc(Cn3cccn3)cc(OC)c12]

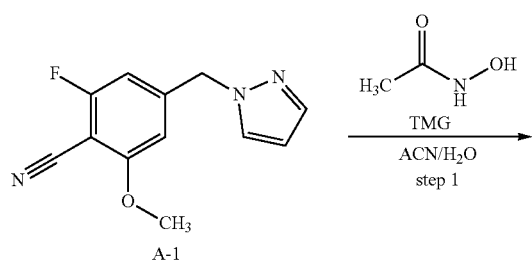

Scheme L

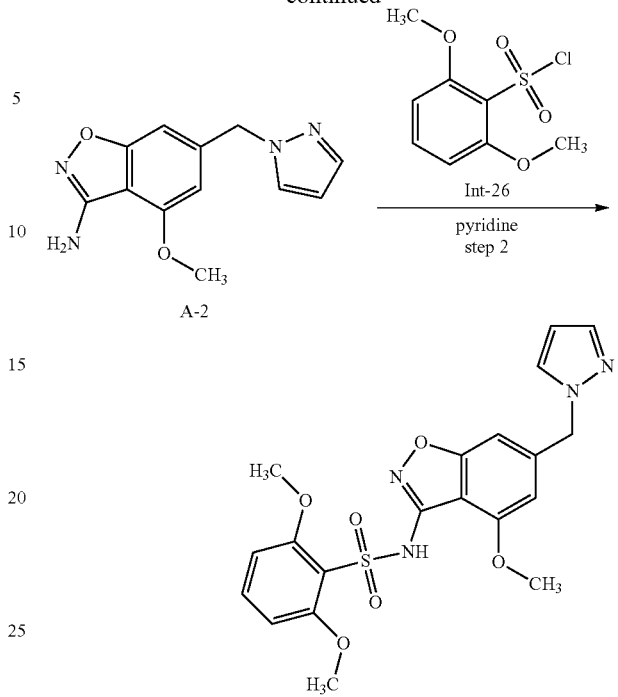

Step 1: Alternate Synthesis of 4-methoxy-6-[(1H-pyrazol-1-yl)methyl]-1,2-benzoxazol-3-amine (A-2) using 1,1,3,3-tetramethylguanidine A suspension of 2-fluoro-6-methoxy-4-(1H-pyrazol-1-ylmethyl)benzonitrile (A-1) (15.43 g, 66.7 mmol), N-hydroxyacetamide (15.0 g, 200 mmol), and 1,1,3,3-TMG (46.1 g, 400 mmol) in acetonitrile (270 mL) and deionized water (30 mL) was heated to 60° C. for 7 hours. The acetonitrile was removed under vacuum, and the residual thick oil was partitioned between ethyl acetate (300 mL) and deionized water (250 mL). The aqueous layer was extracted with ethyl acetate (2×150 mL). All the organic layers were combined and washed with satd. aq. NaCl. Some solids began to form in the organic layer, so methanol (~10 mL) was added and the suspension heated until homogeneous. After cooling to room temperature, the organic layer was dried over sodium sulfate, filtered, and concentrated. The resulting pale-yellow solid was suspended in ethyl acetate (125 mL) and heated briefly to reflux. The suspension was allowed to cool to room temperature, the resulting solids were collected by filtration, and the filter cake was rinsed with heptane. The filtrate and heptane rinse were concentrated to dryness, the residual solid suspended in ethyl acetate (15 mL), the suspension briefly heated to reflux, and a second crop of precipitate was collected as before. The combined precipitate crops were dried under vacuum to give 4-methoxy-6-[(1H-pyrazol-1-yl)methyl]-1,2-benzoxazol-3-amine (A-2) (11.86 g, 48.6 mmol) as a pale-yellow powder. 1H NMR (400 MHz, DMSO-d6) δ 7.87 (d, J=1.8 Hz, 1H), 7.49 (d, J=1.2 Hz, 1H), 6.69 (s, 1H), 6.62 (s, 1H), 6.30 (t, J=2.1 Hz, 1H), 5.93 (s, 2H), 5.41 (s, 2H), 3.86 (s, 3H). LCMS: [M+H]+ 245.

Step 2: Synthesis of 22,6-dimethoxy-N-{4-methoxy-6-[(1H-pyrazol-1-yl)methyl]-1,2-benzoxazol-3-yl}benzene-1-sulfonamide (Example 98)

A mixture of 4-methoxy-6-[(1H-pyrazol-1-yl)methyl]-1,2-benzoxazol-3-amine (A-2) (9.5 g, 39 mmol) and 2,6-dimethoxybenzenesulfonyl chloride (Int-26) (12.1 g, 51.1 mmol) in pyridine (20 mL) was heated to 97° C. internal for 1 hour. After cooling to 50° C., the solution was poured into a flask containing crushed ice (200 g) and 6N HCl (100 mL). The reaction flask was rinsed with dichloromethane to quantitate the transfer. The resulting aqueous mixture was extracted with dichloromethane (4×100 mL). The combined organic extracts were washed with deionized water and satd. aq. NaCl, dried over magnesium sulfate, filtered, and concentrated to a yellow foam. Methyl acetate (50 mL) was added to the foam and the suspension stirred at room temperature for 1 hour. Solids were collected by suction filtration and rinsed with heptane. After drying under vacuum, crude 2,6-dimethoxy-N-[4-methoxy-6-(1H-pyrazol-1-ylmethyl)-1,2-benzoxazol-3-yl]benzenesulfonamide (Example 98)(16.1 g, 95%) was obtained as an orange-tan solid. Trituration of the crude solid with methyl acetate two more times did not remove the orange color, so the crude product was triturated in warm dichloromethane, allowed to cool to room temperature, and filtered to give a cream-colored white solid. The dichloromethane mother liquor was further purified by chromatography (330 g silica column, eluting with 60-100% ethyl acetate in heptane) to give a white solid. The solids from both the DCM trituration and the chromatography of the DCM filtrate were combined, stirred in refluxing methyl acetate, and cooled to room temperature over 2 hours. The resulting solid was collected by suction filtration and dried in a 100° C. vacuum oven overnight, affording purified 2,6-dimethoxy-N-[4-methoxy-6-(1H-pyrazol-1-ylmethyl)-1,2-benzoxazol-3-yl]benzenesulfonamide (Example 98) (15.3 g, 89%) as an off-white powder.

Three batches of Example 98 (total 54.3 g), prepared as described above, were combined, suspended in methyl acetate (250 mL), and heated to reflux for 1 hour. After removing from the heating bath, stirring was continued for 4 hours as the mixture cooled to room temperature. The resulting precipitate was collected by filtration and rinsed with heptane. The solid was dried under vacuum at room temperature for 2 hours, then dried further in a 130° C. vacuum oven for 16 hours, affording 2,6-dimethoxy-N-[4-methoxy-6-(1H-pyrazol-1-ylmethyl)-1,2-benzoxazol-3-yl]benzenesulfonamide (Example 98) (53.55 g, 99%) as an off-white solid. $^1$H NMR (400 MHz, DMSO-$d_6$) δ 9.60 (s, 1H), 7.88 (d, J=1.7 Hz, 1H), 7.45-7.52 (m, 2H), 6.83 (s, 1H), 6.77 (d, J=8.4 Hz, 3H), 6.30 (t, J=2.1 Hz, 1H), 5.44 (s, 2H), 3.87 (s, 3H), 3.76 (s, 6H). LCMS: [M+H]$^+$ 445. Anal. Calcd for $C_{20}H_{20}N_4O_6S$: C, 54.05; H, 4.54; N, 12.61; S, 7.21. Found: C, 53.91; H, 4.58; N, 12.51; S, 7.09.

Example 99: Preparation of N-(6-((1H-pyrazol-1-yl)methyl)-4-methoxybenzo[d]isoxazol-3-yl)-3-methylquinoline-8-sulfonamide according to Method AC

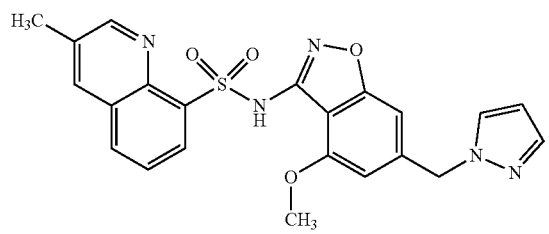 [SMILES: COc1cc(Cn2cccn2)cc2onc(NS(=O)(=O)c3cccc4cc(C)cnc34)c12]

Example 100: Preparation of 2,6-dimethoxy-N-(4-methoxy-6-((4-methyl-1H-pyrazol-1-yl)methyl)benzo[d]isoxazol-3-yl)benzenesulfonamide according to Method AC

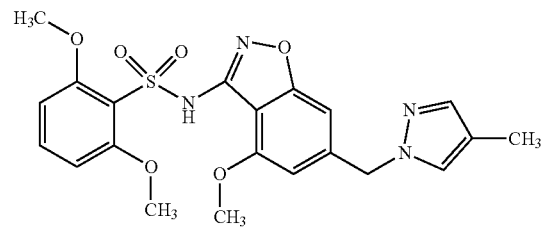 [SMILES: COc1cccc(OC)c1S(=O)(=O)Nc1noc2cc(Cn3cc(C)cn3)cc(OC)c12]

Method AC:

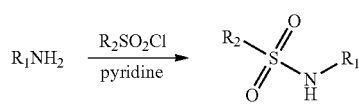

To a solution of the amine (0.2 mmol, 1.0 eq.) in pyridine (2 mL) was added the sulfonyl chloride (1.5 eq.) and the mixture was heated at 120° C. under microwave irradiation for 2 h. The mixture was partitioned between water and EtOAc, the layers were separated, and the organic layer was washed with brine, dried over Na$_2$SO$_4$, filtered and concentrated under reduced pressure. The residue was purified by prep. TLC to give the title compound. Variations to above conditions have been noted in Table 18.

TABLE 18

| Example Name and Structure | Analytical | Intermediates | Notes |
| --- | --- | --- | --- |
| 99 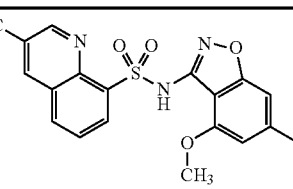<br>N-(6-((1H-pyrazol-1-yl)methyl)-4-methoxybenzo[d]isoxazol-3-yl)-3-methylquinoline-8-sulfonamide | $^1$H NMR (400 MHz, DMSO-d$_6$) δ 8.92 (br. s, 1 H), 8.33 (d, J = 3.2 Hz, 1H), 8.21 (br. s, 1H), 7.99 (br. s, 1H), 7.81 (br. s, 1H), 7.64 (br. s, 1H), 7.43 (br. s, 1H), 6.82-6.47 (m, 2H), 6.24 (s, 1H), 5.32 (s, 2H), 3.82 (s, 3H), 2.43 (s, 3H); m/z 450.0 [M + H]$^+$. | 6-((1H-pyrazol-1-yl)methyl)-4-methoxy-benzo[d]-isoxazol-3-amine (J-2) | 1.2 eq. sulfonyl chloride used; 5 mL pyridine used. Adjusted to pH 5 with 1 M aq. HCl prior to workup. Prep. TLC (Pet. Ether/EtOAc = 1/2) |
| 100 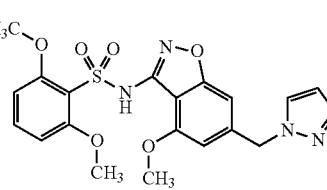<br>2,6-dimethoxy-N-(4-methoxy-6-((4-methyl)-1H-pyrazol-1-yl)methyl)benzo[d]isoxazol-3-yl)benzenesulfonamide | $^1$H NMR (400 MHz, CDCl$_3$) δ 9.83 (br. s, 1H), 8.21 (s, 1H), 7.37-7.35 (m, 2H), 7.19 (s, 1H), 6.76 (s, 1H), 6.58 (d, J = 8.4 Hz, 2H), 6.46 (s, 1H), 5.29 (s, 2H), 3.96 (s, 3H), 3.87 (s, 6H), 2.07 (s, 3H); m/z 459.0 [M + H]$^+$ | dimethoxy benzene-sulfonyl chloride (Int-26) 4-methoxy-6-((4-methyl 1H-pyrazol-1-yl)methyl) benzo[d] isoxazol-3-amine (Int-25) | Reaction mixture was concentrated prior to workup. Prep. TLC (DCM/MeOH H, 20/1) |

Example 101: Preparation 2,6-dimethoxy-N-(4-methoxy-6-(1-methyl-1H-pyrazol-4-yl)benzo[d]isoxazol-3-yl)benzenesulfonamide According to Scheme M Scheme M

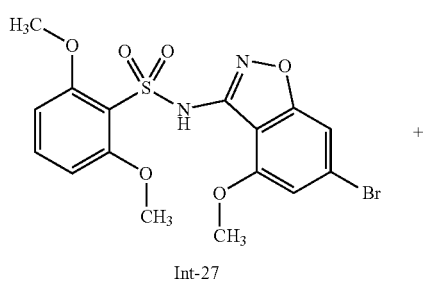

Int-27

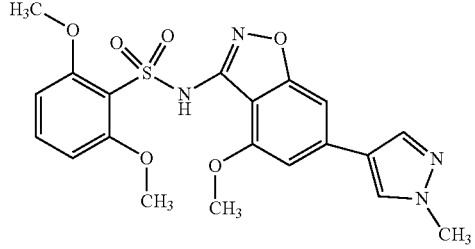 [SMILES: COc1cccc(OC)c1S(=O)(=O)Nc1noc2cc(-c3cnn(C)c3)cc(OC)c12]

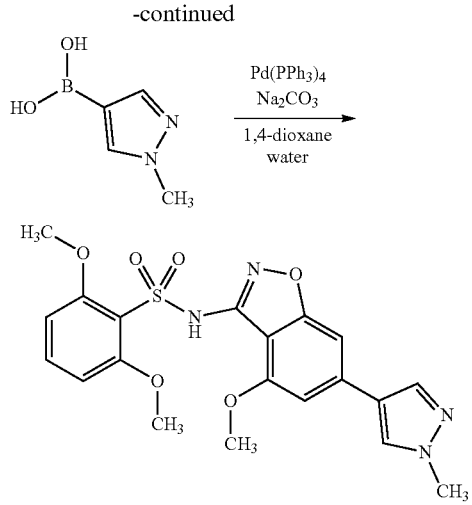

Example 101

To a solution of N-(6-bromo-4-methoxybenzo[d]isoxazol-3-yl)-2,6-dimethoxybenzenesulfonamide (Int-27) (40 mg, 0.09 mmol) in 1,4-dioxane (8 mL) and water (2 mL) was added (1-methyl-1H-pyrazol-4-yl)boronic acid (80 mg, 0.631 mmol), Na$_2$CO$_3$ (100 mg, 0.948 mmol) and Pd(PPh$_3$)$_4$ (37 mg, 0.032 mmol) and the mixture was heated at reflux under a N$_2$ atmosphere overnight. The mixture was adjusted to pH 4-5 with 1 M aqueous HCl, diluted with EtOAc and washed with water, brine, dried over Na$_2$SO$_4$, filtered and concentrated under reduced pressure. The residue was purified by prep. TLC (DCM/MeOH=50/1) to give the title compound (22 mg, 55%) as a white solid. m/z 445.0 [M+H]$^+$. $^1$H NMR (400 MHz, DMSO-d$_6$) δ 9.52 (s, 1H), 8.35 (s, 1H), 8.05 (s, 1H), 7.50 (t, J=8.5 Hz, 1H), 7.38 (s, 1H), 7.05 (s, 1H), 6.78 (d, J=8.5 Hz, 2H), 3.98 (s, 3H), 3.87 (s, 3H), 3.78 (s, 6H).

Example 102: Preparation of 2,6-dimethoxy-N-(5-methyl-7-(1-methyl-1H-pyrazol-4-yl)benzo[d]isoxazol-3-yl)benzenesulfonamide According to Scheme N

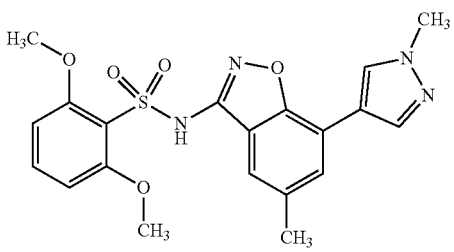

Scheme N

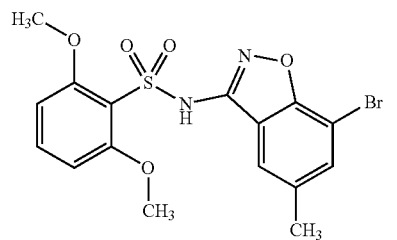

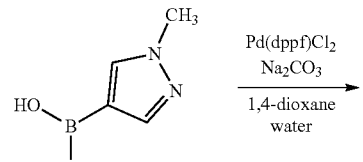

Example 102

To a solution of N-(7-bromo-5-methylbenzo[d]isoxazol-3-yl)-2,6-dimethoxybenzenesulfonamide (Int-29)(50 mg, 0.117 mmol) in 1,4-dioxane (8 mL) and water (2 mL) was added (1-methyl-1H-pyrazol-4-yl)boronic acid (22 mg, 0.176 mmol), Na$_2$CO$_3$ (50 mg, 0.468 mmol) and Pd(dppf)Cl$_2$ (9 mg, 0.012 mmol) and the mixture was heated at reflux under a N$_2$ atmosphere overnight. The mixture was adjusted to pH 5 with 1 M aqueous HCl, diluted with water and extracted with EtOAc (30 mL×3). The combined organic extracts were washed with brine, dried over Na$_2$SO$_4$, filtered and concentrated under reduced pressure. The residue was purified by prep. TLC (Pet. Ether/EtOAc=3/1) to give the title compound (24 mg, 48%) as a white solid. m/z 429.0 [M+H]$^+$. $^1$H NMR (400 MHz, DMSO-d$_6$) δ 8.24 (s, 1H), 7.99 (s, 1H), 7.55 (s, 1H), 7.49-7.22 (m, 2H), 6.67 (d, J=8.6 Hz, 2H), 3.88 (s, 3H), 3.69 (s, 6H), 2.39 (s, 3H) 0.38 (s, 1H), 7.05 (s, 1H), 6.78 (d, J=8.5 Hz, 2H), 3.98 (s, 3H), 3.87 (s, 3H), 3.78 (s, 6H).

Example 103: Preparation of 3-hydroxy-2,6-dimethoxy-N-{4-methoxy-6-[(1H-pyrazol-1-yl)methyl]-1,2-benzoxazol-3-yl}benzene-1-sulfonamide according to Scheme O

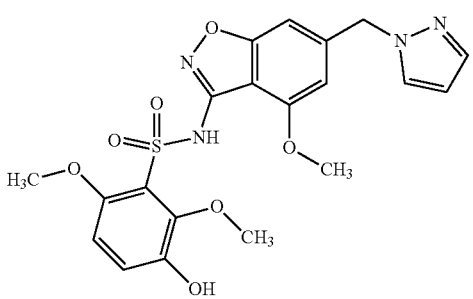 [SMILES: COc1ccc(O)c(OC)c1S(=O)(=O)Nc1noc2cc(Cn3cccn3)cc(OC)c12]

Example 104: Preparation of 2-hydroxy-6-methoxy-N-{4-methoxy-6-[(1H-pyrazol-1-yl)methyl]-1,2-benzoxazol-3-yl}benzene-1-sulfonamide According to Scheme O

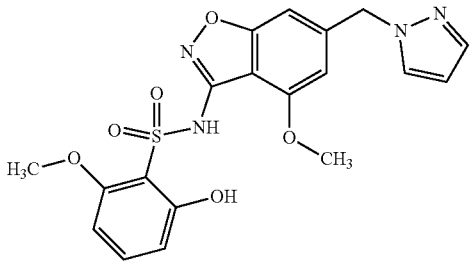 [SMILES: COc1cccc(O)c1S(=O)(=O)Nc1noc2cc(Cn3cccn3)cc(OC)c12]

Example 105: Preparation of N-{6-[(4-hydroxy-1H-pyrazol-1-yl)methyl]-4-methoxy-1,2-benzoxazol-3-yl}-2,6-dimethoxybenzene-1-sulfonamide According to Scheme O

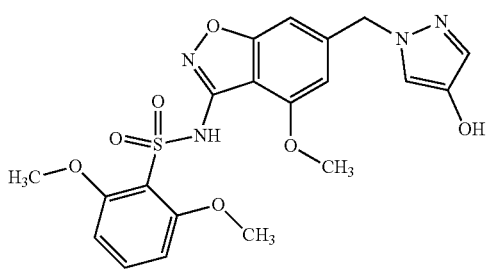 [SMILES: COc1cccc(OC)c1S(=O)(=O)Nc1noc2cc(Cn3cc(O)cn3)cc(OC)c12]

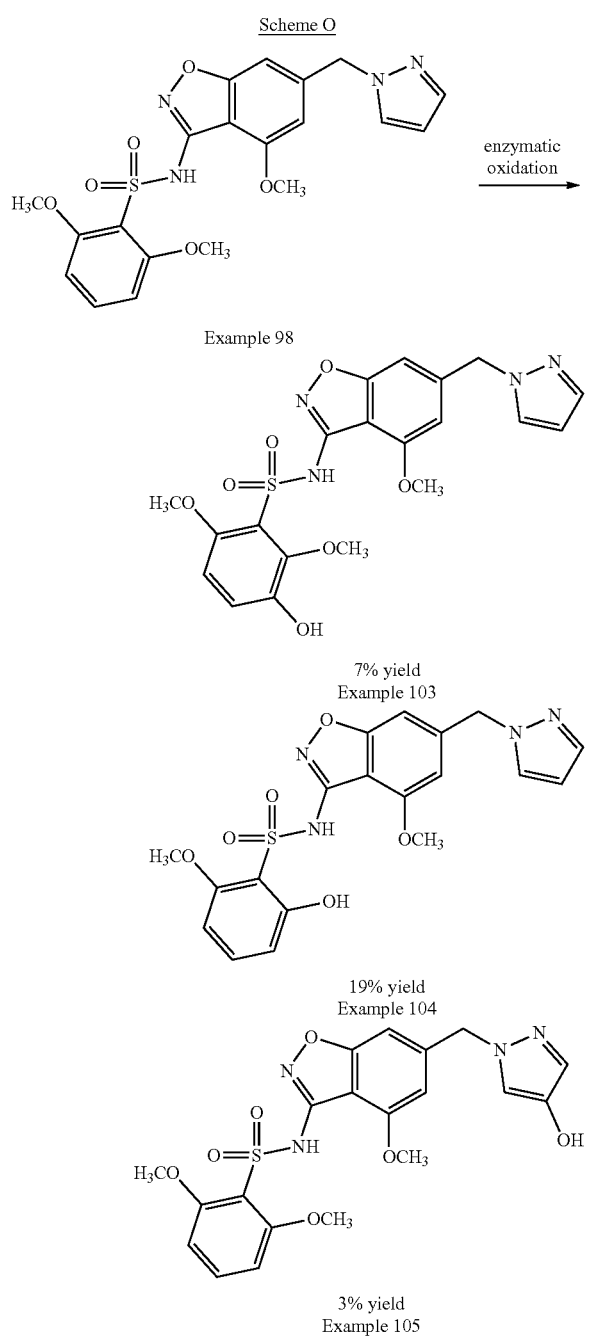

Scheme O

Example 98

7% yield
Example 103

19% yield
Example 104

3% yield
Example 105

To a 500 mL Erlenmeyer flask was added HPLC grade H₂O (27.2 mL), aqueous potassium phosphate buffer (1.0 M, 4.0 mL, pH 7.5), aqueous MgCl₂ (165 mM, 0.8 mL), dexamethasone-induced male rat liver microsomes (4.0 mL, 20 mg/mL, Xenotech) and a solution of 2,6-dimethoxy-N-{4-methoxy-6-[(1H-pyrazol-1-yl)methyl]-1,2-benzoxazol-3-yl}benzene-1-sulfonamide (Prepared as in Example 98, 5 mM in MeCN, 0.20 mL, 1.0 mol). The incubation was commenced with addition of a freshly prepared aqueous solution of NADPH (4.0 mL, 13 mM). The uncapped Erlenmeyer flask was shaken in a water bath maintained at 37° C. for 1.5 h. The incubation mixture was quenched by adding MeCN (40 mL) followed by centrifugation at ~1700 g for 5 min. The supernatant was partially evaporated in a vacuum centrifuge. The remaining solution was treated with MeCN (0.5 mL), neat formic acid (0.5 mL) and de-ionized H₂O to a provide final volume of ~50 mL. The solution was subjected to centrifugation at ~40,000 g for 30 min. The supernatant was adsorbed onto a Zorbax Polaris C18-A HPLC column (250×4.6 mm, 5 m particle size) using a JASCO PU-1580 HPLC pump at a flow rate of 0.8 mL/min over ~60 min. The HPLC column was transferred to a Thermo LTQ Velos mass spectrometer in line with a Waters Acquity UHPLC instrument comprised of a quaternary pump, autosampler and photodiode array UV/vis detector. A gradient of MeCN/H₂O (+0.1% formic acid) was applied to separate products of interest. After passing through the PDA detector, the eluent was split at a ratio of approximately 15:1 with the larger portion going to a fraction collector and the smaller portion to the mass spectrometer. Fractions were collected every 20 s and those containing peaks of interest were analyzed by UHPLC-UV-HRMS using a Thermo Orbitrap Elite high-resolution ion trap mass spectrometer in line with a Thermo Accela UHPLC and diode array UV/vis detector with a CTC Analytics Leap autoinjector (Thermo-Fisher). Samples were injected (10 μL) onto a Phenomenex Kinetex C18 UHPLC column (50×2.1 mm, 1.7 m particle size) maintained at 45° C., which was eluted with a MeCN/H₂O (+0.1% formic acid) gradient with a flow rate of 0.4 mL/min. After UHPLC-UV-HRMS analysis, fractions were pooled, and the solvent was removed by vacuum centrifugation. The dried samples were analyzed by NMR spectroscopy and quantified by external calibration against the ¹H NMR spectrum of a 5.0 mM benzoic acid standard solution in DMSO-d₆ using the ERETIC2 function within Topspin V3.2. N-{6-[(4-hydroxy-1H-pyrazol-1-yl)methyl]-4-methoxy-1,2-benzoxazol-3-yl}-2,6-dimethoxybenzene-1-sulfonamide (Example 105) (0.028 μmol, 3% yield) was obtained as the first-eluting peak. ¹H NMR (600 MHz, DMSO-d₆) δ 8.45 (s, 1H), 7.38 (m, 1H), 7.32 (s, 1H), 7.06 (s, 1H), 6.70 (m, 3H), 6.63 (s, 1H), 5.22 (s, 2H), 3.86 (s, 3H), 3.69 (s, 6H). HRMS (ESI-TOF) calculated for (C₂₀H₂₁N₄O₇S) [M+H]⁺ m/z=461.1125, found 461.1121 (~0.45 ppm). 3-Hydroxy-2,6-dimethoxy-N-{4-methoxy-6-[(1H-pyrazol-1-yl)methyl]-1,2-benzoxazol-3-yl}benzene-1-sulfonamide (Example 103) (0.072 μmol, 7% yield) was obtained as the second-eluting peak. ¹H NMR (600 MHz, DMSO-d₆) δ 9.33 (s, 1H), 7.88 (d, J=2.4 Hz, 1H), 7.50 (s, 1H), 7.01 (d, J=9.0 Hz, 1H), 6.80 (s, 1H), 6.76-6.68 (m, 2H), 6.31 (t, J=2.3 Hz, 1H), 5.44 (s, 2H), 3.87 (s, 3H), 3.76 (s, 3H), 3.65 (s, 3H). HRMS (ESI-TOF) calculated for (C₂₀H₂₁N₄O₇S) [M+H]⁺ m/z=461.1125, found 461.1123 (~0.25 ppm). 2-Hydroxy-6-methoxy-N-{4-methoxy-6-[(1H-pyrazol-1-yl)methyl]-1,2-benzoxazol-3-yl}benzene-1-sulfonamide (Example 104) (0.19 μmol, 19% yield) was obtained as the third eluting peak. ¹H NMR (600 MHz, DMSO-d₆) δ 7.86 (s, 1H), 7.50 (s, 1H), 7.13 (m, 1H), 6.63 (s, 1H), 6.53 (m, 2H), 6.40 (d, J=8.1 Hz, 2H), 6.30 (s, 1H), 5.41 (s, 2H), 3.83 (s, 3H), 3.72 (s, 3H). HRMS (ESI-TOF) calculated for (C₁₉H₁₉N₄O₆S) [M+H]⁺ 431.1020, found 431.1017 (~0.28 ppm).

161

Example 106: Preparation of N-{6-[hydroxy(pyridin-2-yl)methyl]-4-methoxy-1,2-benzoxazol-3-yl}-2,6-dimethoxybenzenesulfonamide According to Scheme P

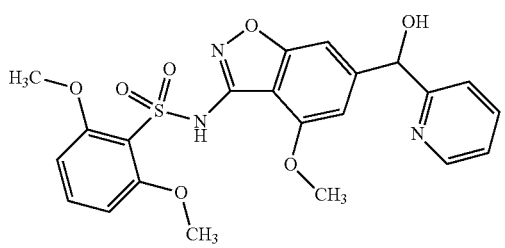 [SMILES: COc1cccc(OC)c1S(=O)(=O)Nc1noc2cc(C(O)c3ccccn3)cc(OC)c12]

Example 107: Preparation of 2,6-dimethoxy-N-[4-methoxy-6-(pyridin-2-ylmethyl)-1,2-benzoxazol-3-yl]benzenesulfonamide According to Scheme P

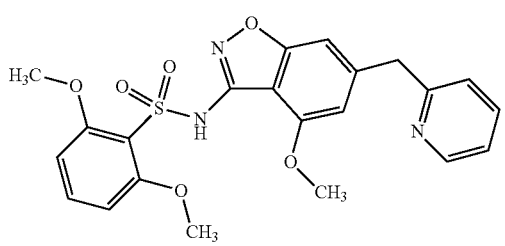 [SMILES: COc1cccc(OC)c1S(=O)(=O)Nc1noc2cc(Cc3ccccn3)cc(OC)c12]

Scheme P

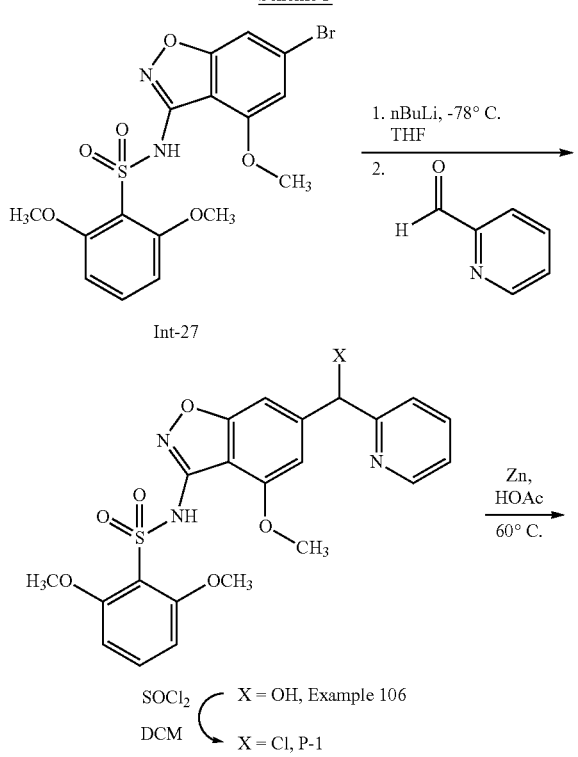

162

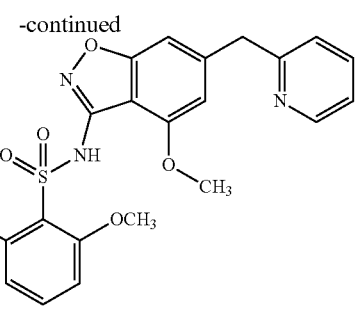

Example 107

Step 1: Synthesis of N-{6-[hydroxy(pyridin-2-yl)methyl]-4-methoxy-1,2-benzoxazol-3-yl}-2,6-dimethoxybenzenesulfonamide (Example 106)

A solution of N-(6-bromo-4-methoxybenzo[d]isoxazol-3-yl)-2,6-dimethoxybenzenesulfonamide (Int-27) (628 mg, 1.42 mmol) in anhydrous THF (20 mL) was cooled to −78° C. n-BuLi (1.20 mL of 2.5 in hexanes, 3.00 mmol) was added dropwise. The resulting slurry was stirred at −78° C. for 1 h. Then, a solution of pyridine-2-aldehyde (187 mg, 1.75 mmol) in anhydrous THF (2 mL) was added dropwise. The resulting reaction mixture was stirred at −78° C. for 1 h. Additional pyridine-2-aldehyde (75 mg, 0.71 mmol) in 1 mL anhydrous THF was added. The resulting reaction mixture was warmed to room temperature and stirred at room temperature for 18 h. The reaction was quenched with HOAc (0.5 mL). The quenched reaction mixture was partitioned between EtOAc (50 mL) and water (50 mL). The organic phase was separated, washed with brine, dried over sodium sulfate, filtered and purified via flash chromatography eluting with a gradient of 0-100% EtOAc in heptane, then 0-20% 2-PrOH in EtOAc to afford N-{6-[hydroxy(pyridin-2-yl)methyl]-4-methoxy-1,2-benzoxazol-3-yl}-2,6-dimethoxybenzenesulfonamide (Example 106) as a solid (247 mg, 37%). $^1$H NMR (400 MHz, CDCl$_3$) δ 8.61 (d, J=4.9 Hz, 1H), 8.23 (s, 1H), 7.82 (t, J=7.7 Hz, 1H), 7.42-7.33 (m, 3H), 7.10 (s, 1H), 6.85 (s, 1H), 6.58 (d, J=8.4 Hz, 2H), 5.99 (s, 1H), 4.01 (s, 3H), 3.88 (s, 6H). m/z 472.2 [M+H].

Step 2: Synthesis of N-(6-(chloro(pyridin-2-yl)methyl)-4-methoxybenzo[d]isoxazol-3-yl)-2,6-dimethoxybenzenesulfonamide (P-1)

To a solution of N-{6-[hydroxy(pyridin-2-yl)methyl]-4-methoxy-1,2-benzoxazol-3-yl}-2,6-dimethoxybenzenesulfonamide (Example 106) (113 mg, 0.240 mmol) in anhydrous DCM (5 mL) was added SOCl$_2$ (0.20 mL, 2.7 mmol). The resulting reaction mixture was stirred at room temperature for 3 h. The solvent was removed, and the resulting residue was partitioned between EtOAc (50 mL) and satd. aqueous NaHCO$_3$ (50 mL). The organic phase was separated, dried over sodium sulfate, and concentrated to afford N-(6-(chloro(pyridin-2-yl)methyl)-4-methoxybenzo[d]isoxazol-3-yl)-2,6-dimethoxybenzenesulfonamide (P-1) (78 mg, 66% yield) which was used in the next step without further purification. $^1$H NMR (400 MHz, CDCl$_3$) δ 8.57 (br. d, J=4.2 Hz, 1H), 8.25 (s, 1H), 7.75 (dt, J=1.7, 7.8 Hz, 1H), 7.57 (d, J=7.8 Hz, 1H), 7.37 (t, J=8.5 Hz, 1H), 7.27-7.22 (m, 1H), 7.10 (s, 1H), 6.82 (s, 1H), 6.57 (d, J=8.6 Hz, 2H), 6.17 (s, 1H), 4.00 (s, 3H), 3.87 (s, 6H), missing the sulfonamide NH; m/z 490.1 [M+H]$^+$.

Step 3: Synthesis of 2,6-dimethoxy-N-[4-methoxy-6-(pyridin-2-ylmethyl)-1,2-benzoxazol-3-yl]benzenesulfonamide (Example 107)

To a solution of N-(6-(chloro(pyridin-2-yl)methyl)-4-methoxybenzo[d]isoxazol-3-yl)-2,6-dimethoxybenzenesulfonamide (P-1) (75 mg, 0.153 mmol) in HOAc (5 mL) was added zinc dust (69 mg, 1.1 mmol) and the solution was heated to 60° C. After 3 h at 60° C., the reaction was complete. The reaction was cooled to room temperature and carefully neutralized with saturated NaHCO$_3$. The organics were extracted with EtOAc (2×50 mL) and the combined organic extract was dried over sodium sulfate, concentrated to dryness and purified via flash chromatography eluting with a gradient of 0-100% EtOAc in heptane followed by 0-20% 2-PrOH in EtOAc. Concentration of the pure fractions afforded 2,6-dimethoxy-N-[4-methoxy-6-(pyridin-2-ylmethyl)-1,2-benzoxazol-3-yl]benzenesulfonamide (Example 107) (38 mg, 55% over two steps) as a solid. $^1$H NMR (400 MHz, CDCl$_3$) δ 8.57 (br. s, 1H), 8.23 (s, 1H), 7.65 (t, J=7.6 Hz, 1H), 7.37 (t, J=8.5 Hz, 1H), 7.19 (br. d, J=6.6 Hz, 2H), 6.89 (s, 1H), 6.64-6.53 (m, 3H), 4.23 (s, 2H), 3.98 (s, 3H), 3.87 (s, 6H). m/z 456.3 [M+H].

Example 108: Preparation of N-{6-[(S*)-hydroxy(1,3-oxazol-2-yl)methyl]-4-methoxy-1,2-benzoxazol-3-yl}-2,6-dimethoxybenzenesulfonamide According to Scheme Q

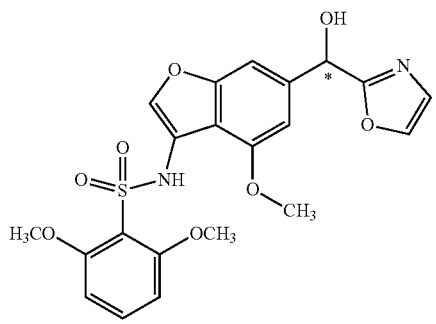 [SMILES: COc1cccc(OC)c1S(=O)(=O)Nc1coc2cc(C(O)c3ncco3)cc(OC)c12]

Example 109: Preparation of N-{6-[(R*)-hydroxy(1,3-oxazol-2-yl)methyl]-4-methoxy-1,2-benzoxazol-3-yl}-2,6-dimethoxybenzenesulfonamide According to Scheme Q

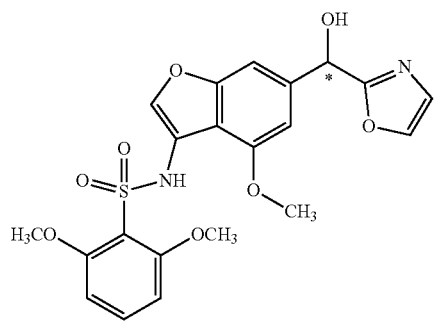 [SMILES: COc1cccc(OC)c1S(=O)(=O)Nc1coc2cc(C(O)c3ncco3)cc(OC)c12]

Example 110: Preparation of 2,6-dimethoxy-N-[4-methoxy-6-(1,3-oxazol-2-ylmethyl)-1,2-benzoxazol-3-yl]benzenesulfonamide According to Scheme Q

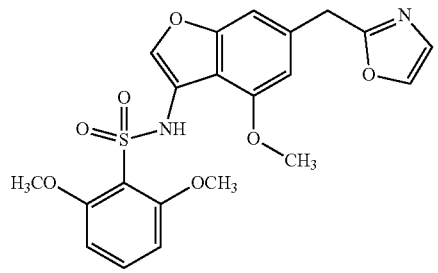 [SMILES: COc1cccc(OC)c1S(=O)(=O)Nc1coc2cc(Cc3ncco3)cc(OC)c12]

Scheme Q

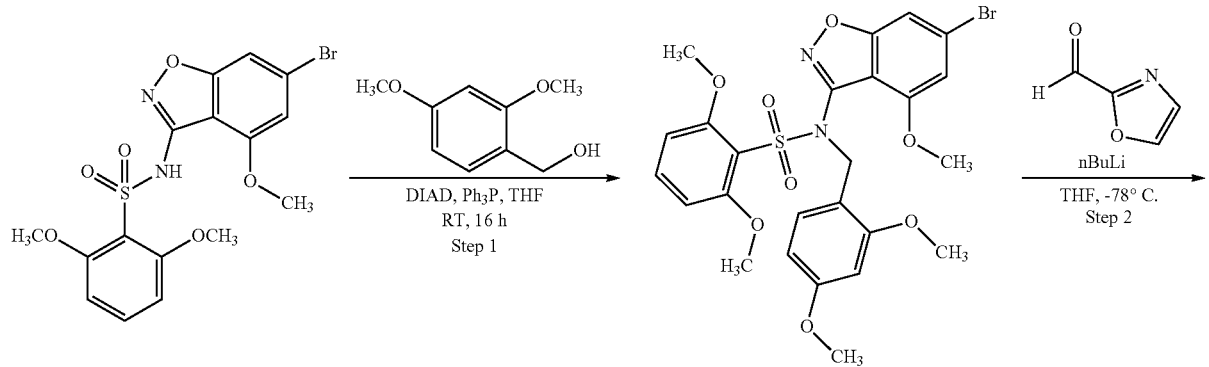

-continued

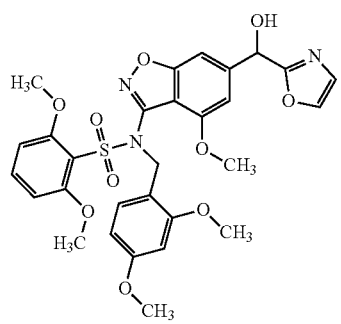

Q-2

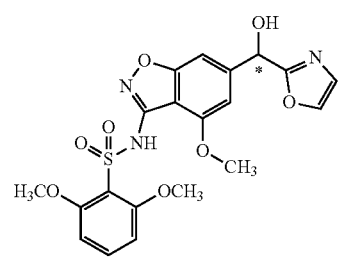

Example 108
Peak 1 from chiral SFC

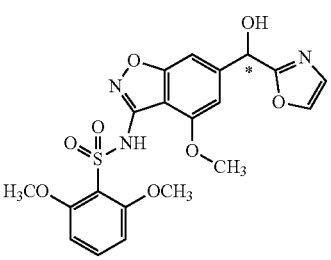

Example 109
Peak 2 from chiral SFC

Step 4 1. SOCl₂, DCM
Step 5 2. Zn, HOAc

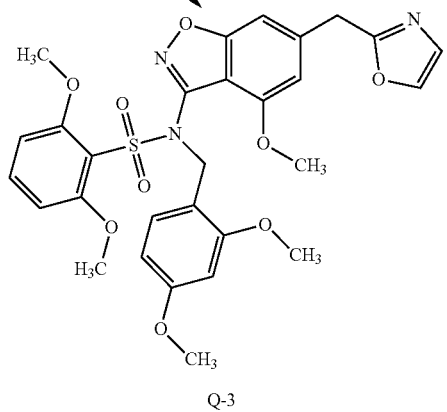

Q-3

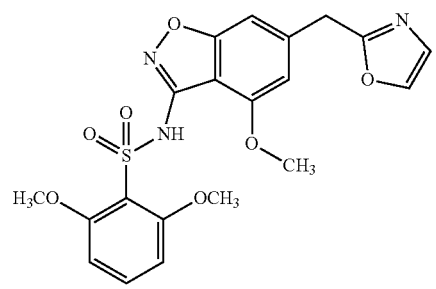

Example 110

Step 1: Synthesis of N-(6-bromo-4-methoxy-1,2-benzoxazol-3-yl)-N-[(2,4-dimethoxyphenyl)methyl]-2,6-dimethoxybenzene-1-sulfonamide (Q-1)

To a solution of N-(6-bromo-4-methoxybenzo[d]isoxazol-3-yl)-2,6-dimethoxybenzenesulfonamide (Int-27) (15 g, 34 mmol) in THF (300 mL) and 2,4-dimethoxybenzyl alcohol (8.54 g, 50.8 mmol), PPh₃ (22.2 g, 84.6 mmol) was added DIAD (13.7 g, 67.7 mmol) dropwise at 0° C. The reaction solution was warmed to room temperature and allowed to stir for 16 h. The reaction mixture was diluted with EtOAc (300 mL), washed with water (150 mL), brine, saturated aq. sodium bicarbonate, and brine again. The organic phase was dried over sodium sulfate and filtered. The solvent was removed under reduced pressure to give a mixture that was purified by flash chromatography eluting with 60%-70% EtOAc in petroleum ether to give crude product with some triphenylphosphine oxide remaining. The crude solid was re-crystalized from MeOH to give N-(6-bromo-4-methoxy-1,2-benzoxazol-3-yl)-N-[(2,4-dimethoxyphenyl)methyl]-2,6-dimethoxybenzene-1-sulfonamide (Q-1) (8.0 g, 40% yield) as a white solid.

Step 2: Synthesis of rac-N-[(2,4-dimethoxyphenyl)methyl]-N-{6-[hydroxy(1,3-oxazol-2-yl)methyl]-4-methoxy-1,2-benzoxazol-3-yl}-2,6-dimethoxybenzene-1-sulfonamide (Q-2)

To a solution of N-(6-bromo-4-methoxy-1,2-benzoxazol-3-yl)-N-[(2,4-dimethoxyphenyl)methyl]-2,6-dimethoxybenzene-1-sulfonamide (Q-1) (500 mg 0.843 mmol) in THF (9.5 mL) was added n-BuLi (0.506 mL of a 2.5 M solution in hexanes, 1.26 mmol) dropwise at −78° C. under an argon atmosphere. After 30 min at −78° C., oxazole-2-carbaldehyde (123 mg 1.26 mmol) was added as a solution in THF (0.5 mL). The reaction was slowly allowed to warm to room temperature and stirred 16 h. The reaction mixture was poured into saturated aq. NH₄Cl (20 mL). The aqueous layer was extracted with two portions of EtOAc (2×20 mL). The combined extract was washed with brine (20 mL), dried over MgSO₄ and concentrated in vacuo. The residue was purified by flash chromatography eluting with 100% EtOAc to give rac-N-[(2,4-dimethoxyphenyl)methyl]-N-{6-[hydroxy(1,3-oxazol-2-yl)methyl]-4-methoxy-1,2-benzoxazol-3-yl}-2,6-dimethoxybenzene-1-sulfonamide (Q-2) (150 mg, 29% yield) as a yellow gum.

Step 3: Synthesis of N-{6-[(S*)-hydroxy(1,3-oxazol-2-yl)methyl]-4-methoxy-1,2-benzoxazol-3-yl}-2,6-dimethoxybenzenesulfonamide (Example 108) and N-{6-[(R*)-hydroxy(1,3-oxazol-2-yl)methyl]-4-methoxy-1,2-benzoxazol-3-yl}-2,6-dimethoxybenzenesulfonamide (Example 109)

A solution of rac-N-[(2,4-dimethoxyphenyl)methyl]-N-{6-[hydroxy(1,3-oxazol-2-yl)methyl]-4-methoxy-1,2-benzoxazol-3-yl}-2,6-dimethoxybenzene-1-sulfonamide (Q-2) (150 mg 0.245 mmol) in TFA (5 mL) was stirred at room temperature for 2 h. A pink solution was observed, and the reaction mixture was concentrated in vacuo. The residue was pre-purified by flash chromatography eluting with EtOAc/MeOH 10:1 to give a racemic mixture of Examples 108 and 109 which was submitted to chiral SFC purification. The compounds were separated from each other using a Chiralpak AS-3 100×4.6 mm I.D., 3 um column with a mobile phase consisting of $CO_2$ (A) and ethanol with 0.05% DEA (B). Gradient elution from 5% to 40% of B in 4 min and hold 40% B for 2.5 min, then 5% of B for 1.5 min. After chiral SFC separation 20 mg of each product was obtained. Peak 1=Example 108 $^1$H NMR (400 MHz, DMSO-$d_6$) δ 8.06 (d, J=0.6 Hz, 1H), 7.45 (br. t, J=8.4 Hz, 1H), 7.18 (d, J=0.6 Hz, 1H), 7.15 (s, 1H), 6.86 (s, 1H), 6.74 (d, J=8.4 Hz, 2H), 6.67 (d, J=5.1 Hz, 1H), 5.93 (d, J=5.3 Hz, 1H), 3.88 (s, 3H), 3.74 (s, 6H), missing sulfonamide NH peak; m/z 462.0 (M+H)$^+$. Peak 2=Example 109 $^1$H NMR (400 MHz, DMSO-$d_6$) δ 8.06 (d, J=0.6 Hz, 1H), 7.50 (t, J=8.5 Hz, 1H), 7.13-7.26 (m, 2H), 6.90 (s, 1H), 6.78 (d, J=8.4 Hz, 2H), 6.70 (d, J=5.4 Hz, 1H), 5.95 (d, J=5.3 Hz, 1H), 3.89 (s, 3H), 3.78 (s, 6H), missing sulfonamide NH peak; m/z 462.0 (M+H)$^+$.

Steps 4 and 5: Synthesis of N-[(2,4-dimethoxyphenyl)methyl]-2,6-dimethoxy-N-{4-methoxy-6-[(1,3-oxazol-2-yl)methyl]-1,2-benzoxazol-3-yl}benzene-1-sulfonamide (Q-3)

To a solution of rac-N-[(2,4-dimethoxyphenyl)methyl]-N-{6-[hydroxy(1,3-oxazol-2-yl)methyl]-4-methoxy-1,2-benzoxazol-3-yl}-2,6-dimethoxybenzene-1-sulfonamide (Q-2) (150 mg 0.245 mmol) in DCM (5 mL) was added thionyl chloride (290 mg 2.44 mmol) at room temperature. The solution was stirred for 1 h while a pale-yellow solution formed. The reaction was complete by TLC and the mixture was quenched with water (20 mL) and extracted with DCM (20 mL). The organic layer was dried over $Na_2SO_4$, filtered and concentrated to give the secondary chloride (150 mg, yellow oil) which was used in the next step without further purification. To a solution of the secondary chloride (150 mg, 0.238 mmol) in HOAc (5 mL) was added zinc dust (467 mg 7.14 mmol) at room temperature. The reaction was allowed to stir at room temperature for 1 h. The reaction was complete by TLC and the mixture was diluted with EtOAc (50 mL) and filtered. The filtrate was adjusted to pH 7-8 using satd. aq. $Na_2CO_3$. The organic layer was dried over $Na_2SO_4$ and concentrated to give a residue which was purified by flash chromatography to afford N-[(2,4-dimethoxyphenyl)methyl]-2,6-dimethoxy-N-{4-methoxy-6-[(1,3-oxazol-2-yl)methyl]-1,2-benzoxazol-3-yl}benzene-1-sulfonamide (Q-3) (80 mg) as yellow oil.

Step 6: Synthesis of 2,6-dimethoxy-N-[4-methoxy-6-(1,3-oxazol-2-ylmethyl)-1,2-benzoxazol-3-yl]benzenesulfonamide (Example 110)

A solution of N-[(2,4-dimethoxyphenyl)methyl]-2,6-dimethoxy-N-{4-methoxy-6-[(1,3-oxazol-2-yl)methyl]-1,2-benzoxazol-3-yl}benzene-1-sulfonamide (Q-3) (80 mg 0.13 mmol) in TFA (5 mL) was stirred for 1 h at room temperature. The reaction was concentrated and pre-purified by flash chromatography eluting with EtOAc/MeOH 10:1. The crude product obtained was further purified by prep. HPLC and the pure fractions were frozen and lyophilized to afford 10 mg of product still contaminated by an impurity as determined by $^1$H NMR. This sample was further purified via prep. TLC to afford 2,6-dimethoxy-N-[4-methoxy-6-(1,3-oxazol-2-ylmethyl)-1,2-benzoxazol-3-yl]benzenesulfonamide (Example 110) (5 mg, 8.4% yield) as a white solid. m/z 446.0 (M+H)$^+$; $^1$H NMR (400 MHz, METHANOL-$d_4$) b 7.87 (s, 1H), 7.43 (t, J=8.5 Hz, 1H), 7.14 (s, 1H), 6.92 (s, 1H), 6.72 (d, J=8.5 Hz, 3H), 4.34-4.11 (m, 2H), 4.00 (s, 3H), 3.81 (s, 7H).

Example 111: Preparation of 2,6-dimethoxy-N-[4-methoxy-6-(pyrazin-2-ylmethyl)-1,2-benzoxazol-3-yl]benzenesulfonamide According to Scheme R

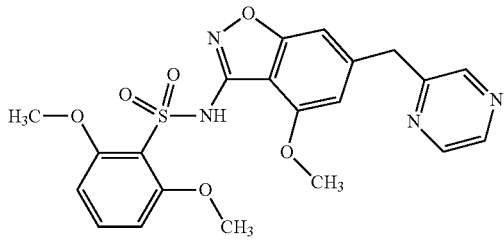

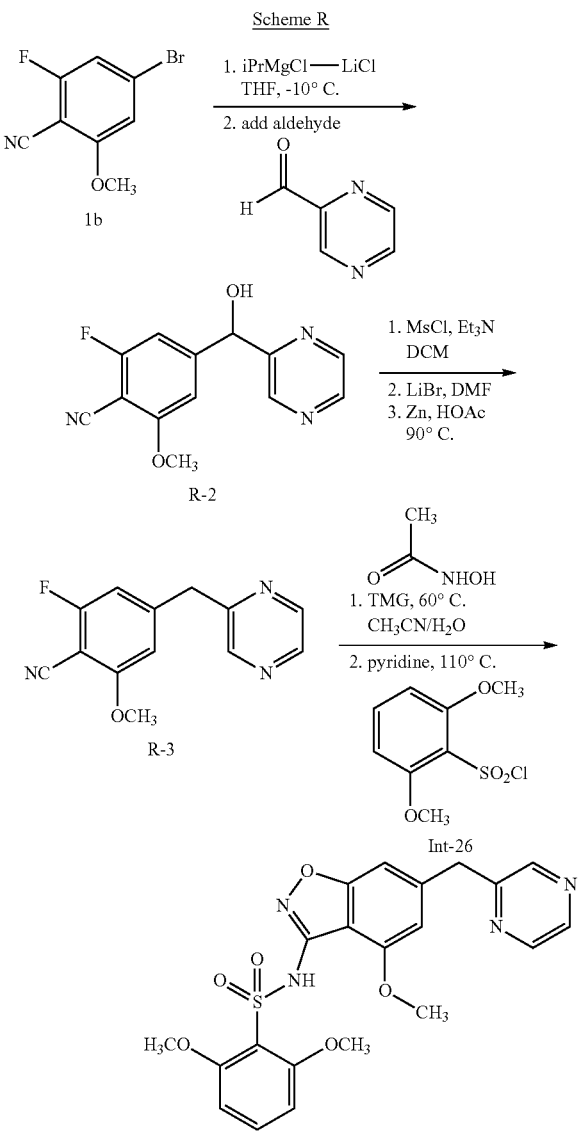

Scheme R

Example 111

Step 1: Synthesis of 2-fluoro-4-[hydroxy(pyrazin-2-yl)methyl]-6-methoxybenzonitrile (R-2)

A 250 mL three-neck round bottom flask was equipped with a thermometer, a stir bar, and a nitrogen inlet. The flask was charged with 4-bromo-2-fluoro-6-methoxybenzonitrile (1b) (4.00 g, 17.4 mmol) and 100 mL anhydrous THF. The flask was capped with a septum stopper, flushed with a nitrogen atmosphere, and cooled down to −20° C. (ice/MeOH bath). iPrMgCl-LiCl (17.5 mL of 1.3 M, 22.8 mmol) was added dropwise, while maintaining the temperature below −15° C. The resulting mixture was stirred at −20° C. for 1 h. Then, pyrazine-2-carboxaldehyde (2.95 g, 1.57 mmol) was added as a solution in 20 mL anhydrous THF while maintaining the temp below −10° C. The resulting reaction was stirred at −10° C. for 1 h and then quenched with 4 N HCl (10 mL). The quenched reaction mixture was partitioned between EtOAc (200 mL) and water (200 mL). The organic phase was separated, and the aqueous phase was extracted with EtOAc again (1×100 mL). The combined organic phases were dried over $Na_2SO_4$, concentrated to dryness and purified via flash chromatography using a gradient of 20-100% EtOAc in heptane to afford 2-fluoro-4-[hydroxy(pyrazin-2-yl)methyl]-6-methoxybenzonitrile (R-2) (2.6 g, 58% yield) as a gum. m/z 260.0 (M+H)$^+$; $^1$H NMR (400 MHz, CDCl$_3$) δ 8.67 (d, J=0.7 Hz, 1H), 8.56-8.50 (m, 2H), 6.93 (s, 1H), 6.87 (d, J=9.2 Hz, 1H), 5.88 (s, 1H), 4.57 (br. s, 1H), 3.94 (s, 3H).

Steps 2-4: Synthesis of 2-fluoro-6-methoxy-4-[(pyrazin-2-yl)methyl]benzonitrile (R-3)

To a solution of 2-fluoro-4-[hydroxy(pyrazin-2-yl)methyl]-6-methoxybenzonitrile (R-2) (145 mg, 0.559 mmol) and Et$_3$N (0.120 mL, 0.861 mmol) in anhydrous THF (10 mL) at 0° C. was added methanesulfonyl chloride (0.050 mL, 0.64 mmol). The resulting mixture was warmed to room temperature and stirred for 30 min. The reaction mixture was diluted with DCM (30 mL), washed with water (1×30 mL) and satd. aq. NaHCO$_3$ (1×30 mL). The extract was dried over Na$_2$SO$_4$ and concentrated to dryness. The material was used in the next step without further purification. A mixture of the crude mesylate (173 mg, 0.513 mmol) and LiBr (137 mg, 1.58 mmol) in anhydrous DMF (4 mL) was stirred at room temperature for 16 h. The reaction mixture was partitioned between EtOAc (50 mL) and water (50 mL). The organic phase was separated, washed with water (1×50 mL) and brine (1×50 mL), dried over Na$_2$SO$_4$, and concentrated. Purification via flash chromatography was accomplished using a gradient of 0-100% EtOAc in heptane to afford 72 mg (44%) of the secondary bromide. The secondary bromide (43 mg, 0.13 mmol) and zinc dust (90 mg, 1.4 mmol) were stirred at 80° C. in HOAc (2 mL) for 8 h. After cooling to room temperature, the reaction was diluted with EtOAc (50 mL) and carefully washed with satd. aq. NaHCO$_3$ (50 mL). The organic layer was then washed with brine (1×50 mL) and dried over Na$_2$SO$_4$. After concentrating to dryness, the crude product was purified via flash chromatography eluting with a gradient 0-100% EtOAc in heptane to afford 10 mg (31%) of 2-fluoro-6-methoxy-4-[(pyrazin-2-yl)methyl]benzonitrile (R-3) (10 mg, 31% yield). $^1$H NMR (400 MHz, CDCl$_3$) b 8.56 (br. s, 3H), 6.74-6.69 (m, 2H), 4.18 (s, 2H), 3.94 (s, 3H); m/z 244.0 (M+H)$^+$.

Steps 5-6: Synthesis of 2,6-dimethoxy-N-[4-methoxy-6-(pyrazin-2-ylmethyl)-1,2-benzoxazol-3-yl]benzenesulfonamide (Example 111)

To a mixture of 2-fluoro-6-methoxy-4-[(pyrazin-2-yl)methyl]benzonitrile (R-3) (178 mg, 0.732 mmol) and N-hydroxyacetamide (165 mg, 2.20 mmol) in CH$_3$CN (5 mL) and water (0.5 mL) was added 1,1,3,3-tetramethylguanidine (0.55 mL, 4.4 mmol). The resulting reaction mixture was stirred at 60° C. for 16 h and then cooled to room temperature. The solvent was removed, and the resulting residue was partitioned between EtOAc and water. The organic phase was separated, and the aqueous phase was extracted a second time with EtOAc (50 mL). The combined organic extract was dried over Na$_2$SO$_4$, concentrated to dryness and purified via flash chromatography eluting with a gradient of 40-100% EtOAc in heptane. This gave 82 mg (44%) of the amine intermediate as an oil. $^1$H NMR (400 MHz, DMSO-d$_6$) δ 8.68 (d, J=1.1 Hz, 1H), 8.60-8.55 (m, 1H), 8.51 (d, J=2.6 Hz, 1H), 6.91 (s, 1H), 6.69 (s, 1H), 5.87 (br. s, 2H), 4.22 (s, 2H), 3.88 (s, 3H); m/z 257.1 (M+H)$^+$. The amine (73 mg, 0.28 mmol) from the above reaction was treated with 2,6-dimethoxybenzene-1-sulfonyl chloride (Int-26) (100 mg, 0.43 mmol) and pyridine (2 mL). The reaction mixture was stirred at 110° C. for 3 h. Then, additional 2,6-dimethoxybenzene-1-sulfonyl chloride (Int-26) (50 mg, 0.21 mmol) was added and heating at 110° C. was continued for an additional 1 h. After cooling to room temperature, the reaction mixture was partitioned between ethyl acetate (20 mL) and 2N HCl (20 mL). The organic phase was separated, dried over Na$_2$SO$_4$, and purified via flash chromatography eluting with a gradient of 20-100% EtOAc in heptane followed by a second gradient of 0-20% 2-PrOH in EtOAc to afford 2,6-dimethoxy-N-[4-methoxy-6-(pyrazin-2-ylmethyl)-1,2-benzoxazol-3-yl]benzenesulfonamide (Example 111) (44 mg, 34% yield) as a solid. $^1$H NMR (400 MHz, DMSO-d$_6$) δ 9.50 (s, 1H), 8.68 (d, J=1.0 Hz, 1H), 8.58-8.53 (m, 1H), 8.50 (d, J=2.4 Hz, 1H), 7.49 (t, J=8.5 Hz, 1H), 7.07 (s, 1H), 6.83 (s, 1H), 6.77 (d, J=8.6 Hz, 2H), 4.25 (s, 2H), 3.89 (s, 3H), 3.77 (s, 6H); m/z 456.8 (M+H)$^+$.

The examples in the table below were synthesized according to the methods used for the synthesis 2,6-dimethoxy-N-[4-methoxy-6-(pyrazin-2-ylmethyl)-1,2-benzoxazol-3-yl]benzenesulfonamide (Example 111). The following examples were synthesized with non-critical changes or substitutions to the exemplified procedures that one skilled in the art would be able to realize. If necessary, separation of regioisomeric mixtures was carried out under standard methods known in the art, such as SFC or HPLC, and was conducted at any suitable step in the synthetic sequence.

TABLE 19

| Example | Name and Structure | Analytical | Notes |
|---|---|---|---|
| 112 | 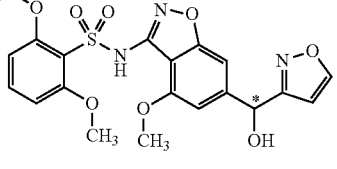<br>N-{6-[(S*)-hydroxy(1,2-oxazol-3-yl)methyl]-4-methoxy-1,2-benzoxazol-3-yl}-2,6-dimethoxybenzenesulfonamide, Isomer-A | $^1$H NMR (400 MHz, METHANOL-$d_4$) δ 8.58 (d, J = 1.4 Hz, 1H), 7.47 (t, J = 8.5 Hz, 1H), 7.19 (s, 1H), 6.88 (s, 1H), 6.74 (d, J = 8.5 Hz, 2H), 6.47 (d, J = 1.6 Hz, 1H), 6.04 (s, 1H), 4.03 (s, 3H), 3.85 (s, 6H); m/z 462.2 [M + H]$^+$. | Single enantiomer, absolute stereochemistry unknown; 1st peak on Chiralpak AS-3 150 × 4.6 mm I.D., 3 μm column. Mobile phase A: $CO_2$ B: iso-propanol (0.05% DEA); Scheme Q |
| 113 | 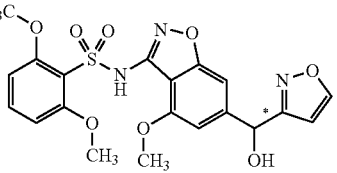<br>N-{6-[(R*)-hydroxy(1,2-oxazol-3-yl)methyl]-4-methoxy-1,2-benzoxazol-3-yl}-2,6-dimethoxybenzenesulfonamide, Isomer-B | $^1$H NMR (400 MHz, METHANOL-$d_4$) δ 8.58 (d, J = 1.5 Hz, 1H), 7.47 (t, J = 8.5 Hz, 1H), 7.19 (s, 1H), 6.88 (s, 1H), 6.74 (d, J = 8.5 Hz, 2H), 6.47 (d, J = 1.6 Hz, 1H), 6.04 (s, 1H), 4.03 (s, 3H), 3.85 (s, 6H); m/z 462.0 [M + H]$^+$. | Single enantiomer, absolute stereochemistry unknown; 2nd peak on Chiralpak AS-3 150 × 4.6 mm I.D., 3 μm column. Mobile phase A: $CO_2$ B: iso-propanol (0.05% DEA); Scheme Q |
| 114 | 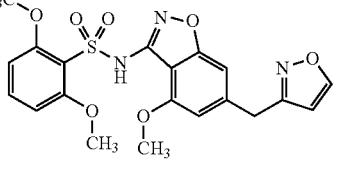<br>N-(6-(isoxazol-3-ylmethyl)-4-methoxybenzo[d]isoxazol-3-yl)-2,6-dimethoxybenzenesulfonamide | $^1$H NMR (400 MHz, METHANOL-$d_4$) δ 8.55 (s, 1H), 8.35 (s, 1H), 7.48 (t, J = 8.6 Hz, 1H), 6.95 (s, 1H), 6.82-6.73 (m, 3H), 4.04 (s, 3H), 3.98 (s, 2H), 3.86 (s, 6H); m/z 446.2 [M + H]$^+$. | Scheme Q |
| 115 | 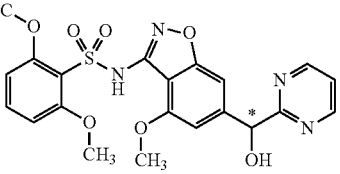<br>N-{6-[(S*)-hydroxy(pyrimidin-2-yl)methyl]-4-methoxy-1,2-benzoxazol-3-yl}-2,6-dimethoxybenzenesulfonamide | $^1$H NMR (400 MHz, METHANOL-$d_4$) δ 8.74 (d, J = 4.8 Hz, 2H), 7.61 (d, J = 8.3 Hz, 1H), 7.46 (t, J = 8.5 Hz, 1H), 7.37 (t, J = 4.9 Hz, 1H), 6.82 (d, J = 8.2 Hz, 1H), 6.72 (d, J = 8.6 Hz, 2H), 6.14 (s, 1H), 4.61 (br. s, 1H), 4.04 (s, 3H), 3.83 (s, 6H); m/z 472.7 [M + H]$^+$. | Single enantiomer, absolute stereochemistry unknown; 2$^{nd}$ Peak on ChiralCel OD-3 150 × 4.6 mm I.D., 3 μm Mobile phase: A: $CO_2$ B: 2-PrOH (0.1% Ethanolamine) Scheme Q |
| 116 | 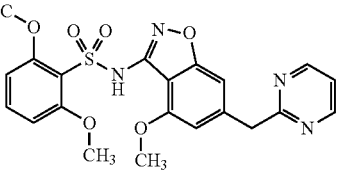<br>2,6-dimethoxy-N-[4-methoxy-6-(pyrimidin-2-ylmethyl)-1,2-bezoxazol-3-yl]benzenesulfonamide | $^1$H NMR (400 MHz, DMSO-$d_6$) δ 9.38 (br. s, 1H), 8.75 (d, J = 4.9 Hz, 2H), 7.48 (t, J = 8.4 Hz, 1H), 7.38 (t, J = 5.0 Hz, 1H), 7.03 (s, 1H), 6.83-6.73 (m, 3H), 4.33 (s, 2H), 3.88 (s, 3H), 3.77 (s, 6H); m/z 456.8 [M + H]$^+$ | Scheme Q but using cat. Pd[PPh$_3$]$_4$ and Et$_2$Zn in DMF for the dechlorination step. |

TABLE 19-continued

| Example | Name and Structure | Analytical | Notes |
| --- | --- | --- | --- |
| 117 | N-{6-[(S*)-hydroxy(1H-pyrazol-3-yl)methyl]-4-methoxy-1,2-benzoxazol-3-yl}-2,6-dimethoxybenzenesulfonamide, Isomer A | $^1$H NMR (400 MHz, DMSO-d$^6$) δ 9.54 (s, 1H), 7.50 (t, J = 8.5 Hz, 2H), 7.15 (s, 1H), 6.89 (s, 1H), 6.77 (d, J = 8.5 Hz, 2H), 6.12 (s, 1H), 5.83 (s, 1H), 3.89 (s, 3H), 3.77 (s, 6H); m/z 461.0 [M + H]$^+$ | Single enantiomer, absolute stereochemistry unknown; Peak 1 on Chiralpak AY-3 100 × 4.6 mm I.D., 3 μm Mobile phase: A: CO$_2$ B: iso-propanol (0.05% DEA). Scheme Q |
| 118 | N-{6-[(R*)-hydroxy(1H-pyrazol-3-yl)methyl]-4-methoxy-1,2-benzoxazol-3-yl}-2,6-dimethoxybenzenesulfonamide, Isomer B | $^1$H NMR (400 MHz, DMSO-d$_6$) δ 9.54 (s, 1H), 7.35-7.59 (m, 2H), 7.15 (s, 1H), 6.89 (s, 1H), 6.77 (d, J = 8.5 Hz, 2H), 6.12 (br. s, 1H), 5.83 (br. s, 1H), 3.89 (s, 3H), 3.77 (s, 6H); m/z 461.0 [M + H]$^+$ | Single enantiomer, absolute stereochemistry unknown; Peak 2 on Chiralpak AY-3 100 × 4.6 mm I.D., 3 μm Mobile phase: A: CO$_2$ B: iso-propanol (0.05% DEA). Scheme Q |
| 119 | 2,6-dimethoxy-N-[4-methoxy-6-(1H-pyrazol-3-yl)methyl)-1,2-benzoxazol-3-yl]benzenesulfonamide | $^1$H NMR (400 MHz, METHANOL-d$_4$) δ 7.55 (br. s, 1H), 7.49 (br. t, J = 8.6 Hz, 1H), 6.92 (s, 1H), 6.82-6.66 (m, 3H), 6.17 (s, 1H), 4.12 (s, 2H), 403 (s 3H), 3.86 (s, 6H); m/z 445.0 [M + H]$^+$ | Scheme Q |
| 120 | N-{6-[(S*)-hydroxy(1,2-oxazol-4-yl)methyl]-4-methoxy-1,2-benzoxazol-3-yl}-2,6-dimethoxybenzenesulfonamide, Isomer A | $^1$H NMR (400 MHz, METHANOL-d$_4$) δ 8.55 (s, 1H), 8.37 (s, 1H), 7.48 (br. t, J = 8.4 Hz, 1H), 7.17 (s, 1H), 6.89 (s, 1H), 6.75 (br. d, J = 8.5 Hz, 2H), 5.92 (s, 1H), 4.05 (s, 3H), 3.86 (s, 6H); m/z 461.7 [M + H]$^+$ | Single enantiomer, absolute stereochemistry unknown; 1st Peak on Chiralpak AS-3 150 × 4.6 mm I.D., 3 μm Mobile phase: A: CO$_2$ B: ethanol (0.05% DEA) Scheme Q |

TABLE 19-continued

| Example | Name and Structure | Analytical | Notes |
|---|---|---|---|
| 121 | 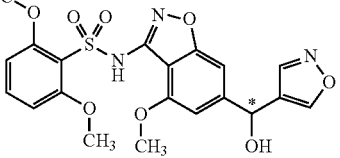<br>N-(6-[(S*)-hydroxy(isoxazol-4-yl)methyl]-4-methoxybenzo[d]isoxazol-3-N-{6-[(R*)-hydroxy(1,2-oxazol-4-yl)methyl]-4-methoxy-1,2-benzoxazol-3-yl}-2,6-dimethoxybenzenesulfonamide, Isomer B | $^1$H NMR (400 MHz, METHANOL-d$_4$) δ 8.55 (s, 1H), 8.37 (s, 1H), 7.48 (br. t, J = 8.5 Hz, 1H), 7.17 (s, 1H), 6.89 (s, 1H), 6.75 (br. d, J = 8.4 Hz, 2H), 5.92 (s, 1H), 4.05 (s, 3H), 3.86 (s, 6H); m/z 461.8 [M + H]$^+$ | Single enantiomer, absolute stereochemistry unknown; 2$^{nd}$ Peak on Chiralpak AS-3 150 × 4.6 mm I.D., 3 μm Mobile phase: A: CO$_2$B: ethanol (0.05% DEA) Scheme Q |
| 122 | 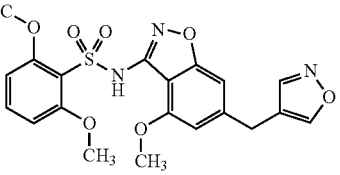<br>2,6-dimethoxy-N-[4-methoxy-6-(1,2-oxazol-4-ylmethyl)-1,2-benzoxazol-3-dimethoxybenzenesulfonamide | $^1$H NMR (400 MHz, METHANOL-d$_4$) δ 8.55 (s, 1H), 8.35 (s, 1H), 7.48 (t, J = 8.6 Hz, 1H), 6.95 (s, 1H), 6.82-6.73 (m, 3H), 4.04 (s, 3H), 3.98 (s, 2H), 3.86 (s, 6H); m/z 446.2 [M + H]$^+$ | Scheme Q |
| 123 | 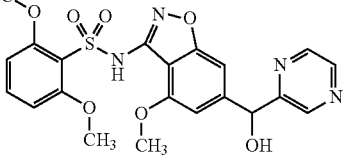<br>rac-N-{6-hydroxy(pyrazin-2-yl)methyl]-4-methoxy-1,2-benzoxazol-3-yl}-2,6-dimethoxybenzenesulfonamide | $^1$H NMR (400 MHz, CDCl$_3$) δ 8.62 (br. s, 1H), 8.55 (br. s, 2H), 8.21 (s, 1H), 7.38 (t, J = 8.50 Hz, 1H), 7.10 (s, 1H), 6.72 (s, 1H), 6.59 (d, J = 8.44 Hz, 2H), 5.94 (s, 1H), 4.44 (br. s, 1H), 4.01 (s, 3H), 3.88 (s, 6H); m/z 473.2 [M + H]$^+$ | Scheme P |
| 124 | 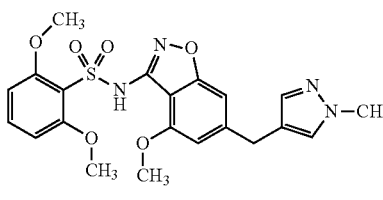<br>2,6-dimethoxy-N-{4-methoxy-6-[(1-methyl-1H-pyrazol-4-yl)methyl]-1,2-benzoxazol-3-yl} benzenesulfonamide | $^1$H NMR (400 MHz, METHANOL-d$_4$) δ 7.46 (t, J = 8.5 Hz, 1H), 7.42 (s, 1H), 7.33 (s, 1H), 6.87 (s, 1H), 6.74 (s, 1H), 6.72 (s, 1H), 6.69 (s, 1H), 4.01 (s, 3H), 3.93-3.90 (m, 2H), 3.84 (s, 6H), 3.83 (s, 3H); m/z 459.1 [M + H]$^+$ | Scheme R |
| 125 | <br>N-(6-[(S*)-hydroxy(1,3-oxazol-4-yl)methyl]-4-methoxy-1,2-benzoxazol-3-yl}-2,6-dimethoxybenzenesulfonamide | $^1$H NMR (400 MHz, METHANOL-d$_4$) δ 8.14 (s, 1H), 7.78 (s, 1H), 7.36 (br. t, J = 8.1 Hz, 1H), 7.03 (br. s, 1H), 6.81 (br. s, 1H), 6.68 (br. d, J = 8.4 Hz, 2H), 5.80 (s, 1H), 3.94 (s, 3H), 3.72 (br. s, 6H); m/z 461.7 [M + H]$^+$ | Single enantiomer, absolute stereochemistry unknown. 1$^{st}$ Peak on Chiralpak IG-3 50 × 4.6 mm I.D., 3 μm Mobile phase: A: CO2B: methanol (0.05% DEA) Isocratic: 40% B. Scheme Q |

TABLE 19-continued

| Example | Name and Structure | Analytical | Notes |
|---|---|---|---|
| 126 | 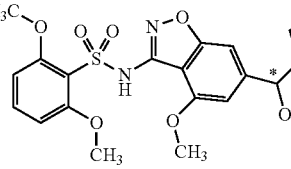<br>N-(6-[(R*)-hydroxy(1,3-oxazol-4-yl)methyl]-4-methoxy-1,2-benzoxazol-3-yl}-2,6-dimethoxybenzenesulfonamide | $^1$H NMR (400 MHz, METHANOL-$d_4$) δ 8.14 (s, 1H), 7.82 (s, 1H), 7.48 (t, J = 8.5 Hz, 1H), 7.16 (s, 1H), 6.94 (s, 1H), 6.74 (d, J = 8.6 Hz, 2H), 5.84 (s, 1H), 4.04 (s, 3H), 3.85 (s, 6H); m/z 461.7 [M + H]$^+$ | Single enantiomer, absolute stereochemistry unknown. 2$^{nd}$ Peak on Chiralpak IG-3 50 × 4.6 mm I.D., 3 μm Mobile phase: A: CO2B: methanol (0.05% DEA) Isocratic: 40% B. Scheme Q |
| 127 | 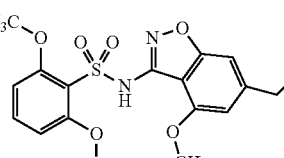<br>2,6-dimethoxy-N-[4-methoxy-6-(1,3-oxazol-4-yl)methyl)-1,2-benzoxazol-3-yl]benzenesulfonamide | $^1$H NMR (400 MHz, METHANOL-$d_4$) δ 1H), 7.44 (t, J = 8.4 Hz, 1H), 6.90 (s, 1H), 6.75-6.72 (m, 2H), 6.71 (s, 1H), 4.00 (d, J = 2.7 Hz, 5H), 3.81 (s, 6H); m/z 445.8 [M + H]$^+$ | Scheme Q |

Example 128: Preparation of N-{5-fluoro-4-methoxy-6-[(1H-pyrazol-1-yl)methyl]-1,2-benzoxazol-3-yl}-2,6-dimethoxybenzene-1-sulfonamide According to Scheme S

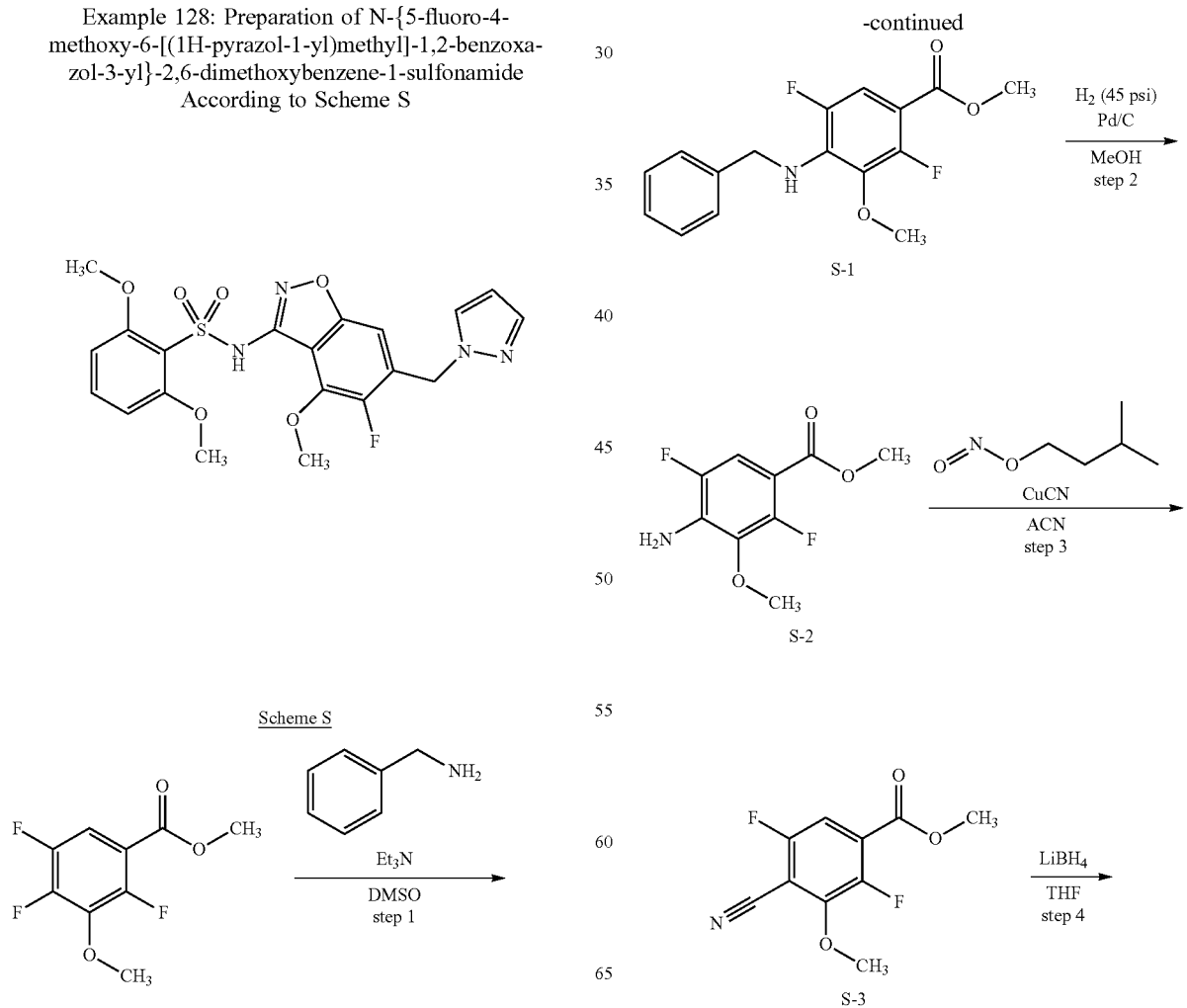

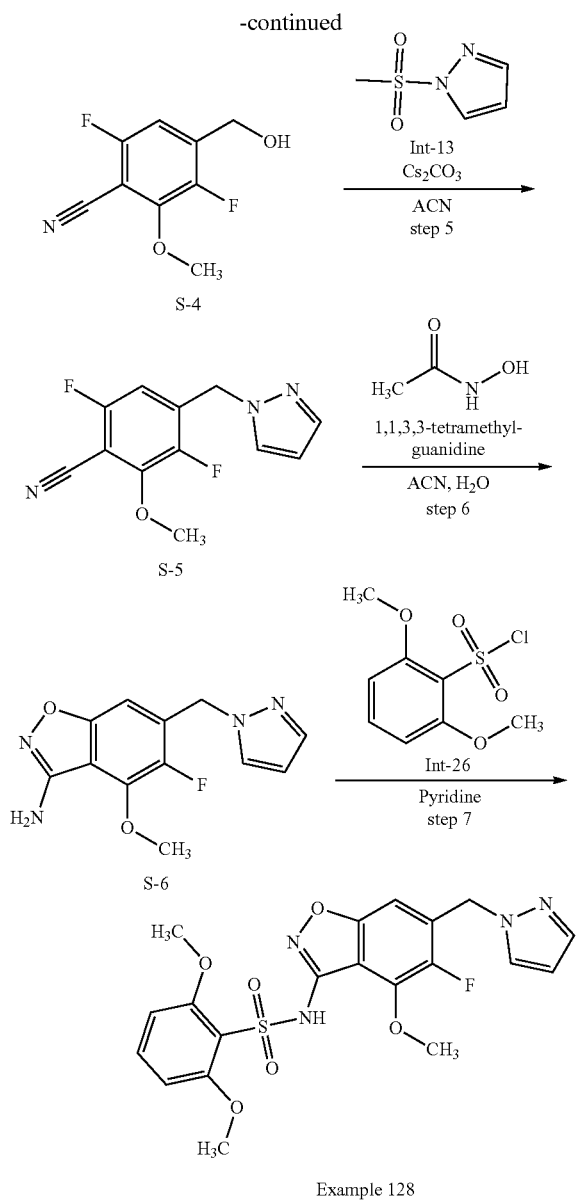

Example 128

Step 1: Synthesis of methyl 4-(benzylamino)-2,5-difluoro-3-methoxybenzoate (S-1)

A solution of benzylamine (38.0 mL, 347 mmol), methyl 2,4,5-trifluoro-3-methoxybenzoate (51.0 g, 232 mmol), and triethylamine (161 mL, 1160 mmol) in DMSO (500 mL) was heated at 100° C. for 18 hours. After cooling to room temperature, the mixture was poured into water and extracted with ethyl acetate. The organic phase was washed with satd. aq. NaCl, dried over sodium sulfate, filtered, and concentrated under vacuum. The residue was purified by silica gel chromatography (eluting with 5/1 pet. ether/ethyl acetate) to give methyl 4-(benzylamino)-2,5-difluoro-3-methoxybenzoate (S-1) (41 g, 57% yield) as a light-yellow oil. LCMS m/z 308.1 [M+H]$^+$; $^1$H NMR (400 MHz, CHLOROFORM-d) b 7.43-7.20 (m, 6H), 4.74 (br s, 1H), 4.63 (br s, 2H), 3.97-3.80 (m, 6H).

Step 2: Synthesis of methyl 4-amino-2,5-difluoro-3-methoxybenzoate (S-2)

A solution of methyl 4-(benzylamino)-2,5-difluoro-3-methoxybenzoate (S-1) (41 g, 133 mmol) in methanol (500 mL) was treated with Pd/C (7.0 g) and stirred at 50° C. under hydrogen (45 psi) for 48 hours. The suspension was filtered through a pad of Celite®, and the filtrate concentrated to give methyl 4-amino-2,5-difluoro-3-methoxybenzoate (S-2) (28.0 g, 96% yield) as an off-white solid. LCMS m/z 217.9 [M+H]$^+$; $^1$H NMR (400 MHz, DMSO-$d_6$) δ 7.27 (dd, J=6.3, 11.6 Hz, 1H), 6.21 (s, 2H), 3.77 (d, J=1.1 Hz, 6H).

Step 3: Synthesis of methyl 4-cyano-2,5-difluoro-3-methoxybenzoate (S-3)

A suspension of methyl 4-amino-2,5-difluoro-3-methoxybenzoate (S-2) (28.0 g, 129 mmol) and copper(I) cyanide (34.6 g, 387 mmol) in $CH_3CN$ (1 L) was warmed to 65° C. Isoamyl nitrite (22.7 g 193 mmol) was added dropwise and the reaction was stirred at 65° C. for 1 h. Analysis by LCMS showed some of the starting material remained and additional isoamyl nitrite (15.1 g 129 mmol) was added. The reaction was heated at 65° C. for 18 h. After cooling to room temperature, the reaction was diluted with EtOAc (200 mL) and filtered. The filtrate was concentrated and purified via flash chromatography eluting with a gradient of 0-50% EtOAc in heptane to give methyl 4-cyano-2,5-difluoro-3-methoxybenzoate (S-3) (14.0 g, 47% yield) as a yellow solid. $^1$H NMR (400 MHz, CHLOROFORM-d) b 7.36 (dd, J=4.8, 8.4 Hz, 1H), 4.21 (d, J=3.1 Hz, 3H), 3.97 (s, 3H).

Step 4: Synthesis of 3,6-difluoro-4-(hydroxymethyl)-2-methoxybenzonitrile (S-4)

To a solution of methyl 4-cyano-2,5-difluoro-3-methoxybenzoate (S-3) (14 g 62 mmol) in THF (400 mL) was added LiBH$_4$ (20 g, 92 mmol) slowly at 0° C. After the addition was complete, the reaction was warmed to room temperature and then heated to 50° C. for 2 h. After cooling to room temperature, the reaction mixture was quenched by the slow addition of H$_2$O (100 mL) and the organics were extracted with EtOAc (2×300 mL). The combined organic extract was washed with brine and satd. NaHCO$_3$, dried over Na$_2$SO$_4$ and filtered. After removing the solvent, 3,6-difluoro-4-(hydroxymethyl)-2-methoxybenzonitrile (S-4) (10 g, 81%) was obtained as a yellow solid. This material was taken on to the next step without further purification. $^1$H NMR (400 MHz, CHLOROFORM-d) b 7.06 (dd, J=4.8, 8.8 Hz, 1H), 4.81 (s, 2H), 4.17 (d, J=3.3 Hz, 3H), 2.48 (br s, 1H).

Step 5: Synthesis of 3,6-difluoro-2-methoxy-4-[(1H-pyrazol-1-yl)methyl]benzonitrile (S-5)

To a solution of 3,6-difluoro-4-(hydroxymethyl)-2-methoxybenzonitrile (S-4) (10 g, 50 mmol) and 1-(methanesulfonyl)-1H-pyrazole (Int-13) (8.8 g, 60 mmol) in $CH_3CN$ (500 mL) was added $Cs_2CO_3$ (24.5 g, 75.3 mmol) was stirred at 70° C. for 2 h. Analysis by LCMS showed that the starting material was consumed. The reaction was cooled to room temperature and filtered. After the filtrate was concentrated, the residue was purified by flash chromatography eluting with a gradient of 20-50% EtOAc in petroleum ether to give 3,6-difluoro-2-methoxy-4-[(1H-pyrazol-1-yl) methyl]benzonitrile (S-5) (8.4 g, 67% yield) as a yellow gum. LCMS m/z 250.0 [M+H]$^+$; $^1$H NMR (400 MHz, DMSO-$d_6$) δ 7.89 (d, J=2.2 Hz, 1H), 7.62-7.40 (m, 1H), 6.76

(dd, J=5.0, 9.1 Hz, 1H), 6.33 (t, J=2.1 Hz, 1H), 5.49 (d, J=1.1 Hz, 2H), 4.13 (d, J=3.2 Hz, 3H).

Step 6: Synthesis of 5-fluoro-4-methoxy-6-[(1H-pyrazol-1-yl)methyl]-1,2-benzoxazol-3-amine (S-6)

To a solution of 3,6-difluoro-2-methoxy-4-[(1H-pyrazol-1-yl)methyl]benzonitrile (S-5) (8.4 g, 34 mmol) and N-hydroxyacetamide (7.6 g, 100 mmol) in CH$_3$CN (400 mL) and water (80 mL) was added 1,1,3,3-tetramethylguanidine (23 g, 200 mmol) slowly. The mixture was heated at 60° C. for 16 h. The mixture was cooled and concentrated to remove the CH$_3$CN. A yellow solid precipitated from solution which was washed with water and then a mixture of 10% EtOAc in petroleum ether. The resulting pale-yellow solid was filtered to give 5-fluoro-4-methoxy-6-[(1H-pyrazol-1-yl)methyl]-1,2-benzoxazol-3-amine (S-6) (6.1 g, 69% yield) as a pale yellow solid. LCMS m/z 262.9 [M+H]$^+$; $^1$H NMR (400 MHz, CHLOROFORM-d) b 7.59 (d, J=1.7 Hz, 1H), 7.43 (d, J=2.2 Hz, 1H), 6.70 (d, J=9.2 Hz, 1H), 6.50 (s, 1H), 6.35 (t, J=2.1 Hz, 1H), 5.31 (s, 2H), 2.23 (tt, J=5.1, 8.4 Hz, 1H), 1.20-1.14 (m, 2H), 0.81-0.73 (m, 2H).

Step 7: Synthesis of N-{5-fluoro-4-methoxy-6-[(1H-pyrazol-1-yl)methyl]-1,2-benzoxazol-3-yl}-2,6-dimethoxybenzene-1-sulfonamide (Example 128)

To a solution of 5-fluoro-4-methoxy-6-[(1H-pyrazol-1-yl)methyl]-1,2-benzoxazol-3-amine (S-6) (6.1 g, 23 mmol) in pyridine (100 mL) was added 2,6-dimethoxybenzenesulfonyl chloride (Int-26) (6.1 g, 26 mmol) and the resulting mixture was stirred at 70° C. for 18 h. The mixture was concentrated and purified by flash chromatography eluting with 10% MeOH in DCM to give crude Example 128 (8 g) as yellow solid. A suspension of the yellow solid in CH$_3$CN (100 mL) was refluxed for 10 min. Most of the solids remained. So, additional CH$_3$CN (500 mL) was added in 100 mL increments until the solid completely dissolved. The solution was allowed to cool to for 5 min and MTBE (400 mL) was added under vigorous stirring. White solids began to form, and the mixture was concentrated to ⅓ volume and the solution was stirred vigorously at 20° C. for 18 h. The precipitate was collected by filtration, washed with heptane, and dried under vacuum to give 3.2 g (30%) of Example 128 as a white solid. The filtrate was concentrated to give 4.7 g of crude Example 128 as yellow solid which was further purified as described below. The 4.7 g was re-purified by flash chromatography eluting with a gradient of 0-20% EtOAc in DCM to afford 3 grams of a white solid which was dissolved in CH$_3$CN (10 mL) and MTBE (25 mL). The colorless solution was stirred until it turned cloudy and a white solid precipitated. The white solid was collected by filtration and washed with MTBE (3×5 mL). This batch of white solid was combined with the 3.2 g batch and the combined solid was suspended in CH$_3$CN (30 mL) and then heated to dissolve. MTBE (60 mL) was added gradually and a white solid precipitated from solution. The mixture was cooled to room temperature and concentrated to a total volume of 30 mL. The resulting white solid was collected by filtration and washed with MTBE (3×10 mL), dried in vacuum oven at 60° C. for 6 h to give N-{5-fluoro-4-methoxy-6-[(1H-pyrazol-1-yl)methyl]-1,2-benzoxazol-3-yl}-2,6-dimethoxybenzene-1-sulfonamide (Example 128) (5.3 g, 49% yield) as a white solid. $^1$H NMR (400 MHz, DMSO-d$_6$) δ 10.13 (br. s, 1H), 7.86 (br. s, 1H), 7.59-7.43 (m, 2H), 6.90 (br. d, J=3.3 Hz, 1H), 6.78 (br. d, J=8.5 Hz, 2H), 6.31 (br. s, 1H), 5.50 (br. s, 2H), 4.04 (br. s, 3H), 3.76 (s, 6H); m/z 463.0 [M+H]$^+$.

The examples in the table below were synthesized according to the methods used for the synthesis of N-{5-fluoro-4-methoxy-6-[(1H-pyrazol-1-yl)methyl]-1,2-benzoxazol-3-yl}-2,6-dimethoxybenzene-1-sulfonamide (Example 128), N-{4-ethyl-6-[(1H-pyrazol-1-yl)methyl]-1,2-benzoxazol-3-yl}-2,6-dimethoxybenzene-1-sulfonamide (Example 95), 5-ethyl-2-methoxy-N-{4-methoxy-6-[(1H-pyrazol-1-yl)methyl]-1,2-benzoxazol-3-yl}benzene-1-sulfonamide (Example 01), 2,6-dimethoxy-N-{4-methoxy-6-[(3-methyl-1H-pyrazol-1-yl)methyl]-1,2-benzoxazol-3-yl}benzene-1-sulfonamide (Example 02), and 2,6-dimethoxy-N-{4-methoxy-6-[(5-methyl-1H-pyrazol-1-yl)methyl]-1,2-benzoxazol-3-yl}benzene-1-sulfonamide (Example 03), and the general sulfonamide formation methods A-D. The following examples were synthesized with non-critical changes or substitutions to the exemplified procedures that someone who is skilled in the art would be able to realize.

TABLE 20

| Example number | Structure/IUPAC Name | Analytical data | Sulfonamide formation method |
|---|---|---|---|
| 129 | 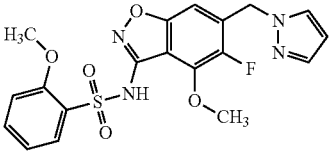<br>N-{5-fluoro-4-methoxy-6-[(1H-pyrazol-1-yl)methyl]-1,2-benzoxazol-3-yl}-2-methoxybenzene-1-sulfonamide | $^1$H NMR (400 MHz, DMSO-d$_6$) δ 10.63 (br s, 1H), 7.86 (d, J = 2.3 Hz, 1H), 7.79 (dd, J = 1.8, 7.8 Hz, 1H), 7.62 (br t, J = 7.3 Hz, 1H), 7.50 (d, J = 1.3 Hz, 1H), 7.21 (d, J = 8.3 Hz, 1H), 7.08 (t, J = 7.7 Hz, 1H), 6.91 (d, J = 4.3 Hz, 1H), 6.31 (t, J = 2.1 Hz, 1H), 5.50 (s, 2H), 4.03 (d, J = 3.0 Hz, 3H), 3.80 (s, 3H), | D |

TABLE 20-continued

| Example number | Structure/IUPAC Name | Analytical data | Sulfonamide formation method |
|---|---|---|---|
| 130 | 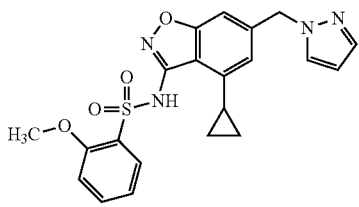<br>N-{4-cyclopropyl-6-[(1H-pyrazol-1-yl)methyl]-1,2-benzoxazol-3-yl}-2-methoxybenzene-1-sulfonamide | $^1$H NMR (400 MHz, DMSO-$d_6$) δ 10.62 (br s, 1H), 7.86 (d, J = 2.0 Hz, 1H), 7.74 (dd, J = 1.6, 7.9 Hz, 1H), 7.63 (br s, 1H), 7.49 (d, J = 1.3 Hz, 1H), 7.23 (br d, J = 8.5 Hz, 1H), 7.14-7.03 (m, 2H), 6.72 (br s, 1H), 6.29 (t, J = 2.1 Hz, 1H), 5.42 (s, 2H), 3.78 (s, 3H), 2.76 (br s, 1H), 1.10-0.95 (m, 2H), 0.80-0.66 (m, 2H); m/z 425.1 (M + H)$^+$ | D |
| 131 | 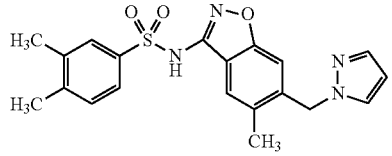<br>3,4-dimethoxy-N-{5-methyl-6-[(1H-pyrazol-1-yl)methyl]-1,2-benzoxazol-3-yl}benzene-1-sulfonamide | $^1$H NMR (400 MHz, DMSO-$d_6$) δ 7.72 (d, J = 2.2 Hz, 1H), 7.57 (s, 1H), 7.53 (br d, J = 7.8 Hz, 1H), 7.49 (d, J = 1.5 Hz, 1H), 7.44 (s, 1H), 7.14 (br d, J = 7.8 Hz, 1H), 6.72 (s, 1H), 6.29 (t, J = 2.0 Hz, 1H), 5.41 (s, 2H), 2.31 (s, 3H), 2.21 (s, 3H), 2.20 (s, 3H); m/z 397.0 (M + H)$^+$ | A |
| 132 | 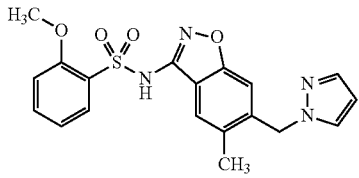<br>2-methoxy-N-{5-methyl-6-[(1H-pyrazol-1-yl)methyl]-1,2-benzoxazol-3-yl}benzene-1-sulfonamide | $^1$H NMR (400 MHz, DMSO-$d_6$) δ 11.58 (br s, 1H), 7.84 (dd, J = 1.3, 7.8 Hz, 1H), 7.78 (d, J = 2.2 Hz, 2H), 7.59 (br t, J = 7.9 Hz, 1H), 7.51 (d, J = 1.5 Hz, 1H), 7.16 (d, J = 8.4 Hz, 1H), 7.08 (t, J = 7.6 Hz, 1H), 6.87 (s, 1H), 6.31 (t, J = 2.0 Hz, 1H), 5.47 (s, 2H), 3.76 (s, 3H), 2.36 (s, 3H); m/z 399.0 (M + H)$^+$ | A |
| 133 | 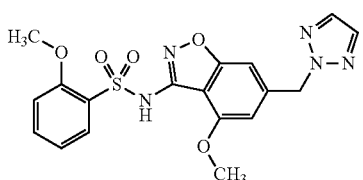<br>2-methoxy-N-{4-methyl-6-[(2H-1,2,3-triazol-2-yl)methyl]-1,2-benzoxazol-3-yl}benzene-1-sulfonamide | $^1$H NMR (400 MHz, DMSO-$d_6$) δ 10.22 (br s, 1H), 7.86 (s, 2H), 7.80 (dd, J = 1.5, 8.0 Hz, 1H), 7.61 (br s, 1H), 7.18 (br d, J = 8.5 Hz, 1H), 7.08 (br t, J = 7.5 Hz, 1H), 6.90 (s, 1H), 6.74 (s, 1H), 5.77 (s, 2H), 3.82 (s, 3H), 3.77 (s, 3H); m/z 416.1 (M + H)$^+$ | D |

Biological Assay Section 1

KAT Assay Protocol:

A. Compound preparation
1. Prepare 10 mM stock solutions in 100% DMSO from solid material
2. Serial dilute 10 mM, 1 mM or 0.1 mM compound stocks 3-fold in 100% DMSO for 11-point dose response B. Reagent preparation
1. Prepare 1× assay buffer containing 10 mM Tris HCL pH 8.0, 2.5 mM NaCl, 0.5 mM EDTA, 0.005% BSG and 0.02% Tween-20
2. Dilute Histone peptide (CPC Scientific) and AcCoA (Sigma) together in assay buffer to 2×.
3. Dilute KAT enzyme in assay buffer to 2×.

C. Enzyme reaction
1. Final reaction conditions for each KAT assay in a 20 ul assay reaction volume:
   i. KAT5 25 nM, 1 uM AcCoA, 2 uM H4 1-21 peptide, 30-minute reaction
   ii. KAT6A 15 nM, 1 uM AcCoA, 2 uM H3 1-21 peptide, 45-minute reaction
   iii. KAT6B 25 nM, 1 uM AcCoA, 2 uM H3 1-21 peptide, 60-minute reaction
   iv. KAT7 12.5 nM, 1 uM AcCoA, 2 uM H3 1-21 peptide, 45-minute reaction
   v. KAT8 15 nM, 1 uM AcCoA, 2 uM H3 1-21 peptide, 45-minute reaction 2. Add 0.5 ul of diluted compound to the assay plate (384-well V-bottom polypropylene plates) or 0.5 ul of DMSO for control wells.
3. Add 10 ul of 2× Histone peptide/2×AcCoA mix to the assay plate.
4. Add 10 ul of 2× enzyme to the assay plate.
5. Stop the reaction after the indicated time with the addition of 2 ul of 5% formic acid
6. Each reaction was analyzed using self-assembled monolayer desorption/ionization time-of-flight mass spectrometry (Mrksich, Milan (2008) Mass Spectrometry of Self-Assembled Monolayers: A New Tool for Molecular Surface Science ACS Nano 2008 2 (1), 7-18; SAMDI Tech, Inc. (Chicago, Ill.)).
7. Area under the curve (AUC) for both substrate and product peaks was determined for KAT5 at M.W. 2561 [Substrate+H]$^+$ and 2603 [Product+H]$^+$ with a +/−1 Da tolerance, respectively
8. Area under the curve (AUC) for both substrate and product peaks was determined for KAT6a, KAT6B, KAT7 and KAT8 at M.W. 2723 [Substrate+H]$^+$ and 2765 [Product+H]$^+$ with a +/−1 Da tolerance, respectively. 9. Percent conversion to product was calculated by: $AUC_{Product}/(AUC_{substrate}+AUC_{Product})$.

D. Data analysis
1. IC$_{50}$ values were determined by fitting the % conversion at each inhibitor concentration to the 4-parameter IC$_{50}$ equation using Pfizer proprietary curve fitting software.
2. K$_i$ values were determined by fitting the % conversion at each inhibitor concentration to the Morrison equation for tightbinding competitive inhibitors using Pfizer proprietary curve fitting software.

Materials

KAT enzymes were expressed using a baculovirus expression system and purified at Pfizer, La Jolla. Histone H3 (1-21) peptide (ARTKQTARKSTGGKAPRKQLA, SEQ ID NO:3) and Histone H4 (1-21) peptide (SGRGKGGKGLGKGGAKRHRKV, SEQ ID NO:4) were purchased from CPC Scientific (Sunnyvale, Calif.). Acetyl coenzyme A was purchased from Sigma-Aldrich (St. Louis, Mo.). All other biochemical reagents were purchased from Sigma-Aldrich or ThermoFisher Scientific (Waltham, Mass.).

KAT Reactions

KAT assays were performed at room temperature in assay buffer containing 1 μM AcCoA, 2 μM histone peptide, 10 mM Tris HCL pH 8.0, 2.5 mM NaCl, 0.5 mM EDTA, 0.005% BSG and 0.02% Tween-20. 10 ul of 2× Histone peptide/AcCoA mix was added to a 384-well V-bottom polypropylene assay plate containing 0.5 ul of serially diluted test compound in 100% dimethyl sulfoxide (DMSO). To start the reaction, 10 ul of 2× enzyme solution was added to the assay plate. KAT assays were terminated after 30-60 minutes with the addition of 2 ul of 5% formic acid. All assays used histone H3 (1-21) peptide except for the KAT5 assay which used histone H4 (1-21) peptide. The final enzyme concentration for each KAT was as follows: KAT5, 25 nM; KAT6A, 15 nM; KAT6B, 25 nM; KAT7, 12.5 nM; KAT8 15 nM. Each reaction was analyzed using self-assembled monolayer desorption/ionization time-of-flight mass spectrometry (Mrksich, Milan (2008) Mass Spectrometry of Self-Assembled Monolayers: A New Tool for Molecular Surface Science ACS Nano 2008 2 (1), 7-18; SAMDI Tech, Inc. (Chicago, Ill.)).

Data Processing and Analysis

Area under the curve (AUC) for both substrate and product peaks was determined for KAT5 at M.W. 2561 [Substrate+H]$^+$ and 2603 [Product+H]$^+$ with a +/−1 Da tolerance, respectively. Area under the curve (AUC) for both substrate and product peaks was determined for KAT6A, KAT6B, KAT7 and KAT8 at M.W. 2723 [Substrate+H]$^+$ and 2765 [Product+H]$^+$ with a +/−1 Da tolerance, respectively. Percent conversion to product was calculated by: $AUC_{Product}/(AUC_{substrate}+AUC_{Product})$. IC50 values were determined by fitting the % conversion at each inhibitor concentration to the 4-parameter IC50 equation using Pfizer proprietary curve fitting software. Ki values were determined by fitting the % conversion at each inhibitor concentration to the Morrison equation for tightbinding competitive inhibitors using Pfizer proprietary curve fitting software.

KAT6a and KAT6b Ki's are provided in Table 21 and KAT5, KAT7, and KAT8 Ki's are provided in Table 22 below.

TABLE 21

| Example No. | KAT6a K$_i$ at 1 μM AcCoA (nM) | KAT6a K$_i$ at 10 μM AcCoA (nM) | KAT6b K$_i$ at 1 μM AcCoA (nM) | KAT6b K$_i$ at 25 μM AcCoA (nM) |
|---|---|---|---|---|
| 1 | 0.55 | 0.43 | 0.68 | 1.14 |
| 2 | 46.9 | N/D | 50.4 | N/D |
| 3 | 3.79 | 1.54 | 8.63 | N/D |
| 4 | 10.3 | N/D | 60.8 | N/D |
| 5 | 1.11 | 1.38 | 2.68 | N/D |
| 6 | 1.50 | 2.32 | 2.50 | N/D |
| 7 | 21.0 | N/D | 28.3 | N/D |
| 8 | 1.54 | 3.23 | 5.74 | 6.63 |
| 9 | 0.74 | 0.83 | 0.42 | 1.55 |
| 10 | 2.72 | 4.65 | 2.27 | N/D |
| 11 | 2.86 | 5.57 | 14.6 | N/D |
| 12 | 1.82 | 1.70 | 1.88 | 2.14 |
| 13 | 17.7 | N/D | N/D | N/D |
| 14 | 1.12 | 0.49 | N/D | 1.05 |
| 15 | 0.65 | 0.35 | N/D | 0.60 |
| 16 | 1.27 | 0.64 | N/D | 1.73 |
| 17 | 0.70 | 0.51 | N/D | 1.21 |
| 18 | 0.83 | 0.38 | N/D | 0.96 |
| 19 | 2.18 | N/D | N/D | 3.44 |
| 20 | 0.34 | 0.87 | 1.78 | 4.08 |
| 21 | 1.23 | N/D | N/D | 1.14 |
| 22 | 16.5 | N/D | 13.2 | N/D |
| 23 | 1.22 | 1.24 | 0.87 | 1.34 |
| 24 | 1.01 | 0.46 | N/D | 1.89 |
| 25 | 2.74 | 1.83 | N/D | 4.46 |
| 26 | 8.01 | 3.16 | N/D | 12.7 |
| 27 | 1.17 | 0.68 | N/D | 2.39 |
| 28 | 4.40 | N/D | N/D | 5.06 |
| 29 | 0.53 | N/D | N/D | 1.40 |
| 30 | 60 | N/D | N/D | N/D |
| 31 | 0.32 | N/D | N/D | 0.89 |
| 32 | 1.4 | N/D | N/D | 2.1 |
| 33 | 3.1 | N/D | N/D | N/D |
| 34 | 30 | N/D | N/D | 4.2 |
| 35 | 15 | N/D | N/D | N/D |
| 36 | 17 | N/D | N/D | N/D |
| 37 | 17 | N/D | N/D | N/D |
| 38 | 16 | N/D | N/D | N/D |
| 39 | 0.74 | N/D | N/D | 0.26 |
| 40 | 0.47 | N/D | N/D | N/D |
| 41 | 0.36 | N/D | N/D | 0.36 |
| 42 | 0.72 | N/D | N/D | 0.48 |
| 43 | 3.6 | N/D | N/D | N/D |
| 44 | 12 | N/D | | 43 |
| 45 | 2.28 | N/D | 2.11 | 1.55 |
| 46 | 32.9 | 13.1 | N/D | N/D |
| 47 | 1.14 | 0.49 | N/D | 1.32 |
| 48 | 14.9 | 6.51 | N/D | N/D |
| 49 | 9.77 | 4.14 | N/D | N/D |
| 50 | 0.46 | 0.40 | N/D | 0.98 |
| 51 | 2.71 | 1.67 | N/D | 4.13 |

TABLE 21-continued

| Example No. | KAT6a $K_i$ at 1 μM AcCoA (nM) | KAT6a $K_i$ at 10 μM AcCoA (nM) | KAT6b $K_i$ at 1 μM AcCoA (nM) | KAT6b $K_i$ at 25 μM AcCoA (nM) |
|---|---|---|---|---|
| 52 | 14.6 | 7.32 | N/D | N/D |
| 53 | 16.1 | 8.78 | N/D | N/D |
| 54 | 57.0 | 38.0 | N/D | N/D |
| 55 | 291 | 178 | N/D | N/D |
| 56 | 14.9 | 7.31 | N/D | N/D |
| 57 | 16.0 | N/D | N/D | N/D |
| 58 | 11.1 | 5.23 | N/D | N/D |
| 59 | 13.0 | 6.25 | N/D | N/D |
| 60 | 9.81 | 4.64 | N/D | N/D |
| 61 | 0.95 | 0.92 | N/D | 1.56 |
| 62 | 9.64 | 3.90 | N/D | N/D |
| 63 | 15.8 | 10.9 | N/D | N/D |
| 64 | 25.3 | 11.0 | N/D | N/D |
| 65 | 6.04 | 4.44 | N/D | 12.1 |
| 66 | 95.4 | 65.6 | N/D | N/D |
| 67 | 20.0 | 10.2 | N/D | N/D |
| 68 | 14.9 | 10.5 | N/D | N/D |
| 69 | N/D | 9.10 | N/D | N/D |
| 70 | 2.28 | 3.27 | N/D | 1.90 |
| 71 | 1.18 | 1.17 | N/D | 2.81 |
| 72 | 2.86 | 2.36 | N/D | 6.97 |
| 73 | 2.31 | 1.70 | N/D | 1.36 |
| 74 | 24.8 | 13.6 | N/D | 0.00 |
| 75 | 9.13 | 6.42 | N/D | 13.8 |
| 76 | 7.89 | 3.62 | N/D | 60.1 |
| 77 | 8.56 | 11.89 | N/D | 29.6 |
| 78 | 5.64 | 5.73 | N/D | 26.0 |
| 79 | 5.11 | 4.98 | N/D | 4.27 |
| 80 | 15.6 | 5.32 | N/D | N/D |
| 81 | 18.2 | 9.96 | N/D | N/D |
| 82 | 16.9 | 12.2 | N/D | N/D |
| 83 | 13.7 | 7.76 | N/D | N/D |
| 84 | 7.86 | 5.61 | N/D | 12.3 |
| 85 | 13.3 | 8.77 | N/D | N/D |
| 86 | 28.9 | 7.11 | N/D | N/D |
| 87 | 38.6 | N/D | 133 | N/D |
| 88 | | | | |
| 89 | | | | |
| 90 | 0.46 | 0.80 | 1.63 | N/D |
| 91 | 0.38 | 0.75 | 1.30 | 1.38 |
| 92 | 1.07 | 0.45 | N/D | 2.73 |
| 93 | 0.64 | 1.02 | 1.20 | 2.33 |
| 94 | 5.15 | N/D | N/D | 2.50 |
| 95 | 9.88 | N/D | N/D | 8.35 |
| 96 | 1.58 | N/D | N/D | 3.67 |
| 97 | 1.10 | N/D | N/D | 2.74 |
| 98 | 0.35 | 0.66 | 1.23 | 2.82 |
| 99 | N/D | N/D | N/D | N/D |
| 100 | 40.3 | N/D | 58.3 | N/D |
| 101 | N/D | N/D | N/D | N/D |
| 102 | N/D | N/D | N/D | N/D |
| 103 | 0.30 | 0.51 | N/D | N/D |
| 104 | 6.11 | 3.89 | N/D | N/D |
| 105 | 3.08 | 6.28 | N/D | N/D |
| 106 | 35 | N/D | N/D | N/D |
| 107 | 1.7 | 2.6 | | 2.9 |
| 108 | 72 | N/D | | N/D |
| 109 | 44 | N/D | | N/D |
| 110 | 2.5 | 2.1 | | 8.8 |
| 111 | 13 | N/D | | N/D |
| 112 | 82 | N/D | | N/D |
| 113 | 14 | N/D | | N/D |
| 114 | 1.9 | N/D | | 2.0 |
| 115 | 1220 | N/D | | N/D |
| 116 | 3.0 | N/D | | 25 |
| 117 | 202 | N/D | | N/D |
| 118 | 357 | N/D | | N/D |
| 119 | 21 | 13 | | N/D |
| 120 | 831 | 212 | | N/D |
| 121 | 1576 | >600 | | N/D |
| 122 | 164 | 25 | | N/D |
| 123 | 138 | N/D | | N/D |
| 124 | 700 | N/D | | N/D |
| 125 | 230 | N/D | | N/D |
| 126 | 230 | N/D | | N/D |
| 127 | 8.6 | N/D | | N/D |
| 128 | 0.54 | 0.59 | | 1.2 |
| 129 | 0.33 | N/D | N/D | N/D |
| 130 | 0.77 | N/D | | N/D |
| 131 | 28.3 | N/D | N/D | N/D |
| 132 | 4.1 | N/D | N/D | N/D |
| 133 | 2.9 | N/D | N/D | N/D |

TABLE 22

| Example No. | KAT5 $K_i$ at 1 μM AcCoA (μM) | KAT7 $K_i$ at 1 μM AcCoA (μM) | KAT8 $K_i$ at 1 μM AcCoA (μM) |
|---|---|---|---|
| 1 | 0.12 | 0.05 | 0.11 |
| 2 | 13.0 | 0.70 | 36.7 |
| 3 | 9.79 | 1.72 | 17.4 |
| 4 | 5.98 | 0.90 | 20.6 |
| 5 | 0.53 | 0.08 | 0.66 |
| 6 | 0.98 | 0.12 | 3.32 |
| 7 | 4.53 | 0.23 | 4.46 |
| 8 | 1.71 | 0.06 | 2.87 |
| 9 | 0.62 | 0.05 | 0.82 |
| 10 | 60.2 | 9.32 | 19.4 |
| 11 | 12.5 | 5.96 | 3.26 |
| 12 | 1.17 | 0.92 | 1.07 |
| 13 | N/D | 1.04 | N/D |
| 14 | 0.27 | 0.05 | 0.42 |
| 15 | 0.07 | 0.03 | 0.17 |
| 16 | 0.83 | 0.12 | 1.75 |
| 17 | 0.15 | 0.09 | 0.22 |
| 18 | 0.13 | 0.12 | 0.10 |
| 19 | 0.80 | 0.15 | 0.96 |
| 20 | 0.15 | 0.00 | 0.47 |
| 21 | 1.03 | 0.12 | 0.83 |
| 22 | 11.7 | 12.9 | 17.4 |
| 23 | 2.07 | 0.04 | 1.97 |
| 24 | 0.19 | 0.02 | 0.16 |
| 25 | 12.5 | 1.08 | 12.5 |
| 26 | 125 | 7.79 | 27.1 |
| 27 | 0.22 | 0.05 | 0.53 |
| 28 | 3.05 | 0.45 | 3.26 |
| 29 | 0.18 | 0.06 | 1.01 |
| 30 | | 1.1 | |
| 31 | | 0.056 | |
| 32 | | 0.060 | |
| 33 | | 0.31 | |
| 34 | | 1.2 | |
| 35 | | 0.42 | |
| 36 | | 0.98 | |
| 37 | | 4.6 | |
| 38 | | 0.53 | |
| 39 | | 0.008 | |
| 40 | | 0.38 | |
| 41 | | 0.23 | |
| 42 | | 0.16 | |
| 43 | | 0.57 | |
| 44 | | 0.63 | |
| 45 | 0.32 | 0.09 | 0.90 |
| 46 | N/D | 1.03 | N/D |
| 47 | 0.18 | 0.04 | 0.56 |
| 48 | N/D | 0.41 | N/D |
| 49 | N/D | 0.37 | N/D |
| 50 | 0.26 | 0.02 | 0.35 |
| 51 | 0.77 | 0.09 | 1.11 |
| 52 | N/D | 0.66 | N/D |
| 53 | N/D | 0.30 | N/D |
| 54 | N/D | 1.16 | N/D |
| 55 | N/D | 15.0 | N/D |
| 56 | N/D | 0.60 | N/D |
| 57 | N/D | 0.45 | N/D |
| 58 | N/D | 0.86 | N/D |
| 59 | N/D | 0.22 | N/D |
| 60 | N/D | 0.42 | N/D |

TABLE 22-continued

| Example No. | KAT5 $K_i$ at 1 µM AcCoA (µM) | KAT7 $K_i$ at 1 µM AcCoA (µM) | KAT8 $K_i$ at 1 µM AcCoA (µM) |
|---|---|---|---|
| 61 | 0.20 | 0.04 | 0.54 |
| 62 | N/D | 0.36 | N/D |
| 63 | N/D | 0.94 | N/D |
| 64 | N/D | 0.63 | N/D |
| 65 | 3.06 | 0.22 | 12.50 |
| 66 | N/D | 4.05 | N/D |
| 67 | N/D | 1.76 | N/D |
| 68 | N/D | 0.25 | N/D |
| 69 | N/D | 0.37 | N/D |
| 70 | 0.41 | 0.14 | 3.26 |
| 71 | 0.32 | 0.03 | 1.44 |
| 72 | 2.96 | 0.14 | 12.5 |
| 73 | 0.71 | 0.25 | 3.26 |
| 74 | N/D | 2.87 | N/D |
| 75 | 5.70 | 0.32 | 12.50 |
| 76 | 4.38 | 0.33 | 12.5 |
| 77 | 8.45 | 0.46 | 12.5 |
| 78 | 9.92 | 0.54 | 12.5 |
| 79 | 1.44 | 0.22 | 3.26 |
| 80 | N/D | 0.36 | N/D |
| 81 | N/D | 1.62 | N/D |
| 82 | N/D | 0.64 | N/D |
| 83 | N/D | 0.78 | N/D |
| 84 | 4.63 | 0.19 | 12.50 |
| 85 | N/D | 1.14 | N/D |
| 86 | N/D | 0.37 | N/D |
| 87 | 10.8 | 1.84 | 17.9 |
| 88 |  |  |  |
| 89 |  |  |  |
| 90 | 0.61 | 0.06 | 0.73 |
| 91 | 0.57 | 0.06 | 0.66 |
| 92 | 0.11 | 0.03 | 0.24 |
| 93 | 0.43 | 0.05 | 0.47 |
| 94 | 3.64 | 0.63 | 3.26 |
| 95 | 12.5 | 4.34 | 3.26 |
| 96 | 11.7 | 0.90 | 12.5 |
| 97 | 1.03 | 0.12 | 1.51 |
| 98 | 0.37 | 0.04 | 0.50 |
| 99 | N/D | N/D | N/D |
| 100 | 6.22 | 0.61 | 4.95 |
| 101 | N/D | N/D | N/D |
| 102 | N/D | N/D | N/D |
| 103 | NA | 0.15 | N/D |
| 104 | N/D | 2.06 | N/D |
| 105 | N/D | 0.23 | N/D |
| 106 |  | 1.9 |  |
| 107 |  | 0.37 |  |
| 108 |  | 1.3 |  |
| 109 |  | 3.1 |  |
| 110 |  | 0.23 |  |
| 111 |  | 0.39 |  |
| 112 |  | 1.5 |  |
| 113 |  | 2.8 |  |
| 114 |  | 0.22 |  |
| 115 |  | >15 |  |
| 116 |  | 0.095 |  |
| 117 |  | 0.20 |  |
| 118 |  | 2.3 |  |
| 119 |  | 0.65 |  |
| 120 |  | 2.4 |  |
| 121 |  | >15 |  |
| 122 |  | 7.4 |  |
| 123 |  | 4.6 |  |
| 124 |  | 6.287 |  |
| 125 |  | 7.509 |  |
| 126 |  | 4.152 |  |
| 127 |  | 0.137 |  |
| 128 |  | 0.049 |  |
| 129 | N/D | 0.0106 | N/D |
| 130 | N/D | 0.1000 | N/D |
| 131 | N/D | 0.662 | N/D |
| 132 | N/D | 0.124 | N/D |
| 133 | N/D | 0.0192 | N/D |

Biological Assay Section 2
Protein Preparation
KAT5

Molecular Biology: A codon optimized DNA sequence (for expression in *Escherichia coli*) encoding amino acid residues 2 to 461 (Uniprot Q92993-2) of human KAT5 isoform was synthesised by GenScript USA Inc (Piscataway, N.J., USA). This was ligated into a modified pET43a *E. coli* expression vector designed to encode an N-terminal hexahistidine tag followed by a tobacco etch virus protease (TEV) cleavage site and by the KAT5 sequence. The resulting protein sequence is listed below (SEQ ID NO:5).

MGHHHHHHGTENLYFQGSAEVGEIIEGCRLPVLRRNQDNEDEWPLAEILS

VKDISGRKLFYVHYIDFNKRLDEWVTHERLDLKKIQFPKKEAKTPTKNGL

PGSRPGSPEREVKRKVEVVSPATPVPSETAPASVFPQNGAARRAVAAQPG

RKRKSNCLGTDEDSQDSSDGIPSAPRMTGSLVSDRSHDDIVTRMKNIECI

ELGRHRLKPWYFSPYPQELTTLPVLYLCEFCLKYGRSLKCLQRHLTKCDL

RHPPGNEIYRKGTISFFEIDGRKNKSYSQNLCLLAKCFLDHKTLYYDTDP

FLFYVMTEYDCKGFHIVGYFSKEKESTEDYNVACILTLPPYQRRGYGKLL

IEFSYELSKVEGKTGTPEKPLSDLGLLSYRSYWSQTILEILMGLKSESGE

RPQITINEISEITSIKKEDVISTLQYLNLINYYKGQYILTLSEDIVDGHE

RAMLKRLLRIDSKCLHFTPKDWSKRGKWAS*

Protein Expression: To produce recombinant KAT5 protein, expression plasmid was transformed into *E. coli* BL21 DE3 strain and grown with shaking at 37° C. in 1 L volumes of Terrific broth (TB) supplemented with 100 µg/mL Ampicillin and 50 µM zinc until an OD600 of 0.8 was reached. Cultures were transferred to 18° C. and protein expression induced by the addition of Isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −20° C.

Protein Purification: Protein purification was initiated by thawing the cell pellet (25 g wet weight) in Lysis buffer (50 mM Hepes pH 7.4, 500 mM NaCl, 5 mM imidazole, 5% [v/v] glycerol, 0.1% [w/v] CHAPS, 2 mM 2-mercaptoethanol, 3 mM MgCl$_2$, 0.5 mg/mL lysozyme, benzonase endonuclease [EMD Millipore], 1 mM PMSF, complete protease inhibitor tablets EDTA-free [Roche]) using a ratio of 6 mL of buffer per 1 g of cells. Cells were further lysed by sonication using a Misonix Liquid Processor (6×30 second pulses, amplitude 60 [70 watts]) and then centrifuged at 48,000×g at 4° C. Supernatant (cell lysate) was mixed with 20 mL of Q-Sepharose FF resin (GE Healthcare) pre-equilibrated with Q buffer (20 mM Hepes pH 7.4, 1 M NaCl). The unbound fraction from Q-Sepharose FF was then incubated with 5 mL of cOmplete His-Tag Purification Resin (Roche), pre-equilibrated with IMAC Wash Buffer (20 mM hepes pH 7.4, 500 mM NaCl, 35 mM imidazole). The resin was washed with IMAC Wash Buffer, and bound KAT5 eluted with IMAC Elution buffer (20 mM hepes pH 7.4, 500 mM NaCl, 300 mM imidazole). IMAC-eluted protein was immediately desalted into Storage buffer (50 mM Na citrate pH 6.5, 500 mM NaCl, 5% [v/v] glycerol) using 2× HiPrep 26/10 desalting columns (GE Healthcare) in series. Desalted protein was further purified by passing through a HiLoad 26/60 Superdex 75 column pre-equilibrated in Storage buffer. Finally, KAT5 protein was concentrated to 1.5 mg/mL

KAT6A

Molecular Biology: The DNA sequence encoding amino acid residues 507 to 778 (Uniprot Q92794-1) of human KAT6A was amplified by PCR and was ligated into a modified pET E. coli expression vector designed to encode a NusA solubility tag followed by a hexahistidine tag and a tobacco etch virus protease (TEV) cleavage site and by the KAT6A sequence. The resulting protein sequence is listed below (SEQ ID NO:6).

MNKEILAVVEAVSNEKALPREKIFEALESALATATKKKYEQEIDVRVQID

RKSGDFDTFRRWLVVDEVTQPTKEITLEAARYEDESLNLGDYVEDQIESV

TFDRITTQTAKQVIVQKVREAERAMVVDQFREHEGEIITGVVKKVNRDNI

SLDLGNNAEAVILREDMLPRENFRPGDRVRGVLYSVRPEARGAQLFVTRS

KPEMLIELFRIEVPEIGEEVIEIKAAARDPGSRAKIAVKTNDKRIDPVGA

CVGMRGARVQAVSTELGGERIDIVLWDDNPAQFVINAMAPADVASIVVDE

DKHTMDIAVEAGNLAQAIGRNGQNVRLASQLSGWELNVMTVDDLQAKHQA

EAHAAIDTFTKYLDIDEDFATVLVEEGFSTLEELAYVPMKELLEIEGLDE

PTVEALRERAKNALATIAQAQEESLGDNKPADDLLNLEGVDRDLAFKLAA

RGVCTLEDLAEQGIDDLADIEGLTDEKAGALIMAARNICWFGDEATSGSG

HHHHHHSAGENLYFQGAMGRCPSVIEFGKYEIHTWYSSPYPQEYSRLPKL

YLCEFCLKYMKSRTILQQHMKKCGWFHPPVNEIYRKNNISVFEVDGNVST

IYCQNLCLLAKLFLDHKTLYYDVEPFLFYVLTQNDVKGCHLVGYFSKEKH

CQQKYNVSCIMILPQYQRKGYGRFLIDFSYLLSKREGQAGSPEKPLSDLG

RLSYMAYWKSVILECLYHQNDKQISIKKLSKLTGICPQDITSTLHHLRML

DFRSDQFVIIRREKLIQDHMAKLQLNLRPVDVDPECLRWTP

Protein Expression: To produce recombinant KAT6A protein, expression plasmid was transformed into E. coli BL21 DE3 strain and grown with shaking at 37° C. in 1 L volumes of Terrific broth (TB) supplemented with 100 µg/mL Ampicillin until an OD600 of 0.8 was reached. Cultures were transferred to 18° C. and protein expression induced by the addition of Isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −20° C.

Protein Purification: Protein purification was initiated by thawing the cell pellet (40 g wet weight) in Lysis buffer (25 mM Tris-HCl pH 7.8, 500 mM NaCl, 5 mM DTT, 0.01% [v/v] Triton-X 100, 5% [v/v] glycerol, 2 mM MgCl₂, 10 mM Imidazole, 0.5 mg/mL lysozyme, benzonase endonuclease [EMD Millipore], 1 mM PMSF, complete protease inhibitor tablets EDTA-free [Roche]) using a ratio of 5 mL of buffer per 1 g of cells. Cells were further lysed by 3 passes (at 15000 psi) through an ice cooled Avestin C5 cell crusher and then centrifuged at 48,000×g at 4° C. Supernatant (cell lysate) was filtered through a 5 µm filter and applied onto 5 mL HiTrap IMAC Sepharose FF column (GE Healthcare) pre-equilibrated with IMAC wash buffer (25 mM Tris-HCl pH 7.8, 500 mM NaCl, 5 mM DTT, 0.01% [v/v] Triton-X 100, 5% [v/v] glycerol, 20 mM Imidazole) using a Profinia Affinity chromatography purification system (Bio-Rad). The IMAC column was then washed with IMAC Wash buffer and bound KAT6A protein eluted with IMAC Elution buffer (25 mM Tris-HCl pH 7.8, 500 mM NaCl, 5% [v/v] glycerol, 5 mM DTT, 250 mM Imidazole). IMAC-eluted protein was further purified by passing through a HiLoad 26/60 Superdex 200 column pre-equilibrated in Storage buffer (25 mM Tris-HCl pH 7.8, 500 mM NaCl, 5 mM DTT, 5% [v/v] glycerol). Finally, KAT6A protein was concentrated to <; 1 mg/mL using Amicon Ultra centrifugal filter unit (Utra-15 MWCO 10 kDa), flash-frozen in liquid nitrogen and stored in −70° C. freezer.

KAT7

Molecular Biology: A codon optimized DNA sequence encoding amino acid residues 325 to 611 (Uniprot O95251-1) of human KAT7 was synthesised by GenScript USA Inc (Piscataway, N.J., USA). This was ligated into a modified pET43a E. coli expression vector designed to encode an N-terminal hexahistidine tag followed by a tobacco etch virus protease (TEV) cleavage site and by the KAT7 sequence. The resulting protein sequence is listed below (SEQ ID NO:7).

MGHHHHHHGTENLYFQGSRLQGQITEGSNMIKTIAFGRYELDTWYHSPYP

EEYARLGRLYMCEFCLKYMKSQTILRRHMAKCVWKHPPGDEIYRKGSISV

FEVDGKKNKIYCQNLCLLAKLFLDHKTLYYDVEPFLFYVMTEADNTGCHL

IGYFSKEKNSFLNYNVSCILTMPQYMRQGYGKMLIDFSYLLSKVEEKVGS

PERPLSDLGLISYRSYWKEVLLRYLHNFQGKEISIKEISQETAVNPVDIV

STLQALQMLKYWKGKHLVLKRQDLIDEWIAKEAKRSNSNKTMDPSCLKWT

PPKGTAS

Protein Expression: To produce recombinant KAT7 protein, expression plasmid was transformed into E. coli BL21 DE3 RIL strain and grown with shaking at 37° C. in 1 L volumes of Terrific broth (TB) supplemented with 100 µg/mL Ampicillin and 50 µM zinc until an OD600 of 0.8 was reached. Cultures were transferred to 18° C. and protein expression induced by the addition of Isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −20° C.

Protein Purification: Protein purification was initiated by thawing the cell pellet (10 g wet weight) in Lysis buffer (50 mM Hepes pH 7.5, 300 mM NaCl, 5 mM DTT, 5 mM Imidazole, 0.05% [v/v] Brij 35, 10% [v/v] glycerol, 3 mM MgCl₂, 0.5 mg/mL lysozyme, benzonase endonuclease [EMD Millipore], 1 mM PMSF, complete protease inhibitor tablets EDTA-free [Roche]) using a ratio of 10 mL of buffer per 1 g of cells. Cells were further lysed by sonication using a Misonix Liquid Processor (6×30 second pulses, amplitude 60 [70 watts]) and then centrifuged at 48,000×g at 4° C. Supernatant (cell lysate) was incubated with 1 mL of cOmplete His-Tag Purification Resin (Roche), pre-equilibrated with IMAC Wash Buffer 1 (25 mM Hepes pH 7.5, 800 mM NaCl, 5 mM imidazole, 10% [v/v] glycerol, 5 mM DTT, 0.01% [v/v] Brij 35, 50 mM arginine, 50 mM glutamic acid). The resin was sequentially washed with IMAC Wash buffer 1 and IMAC Wash buffer 2 (25 mM hepes pH 7.5, 300 mM NaCl, 20 mM imidazole, 10% [v/v]glycerol, 5 mM DTT, 0.01% [v/v] Brij 35, 50 mM arginine, 50 mM glutamic acid). Bound KAT7 protein was eluted with IMAC Elution buffer (25 mM hepes pH 7.5, 200 mM NaCl, 500 mM imidazole, 10% [v/v] glycerol, 5 mM DTT 0.01% [v/v] Brij 35, 50 mM arginine, 50 mM glutamic acid). The eluting protein was collected directly into 4 volumes of Desalt Buffer (50 mM Na citrate pH 6.5, 200 mM NaCl, 0.01% [v/v] Brij 35, 10% [v/v]glycerol, 5 mM DTT) to bring the final imidazole concentration to 100 mM. IMAC-eluted protein was immediately desalted into Desalt buffer using 2× HiPrep 26/10 desalting columns (GE Healthcare) in series. Desalted protein was further purified by passing through a HiLoad 26/60 Superdex 75 column pre-equilibrated in Storage Buffer (50 mM Na citrate pH 6.5, 200 mM NaCl, 10% [v/v] glycerol, 5 mM DTT). Finally, KAT7 protein was concentrated to 3.5 mg/mL using Amicon Ultra centrifugal filter unit (Utra-15 MWCO 10 kDa), flash-frozen in liquid nitrogen and stored in −70° C. freezer.

Acetyltransferase Biochemical Assay

To determine the inhibition of KAT enzymatic activity by test compounds, assay reactions were conducted in a volume of 8 µL in 384-well low volume assay plates. The reactions were performed in assay buffer (100 mM Tris-HCl, pH 7.8, 15 mM NaCl, 1 mM EDTA, 0.01% Tween-20, 1 mM Dithiothreitol, and 0.01% m/v chicken egg white albumin).

Reactions were set up with 1 µM Acetyl coenzyme A, 100 nM of full-length recombinant histone labelled by limited biotinylation (KAT6 Å, KAT7: H3.1, KAT5), 10/5/8/40/20 nM of KAT5/KAT6 Å/KAT7 enzyme respectively, and an acetyl-lysine specific antibody (H3.1: Cell Signaling Technology, H4: Abcam). 11-point dilution series of the test compounds were prepared in DMSO; a volume of 100 nL was transferred using a pin tool into assay plates containing substrates, before adding enzyme to start the reaction. Positive (no compound, DMSO only) and negative (AcCoA omitted) control reactions were included on the same plates and received the same amount of DMSO as the compound treated wells. After adding all reagents, the plates were sealed with adhesive seals and incubated for 90 min at room temperature. An additional 4 µL of assay buffer containing AlphaScreen® Protein A acceptor beads and Streptavidin donor beads (PerkinElmer, Waltham, Mass.) to a final concentration of 8 µg/mL was then added. After incubation for 2 hours the plates were read using an EnVision 2103 multi label plate reader (PerkinElmer) in HTS AlphaScreen® mode, IC50 values were obtained from the raw readings by calculating percent inhibition (% I) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, B is the upper asymptote, C is the IC50 value, and D is the slope.

The results are shown in the Table 23 below:

TABLE 23

| Example | TIP60-KAT5 IC50 (µM) | MOZ-KAT6A IC50 (µM) | HBO1-KAT7 IC50 (µM) |
|---|---|---|---|
| 98 | =0.256 | =0.0059 | =0.035 |
| 99 | =0.98 | =0.013 | =0.12 |
| 100 | =11.17 | =0.03 | =0.34 |
| 101 | =11.23 | =1.26 | =1.55 |
| 102 | >125.00 | =48.75 | =1.40 |

Histone H3 Lysine 23 Acetylation Biomarker Assay

Compounds were tested for their ability to inhibit acetylation of the histone H3K23 marker in the following assay:

The cell line U2OS was seeded at a density of 9,000 cells per well in 96 well optical quality tissue culture plates in RPMI medium and 10% foetal bovine serum, and allowed to adhere for 24 hours under standard culture conditions (37 degree Celsius, 5% $CO_2$). At the end of this period the medium was aspirated. Compound dilutions prepared in DMSO were added to medium, with negative control wells reserved for treatment with DMSO only and 100% inhibition positive controls receiving a potent inhibitor compound (e.g. cas 2055397-28-7, benzoic acid, 3-fluoro-5-(2-pyridinyl)-, 2-[(2-fluorophenyl)sulfonyl]hydrazide) (Baell, J., Nguyen, H. N., Leaver, D. J., Cleary, B. L., Lagiakos, H. R., Sheikh, B. N., Thomas. T. J., Aryl sulfonohydrazides, WO2016198507A1, 2016) at 10 µM concentration and 200 µL transferred to the cells. After incubation for 24 hours, the cells were fixed with 3.7% formaldehyde in PBS for 20 minutes at room temperature, washed (5×5 minutes) with phosphate buffer saline containing 0.1% Tween 20 and blocked with Odyssey blocking buffer (LI-COR, Lincoln, Nebr.) containing 0.1% TritonX100. Anti-H3K23ac specific antibody (Abcam ab177275) in Odyssey blocking buffer containing 0.1% Tween 20 was added and incubated for 16 hours at 4 degree Celsius. After washing (as above), a secondary antibody labelled with Alexa647 dye (LifeTechnologies) and Hoechst 33342 (1 µg/mL, SigmaAldrich) were added for 1 hour incubation. Plates were washed as previously and read on a PerkinElmer Phenix high content imaging platform. Using a Columbus image analysis pipeline, individual nuclei were located by Hoechst 33342 stain and the acetylation level was calculated from the Alexa647-related intensity in the same area. The resulting mean intensity per cell was directly converted to percent inhibition relative to controls on the same plate and the data fitted against a four-parameter logistic model to determine the 50% inhibitory concentration (IC50).

The results are shown in Table 24 below:

TABLE 24

| Example | Histone H3 Lysine 23 Biomarker IC50 (µM) |
|---|---|
| 98 | =0.0006 |
| 99 | N/D |
| 100 | =0.046 |
| 101 | N/D |
| 102 | N/D |

Histone H3 Lysine 14 Acetylation BiomarkerAssay

Compounds were tested for their ability to inhibit acetylation of the histone H3 Lysine 14 marker in the following assay:

The cell line U2OS was seeded at a density of 3,000 cells per well in 384-well optical quality tissue culture plates in RPMI medium supplemented with 10% foetal bovine serum and 10 mM Hepes. The cells were allowed to adhere for 24 hours under standard culture conditions (37 degree Celsius, 5% CO2). At the end of this period the cells were washed with serum free medium. Compound dilutions prepared in DMSO were added to the serum free medium, with negative control wells reserved for treatment with DMSO only and 100% inhibition positive controls receiving a potent inhibitor compound (e.g. (Z)-4-fluoro-N-((3-hydroxyphenyl) sulfonyl)-5-methyl-[1,1'-biphenyl]-3-carbohydrazonic acid) at 10 µM concentration. After incubation for 24 hours, the cells were fixed with 4% formaldehyde in PBS for 15 minutes at room temperature, washed with phosphate buffer saline and blocked with blocking buffer containing 0.2% TritonX100 and 2% BSA. Anti-H3K14ac specific antibody (Cell Signalling Technologies) in blocking buffer was added and incubated overnight at 4 degree Celsius. After washing, a secondary antibody labelled with AlexaFluor 488 dye (ThermoFisher) and Hoechst 33342 (1 μg/mL, Life Technologies) were added for 2 hours incubation at room temperature. Plates were washed and read on a PerkinElmer Opera HCS high content imaging platform. Using a Columbus image analysis pipeline, individual nuclei were located by Hoechst 33342 stain and the acetylation level was calculated from the AlexaFluor 488-related intensity in the same area. The resulting mean intensity per cell was converted to percent inhibition relative to controls on the same plate and the data fitted against a four-parameter logistic model to determine the 50% inhibitory concentration (IC50).

The results are shown in Table 25 below:

TABLE 25

| Example | Histone H3 Lysine 14 Biomarker IC50 (μM) |
|---|---|
| 98 | N/D |
| 99 | =1.55 |
| 100 | =1.36 |
| 101 | N/D |
| 102 | =28.33 |

H2A.Z Lysine 7 Acetylation BiomarkerAssay

Compounds were tested for their ability to inhibit the histone H2A.Z Lysine 7 acetylation marker in the following assay: The cell line U2OS was seeded at a density of 3,000 cells per well in 384-well optical quality tissue culture plates in RPMI medium supplemented with 10% foetal bovine serum and 10 mM Hepes. The cells were allowed to adhere for 24 hours under standard culture conditions (37 degree Celsius, 5% CO2). At the end of this period the cells were washed with serum free medium. Compound dilutions prepared in DMSO were added to the serum free medium, with negative control wells reserved for treatment with DMSO only and 100% inhibition positive controls receiving a potent inhibitor compound enantiomer 1 of 7-iodo-N-(2-(oxazol-2-yl)-2-phenylethyl)-2H-benzo[e][1,2,4]thiadiazine-3-carboxamide 1,1-dioxide, which is compound 146 of co-pending application GB1713962.7, filed on 31 Aug. 2018, at 30 μM concentration. After incubation for 24 hours, the cells were fixed with 4% formaldehyde in PBS for 15 minutes at room temperature, washed with phosphate buffer saline and blocked with blocking buffer containing 0.2% TritonX100 and 2% BSA. Anti-H2A.ZK7ac specific antibody (Abcam) in blocking buffer was added and incubated overnight at 4 degree Celsius. After washing, a secondary antibody labelled with AlexaFluor 488 dye (ThermoFisher) and Hoechst 33342 (1 μg/mL, Life Technologies) were added for 2 hours incubation at room temperature. Plates were washed and read on a PerkinElmer Opera HCS high content imaging platform. Using a Columbus image analysis pipeline, individual nuclei were located by Hoechst 33342 stain and the acetylation level was calculated from the AlexaFluor 488-related intensity in the same area. The resulting mean intensity per cell was converted to percent inhibition relative to controls on the same plate and the data fitted against a four-parameter logistic model to determine the 50% inhibitory concentration (IC50).

The results are shown in Table 26 below:

TABLE 26

| Example | H2A.Z Lysine 7 Biomarker IC50 (μM) |
|---|---|
| 98 | N/D |
| 99 | =11.40 |
| 100 | =14.98 |
| 101 | N/D |
| 102 | >40.00 |

REFERENCES

Aggarwal and Calvi, Nature, 2004, 430, 372-376 doi: 10.1038/nature02694
Avvakumov et al., Oncogene, 2007, 26, 5395-5407 doi: 10.1038/sj.onc.1210608
Berge et al., J. Pharm. Sci., 1977, 66, 1-19 doi:10.1002/jps.2600660104
Borrow et al., Nat. Genet., 1996, 14, 33-41 doi:10.1038/ng0996-33
Dekker et al., Drug. Discov. Today, 2014, 19, 654-660 doi:10.1016/j.drudis.2013.11.012
Doyon et al., Mol. Cell., 2006, 21, 51-64 doi:10.1016/j.molcel.2005.12.007
Dhuban et al., Sci. Immunol., 2017, 2, 9297 doi:10.1126/sciimmunol.aai9297
Duong et al., Cancer Res., 2013, 73, 5556-5568 doi: 10.1158/0008-5472.CAN-13-0013
Ghizzoni et al., Eur. J. Med. Chem., 2012, 47, 337-344 doi:10.1016/j.ejmech.2011.11.001
Gil et al., J. Proteomics, 2017, 150, 297-309 doi:10.1016/j.jprot.2016.10.003
Gobert, M. et al., Cancer Research, 2009, 69, 2000-2009 doi:10.1158/0008-5472.CAN-08-2360
Holbert et al., J. Biol. Chem., 2007, 282, 36603-36613 doi:10.1074/jbc.M705812200
Iizuka et al., Mol. Cell. Biol., 2006, 26, 1098-1108 doi: 10.1128/MCB.26.3.1098-1108.2006
Iizuka et al., Cancer Sci., 2013, 104, 1647-1655 doi: 10.1111/cas.12303
Jeong, et al., Blood Res 2016 51(3), 152-154 doi:10.5045/br.2016.51.3.152
Joshi, et al., Immunity 2015, 43, 579-590 doi:10.1016/j.immuni.2015.08.006
Li, B. et al., PNAS, 2007, 104, 4571-4576 doi:10.1073/pnas.0700298104
Melero, et al. Nature Reviews Cancer, 2015, 15, 457-472 doi:10.1038/nrc3973
Merson et al., J. Neurosci., 2006, 26, 11359-11370 doi: 10.1523/JNEUROSCI.2247-06.2006
Miller, A. M. et al. J. Immunol., 2006, 177, 7398-7405 doi:10.4049/jimmunol.177.10.7398
Persa, E. et al. Cancer Letters, 2015 368(2), 252-261 doi: 10.1016/j.canlet.2015.03.003
Sheikh et al., Blood, 2015, 125(12), 1910-21 doi:10.1182/blood-2014-08-594655
Shi et al, Nature Biotech, 2015, 33, 661-667 doi:10.1038/nbt.3235
Su et al., Int. J. Mol. Sci., 2016, 17, 1-18 doi:10.3390/ijms17101594
Stern et al., Crit. Rev. Oncol. Hematol., 2005, 54, 11-29 doi:10.1016/j.critrevonc.2004.10.011
Thomas et al., Development, 2000, 127, 2537-2548 PMID: 10821753
Tao, H. et al., Lung Cancer, 2012, 75, 95-101 doi:10.1016/j.lungcan.2011.06.002
Turner-Ivey et al., Neoplasia, 2014, 16(8): 644-655 doi: 10.1016/j.neo.2014.07.007

Valerio et al., *Cancer Research*, 2017, 77(7), 1753-62 doi: 10.1158/0008-5472.CAN-16-2374

Vizmanos et al., *Genes Chromosomes Cancer*, 2003, 36(4), 402-405 doi:10.1002/gcc.10174

Voss et al., *BioEssays*, 2009, 31(10), 1050-1061 doi: 10.1002/bies.200900051

Wang, L., et al. *EBioMedicine*, 2016, 13, 99-112 doi: 10.1016/j.ebiom.2016.10.018

Wang, X. et al., *Oncogene*, 2017, 36, 3048-3058 doi: 10.1038/onc.2016.458

Xiao, Y. et al., *Cell reports*, 2014, 7, 1471-1480 doi:10.1016/j.celrep.2014.04.021

Yan, M. et al., *Breast Cancer Research*, 2011, 13, R47 doi:10.1186/bcr2869

Zack et al., *Nature Genetics* 2013 45, 1134-1140 doi: 10.1038/ng.2760

Zhang et al., *Mini. Rev. Med. Chem.*, 2017, 17, 1-8 doi: 10.2174/1389557516666160923125031

---

What is claimed is:

1. A compound

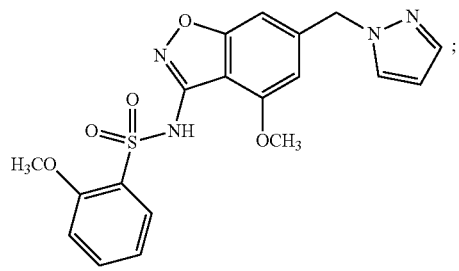 [SMILES: COc1ccccc1S(=O)(=O)Nc1noc2cc(Cn3cccn3)cc(OC)c12 ; ";"]

or a pharmaceutically acceptable salt thereof.

2. 2-Methoxy-N-{4-methoxy-6-[(1H-pyrazol-1-yl)methyl]-1,2-benzoxazol-3-yl}benzene-1-sulfonamide.

3. A pharmaceutical composition comprising the compound of claim 1, or a pharmaceutically acceptable salt thereof, and a pharmaceutically acceptable carrier or diluent.

4. A pharmaceutically acceptable salt of 2-methoxy-N-{4-methoxy-6-[(1H-pyrazol-1-yl)methyl]-1,2-benzoxazol-3-yl}benzene-1-sulfonamide.

5. A pharmaceutical composition comprising 2-methoxy-N-{4-methoxy-6-[(1H-pyrazol-1-yl)methyl]-1,2-benzoxazol-3-yl}benzene-1-sulfonamide, and a pharmaceutically acceptable carrier or diluent.

6. A pharmaceutical composition comprising a pharmaceutically acceptable salt of 2-methoxy-N-{4-methoxy-6-[(1H-pyrazol-1-yl)methyl]-1,2-benzoxazol-3-yl}benzene-1-sulfonamide, and a pharmaceutically acceptable carrier or diluent.

* * * * *

SEQUENCE LISTING

```
<160> NUMBER OF SEQ ID NOS: 7

<210> SEQ ID NO 1
<211> LENGTH: 20
<212> TYPE: PRT
<213> ORGANISM: Homo sapiens

<400> SEQUENCE: 1

Ala Arg Thr Lys Gln Thr Ala Arg Lys Ser Thr Gly Gly Lys Ala Pro
1               5                   10                  15

Arg Lys Gln Leu
            20

<210> SEQ ID NO 2
<211> LENGTH: 20
<212> TYPE: PRT
<213> ORGANISM: Homo sapiens

<400> SEQUENCE: 2

Ser Gly Arg Gly Lys Gly Gly Lys Gly Leu Gly Lys Gly Gly Ala Lys
1               5                   10                  15

Arg His Arg Lys
            20

<210> SEQ ID NO 3
<211> LENGTH: 21
<212> TYPE: PRT
<213> ORGANISM: Homo sapiens

<400> SEQUENCE: 3

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 4
<211> LENGTH: 21
<212> TYPE: PRT
<213> ORGANISM: Homo sapiens

<400> SEQUENCE: 4

Ser Gly Arg Gly Lys Gly Gly Lys Gly Leu Gly Lys Gly Gly Ala Lys
1               5                   10                  15

Arg His Arg Lys Val
            20

<210> SEQ ID NO 5
<211> LENGTH: 480
<212> TYPE: PRT
<213> ORGANISM: Artificial Sequence
<220> FEATURE:
<223> OTHER INFORMATION: modified KAT5 protein
```

<400> SEQUENCE: 5

```
Met Gly His His His His His Gly Thr Glu Asn Leu Tyr Phe Gln
1               5                   10                  15

Gly Ser Ala Glu Val Gly Glu Ile Ile Glu Gly Cys Arg Leu Pro Val
            20                  25                  30

Leu Arg Arg Asn Gln Asp Asn Glu Asp Glu Trp Pro Leu Ala Glu Ile
        35                  40                  45

Leu Ser Val Lys Asp Ile Ser Gly Arg Lys Leu Phe Tyr Val His Tyr
    50                  55                  60

Ile Asp Phe Asn Lys Arg Leu Asp Glu Trp Val Thr His Glu Arg Leu
65                  70                  75                  80

Asp Leu Lys Lys Ile Gln Phe Pro Lys Lys Glu Ala Lys Thr Pro Thr
                85                  90                  95

Lys Asn Gly Leu Pro Gly Ser Arg Pro Gly Ser Pro Glu Arg Glu Val
            100                 105                 110

Lys Arg Lys Val Glu Val Val Ser Pro Ala Thr Pro Val Pro Ser Glu
        115                 120                 125

Thr Ala Pro Ala Ser Val Phe Pro Gln Asn Gly Ala Ala Arg Arg Ala
    130                 135                 140

Val Ala Ala Gln Pro Gly Arg Lys Arg Lys Ser Asn Cys Leu Gly Thr
145                 150                 155                 160

Asp Glu Asp Ser Gln Asp Ser Ser Asp Gly Ile Pro Ser Ala Pro Arg
                165                 170                 175

Met Thr Gly Ser Leu Val Ser Asp Arg Ser His Asp Asp Ile Val Thr
            180                 185                 190

Arg Met Lys Asn Ile Glu Cys Ile Glu Leu Gly Arg His Arg Leu Lys
        195                 200                 205

Pro Trp Tyr Phe Ser Pro Tyr Pro Gln Glu Leu Thr Thr Leu Pro Val
    210                 215                 220

Leu Tyr Leu Cys Glu Phe Cys Leu Lys Tyr Gly Arg Ser Leu Lys Cys
225                 230                 235                 240

Leu Gln Arg His Leu Thr Lys Cys Asp Leu Arg His Pro Pro Gly Asn
                245                 250                 255

Glu Ile Tyr Arg Lys Gly Thr Ile Ser Phe Phe Glu Ile Asp Gly Arg
            260                 265                 270

Lys Asn Lys Ser Tyr Ser Gln Asn Leu Cys Leu Leu Ala Lys Cys Phe
        275                 280                 285

Leu Asp His Lys Thr Leu Tyr Tyr Asp Thr Asp Pro Phe Leu Phe Tyr
    290                 295                 300

Val Met Thr Glu Tyr Asp Cys Lys Gly Phe His Ile Val Gly Tyr Phe
305                 310                 315                 320

Ser Lys Glu Lys Glu Ser Thr Glu Asp Tyr Asn Val Ala Cys Ile Leu
                325                 330                 335

Thr Leu Pro Pro Tyr Gln Arg Arg Gly Tyr Gly Lys Leu Leu Ile Glu
            340                 345                 350

Phe Ser Tyr Glu Leu Ser Lys Val Glu Gly Lys Thr Gly Thr Pro Glu
        355                 360                 365

Lys Pro Leu Ser Asp Leu Gly Leu Leu Ser Tyr Arg Ser Tyr Trp Ser
    370                 375                 380

Gln Thr Ile Leu Glu Ile Leu Met Gly Leu Lys Ser Glu Ser Gly Glu
385                 390                 395                 400

Arg Pro Gln Ile Thr Ile Asn Glu Ile Ser Glu Ile Thr Ser Ile Lys
                405                 410                 415
```

```
Lys Glu Asp Val Ile Ser Thr Leu Gln Tyr Leu Asn Leu Ile Asn Tyr
            420                 425                 430

Tyr Lys Gly Gln Tyr Ile Leu Thr Leu Ser Glu Asp Ile Val Asp Gly
            435                 440                 445

His Glu Arg Ala Met Leu Lys Arg Leu Arg Ile Asp Ser Lys Cys
450                 455                 460

Leu His Phe Thr Pro Lys Asp Trp Ser Lys Arg Gly Lys Trp Ala Ser
465                 470                 475                 480

<210> SEQ ID NO 6
<211> LENGTH: 791
<212> TYPE: PRT
<213> ORGANISM: Artificial Sequence
<220> FEATURE:
<223> OTHER INFORMATION: modified KAT6A protein

<400> SEQUENCE: 6

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
            35                  40                  45

Ile Asp Arg Lys Ser Gly Asp Phe Asp Thr Phe Arg Arg Trp Leu Val
50                  55                  60

Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
            85                  90                  95

Ile Glu Ser Val Thr Phe Asp Arg Ile Thr Thr Gln Thr Ala Lys Gln
            100                 105                 110

Val Ile Val Gln Lys Val Arg Glu Ala Glu Arg Ala Met Val Val Asp
            115                 120                 125

Gln Phe Arg Glu His Glu Gly Glu Ile Ile Thr Gly Val Val Lys Lys
130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
            165                 170                 175

Asp Arg Val Arg Gly Val Leu Tyr Ser Val Arg Pro Glu Ala Arg Gly
            180                 185                 190

Ala Gln Leu Phe Val Thr Arg Ser Lys Pro Glu Met Leu Ile Glu Leu
            195                 200                 205

Phe Arg Ile Glu Val Pro Glu Ile Gly Glu Val Ile Glu Ile Lys
210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
            245                 250                 255

Ala Arg Val Gln Ala Val Ser Thr Glu Leu Gly Gly Glu Arg Ile Asp
            260                 265                 270

Ile Val Leu Trp Asp Asp Asn Pro Ala Gln Phe Val Ile Asn Ala Met
            275                 280                 285

Ala Pro Ala Asp Val Ala Ser Ile Val Val Asp Glu Asp Lys His Thr
            290                 295                 300
```

-continued

```
Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
            325                 330                 335

Asn Val Met Thr Val Asp Asp Leu Gln Ala Lys His Gln Ala Glu Ala
        340                 345                 350

His Ala Ala Ile Asp Thr Phe Thr Lys Tyr Leu Asp Ile Asp Glu Asp
    355                 360                 365

Phe Ala Thr Val Leu Val Glu Glu Gly Phe Ser Thr Leu Glu Glu Leu
370                 375                 380

Ala Tyr Val Pro Met Lys Glu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
    450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala Thr
                485                 490                 495

Ser Gly Ser Gly His His His His His Ser Ala Gly Glu Asn Leu
            500                 505                 510

Tyr Phe Gln Gly Ala Met Gly Arg Cys Pro Ser Val Ile Glu Phe Gly
        515                 520                 525

Lys Tyr Glu Ile His Thr Trp Tyr Ser Ser Pro Tyr Pro Gln Glu Tyr
    530                 535                 540

Ser Arg Leu Pro Lys Leu Tyr Leu Cys Glu Phe Cys Leu Lys Tyr Met
545                 550                 555                 560

Lys Ser Arg Thr Ile Leu Gln Gln His Met Lys Lys Cys Gly Trp Phe
                565                 570                 575

His Pro Pro Val Asn Glu Ile Tyr Arg Lys Asn Asn Ile Ser Val Phe
            580                 585                 590

Glu Val Asp Gly Asn Val Ser Thr Ile Tyr Cys Gln Asn Leu Cys Leu
        595                 600                 605

Leu Ala Lys Leu Phe Leu Asp His Lys Thr Leu Tyr Tyr Asp Val Glu
    610                 615                 620

Pro Phe Leu Phe Tyr Val Leu Thr Gln Asn Asp Val Lys Gly Cys His
625                 630                 635                 640

Leu Val Gly Tyr Phe Ser Lys Glu Lys His Cys Gln Gln Lys Tyr Asn
                645                 650                 655

Val Ser Cys Ile Met Ile Leu Pro Gln Tyr Gln Arg Lys Gly Tyr Gly
            660                 665                 670

Arg Phe Leu Ile Asp Phe Ser Tyr Leu Leu Ser Lys Arg Glu Gly Gln
        675                 680                 685

Ala Gly Ser Pro Glu Lys Pro Leu Ser Asp Leu Gly Arg Leu Ser Tyr
    690                 695                 700

Met Ala Tyr Trp Lys Ser Val Ile Leu Glu Cys Leu Tyr His Gln Asn
705                 710                 715                 720
```

```
Asp Lys Gln Ile Ser Ile Lys Lys Leu Ser Lys Leu Thr Gly Ile Cys
                725                 730                 735

Pro Gln Asp Ile Thr Ser Thr Leu His His Leu Arg Met Leu Asp Phe
            740                 745                 750

Arg Ser Asp Gln Phe Val Ile Ile Arg Arg Glu Lys Leu Ile Gln Asp
            755                 760                 765

His Met Ala Lys Leu Gln Leu Asn Leu Arg Pro Val Asp Val Asp Pro
    770                 775                 780

Glu Cys Leu Arg Trp Thr Pro
785                 790

<210> SEQ ID NO 7
<211> LENGTH: 307
<212> TYPE: PRT
<213> ORGANISM: Artificial Sequence
<220> FEATURE:
<223> OTHER INFORMATION: modified KAT7 protein

<400> SEQUENCE: 7

Met Gly His His His His His Gly Thr Glu Asn Leu Tyr Phe Gln
1               5                   10                  15

Gly Ser Arg Leu Gln Gly Gln Ile Thr Glu Gly Ser Asn Met Ile Lys
            20                  25                  30

Thr Ile Ala Phe Gly Arg Tyr Glu Leu Asp Thr Trp Tyr His Ser Pro
        35                  40                  45

Tyr Pro Glu Glu Tyr Ala Arg Leu Gly Arg Leu Tyr Met Cys Glu Phe
    50                  55                  60

Cys Leu Lys Tyr Met Lys Ser Gln Thr Ile Leu Arg Arg His Met Ala
65                  70                  75                  80

Lys Cys Val Trp Lys His Pro Pro Gly Asp Glu Ile Tyr Arg Lys Gly
                85                  90                  95

Ser Ile Ser Val Phe Glu Val Asp Gly Lys Lys Asn Lys Ile Tyr Cys
            100                 105                 110

Gln Asn Leu Cys Leu Leu Ala Lys Leu Phe Leu Asp His Lys Thr Leu
        115                 120                 125

Tyr Tyr Asp Val Glu Pro Phe Leu Phe Tyr Val Met Thr Glu Ala Asp
    130                 135                 140

Asn Thr Gly Cys His Leu Ile Gly Tyr Phe Ser Lys Glu Lys Asn Ser
145                 150                 155                 160

Phe Leu Asn Tyr Asn Val Ser Cys Ile Leu Thr Met Pro Gln Tyr Met
                165                 170                 175

Arg Gln Gly Tyr Gly Lys Met Leu Ile Asp Phe Ser Tyr Leu Leu Ser
            180                 185                 190

Lys Val Glu Glu Lys Val Gly Ser Pro Glu Arg Pro Leu Ser Asp Leu
        195                 200                 205

Gly Leu Ile Ser Tyr Arg Ser Tyr Trp Lys Glu Val Leu Leu Arg Tyr
    210                 215                 220

Leu His Asn Phe Gln Gly Lys Glu Ile Ser Ile Lys Glu Ile Ser Gln
225                 230                 235                 240

Glu Thr Ala Val Asn Pro Val Asp Ile Val Ser Thr Leu Gln Ala Leu
                245                 250                 255

Gln Met Leu Lys Tyr Trp Lys Gly Lys His Leu Val Leu Lys Arg Gln
            260                 265                 270

Asp Leu Ile Asp Glu Trp Ile Ala Lys Glu Ala Lys Arg Ser Asn Ser
        275                 280                 285
```

```
Asn Lys Thr Met Asp Pro Ser Cys Leu Lys Trp Thr Pro Pro Lys Gly
    290                 295                 300
Thr Ala Ser
305
```